United States Patent
Meiyappan et al.

(10) Patent No.: US 9,957,494 B2
(45) Date of Patent: May 1, 2018

(54) CRYSTAL STRUCTURE OF HUMAN FOUR-PHOSPHATE ADAPTOR PROTEIN 2 GLYCOLIPID TRANSFER PROTEIN LIKE DOMAIN

(71) Applicants: Shire Human Genetic Therapies, Inc., Lexington, MA (US); Fondazione Telethon, Rome (IT)

(72) Inventors: Muthuraman Meiyappan, Lexington, MA (US); Maria A. DeMatteis, Rome (IT)

(73) Assignees: SHIRE HUMAN GENETIC THERAPIES, INC., Lexington, MA (US); FONDAZIONE TELETHON, Roma (IT)

( * ) Notice: Subject to any disclaimer, the term of this patent is extended or adjusted under 35 U.S.C. 154(b) by 0 days. days.

(21) Appl. No.: 15/327,583

(22) PCT Filed: Jul. 23, 2015

(86) PCT No.: PCT/US2015/041683
§ 371 (c)(1),
(2) Date: Jan. 19, 2017

(87) PCT Pub. No.: WO2016/014758
PCT Pub. Date: Jan. 28, 2016

(65) Prior Publication Data
US 2017/0349889 A1   Dec. 7, 2017

Related U.S. Application Data

(60) Provisional application No. 62/029,180, filed on Jul. 25, 2014.

(51) Int. Cl.
| | | |
|---|---|---|
| C12N 9/36 | (2006.01) | |
| G01N 33/68 | (2006.01) | |
| G06F 19/12 | (2011.01) | |
| G06F 19/16 | (2011.01) | |

(52) U.S. Cl.
CPC .... *C12N 9/2462* (2013.01); *C12Y 302/01017* (2013.01); *G01N 33/6803* (2013.01); *G06F 19/12* (2013.01); *G06F 19/16* (2013.01)

(58) Field of Classification Search
None
See application file for complete search history.

(56) References Cited

U.S. PATENT DOCUMENTS

2016/0250221 A1* 9/2016 La Montagna ...... A61K 31/192
514/225.8

FOREIGN PATENT DOCUMENTS

WO   WO-2007/137072 A2   11/2007
WO   WO-2015/011284 A2   1/2015

OTHER PUBLICATIONS

Cao et al. PNAS 2009 (106) p. 21121-21125 (Year: 2009).*
D'Angelo, G. et al., Vesicular and non-vesicular transport feed distinct glycosylation pathways in the Golgi, Nature, 501(7465): 116-120 (2013).
Dowler, S. et al., Identification of Pleckstrin-Homology-Domain-Containing Proteins with Novel Phosphoinositide-Binding Specificities, Biochemical Journal, 351: 19-31 (2000).
International Search Report for PCT/US15/041683, 9 pages (dated Nov. 17, 2015).
Patzer, S. I. et al., Structural and Mechanistic Studies of Pesticin. a Bacterial Homolog of Phage Lysozymes, Journal of Biological Chemistry, 287(28): 23381-23396 (2012).
Prashek, J. et al., Crystal Structure of the Pleckstrin Homology Domain from the Ceramide Transfer Protein: Implications for Conformational Change upon Ligand Binding, PLOS ONE, 8(11): e79590 (2013).
Thurberg, B.L. et al., Globotriaosylceramide accumulation in the Fabry kidney is cleared from multiple cell types after enzyme replacement therapy, Kidney International, Nature Publishing Group, 62: 1933-1945 (2002).
Written Opinion for PCT/US15/041683, 11 pages (dated Nov. 17, 2015).
Zou, Y. et al., N-Terminal T4 Lysozyme Fusion Facilitates Crystallization of a G Protein Coupled Receptor, PLOS ONE 7(10): e46039 (2012).

* cited by examiner

*Primary Examiner* — Jeffrey S Lundgren
*Assistant Examiner* — Michael J Schmitt
(74) *Attorney, Agent, or Firm* — Choate, Hall & Stewart LLP; Brian E. Reese

(57) ABSTRACT

In some embodiments, the present invention provides method of identifying compounds that bind to phosphoinositol 4-phosphate adaptor protein-2 (FAPP2), including the steps of computationally identifying a compound that binds to FAPP2 using the atomic coordinates of at least the amino acids which make up the substrate binding pocket of FAPP2. Also provided are methods of designing, selecting and/or optimizing a compound that binds to FAPP2.

14 Claims, 7 Drawing Sheets

Monosulfo-Galactosyl
Ceramide bound to
hGLTP

SEQUENCE LISTING

<160> NUMBER OF SEQ ID NOS: 7

<210> SEQ ID NO 1
<211> LENGTH: 212

```
<212> TYPE: PRT
<213> ORGANISM: Homo sapiens

<400> SEQUENCE: 1

Ile Pro Thr Phe Phe Ser Thr Met Asn Thr Ser Phe Ser Asp Ile Glu
1               5                   10                  15

Leu Leu Glu Asp Ser Gly Ile Pro Thr Glu Ala Phe Leu Ala Ser Cys
            20                  25                  30

Tyr Ala Val Val Pro Val Leu Asp Lys Leu Gly Pro Thr Val Phe Ala
        35                  40                  45

Pro Val Lys Met Asp Leu Val Gly Asn Ile Lys Lys Val Asn Gln Lys
    50                  55                  60

Tyr Ile Thr Asn Lys Glu Glu Phe Thr Thr Leu Gln Lys Ile Val Leu
65                  70                  75                  80

His Glu Val Glu Ala Asp Val Ala Gln Val Arg Asn Ser Ala Thr Glu
                85                  90                  95

Ala Leu Leu Trp Leu Lys Arg Gly Leu Lys Phe Leu Lys Gly Phe Leu
            100                 105                 110

Thr Glu Val Lys Asn Gly Glu Lys Asp Ile Gln Thr Ala Leu Asn Asn
        115                 120                 125

Ala Tyr Gly Lys Thr Leu Arg Gln His His Gly Trp Val Val Arg Gly
    130                 135                 140

Val Phe Ala Leu Ala Leu Arg Ala Ala Pro Ser Tyr Glu Asp Phe Val
145                 150                 155                 160

Ala Ala Leu Thr Val Lys Glu Gly Asp His Gln Lys Glu Ala Phe Ser
                165                 170                 175

Ile Gly Met Gln Arg Asp Leu Ser Leu Tyr Leu Pro Ala Met Glu Lys
            180                 185                 190

Gln Leu Ala Ile Leu Asp Thr Leu Tyr Glu Val His Gly Leu Glu Ser
        195                 200                 205

Asp Glu Val Val
    210

<210> SEQ ID NO 2
<211> LENGTH: 163
<212> TYPE: PRT
<213> ORGANISM: Enterobacteria phage T4

<400> SEQUENCE: 2

Asn Ile Phe Glu Met Leu Arg Ile Asp Glu Gly Leu Arg Leu Lys Ile
1               5                   10                  15

Tyr Lys Asp Thr Glu Gly Tyr Tyr Thr Ile Gly Ile Gly His Leu Leu
            20                  25                  30

Thr Lys Ser Pro Ser Leu Asn Ala Ala Lys Ser Glu Leu Asp Lys Ala
        35                  40                  45

Ile Gly Arg Asn Thr Asn Gly Val Ile Thr Lys Asp Glu Ala Glu Lys
    50                  55                  60

Leu Phe Asn Gln Asp Val Asp Ala Ala Val Arg Gly Ile Leu Arg Asn
65                  70                  75                  80

Ala Lys Leu Lys Pro Val Tyr Asp Ser Leu Asp Ala Val Arg Arg Ala
                85                  90                  95

Ala Leu Ile Asn Met Val Phe Gln Met Gly Glu Thr Gly Val Ala Gly
            100                 105                 110

Phe Thr Asn Ser Leu Arg Met Leu Gln Gln Lys Arg Trp Asp Glu Ala
        115                 120                 125
```

```
Ala Val Asn Leu Ala Lys Ser Arg Trp Tyr Asn Gln Thr Pro Asn Arg
    130                 135                 140

Ala Lys Arg Val Ile Thr Thr Phe Arg Thr Gly Thr Trp Asp Ala Tyr
145                 150                 155                 160

Lys Asn Leu

<210> SEQ ID NO 3
<211> LENGTH: 419
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 3

Met Arg Gly Ser His His His His His His Gly Met Ala Ser Met Thr
1               5                   10                  15

Gly Gly Gln Gln Met Gly Arg Asp Leu Tyr Asp Asp Asp Lys Asp
            20                  25                  30

Arg Trp Gly Ser Glu Asn Leu Tyr Phe Gln Gly Asn Ile Phe Glu Met
            35                  40                  45

Leu Arg Ile Asp Glu Gly Leu Arg Leu Lys Ile Tyr Lys Asp Thr Glu
50                  55                  60

Gly Tyr Tyr Thr Ile Gly Ile Gly His Leu Leu Thr Lys Ser Pro Ser
65                  70                  75                  80

Leu Asn Ala Ala Lys Ser Glu Leu Asp Lys Ala Ile Gly Arg Asn Thr
                85                  90                  95

Asn Gly Val Ile Thr Lys Asp Glu Ala Glu Lys Leu Phe Asn Gln Asp
            100                 105                 110

Val Asp Ala Ala Val Arg Gly Ile Leu Arg Asn Ala Lys Leu Lys Pro
            115                 120                 125

Val Tyr Asp Ser Leu Asp Ala Val Arg Arg Ala Ala Leu Ile Asn Met
            130                 135                 140

Val Phe Gln Met Gly Glu Thr Gly Val Ala Gly Phe Thr Asn Ser Leu
145                 150                 155                 160

Arg Met Leu Gln Gln Lys Arg Trp Asp Glu Ala Val Asn Leu Ala
                165                 170                 175

Lys Ser Arg Trp Tyr Asn Gln Thr Pro Asn Arg Ala Lys Arg Val Ile
                180                 185                 190

Thr Thr Phe Arg Thr Gly Thr Trp Asp Ala Tyr Lys Asn Leu Gly Ile
            195                 200                 205

Pro Thr Phe Phe Ser Thr Met Asn Thr Ser Phe Ser Asp Ile Glu Leu
210                 215                 220

Leu Glu Asp Ser Gly Ile Pro Thr Glu Ala Phe Leu Ala Ser Cys Tyr
225                 230                 235                 240

Ala Val Val Pro Val Leu Asp Lys Leu Gly Pro Thr Val Phe Ala Pro
                245                 250                 255

Val Lys Met Asp Leu Val Gly Asn Ile Lys Val Asn Gln Lys Tyr
            260                 265                 270

Ile Thr Asn Lys Glu Glu Phe Thr Thr Leu Gln Lys Ile Val Leu His
            275                 280                 285

Glu Val Glu Ala Asp Val Ala Gln Val Arg Asn Ser Ala Thr Glu Ala
            290                 295                 300

Leu Leu Trp Leu Lys Arg Gly Leu Lys Phe Leu Lys Gly Phe Leu Thr
305                 310                 315                 320
```

```
Glu Val Lys Asn Gly Glu Lys Asp Ile Gln Thr Ala Leu Asn Asn Ala
                325                 330                 335

Tyr Gly Lys Thr Leu Arg Gln His His Gly Trp Val Val Arg Gly Val
            340                 345                 350

Phe Ala Leu Ala Leu Arg Ala Ala Pro Ser Tyr Glu Asp Phe Val Ala
        355                 360                 365

Ala Leu Thr Val Lys Glu Gly Asp His Gln Lys Glu Ala Phe Ser Ile
    370                 375                 380

Gly Met Gln Arg Asp Leu Ser Leu Tyr Leu Pro Ala Met Glu Lys Gln
385                 390                 395                 400

Leu Ala Ile Leu Asp Thr Leu Tyr Glu Val His Gly Leu Glu Ser Asp
                405                 410                 415

Glu Val Val

<210> SEQ ID NO 4
<211> LENGTH: 519
<212> TYPE: PRT
<213> ORGANISM: Homo sapiens

<400> SEQUENCE: 4

Met Glu Gly Val Leu Tyr Lys Trp Thr Asn Tyr Leu Ser Gly Trp Gln
1               5                   10                  15

Pro Arg Trp Phe Leu Leu Cys Gly Gly Ile Leu Ser Tyr Tyr Asp Ser
            20                  25                  30

Pro Glu Asp Ala Trp Lys Gly Cys Lys Gly Ser Ile Gln Met Ala Val
        35                  40                  45

Cys Glu Ile Gln Val His Ser Val Asp Asn Thr Arg Met Asp Leu Ile
    50                  55                  60

Ile Pro Gly Glu Gln Tyr Phe Tyr Leu Lys Ala Arg Ser Val Ala Glu
65                  70                  75                  80

Arg Gln Arg Trp Leu Val Ala Leu Gly Ser Ala Lys Ala Cys Leu Thr
                85                  90                  95

Asp Ser Arg Thr Gln Lys Glu Lys Glu Phe Ala Glu Asn Thr Glu Asn
            100                 105                 110

Leu Lys Thr Lys Met Ser Glu Leu Arg Leu Tyr Cys Asp Leu Leu Val
        115                 120                 125

Gln Gln Val Asp Lys Thr Lys Glu Val Thr Thr Thr Gly Val Ser Asn
    130                 135                 140

Ser Glu Glu Gly Ile Asp Val Gly Thr Leu Leu Lys Ser Thr Cys Asn
145                 150                 155                 160

Thr Phe Leu Lys Thr Leu Glu Glu Cys Met Gln Ile Ala Asn Ala Ala
                165                 170                 175

Phe Thr Ser Glu Leu Leu Tyr Arg Thr Pro Pro Gly Ser Pro Gln Leu
            180                 185                 190

Ala Met Leu Lys Ser Ser Lys Met Lys His Pro Ile Ile Pro Ile His
        195                 200                 205

Asn Ser Leu Glu Arg Gln Met Glu Leu Ser Thr Cys Glu Asn Gly Ser
    210                 215                 220

Leu Asn Met Glu Ile Asn Gly Glu Glu Ile Leu Met Lys Asn Lys
225                 230                 235                 240

Asn Ser Leu Tyr Leu Lys Ser Ala Glu Ile Asp Cys Ser Ile Ser Ser
                245                 250                 255

Glu Glu Asn Thr Asp Asp Asn Ile Thr Val Gln Gly Glu Ile Arg Lys
            260                 265                 270
```

```
Glu Asp Gly Met Glu Asn Leu Lys Asn His Asp Asn Leu Thr Gln
        275                 280                 285

Ser Gly Ser Asp Ser Ser Cys Ser Pro Glu Cys Leu Trp Glu Gly
        290                 295                 300

Lys Glu Val Ile Pro Thr Phe Phe Ser Thr Met Asn Thr Ser Phe Ser
305                 310                 315                 320

Asp Ile Glu Leu Leu Glu Asp Ser Gly Ile Pro Thr Glu Ala Phe Leu
                325                 330                 335

Ala Ser Cys Tyr Ala Val Val Pro Val Leu Asp Lys Leu Gly Pro Thr
                340                 345                 350

Val Phe Ala Pro Val Lys Met Asp Leu Val Gly Asn Ile Lys Lys Val
                355                 360                 365

Asn Gln Lys Tyr Ile Thr Asn Lys Glu Glu Phe Thr Thr Leu Gln Lys
        370                 375                 380

Ile Val Leu His Glu Val Glu Ala Asp Val Ala Gln Val Arg Asn Ser
385                 390                 395                 400

Ala Thr Glu Ala Leu Leu Trp Leu Lys Arg Gly Leu Lys Phe Leu Lys
                405                 410                 415

Gly Phe Leu Thr Glu Val Lys Asn Gly Glu Lys Asp Ile Gln Thr Ala
                420                 425                 430

Leu Asn Asn Ala Tyr Gly Lys Thr Leu Arg Gln His His Gly Trp Val
        435                 440                 445

Val Arg Gly Val Phe Ala Leu Ala Leu Arg Ala Ala Pro Ser Tyr Glu
        450                 455                 460

Asp Phe Val Ala Ala Leu Thr Val Lys Glu Gly Asp His Gln Lys Glu
465                 470                 475                 480

Ala Phe Ser Ile Gly Met Gln Arg Asp Leu Ser Leu Tyr Leu Pro Ala
                485                 490                 495

Met Glu Lys Gln Leu Ala Ile Leu Asp Thr Leu Tyr Glu Val His Gly
                500                 505                 510

Leu Glu Ser Asp Glu Val Val
        515

<210> SEQ ID NO 5
<211> LENGTH: 1260
<212> TYPE: DNA
<213> ORGANISM: Homo sapiens

<400> SEQUENCE: 5
atgcggggtt ctcatcatca tcatcatcat ggtatggcta gcatgactgg tggacagcaa      60
atgggtcggg atctgtacga cgatgacgat aaggatcgat ggggatccga gaacctgtac     120
ttccagggca atatatttga aatgttacgt atagatgaag gtcttagact taaaatctat     180
aaagacacag aaggctatta cactattggc atcggtcatt tgcttacaaa aagtccatca     240
cttaatgctg ctaaatctga attagataaa gctattgggc gtaataccaa tggtgtaatt     300
acaaaagatg aggctgaaaa actctttaat caggatgttg atgctgctgt tcgcggtatt     360
ctgagaaatg ctaaattaaa accggtttat gattctcttg atgcggttcg tcgcgctgca     420
ttgattaata tggttttcca aatgggagaa accggtgtgg caggatttac taactctttg     480
cgtatgcttc aacaaaaacg ctgggatgaa gcagcagtta acttagctaa agtagatgg      540 tataatcaaa cacctaatcg cgcaaaacga gtcattacaa cgtttagaac tggcacttgg     600
gacgcgtata aaaatctagg tatcccaact ttctttagta ccatgaacac aagctttagt     660
```

```
gacattgaac ttctggaaga cagtggcatt cccacagaag cattcttggc atcatgttat    720
gctgtggttc cagtattaga caaacttggc cctacagtgt ttgctcctgt taagatggat    780
cttgttggaa atattaagaa agtaaatcag aagtatataa ccaacaaaga agagtttacc    840
actctccaga agatagtgct gcacgaagtg gaggcggatg tagcccaggt taggaactca    900
gcgactgaag ccctcttgtg gctgaagaga ggtctcaaat ttttgaaggg atttttgaca    960
gaagtgaaaa atggggagaa ggatatccag acagccctaa ataatgcata tggtaaaaca    1020
ttgcggcaac accatggctg ggtagttcga ggggtttttg cgttagcttt aagggcagct    1080
ccatcctatg aagattttgt ggccgcgtta accgtaaagg aaggtgacca ccagaaagaa    1140
gctttcagta ttgggatgca gagggacctc agcctttacc tccctgccat ggagaagcag    1200
ctggccatac tggacacttt atatgaggtc cacgggctgg aatctgatga ggtggtatga    1260
```

<210> SEQ ID NO 6
<211> LENGTH: 7
<212> TYPE: PRT
<213> ORGANISM: Homo sapiens

<400> SEQUENCE: 6

Ile Pro Thr Phe Phe Ser Thr
1               5

<210> SEQ ID NO 7
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Pro Pro Phe Phe Cys Asp
1               5

CRYSTAL STRUCTURE OF HUMAN FOUR-PHOSPHATE ADAPTOR PROTEIN 2 GLYCOLIPID TRANSFER PROTEIN LIKE DOMAIN

FIELD OF THE INVENTION

This invention relates to the provision of a high resolution crystal structure of the human four-phosphate adaptor protein 2 (FAPP2) glycolipid transfer protein (GLTP) like domain and the use of this structure in drug discovery.

BACKGROUND TO THE INVENTION

Fabry disease (sometimes also called Anderson-Fabry disease) is a rare X-linked disorder characterized by the absence of α-galactosidase A (α-Gal A), an enzyme required for the normal processing of glycosphingolipids in mammalian lysosomes. The loss of α-Gal A leads to accumulation of the neutral globotriaosylceramide (Gb3), also known as ceramide trihexoside (CTH), within the heart, kidney, liver, and vascular endothelial cells. Renal and cardiac diseases are the most common cause of mortality and morbidity in Fabry patients [1, 2]. Hemizygous males, homozygous females, and some heterozygous females experience progressive organ dysfunction manifesting clinically as angiokeratomas, acroparathesis, stroke, cardiomyopathies, myocardian infarction and renal failure [1]. The kidney is exceptionally susceptible to damage from Gb3 deposition with several published reports of glycosphingolipid localized to the podocytes, vascular endothelial cells, and epithelial cells of the glomerulus. Loss of podocytes by apoptosis leads to glomerulosclerosis and drastically reduced kidney function. Affected individuals vary in disease progression and severity of symptoms.

Historically, treatment options for Fabry patients were limited to symptomatic relief of renal and cardiovascular complications [3]. Attempts at more severe treatments, namely organ transplantation [4,5] and plasmapheresis [6], did not prove successful. Currently, two galactosidase drugs are available for treatment of Fabry disease via enzyme replacement therapy (ERT): agalsidase alfa (Replagal®, TKT/Shire) and agalsidase beta (Fabrazyme®, Genzyme). These protein based therapeutics are administered by (approved for) intravenous injection and deliver galactosidase activity to the lysosomes of affected organs in order to reduce the level of Gb3 accumulation. Additional approaches to ERT for treatment of lysosomal storage diseases, such as Fabry disease, are needed.

An alternative strategy to ERT is substrate reduction therapy (SRT). This works on the basis of limiting the amount of pathologic substrate (i.e. Gb3) in the patient. The pathology of Fabry disease arises as a result of the patient's reduced ability to degrade Gb3 and the resulting accumulation of the substrate, and the aim of SRT is to reduce the amount of this pathologic substance that is present.

Gb3, like the other complex glycosphingolipids is synthesised from glucosylceramide (GlcCer) in the Golgi. It has recently been shown that FAPP2, a cytosolic transfer protein, has an important role in partitioning GlcCer into different pathways for downstream synthesis of different GSLs in different cellular compartments. FAPP2 has been shown to be responsible for delivering GlcCer directly to the Trans Golgi network (TGN). In the TGN the globo- and asialo-sphingolipids, including Gb3, are synthesised from GlcCer. Other GlcCer is moved through the vesicular route to the Golgi cisternae, to make the ganglio-series of sphingolipids in the Golgi cisternae. It has further been shown that FAPP-2−/− mice have a selective decrease in Gb3 in the kidneys [7].

In view of the role of FAPP2 in the synthesis of Gb3, FAPP2 represents a target for SRT for the treatment of Fabry disease. SRT has been proposed for lysosomal storage disorders such as Gaucher disease and Niemann-Pick type-C disease, and Zavesca® (Actelion) has been approved for the treatment of mild to moderate type-1 Gaucher disease patients who cannot receive the standard treatment of ERT and for the treatment of the neurological symptoms of the disease patients of all ages with Niemann-Pick type-C disease. Inhibitors of FAPP2 that are suitable for SRT of Fabry disease are, however, not currently available.

Whilst the structure of the GLTP domain of human FAPP2 has been modelled, based on the crystal structure of the human glycolipid transfer protein (GLTP) [8], a high resolution crystal structure of the glycolipid binding portion of FAPP2 is needed in order to develop FAPP2 inhibitors suitable for SRT. In particular, it is known that FAPP2 has a different lipid transfer specificity to GLTP, with FAPP2 being unable to transfer certain glycolipids that are readily transferred by GLTP, such as negatively charged glycolipids. Further, there are differences in the structure of the two proteins, which is reflected in their different helix content and the relatively low Tm for the GLTP domain of FAPP2, which exhibits thermal unfolding with a Tm of about 41° C., compared to 53° C. for GLTP [8].

Developing inhibitors that are specific for FAPP2 is of particular interest, and understanding the structure of FAPP2 and how it may differ from other related and non-related molecules is important in this process.

SUMMARY OF THE INVENTION

A high resolution crystal structure of the GLTP domain of FAPP2 (FAPP2-C212) has now been generated. The structure shows that the residues that interact with the sugar headgroup of GlcCer (including D360, N364, W407) are well refined and so are other (e.g. hydrophobic) residues that interact with the acyl/sphingosine chains of ceramide. The high resolution structure can be used to design and to optimise inhibitors of FAPP2. Atomic level structural information was not available for the GLTP domain of FAPP2 before the present invention and this information is crucial for understanding the structure-function relationships in FAPP2 activity and allows the design and testing of novel inhibitors of FAPP2.

Aspects of the invention are based on the inventor's successful crystallisation of the GLTP domain of FAPP2 and the subsequent determination of the three dimensional polypeptide structure. The GLTP domain of FAPP2 is the C terminal 212 amino acids in human FAPP2 (residues 308-519 using the numbering of human FAPP2). It is particularly surprising that it has been possible to crystallise the GLTP domain of FAPP2, as this is a relatively flexible and unstable molecule (as evidenced by its low Tm) and it becomes completely unfolded even at around 45° C. Extensive previous efforts to generate crystals of the GLTP domain of FAPP2 were unsuccessful. Only when lysozyme T4L was chosen as a crystallisable fusion tag by the inventor was it possible to generate crystals, from which the structure as defined in more detail below was generated.

In a first aspect therefore the invention provides a polypeptide comprising the GLTP domain of FAPP2, fused to T4L. Encoding nucleic acid molecules and vectors are further provided, as are host cells containing these.

A further aspect is the crystalline form of the polypeptide of the invention.

In a further aspect the invention provides a method of obtaining the crystalline form of the invention comprising providing a polypeptide of the invention, and concentrating the polypeptide to a polypeptide concentration at which it precipitates and forms crystals. The crystalline form obtainable from this method is also provided.

The atomic coordinates provided herein for the GLTP domain of FAPP2, and subsets thereof and the three dimensional structural models that may be generated using the atomic coordinates provided herein can be used for identifying, designing, selecting, and/or optimising FAPP2 binding compounds. Such compounds could be used to inhibit FAPP2, and hence reduce Gb3 levels.

Aspects of the invention thus relate to methods of identifying a compound that binds to FAPP2. This method may comprise computationally identifying a compound that binds to FAPP2 using the atomic coordinates of at least the amino acids which make up the substrate binding pocket of FAPP2, e.g. as set forth in Table 2, or using the atomic coordinates for at least the GLTP domain of FAPP2, as set forth in Table 3. A compound that binds to a FAPP2 polypeptide may be computationally identifying using said coordinates.

In a further aspect the invention provides a method of designing, selecting and/or optimising a compound that binds to FAPP2 comprising: a) providing a set of atomic coordinates of at least the amino acids which make up the substrate binding pocket of FAPP2, e.g. as set forth in Table 2 and b) computationally designing, selecting and/or optimising said compound by performing a fitting operation between said compound and all or part of the three dimensional structure information that is generated from the atomic coordinates.

In a further aspect the invention provides a method of designing, selecting and/or optimising a compound that binds to FAPP2 comprising: a) providing a set of atomic coordinates for at least the GLTP domain of FAPP2 as set forth in Table 3 and b) computationally designing, selecting and/or optimising said compound by performing a fitting operation between said compound and all or part of the three dimensional structure information that is generated from the atomic coordinates.

In a further aspect the invention provides a method for evaluating the ability of a compound to associate with FAPP2 comprising: a) providing a set of atomic coordinates of at least the amino acids which make up the substrate binding pocket of FAPP2, e.g. as set forth in Table 2; b) computationally performing a fitting operation between said compound and all or part of the three dimensional structure information that is generated from the atomic coordinates; and c) analysing the results of said fitting operation to quantitate the association between the compound and FAPP2.

In a further aspect the invention provides a method for evaluating the ability of a compound to associate with FAPP2 comprising: a) providing a set of atomic coordinates for at least the GLTP domain of FAPP2 as set forth in Table 3 and b) computationally performing a fitting operation between said compound and all or part of the three dimensional structure information that is generated from the atomic coordinates; and c) analysing the results of said fitting operation to quantitate the association between the compound and FAPP2.

In a further aspect the invention provides a method of using a computer for evaluating the ability of a compound to associate with FAPP2 wherein said computer comprises a machine readable data storage medium comprising a data storage material encoded with the atomic coordinates of at least the amino acids which make up the substrate binding pocket of FAPP2, e.g. as set forth in Table 2 and means for generating a three dimensional graphical representation of the structure of said amino acids and said method comprises: a) positioning a first compound using a graphical three dimensional representation of the structure of the compound and all or part of the substrate binding pocket of FAPP2; b) performing a fitting operation between the compound and the substrate binding pocket of FAPP2 by employing computational means; and c) analysing the results of said fitting operation to quantitate the association between the compound and the substrate binding pocket of FAPP2.

In a further aspect the invention provides a method of using a computer for evaluating the ability of a compound to associate with FAPP2 wherein said computer comprises a machine readable data storage medium comprising a data storage material encoded with the atomic coordinates for at least the GLTP domain of FAPP2 as set forth in Table 3 and means for generating a three dimensional graphical thereof and said method comprises: a) positioning a first compound using a graphical three dimensional representation of the structure of the compound and all or part of the GLTP domain of FAPP2; b) performing a fitting operation between said compound and the GLTP domain of FAPP2 by employing computational means; and c) analysing the results of said fitting operation to quantitate the association between said compound and the GLTP domain of FAPP2.

In a further aspect the invention provides a computer readable medium comprising the atomic coordinates for the polypeptide of the invention or a subset thereof, and a computer comprising the computer-readable medium of the invention.

A computer system comprising a memory unit comprising x-ray crystallographic structure coordinates defining the polypeptide of the invention or a subset thereof; and a processor in electrical communication with the memory unit; wherein the processor generates a molecular model having a three dimensional structure representative of at least a portion of said polypeptide also forms part of the invention.

A further aspect of the invention provides a method of producing a pharmaceutical composition comprising designing, selecting and/or optimising a compound with the methods of the invention, modifying the identified compound for administration as a pharmaceutical and formulating the product obtained with a pharmaceutically acceptable carrier or diluent.

In a further aspect the invention provides the use of the structure of the crystalline form of the invention or a portion of the structure in modelling a binding compound which binds to FAPP2, as well as the use of the atomic coordinates of the crystalline form of the invention or a subset of the atomic coordinates, in modelling a binding compound which binds to FAPP2.

A compound identified, designed, selected and/or optimised by a method of the invention, and optionally which has been modified for administration as a pharmaceutical, and/or which has been formulated as a pharmaceutical is provided in a further aspect of the invention. Such compounds may be used as a medicament, e.g. in treating Fabry's disease. Methods of treating or preventing Fabry's disease comprising administering an effective amount of such a compound or pharmaceutical to a patient in need thereof are furthermore provided.

Polypeptide

It has not previously been possible to crystallise the GLTP domain of FAPP2, at least because it is a very flexible peptide with a low melting temperature. By fusing amino acids 2-164 of the lysozyme sequence from phage T4 to the GLTP domain of FAPP2 (amino acids 308-519 of FAPP2), the inventors surprisingly found that it was possible to generate crystals. The crystals of the fusion protein that were generated contained two molecules of the fusion protein in each asymmetric unit. The T4L from adjacent molecules in the crystal lattice make extensive contacts that appear to have facilitated crystallisation (FIGS. 1A and B). The fusion of the T4L sequence to the GLTP domain of FAPP2 thus has advantages in that it allows crystals of this polypeptide to be generated for analysis. T4L has previously been used as a fusion only with G protein coupled receptors (GPCR), either at the N-terminus or in the middle of the molecule [9,10,11]. These are proteins of a very different nature to the GLTP domain of FAPP2.

The invention thus provides a polypeptide comprising the GLTP domain of FAPP2, fused to a T4L polypeptide. The GLTP domain of FAPP2 may be C terminal or N terminal to the T4L polypeptide. In certain embodiments the FAPP2 is human FAPP2. The full length sequence for human FAPP2 is set out in SEQ ID NO:4. The sequence of the C terminal 212 amino acids of human FAPP2 (amino acids 308-519 of FAPP2) which make up the GLTP domain is set out in SEQ ID NO:1 and the sequence of amino acids 2-164 of the T4L polypeptide is set out in SEQ ID NO:2.

A polypeptide comprising an amino acid sequence with at least 95% sequence identity to amino acids 308-519 of FAPP2 (SEQ ID NO:1) and an amino acid sequence with at least 95% sequence identity to amino acids 2-164 of lysozyme T4L (SEQ ID NO:2) thus forms part of the invention. Optionally the polypeptide has at least 95% sequence identity to the sequence SEQ ID NO:3.

The polypeptide of the invention comprises residues L349, D360 N364, K367, W407 R410, F414, I429, Y437, L441, H445, V449, F453, A456, F466, L470, V342, L346, V357, L361, L433, V452, L488, Y491, V345, N399, E403, R398, F311 and F312 in one embodiment, and in a further embodiment comprises sequence SEQ ID NO:3 or a fragment thereof. In another embodiment the polypeptide of the invention consists of the sequence SEQ ID NO:3 or a fragment thereof. The polypeptide consisting of the sequence SEQ ID NO:3 may be referred to as T4L-FAPP2-C212.

More preferred polypeptides have a percentage of identity of greater than 96%, 97%, 98%, 99% or 99.5%, respectively with the sequence of amino acids 308-519 of FAPP2 (SEQ ID NO:1) and/or amino acids 2-164 of lysozyme T4L (SEQ ID NO:2), and/or may have a percentage of identity of greater than 96%, 97%, 98%, 99% or 99.5%, respectively with the sequence of amino acids SEQ ID NO:3. Percentage identity, as referred to herein, is as determined using BLAST version 2.1.3 using the default parameters specified by the NCBI (the National Center for Biotechnology Information; www.ncbi.nlm.nih.gov/) [Blosum 62 matrix; gap open penalty=11 and gap extension penalty=1].

Such polypeptides may contain a sequence which differs from the reference sequences by amino acid substitutions, insertions or deletions from the reference sequence, for example, of 1, 2, 3, 4, 5, 6, 7, 8, 9 or 10, 15, 20 25, 30 or 35 or more amino acids, or up to this number of amino acids. Such sequences include proteins containing conservative amino acid substitutions that do not affect the function or activity of the protein in an adverse manner.

Insertions may include linkers e.g. between the T4L sequence and the FAPP2 sequence. Suitable examples of amino acids that may be used in linkers include threonine, serine, proline, asparagine, glycine. Preferably the linker comprises one or more glycine residue. More preferably the linker consists of one or more glycine residue (e.g. is a single glycine).

Fragments of the reference polypeptides thus contain deletions (e.g. from the N or C terminus or internally) of up to 1, 2, 3, 4, 5, 6, 7, 8, 9 or 10 amino acids.

The polypeptide of the invention may additionally comprise a tag, e.g. of use in the preparation and/or purification of the peptide. Such tags are well known in the art and thus include his tags. A linker may also be present between any tag and the T4L sequence or FAPP2 sequence.

In certain embodiments, nucleic acids encoding the polypeptide of the invention are provided. In certain embodiments, the nucleic acid comprises the sequence as set forth in SEQ ID NO: 5, or a fragment thereof.

Substitutions, additions and deletions in the polypeptide of the invention may be generated by making appropriate changes to the encoding nucleic acid molecule of the invention and as such, the nucleic acid of the invention may comprise one or more nucleotide substitutions, additions, deletions, or duplications.

Modifications and mutations which create a polypeptide with a substitution, addition and/or deletions variant can be made within the nucleic acid sequence which encodes the polypeptide of the invention.

Modifications and mutations include deletions, point mutations, truncations, nucleic acid changes that lead to amino acid substitutions, and nucleic acid changes that lead to the addition of amino acids.

Nucleic acid modifications can be made to generate variants that are silent with respect to the amino acid sequence of the encoded polypeptide, but which provide preferred codons for translation in a particular host. The preferred codons for translation of a nucleic acid in specific non-mammalian expression systems, such as prokaryotic systems, are well known in the art, e.g. [12;13;14]. Still other modifications can be made to the non-coding sequences to enhance or control the expression of the encoding gene.

The encoding nucleic acid sequence may be present in a vector. The vector may include a coding sequence operably associated with one or more regulatory sequences. A coding sequence and regulatory sequences are "operably associated with" when they are covalently linked to place the expression or transcription of the coding sequence under the control of the regulatory sequence. A promoter region is operably associated with a coding sequence if the promoter region is capable of modulating transcription of the coding sequence.

The nature of the regulatory sequences needed for gene expression may vary between species or cell types, but may generally include 5' non-transcribed and 5' non-translated sequences involved with initiation of transcription and translation respectively, such as, for example, TATA box, capping sequence, CAAT sequence. 5' non-transcribed regulatory sequences may include a promoter region which includes a promoter sequence for transcriptional control of the operably associated gene. Promoters may be constitutive or inducible. Regulatory sequences may also include enhancer sequences or upstream activator sequences.

A DNA sequence operably associated with a regulatory sequence may be inserted by restriction and ligation into a vector, e.g., for transport between different genetic environments or for expression in a host cell. Vectors are typically composed of DNA or RNA. Vectors include, but are not limited to, plasmids, viral vectors, cosmids, artificial chromosomes, and phagemids. A cloning vector is one which is able to replicate in a host cell, and which is further characterized by one or more endonuclease restriction sites at which the vector may be cut and into which a desired nucleic acid sequence (e.g., an open reading frame) may be inserted. Vectors may contain one or more marker sequences suitable for use in the identification of cells which have or have not been transformed or transfected with the vector. Markers include, for example, genes encoding proteins which increase or decrease either resistance or sensitivity to antibiotics or other compounds, genes which encode enzymes whose activities are detectable by standard assays known in the art (e.g., β-galactosidase, alkaline phosphatase or luciferase), and genes which visibly affect the phenotype of transformed or transfected cells, hosts, colonies or plaques.

For prokaryotic systems, plasmid vectors that contain replication sites and control sequences derived from a species compatible with the host may be used. Preferably, the vector has the capacity to autonomously replicate in the host cell. Useful prokaryotic hosts include bacteria such as *E. coli*. To express a polypeptide in a prokaryotic cell, it is desirable to operably join its nucleic acid sequence (e.g. cDNA) to a functional prokaryotic promoter. Such promoter may be either constitutive or regulatable (e.g. by induction or derepression).

Eukaryotic hosts include, for example, yeast, fungi, insect cells, and mammalian cells. In addition, plant cells are also available as hosts, and control sequences compatible with plant cells are known in the art.

A wide variety of transcriptional and translational regulatory sequences may be employed, depending upon the nature of the host. The transcriptional and translational regulatory signals may be derived from viral sources, such as adenovirus, bovine papilloma virus and simian virus. Mammalian promoters, such as, for example, actin, collagen, and myosin may be employed. Transcriptional initiation regulatory signals may be selected which allow for repression or activation, so that expression of the gene sequences can be modulated, for example by regulatory signals, such as repression/initiation through changes in temperature or by addition of a chemical or biological modulating molecule.

Vectors can be employed which are capable of integrating a desired gene sequences into the host cell chromosome. Cells which have stably integrated the introduced nucleic acid into their chromosomes can be selected by also introducing one or more markers which allow for selection of host cells which contain the expression vector. The selectable marker gene sequence can either be directly linked to the gene sequences to be expressed, or introduced into the same cell by co-transfection. Additional elements, such as splice signals, transcription promoters, enhancers, and termination signals may also be needed for optimal synthesis of mRNA.

Once a desired vector or desired nucleic acid sequence has been prepared, the vector or nucleic acid sequence is introduced into an appropriate host cell by any of a variety of suitable means, for example, transformation, transfection, conjugation, protoplast fusion, electroporation, calcium phosphate-precipitation, or direct microinjection. After the introduction of the vector, recipient cells are grown in a selective medium, which selects for the growth of vector-containing cells. Expression of the cloned gene sequence results in the production of recombinant polypeptide.

Preparing Crystals

In another aspect the invention provides methods for crystallizing the polypeptide of the invention, e.g. by providing a polypeptide of the invention, and concentrating the polypeptide to a polypeptide concentration at which it precipitates and forms crystals.

In certain embodiments, methods for crystallizing the polypeptide of the invention involve crystallizing purified recombinant polypeptide of the invention.

A wide variety of crystallization conditions may be employed to provide crystals of the polypeptide of the invention, therefore, a wide variety of crystallization conditions are envisioned and encompassed by the present invention. Every protein crystallizes under a unique set of conditions, such as, for example, supersaturating the solution containing the protein; and/or adding precipitating or crystallizing agents, salts, metals, and/or buffers to the solution containing the protein.

Any crystallization technique known to those skilled in the art may be employed to obtain the crystals of the present invention, including, but not limited to, batch crystallization, vapor diffusion (e.g., either by sitting drop or hanging drop), and micro dialysis. Seeding in some instances may be required to obtain x-ray quality crystals. Standard micro and/or macro seeding of crystals may therefore be used. In certain embodiments, the crystals of the present invention are grown using the hanging-drop vapor-diffusion method.

The crystals of the polypeptide of the invention may be grown at any temperature suitable for crystallization. For example, the crystals may be grown at temperatures ranging from approximately 0° C. to approximately 30° C. In certain embodiments, the crystals of the present invention are grown at a temperature of between approximately 0° C. to approximately 10° C. In certain embodiments, the crystals of the present invention are grown at a temperature of between approximately 0° C. to approximately 5° C. In other embodiments the crystals of the present invention are grown at a temperature of between approximately 5° C.-approximately 10° C., approximately 10° C. to approximately 15° C., approximately 15° C. to approximately 20° C., approximately 20° C. to approximately 25° C., approximately 25° C. to approximately 30° C.

In certain embodiments, the crystals of the present invention are grown at a temperature of approximately, 10° C., 11° C., 12° C., 13° C., 14° C., 15° C., 16° C., 17° C., 18° C., 19° C., 20° C. or room temperature.

Crystals of the present invention are typically grown from a crystallization solution comprising one or more precipitants. In certain embodiments the precipitants may be selected from polymers, polyethers, alcohols, salts, and/or polyols. In certain embodiments, these precipitants are selected from the group consisting of monomethyl ether (ME); polyethylene glycol PEG-400; PEG-1000; PEG-2000; PEG-3000; PEG-8000; PEG 20,000; (($NH_4$)$_2SO_4$); 2-propanol; 1,4-butanediol; K/Na tartrate; ethanol; NaCl; sodium citrate; $NaH_2PO_4$/$K_2HPO_4$; ethylene glycol; dioxane; 2-methyl-2,4-pentanediol (MPD); polyethyleneimine; tert-butanol; and 1,6-hexanediol.

In certain embodiments, the crystallization conditions may further comprise one or more salts. Thus, in certain embodiments the crystallization conditions further comprises one or more salts selected from the group consisting of $MgCl_2$; Zn(OAc)$_2$, Li $SO_4$, Ca(OAc)$_2$, NaCl; ($NH_4$)$_2SO_4$, $CdCl_2$, $CoCl_2$, $MgSO_4$, and $NiCl_2$, preferably $MgCl_2$ and/or NaCl. In certain embodiments, the crystallization conditions further comprises one or more buffers selected from the group consisting of 2-(cyclohexylamino)ethanesulfonic acid (CHES); 2-(N-morpholino)ethanesulfonic acid (MES); N-cyclohexyl-3-aminopropanesulfonic acid (CAPS); N-cyclohexyl-2-hydroxyl3-aminopropanesulfonic acid (CASPO); 4-(2-hydroxyethyl)piperazine-1-ethane sulfonic acid (HEPES); 3-(N-morpholino)propanesulfonic acid (MOPS); 2-amino-2-(hydroxymethyl)-1,3-propanediol (Tris); piperazine-N,N'-bis(2-ethanesulfonic acid) (PIPES); N-(2-Acetamido)-2-aminoethanesulfonic acid (ACES); N,N-Bis(2-hydroxyethyl)-2-aminoethanesulfonic acid (BES); N-Tris(hydroxymethyl)methyl-2-aminoethanesulfonic acid (TES); N-(2-acetamido)iminodiacetic acid (ADA); tris(2-carboxylethyl)phosphine (TCEP); acetamido glycine; cholamine chloride; glycinamide; bicine; N-(2-Hydroxy-1, 1-bis(hydroxymethyl)ethyl)glycine (tricine); imidazole; sodium citrate; sodium acetate; cacodylate; Na/K phosphate, and buffers as described in [15], preferably tris. Precipitants that may be used to crystallize the polypeptide of the invention include, but are not limited to, lithium sulfate; PEG-400; PEG-550 MME; PEG-2000; PEG-6000; PEG-8000; PEG 20,000; and/or 2-methyl-2,4-pentanediol (MPD).

In certain embodiments, the pH of the crystallization solution is between about a pH of approximately 4 to pH of approximately 9. In certain embodiments, the pH of the crystallization solution is between about a pH of approximately 6.5 to a pH of approximately 9. In certain embodiments, the pH of the crystallization solution is approximately 7.0. In certain embodiments, the pH of the crystallization solution is near the isoelectric point of the protein.

In a specific embodiment, the polypeptide of the invention at a concentration of about 6 mg/ml is screened for crystallization conditions using the sitting drop vapor diffusion method employing a random matrix crystallization screening kit. Such kits are commercially available, for example, Qiagen JCSG-I random matrix crystallisation kit. In a specific embodiment, the polypeptide of the invention is crystallized under #6 conditions (0.2 M $MgCl_2$, 0.1 M Tris, pH 7.0, 2.5M NaCl). In other embodiments the conditions are 0.1-0.3M $MgCl_2$, 1.5-3M NaCl, 0.1M Tris pH7. Approximately 6-20 mg/ml protein may be used In certain embodiments, the crystals are screened for optimal cryo-conditions to freeze the crystals at the temperature of liquid nitrogen, for example, to attenuate the radiation damage to crystals that occurs during data collection. In certain embodiments, screening for optimal cryo-conditions can be carried out in crystallization buffers containing 20-35% v/v of polyols, such as glycerol, ethylene glycol or 2-methyl-2,4-pentanediol (MPD), or 35-70% w/v of sugars, such as sucrose or xylitol. Crystals may be soaked in the cryo-buffer for about 5-15 minutes. In a specific embodiment, cryo-protection of crystals of the invention, grown in condition #6 (0.2 M $MgCl_2$, 0.1 M Tris, pH 7.0, 2.5M NaCl) is achieved by soaking the crystals in a cryo-buffer containing glycerol and xylitol (0.2 M $MgCl_2$, 0.1 M Tris, pH 7.0, 2.5M NaCl, 10% glycerol and 5% xylitol).

The crystals of the invention may also include a binding compound bound to the GLTP domain of FAPP2 polypeptide. The complex of the polypeptide and binding compound may be formed before, after, or during crystallization. In certain embodiments, the crystals of the present invention and the crystallization conditions further comprise a binding compound. Thus, in certain embodiments, the crystallization solution of the above method further comprises a binding compound in order to provide a FAPP2 GLTP domain polypeptide-binding compound complex. In certain embodiments, the FAPP2 GLTP domain polypeptide provided by the above method is soaked in a solution of a binding compound to provide a FAPP2 GLTP domain polypeptide-binding compound complex.

In certain embodiments, a binding compound is bound in the substrate binding pocket of FAPP2 GLTP domain polypeptide. In some embodiments, the inhibitor is a reversible inhibitor.

In other embodiments, the binding compound is bound outside the substrate binding pocket at one or more exosites. In some embodiments, the binding compound, whether bound in the substrate binding pocket or at one or more exo sites, aids in stabilizing the protein for crystallization and/or x-ray diffraction.

The step of providing the polypeptide of the invention may optionally comprise expressing an appropriate polypeptide in a host cell and may optionally further comprise purifying said polypeptide.

The polypeptide which is expressed is any polypeptide from which the polypeptide of the invention may then be derived, e.g. by proteolytic cleavage. The polypeptide which is expressed may thus contain a tag, which is subsequently removed during or following purification of the protein from the host cell. The tag may be used to facilitate purification e.g. by allowing binding to a matrix, or by allowing secretion of the polypeptide from the host cell.

Examples of appropriate purification methods include a Ni column step. Ni column binds to histidine resides, e.g. in a his tag. A size exclusion chromatography step (SEC) step may also be used, e.g. to separate polypeptides of different sizes. An anion exchange column may additionally or alternatively be used e.g. after the Ni-column. This may increase the purity of the protein.

Crystalline Form of the Polypeptide

The invention also provides a crystalline form of the polypeptide of the invention. In certain embodiments, the crystals are of the GLTP domain of human FAPP2, fused to a T4L polypeptide. In certain embodiments, the crystals are of a polypeptide comprising or consisting of the amino acid sequence set forth in SEQ ID NO: 3.

A crystal of the present invention may take a variety of forms, all of which are contemplated by the present invention. In certain embodiments, the crystal may have a size of about 50-100×30-50×20-30 μm. In certain embodiments, the crystals have the optical appearance as illustrated in FIG. 5 and/or the crystals may grow as rod shaped, some without clear faces. A crystal of the present invention may be obtainable by the methods of polypeptide crystallization referred to elsewhere herein.

The crystalline form of the polypeptide of the invention may be characterised with space group $P2_12_12$ and have unit cell parameters of +/−5%, 4%, 3%, 2%, 1% of a=100.02 Å, b=130.87 Å, c=88.73 Å, α=90°, β=90°, γ=90°, optionally unit cell parameters of a=100.02 Å, b=130.87 Å, c=88.73 Å, α=90°, β=90°, γ=90°, unit cell parameters of a=100.02 Å, b=130.87 Å, c=88.73 Å, unit cell parameters of α=90°, β=90°, γ=90°. The a, b and c values may be defined to a further decimal place (e.g. a=100.020, b=130.872, c=88.733).

The term "space group" refers to the arrangement of symmetry elements in a crystal. The term "unit cell" refers to the basic parallelipiped shaped block. The entire volume of a crystal may be constructed by regular assembly of such blocks.

Crystal Structure of GLTP Domain of FAPP2

In another aspect, the present invention provides three-dimensional structural information for the polypeptide of the invention. In other aspects the invention provides three-dimensional structural information for a subset of amino acids of the polypeptide of the invention. For example this subset may be the amino acids making up the substrate binding pocket of FAPP2, the amino acids making up the sugar headgroup recognition site of FAPP2, and/or the amino acids making up the GLTP domain of FAPP2.

In certain embodiments, X-ray diffraction data collection can be performed in an X-ray crystallography facility. One, two, three, or more diffraction data sets may be collected from one or more crystals. In certain embodiments, the crystals of the present invention diffract to a resolution limit of at least approximately 8 angstrom (Å). In certain embodiments, the crystals diffract to a resolution limit of at least approximately 6 Å, 4 Å or 3 Å.

In certain embodiments, the crystal diffracts x-rays for a determination of structural coordinates to a maximum resolution of about 3.9 Å, of about 3.2 Å, of about 2.9 Å, or about 2.6 Å. The crystals may diffract to a maximum resolution of about 2.0-4.0 Å (e.g. about 2.5 Å to about 3.5 Å, of about 2.0 Å to about 3.0 Å, of about 2.5 Å to about 3.0 Å, or of about 3.0 Å to about 3.5 Å).

Diffraction data can be collected using a variable oscillation angles, number of frames and exposure times that all depend on the equipment used and on the quality of the crystal(s) used to collect the data. One of ordinary skill would know how to optimize these parameters [16; 17]). In certain embodiments, diffraction data can be collected with 1° oscillation. Other oscillation may be used, e.g. oscillations of less than or greater than 1°. For example, diffraction data can be collected with 0.1°, 0.3°, 0.5°, 1°, 1.5°, 2°, 3°, 4°, 5°, or 10° oscillation, or any oscillation angle in between these angles. In certain embodiments, 120 frames are collected. More or fewer than 120 frames may be collected. For example, 10, 20, 50, 100, 200, 300, 400, 500, 1000, or 5000 frames may be collected, or any number of frames in between these numbers. In certain embodiments, the exposure is 10 minutes per frame. Other frame exposure times may also be used, such as, for example 5 seconds, 10 seconds, 20 seconds, 30 seconds, 40 seconds, 50 seconds, 60 seconds, 120 seconds, 180 seconds, 3 minutes, 4 minutes, 5 minutes, 15 minutes, 20 minutes, 30 minutes per frame or any exposure time in between these times. Data merging and scaling can be done, for example, using HKL2000 software suite (HKL Research, Inc., Charlottesville, Va.). Structure determination, model building, and refinement can be performed, for example, using software such as Molrep, coot and Refmac that are part of CCP4 software suite. MolRep is a program for automated molecular replacement (e.g., MolRep, version 10.2.35). Coot Graphical Interface by Paul Emsley (www.ysbl.york.ac.uk/~emsley) for model building includes an interface to refmac5 (Gnu Public License; refmac5, e.g. version 5.5.0072 or version 5.5.0109). A macromolecular refinement program by Garib Murshudov et al. is integrated into the CCP4 program suite (www.ccp4.ac.uk, CCP4, version 6.1.3). Structural analyses may be performed using molecular viewer software PYMOL (pymol.org). In certain embodiments, models of the polypeptide may be obtained by the molecular replacement method using the program Molrep and the structural information available for T4L (PDB ID:3G3V) and human GLTP (PDB ID 1SWX) as search models. For example, initial phases may be obtained removing from the coordinates of the search models all of the side chains resulting in a poly-alanine model. Such models may be used for further model building and refinement, for example using programs such as coot and Refmac.

The term "molecular replacement" refers to a method that involves generating a preliminary model of the three-dimensional structure of a polypeptide or a polypeptide complexed with a binding compound whose structure coordinates are not known by orienting and positioning a polypeptide structure whose atomic coordinates are known. Phases are calculated from this model and combined with the observed amplitudes of the unknown crystal structure to give an approximate structure. This structure is then subject to any of several forms of refinement to provide a final, accurate structure. Any program known to the skilled artisan may be employed to determine the structure by molecular replacement. Suitable molecular replacement programs include, but are not limited to, AMORE (1994) [18;19] and CNS (1998) [20].

In certain embodiments, the atomic coordinates of the crystalline polypeptide of the invention, or a subset thereof (e.g. for the sugar headgroup binding residues, substrate binding pocket and/or the GLTP domain of FAPP2) are provided. In one embodiment, wherein the crystal diffracts at a resolution of 3 Å the model may be refined to a final R factor of 25.5% and Rfree of 32.4%. In a further embodiment wherein the crystal diffracts at a resolution of 2.6 Å the model may be refined to a final R factor of 20.5% and Rfree of 25.7%.

In certain embodiments, atomic coordinates of crystalline T4L-FAPP2-C212 (SEQ ID NO:3) are provided. The parameters for residues 36-207 of SEQ ID NO:3 are set forth in Table 1, in which they are referred to as residues 136-307 to reflect their positions relative to residues 308 onwards of human FAPP2 in the fusion protein. The parameters for substrate binding pocket residues are set forth in Table 2 and the parameters for the GLTP domain of FAPP2 are set forth in Table 3. Residue numbering in Tables 2 and 3 is accordance with residue numbering in full length human FAPP2 (residues 308 onwards are referred to with numbering that is used for these residues in full length human FAPP2 (e.g. 308 is Ile, 309 is Pro, 310 is Thr, 311 and 312 are both Phe etc.). Atomic coordinates for residues 308-514 of human FAPP2 are provided in Table 3. Only the coordinates for the molecule A are provided.

In one embodiment, crystalline T4L-FAPP2-C212 at 3 Å has a space group of $P2_12_12$ and unit cell parameters of +/−5%, 4%, 3%, 2%, 1% of a=99.8 Å, b=130.6 Å, c=88.6 Å, $\alpha$=90°, $\beta$=90°, $\gamma$=90°, optionally unit cell parameters of a=99.8 Å, b=130.6 Å, c=88.6 Å, $\alpha$=90°, $\beta$=90°, $\gamma$=90°. Crystalline T4L-FAPP2-C212 At 2.6 Å has a space group of $P2_12_12$ and unit cell parameters of +/−5%, 4%, 3%, 2%, 1% of a=100.02 Å, b=130.87 Å, c=88.73 Å, $\alpha$=90°, $\beta$=90°, $\gamma$=90°, optionally unit cell parameters of a=100.02 Å, b=130.87 Å, c=88.73 Å, $\alpha$=90°, $\beta$=90°, $\gamma$=90° (the a, b and c values may be defined to a further decimal place (e.g. a=100.020, b=130.872, c=88.733).

The term "atomic coordinates" refers to mathematical coordinates derived from mathematical equations related to the patterns obtained on diffraction of a monochromatic beam of X-rays by the atoms (scattering centers) of a protein molecule in crystal form. The diffraction data are used to calculate an electron density map of the repeating unit of the crystal. The electron density map is then used to establish the positions of the individual atoms within the unit cell of the crystal. The coordinates can also be obtained by means of computational analysis.

Crystalline T4L-FAPP2-C212 has two molecules of T4L-FAPP2-C212 in the asymmetric unit, referred as Mol-A and Mol-B (FIG. 1). T4L from adjacent molecules in the crystal lattice make extensive contacts that appear to have facilitated crystallization (FIG. 1). Only the coordinates for the molecule A are shown in the Tables.

Analysis shows that the residues of FAPP2 involved in glucosylceramide binding, including D360, N364, W407 (which are believed to be sugar headgroup binding residues) and other (e.g. hydrophobic) residues that accommodate and may interact with the acyl/sphingosine chains of glucosylceramide are well refined in the electron density map. Glucosylceramide containing oleoyl acyl chain (18:1) from PDB ID: 3S0K was docked into the ligand binding pocket of the FAPP2 structure (FIG. 3, where amino acid residues are numbered according to SEQ ID NO:4) and the corresponding electron density map is shown in FIG. 4. No energy minimization was done after docking.

The FAPP2-C212 structure takes the general GLTP fold with eight alpha helices (FIG. 6). W407 is located in helix-4. The sugar head group would stack on this tryptophan and further makes contacts with D360 and N364. In FAPP2, E403 is also located at the sugar binding pocket which would provide additional interaction with the sugar ring. E403 has been reported in the literature, based on homology modeling, as being located in the sugar binding pocket and as being able to discriminate negatively charged sugar head groups. However in the present structure, it appears as a residue that could stabilise sugar ring binding.

K367 that is hydrogen bonded with N399 and the projected loop around N399 appear to be responsible for discriminating negatively charged sugar head groups in FAPP2 (FIG. 7).

Most of the residues that form the ceramide binding tunnel are either conserved or similar in FAPP2 and hGLTP. There are however also two phenylalanines, that are not present in hGLTP, F311 and F312 that are located at the end of the ceramide binding tunnel (FIGS. 6 and 8—in FIG. 8 24:1 Galactosyl Cer bound hGLTP (PDB ID:2EUK) has been superimposed on FAPP2). These two phenylalanines are unique to FAPP2 and are located at the N-terminus of the FAPP2 GLTP domain. These two residues sit at the end of the hydrophobic tunnel and also make hydrophobic contacts with helices 1, 7 and 8 thus stabilizing the GLTP fold. Moreover these two phenylalanine residues are part of a FFAT-like motif which is known to interact with VAP (vesicle-associated membrane protein associated proteins). F311 of FAPP2 takes the same place as F33 of hGLTP located in between helices 1 and 2. These two residues may play a role in ceramide release. Inhibition of the transfer activity of FAPP2 may be achieved by displacing them.

The term "binding pocket" is used herein to refer to the site at which the molecule to be transferred (i.e. the substrate) binds to FAPP2. The structure and chemical properties of the binding pocket allow the recognition and binding of a binding compound or substrate. The binding pocket typically includes residues responsible for the binding specificity (e.g., charge, hydrophobicity, and/or steric hindrance) of the molecule. 30 residues have been identified by the inventor as being within 5 Å of the docked substrate in the ceramide docked model (see Table 4). In one embodiment the substrate binding pocket comprises the residues of Table 4. These residues have the potential to make contact with the substrate.

In certain embodiments, the binding pocket may be defined as comprising the sugar headgroup binding residues.

The sugar headgroup binding residues are residues which make contact with the glucosyl headgroup of the substrate (e.g. GlcCer). At least residues D360, N364, and W407 are believed to make contact with the glucosyl head group of GlcCer, based on mutational studies on hGLTP [21] (see also FIG. 3). The sugar headgroup binding residues may contribute to selectivity of FAPP2 for certain substrates. For example it has been shown that FAPP2 shows a different substrate selectivity to the related molecule GLTP. FAPP2 shows a preference for uncharged monohexosyl and dihexosylceramides, compared to the broadly selective human GLTP [8]. FAPP2 has been shown to efficiently transfer GlcCer and other simple neutral glycosylceramides such as GlaCer and LacCer, but not negatively charged molecules such as sulfatide. The atomic coordinates of the sugar headgroup binding residues are included in Table 2.

In addition to the sugar headgroup binding residues the substrate binding pocket may also comprise residues that allow FAPP2 to accommodate the non-sugar portion of the substrate such as GlcCer, e.g. the ceramide portion thereof. A substrate or ceramide (fatty acid chain) accommodating tunnel is present, which comprises hydrophobic residues (see Table 4). This tunnel, which may be defined as being hydrophobic, will have a shape which depends on substrate binding (helices 2, 4, 5 and 6 can slightly move to accommodate fatty acid chains). The role of the two key phenylalanine resides F311 and F312 in the ceramide accommodating tunnel is discussed above. Residues in the ceramide accommodating tunnel include L441, F453, Y491 (as identified e.g. in [21]), in addition to other hydrophobic residues referred to in Table 4).

It will be seen from Table 4 that some of the key residues in the substrate binding pocket are identical to those in hGLTP, others are similar but a small number are unique to FAPP2, including V345, N399, E403, R398, F311 and F312.

The present structure has identified V345, N399, E403, R398, F311 and F312 as residues of the substrate binding pocket which are unique to human FAPP2 compared to human GLTP. They may be absent from human GLTP (in the case of R398, F311 and F312) or different to the equivalent residues in human GLTP. The potential role of F311 and F312 is discussed above. N399, E403 and R398 are found near to the sugar headgroup.

In one embodiment, the model created based on the structural information obtained contains positional information for the sugar headgroup binding residues. In other embodiments the model created based on the structural information obtained additionally or alternatively contains positional information for residues in the ceramide accommodating tunnel, including L441, F453, Y491 (and optionally other hydrophobic residues referred to in Table 4). In further embodiments the model created based on the structural information obtained additionally or alternatively contains positional information of the residues referred to in Table 4 as unique to human FAPP2.

It should be understood that while Tables 1-3 provide atomic coordinates for crystalline T4L-FAPP2-C212 and portions thereof, the present invention also contemplates structural modifications thereof, for example, for polypeptides having significant structural homology (e.g., significant structural overlap), particularly in the areas recognized as active, and thus providing the same or similar structural information as provided herewith. Significant structural homology refers to at least one of the following criteria: (i) at least 60%, 65%, 70%, 75%, 80%, 85%, 90%, 95%, or 99% structural homology with crystalline T4L-FAPP2-C212 or the GLTP domain thereof; or (ii) at least 60%, 65%, 70%, 75%, 80%, 85%, 90%, 95%, or 99% structural homology with a recognized binding pocket of crystalline T4L-FAPP2-C212 or the GLTP domain thereof. In certain embodiments, significant structural homology may also refer to at least 60%, 65%, 70%, 75%, 80%, 85%, 90%, 95%, or 99% structural homology with the primary amino acid sequence of T4L-FAPP2-C212 or the GLTP domain thereof. Furthermore, the primary amino acid sequence of T4L-FAPP2-C212 may be a sequence included as a segment in a larger amino acid sequence, or may be a fragment thereof (e.g. the GLTP domain). In some embodiments, a fragment of a full-length, T4L-FAPP2-C212 polypeptide is provided or used in an inventive method or system provided herein. In some embodiments, a fragment comprises a sequence of (or of at least) 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 50-75, 75-100, 100-150, 150-200 amino acids. In some embodiments, a fragment of T4L-FAPP2-C212 does not comprise a full-length T4L-FAPP2-C212 sequence, for example, a full-length human T4L-FAPP2-C212 sequence. In some embodiments, a fragment of T4L-FAPP2-C212 comprises all or at least part of the portion responsible for the transfer activity of FAPP2. In some embodiments, fragments include fragments that contain the residues that have been shown to make contact with the glucosyl head group of GlcCer (e.g. D360, N364, W407) The present invention contemplates any and all such variations and modifications of T4L-FAPP2-C212 or the GLTP domain thereof, and which may be used in the methods and uses of the invention (e.g. 308-515, 308-514, 308-513, 308-512 of FAPP2).

Table 1 provides a set of atomic coordinates for T4L-FAPP2-C212 and Table 3 provides the atomic coordinates for the GLTP domain thereof.

Uses of Structural Information

In another aspect the invention provides methods and/or uses of the structural information, for example methods for designing, identifying, and/or screening binding compounds to FAPP2 that may be useful in treating Fabry disease.

In certain embodiments, methods for identifying, designing, selecting, and/or optimising binding compounds to FAPP2 are provided, as are methods of evaluating the ability of a compound to associate with FAPP2. These binding compounds may be useful in the treatment of Fabry disease. Since Fabry disease is caused by the absence of α-galactosidase A (α-Gal A), an enzyme required for the normal processing of glycosphingolipids in mammalian lysosomes, reducing the amount of substrate for this enzyme may be particularly useful in the treatment of Fabry disease. In certain embodiments, the binding compound may affect enzyme stabilization, e.g. during protein folding. The compound may also affect aspects of intracellular trafficking of the enzyme or aspects of transfer function, such as substrate recognition and/or transfer activity.

In certain embodiments, methods are provided for the in silico design, identification, selection and/or optimisation of FAPP2 binding compounds using the three-dimensional structural information provided herein. In certain embodiments, methods are provided that can be used to identify inhibitors, reversible inhibitors, activators and/or stabilizers of FAPP2 activity. In certain embodiments, methods are provided that can be used to identify binding compounds that modulate FAPP2 stability. In certain embodiments, methods are provided that can be used to identify binding compounds that modulate FAPP2 stability, activity, and/or intracellular trafficking. In certain embodiments, methods are provided that can be used to test potential binding compounds for their ability to bind to, to modulate stability, to modulate activity, and or to modulate intracellular trafficking of FAPP2. In certain embodiments, these methods include in silico, in vitro, and in vivo methods.

Design, Identification, Selection and/or Optimisation of Potential FAPP2 Binding Compounds It is one object of the present invention to use the atomic coordinates provided for T4L-FAPP2-C212 (Tables 1 and 3) or a subset thereof (e.g. those provided for the substrate binding pocket residues and/or those provided for the GLTP domain of FAPP2) to design, identify, select and/or optimise potential binding compounds for FAPP2. In all cases where FAPP2 is referred to herein it is preferably human FAPP2. Compounds obtained from this method may further be identified as being able to treat Fabry disease in human subjects. As discussed elsewhere, the methods may utilise the atomic coordinates of at least the amino acids which are the sugar headgroup binding residues and/or additional residues in the substrate binding pocket. Table 3 provides the atomic coordinates for residues 308-514 of human FAPP2. The methods may utilise these atomic coordinates of at least amino acids 308-514 of human FAPP2.

In a further aspect the invention thus provides a method of identifying a compound that binds to FAPP2, comprising computationally identifying a compound that binds to FAPP2 using the atomic coordinates of at least the substrate binding pocket of FAPP2, e.g. as set forth in Table 2. The invention further provides a method of identifying a compound that binds to FAPP2, comprising a) providing a set of atomic coordinates for at least the GLTP domain of FAPP2, as set forth in Table 3 and b) computationally identifying a compound that binds to FAPP2 using said coordinates.

In a further aspect the invention provides a method of designing, selecting and/or optimising a compound that binds to FAPP2 comprising: a) providing a set of atomic coordinates of at least the amino acids which make up the substrate binding pocket of FAPP2, e.g. as set forth in Table 2 and b) computationally designing, selecting and/or optimising said compound by performing a fitting operation between said compound and all of part of the three dimensional structure information that is generated from the atomic coordinates. The invention further provides a method of designing, selecting and/or optimising a compound that binds to FAPP2 comprising: a) providing a set of atomic coordinates for at least the GLTP domain of FAPP2 as set forth in Table 3 and b) computationally designing, selecting and/or optimising said compound by performing a fitting operation between said compound and all or part of the three dimensional structure information that is generated from the atomic coordinates.

In a further aspect the invention provides a method for evaluating the ability of a compound to associate with FAPP2 comprising: a) providing a set of atomic coordinates of at least the amino acids which make up the substrate binding pocket of FAPP2, e.g. as set forth in Table 2; b) computationally performing a fitting operation between said compound and all or part of the three dimensional structure information that is generated from the atomic coordinates; and c) analysing the results of said fitting operation to quantitate the association between the compound and said FAPP2 polypeptide. The invention further provides a method for evaluating the ability of a compound to associate with FAPP2 comprising: a) providing a set of atomic coordinates for at least the GLTP domain of FAPP2 as set forth in Table 3 and b) computationally performing a fitting operation between said compound and all or part of the three dimensional structure information that is generated from the atomic coordinates; and c) analysing the results of said fitting operation to quantitate the association between the compound and FAPP2.

In one embodiment the methods of the invention further comprise generating a three dimensional graphical representation of the structure prior to step (b).

In a further aspect the invention provides a method of using a computer for evaluating the ability of a compound to associate with FAPP2 wherein said computer comprises a machine readable data storage medium comprising a data storage material encoded with the atomic coordinates of at least the amino acids which make up substrate binding pocket of FAPP2, e.g. as set forth in Table 2 and means for generating a three dimensional graphical representation of the structure of said amino acids and said method comprises: a) positioning a first compound using a graphical three dimensional representation of the structure of the compound and all or part of the substrate binding pocket of FAPP2; b) performing a fitting operation between the compound and the substrate binding pocket of FAPP2 by employing computational means; and c) analysing the results of said fitting operation to quantitate the association between the compound and the substrate binding pocket of FAPP2.

The method further provides a method of using a computer for evaluating the ability of a compound to associate with FAPP2 wherein said computer comprises a machine readable data storage medium comprising a data storage material encoded with the atomic coordinates for at least the GLTP domain of FAPP2 as set forth in Table 3 and means for generating a three dimensional graphical representation of the structure of the GLTP domain of FAPP2 and said method comprises: a) positioning a first compound using a graphical three dimensional representation of the structure of the compound and all or part of the GLTP domain of FAPP2; b) performing a fitting operation between said compound and the GLTP domain of FAPP2 by employing computational means; and c) analysing the results of said fitting operation to quantitate the association between said compound and the GLTP domain of FAPP2.

The method of using a computer for evaluating the ability of a compound to associate with FAPP2 may further comprise the steps of (d) repeating steps (a) to (c) with a second chemical entity; and (e) selecting at least one of the first or second chemical entity that associates with the GLTP domain of FAPP2 or the substrate binding pocket based on the quantitated association of the first or second chemical entity.

The above methods may additionally be performed based on the atomic coordinates of the sugar head group binding residues alone, or with the ceramide accommodating tunnel residues and/or the residues defined as unique to FAPP2.

Also provided is the use of the structure of the crystalline form of the invention, or a subset thereof in modelling a binding compound which binds to FAPP2, and the use of the atomic coordinates of the crystalline form of the invention, or a subset thereof in modelling a binding compound which binds to FAPP2.

Useful subsets of structure coordinates that can be used in the method of the invention include structure coordinates defining a) are the sugar headgroup binding residues of FAPP2 b) the substrate binding pocket residues of FAPP2 and c) the GLTP domain of FAPP2.

It should be understood that a potential binding compound according to this invention may bind anywhere on FAPP2. In one embodiment a potential binding compound according to this invention may bind on the GLTP domain of FAPP2. The binding compound may bind to the binding pocket or to any other site which is not identified as a binding pocket, e.g. to a site which is adjacent to a binding pocket. In certain embodiments, the potential binding compound according to this invention may bind specifically to one or more sites on the FAPP2 polypeptide (be it nascent, partially or fully folded).

In many embodiments the binding molecule will bind to the binding pocket of FAPP2. In many embodiments the binding molecule will bind to the sugar headgroup binding residues, of FAPP2, or the ceramide accommodating tunnel residues. "Binding to" a molecule or a defined portion thereof encompasses binding to all or a part of a molecule or a defined portion thereof, such that reference to binding to a molecule or a defined portion thereof does not require an interaction to be made with each residue of that molecule or portion.

In line with this, where binding compounds are identified using the methods of the invention the identification of a binding compound may use information about the relevant molecule or the defined portion thereof, or a part of the defined molecule or portion thereof. It may thus use information about the structure of the GLTP domain of FAPP2, the structure of the binding pocket of FAPP2, the structure of the sugar headgroup binding residues, or a portion of any of these.

As used herein, a "binding compound" refers to a compound which reversibly or irreversibly binds to FAPP2. In certain embodiments, the binding compound binds in a binding pocket of FAPP2. Binding may involve the formation of bonds which may be covalent or non-covalent. Non-covalent bonds may be e.g. hydrogen bonds, ionic binds or hydrophobic bonds.

A binding compound may affect the activity of FAPP2. This may be achieved directly by modulating the ability of the FAPP2 to transfer its substrate, which may be achieved by being an inhibitor of FAPP2 (i.e. eliciting inhibition or reduction in transfer activity), or an activator of FAPP2 (i.e. eliciting an increase in transfer activity). In some cases the binding compound may affect the stability of FAPP2 which in turn may result in an effect on the activity of FAPP2 in which case the binding molecule is a stabilizer or destabilizer of FAPP2 (i.e. may elicit a change in stability of FAPP2). In other cases the binding molecule may affect the intracellular trafficking of FAPP2. FAPP2 picks up its substrate in the Golgi, so binding molecules which influence the ability of FAPP2 to localise at the Golgi (e.g. which prevent FAPP2 from localizing to the Golgi, or which reduce the ability of FAPP2 to localise to the Golgi, or which increase the ability of FAPP2 to localise to the Golgi) are also contemplated.

In certain embodiments, the potential binding compound is a potential inhibitor or activator compound. In certain embodiments, the potential binding compound is a potential FAPP2 inhibitor or activator compound. In certain embodiments, the potential inhibitor or activator compound is a competitive, uncompetitive or non-competitive inhibitor or activator compound. In certain embodiments, the potential inhibitor is a reversible inhibitor. Those of skill in the art may identify potential inhibitors or activators as competitive, uncompetitive or non-competitive or reversible inhibitors or activators by computer fitting kinetic data using standard equations [22], or by employing assays which measure the ability of a potential inhibitor or activator to modulate FAPP2 transfer activity.

FAPP2 is known to at least function to transfer glycolipids such as GlcCer from the cis-Golgi to the TGN. The activity of FAPP2 thus includes its transfer activity, i.e. transferring its substrate from one membrane to another membrane. This transfer activity can be measured by measuring the substrate transfer in vitro, e.g. from one membrane to another. The assays in general involve donor and acceptor vesicles and the transfer of labelled substrate is measured. At least two established assays exist. In one example substrate transfer is measured by liquid scintillation counting of acceptor vesicles when the substrate is radiolabeled. In another example real time monitoring of glycolipid transfer activity is carried out using Förster resonance energy transfer (FRET), where FRET between an appropriately labelled substrate molecule and a labelled non-transferable molecule in the donor membrane is determined. Recovery of emission of the appropriately labelled substrate molecule is indicative of transfer. [23, 24, 25, 26, 27]

Inhibitors or activators of FAPP2 may in one embodiment lead to a statistically significant decrease or increase, respectively of FAPP2 activity.

An inhibitor of FAPP2 may be a catalytic substrate of FAPP2. Such compounds may be analogues of the natural substrate of FAPP2, GlcCer, or of other molecules which bind to the binding pocket e.g. GalCer or LacCer. Such analogues may have modifications which cause them to inhibit FAPP2.

Further examples of possible inhibitors include molecules with a hydrophilic or hydrogen bond forming head group, e.g. that can stack over W407 and fill the sugar headgroup binding pocket; (2) hydrophobic molecules that can bind to the ceramide accommodating tunnel; (3) small molecules that can displace F311/F312 located at the end of ceramide accommodating tunnel (at the opposite face to sugar binding pocket).

A binding compound may be a small molecule. The term "small molecule" as used herein is meant to describe a low molecular weight organic compound which is not a polymer. A small molecule may bind with high or low affinity to a biopolymer such as protein, nucleic acid, or polysaccharide and may in addition alter the activity or function of the biopolymer. The molecular weight of the small organic compound may generally be smaller than about 1500 Da. Small molecules may be smaller than about 1000 Da, smaller than about 800 Da, or smaller than about 500 Da. Small molecules may rapidly diffuse across cell membranes and may have oral bioavailability. These compounds can be natural or synthetic.

It is useful to be able to identify binding molecules that are specific to FAPP2 (e.g. to human FAPP2). By specific it is meant that the binding molecule has a preference for binding to FAPP2 (e.g. it does not bind to one or more other molecules or it shows reduced binding e.g. at least 5, 10, 20, 50, 100, 200, 500, 1000 fold reduced affinity to the one or more other molecules). Binding can be quantitated in accordance with methods known in the art.

Preferably the binding molecule is specific for FAPP2 in comparison to GLTP (e.g. specific for human FAPP2 in comparison to human GLTP). The GLTP domain of human FAPP2 is similar in structure to human GLTP, but not identical, as determined by the inventor, and there are key differences between these two molecules. The identification of the structure of FAPP2 by the inventor means that binding molecules that have a required specificity can be obtained.

The availability of structural information for human GLTP (e.g. PDB ID 1SWX, PDB ID 2EUK, PDB ID 4H2Z) also means that in addition to the methods above (using the structure of the GLTP domain of human FAPP2 (or portions thereof)) methods can be carried out in which the steps described above using the atomic coordinates or structural information for the GLTP domain of human FAPP2 (or portions thereof) are carried out using the atomic coordinates or structural information for human GLTP. This can be done in parallel or in sequence with methods using the structure of the GLTP domain of human FAPP2 (or portions thereof). Such methods are a further way to determine whether a binding molecule that binds to FAPP2 is specific for FAPP2 over GLTP.

Similarly the information provided herein can be used to identify binding compounds which bind to both human GLTP and human FAPP2 (e.g. with equal or about equal affinity), or which are specific for human GLTP over human FAPP2. The methods referred to above can be carried out using the atomic coordinates or structural information available for GLTP, and the equivalent information provided herein for FAPP2, simultaneously or sequentially, to identify binding compounds which bind to both human GLTP and human FAPP2, or which are specific for human GLTP over human FAPP2.

By way of example, methods referred to above which identify, design, select, optimise and/or evaluate a compound that binds to FAPP2 may thus additionally comprise a step of determining whether said compound binds to GLTP, and/or performing a fitting operation between the compound and all or part of the three dimensional structural information of GLTP.

Methods referred to above which relate to using a computer for evaluating the ability of a compound to associate with FAPP2 may additionally require the data storage material to be encoded with the atomic coordinates of at least the amino acids which make up the substrate binding pocket of GLTP (or the whole molecule) and additionally require the steps to quantitate the association between the compound and the substrate binding pocket of GLTP.

Uses referred to above may additionally incorporate the use of the structure of GLTP.

Such methods and uses may thus be methods which identify, design, select, optimise and/or evaluate a compound that binds specifically to FAPP2 (e.g. over GLTP), or which binds to FAPP2 and GLTP.

As a further example methods which identify, design, select, optimise and/or evaluate a compound that binds specifically to GLTP over FAPP2 are also provided. For example a method of identifying a compound that binds specifically to GLTP over FAPP2, comprises computationally identifying a compound that binds specifically to GLTP over FAPP2 using (i) the atomic coordinates of at least the substrate binding pocket of FAPP2, e.g. as set forth in Table 2 and the atomic coordinates of at least the substrate binding pocket of GLTP or (ii) the atomic coordinates for at least the GLTP domain of FAPP2, as set forth in Table 3 and the atomic coordinates for GLTP.

A method of designing, selecting and/or optimising a compound that binds specifically to GLTP over FAPP2 may comprise: a) providing a set of atomic coordinates of i) at least the amino acids which make up the substrate binding pocket of FAPP2, e.g. as set forth in Table 2 and at least the amino acids which make up the substrate binding pocket of GLTP, or ii) at least the GLTP domain of FAPP2 as set forth in Table 3, and GLTP b) computationally designing, selecting and/or optimising said compound by performing a fitting operation between said compound and all of part of the three dimensional structure information that is generated from the atomic coordinates.

In one embodiment the methods of the invention further comprise generating a three dimensional graphical representation of the structure prior to step (b).

The potential binding compound may be identified or selected from a library of compounds, or identified or selected from a database. In such cases the identification is made from a pre-existing molecular structure and the potential binding compound is chosen, for example, from a group of pre-existing compounds. One or more members, such as a small molecule or a substrate analogue that have or exhibit a desired property or characteristic are chosen.

The potential binding compound is in some embodiments designed, e.g. in silico. When the binding compound is designed in silico this may be from a known compound. "Design" or "designing" as used herein is meant to provide a novel molecular structure of, for example, a compound, such as a small molecule or a substrate analogue.

Suitable computer programs which may be used in the design and identification of potential binding compounds (e.g., by selecting suitable chemical fragments) include, but are not limited to, GRID [28], MCSS [29], AUTODOCK [30]; and DOCK [31].

Suitable computer programs which may be used in connecting the individual chemical entities or fragments include, but are not limited to, CAVEAT (Bartlett, (1989) Molecular Recognition in Chemical and Biological Problems, Special Pub., Royal Chem. Soc. 78:182-19632); and 3D Database systems such as MACCS-3D by MDL Information Systems, San Leandro, Calif.), HOOK (Molecular Simulations, Burlington, Mass.) and as reviewed in reference [33].

In addition to methods in which potential binding compounds are built or identified in a step-wise fashion (e.g., one fragment or chemical entity at a time as described above), potential binding compounds may be designed as a whole or "de novo" using either an empty active site or, optionally, including some portion(s) of a known inhibitor(s), activator(s) or stabilizer (s). Suitable computer programs include, but are not limited to, LUDI [34], LEGEND [35]; and LEAPFROG (Tripos Associates, St. Louis, Mo.). Other molecular modeling techniques may also be employed in accordance with this invention [36,37].

Once a potential binding compound has been designed, selected, identified, synthesized, or chosen by the methods described herein, the affinity with which that compound binds to FAPP2 (and/or GLTP) may be tested and optimized by computational evaluation. A compound designed, or selected, or synthesized, or chosen as potential binding compound or may be further computationally optimized so that in its bound state it would preferably lack repulsive electrostatic interaction with the target site. Such non-complementary (e.g., electrostatic) interactions include repulsive charge-charge, dipole-dipole and charge-dipole interactions. Specifically, the sum of all electrostatic interactions between the potential binding compound and the site at which it is bound to FAPP2, in certain embodiments, make a neutral or favorable contribution to the enthalpy of binding. Suitable computer software which may be used to evaluate compound deformation energy and electrostatic interactions, includes, but is not limited to, Gaussian 92, revision C by M. J. Frisch, Gaussian, Inc., (1992) Pittsburgh, Pa.; AMBER, version 4.0 by P. A. Kollman, (1994) University of California at San Francisco; QUANTA/CHARMM by Molecular Simulations, Inc., (1994) Burlington, Mass.; and Insight II/Discover by Biosysm Technologies Inc., (1994) San Diego, Calif. These programs may be implemented, for example, using a Silicon Graphics workstation, IRIS 4D/35 or IBM RISC/6000 workstation model 550. Hardware systems, such as an IBM thinkpad with LINUX operating system or a DELL latitude D630 with WINDOWS operating system, may be used. Other hardware systems and software packages will be known to those skilled in the art of which the speed and capacity are continually modified.

In certain embodiments, binding compounds may be specifically designed and/or selected and/or synthesized and/or chosen by the above methods to induce non-complementary (e.g., electrostatic) interactions, such as repulsive charge-charge, dipole-dipole and charge-dipole interactions. In certain embodiments, the sum of all electrostatic interactions between the potential binding compound and the site at which it is bound to FAPP2 make a contribution to the enthalpy of binding that is not neutral.

In certain embodiments, the above method comprises using a suitable computer program in designing and/or selecting a potential binding compound.

Additionally, in certain embodiments, the above methods comprise using a suitable computer program in conjunction with synthesizing and/or choosing the potential binding compound.

Furthermore, in certain embodiments, the above method further comprises the steps of using a suitable assay, as described herein, to characterize the potential binding compound's ability to bind to FAPP2 (and/or GLTP). This may involve directly testing the compound's ability to bind, and/or determining whether the compound has an influence on FAPP2 activity (e.g. by affecting its transfer activity, stability, folding, and/or intracellular localization).

To evaluate binding properties of binding compounds, assays may be used, such as, calorimetric techniques (e.g. isothermal titration calometry, differential scanning calometry), or Biacore™.

In certain embodiments, the above methods may further comprise determining whether the potential binding compound modulates the activity (e.g. transfer activity), stability or intracellular trafficking of FAPP2 (and/or GLTP). This may be carried out using a biological assay.

Determining whether the potential binding compound modulates the transfer activity of FAPP2 may involve contacting the potential binding compound with FAPP2 in the presence of a substrate (e.g. GlcCer) and determining the amount of substrate transfer. This can be compared to the amount of substrate transfer in the absence of the potential binding compound to determine the effect of the potential binding compound on FAPP2 transfer activity. Suitable assays for FAPP2 are known in the art and discussed above.

Determining whether the potential binding compound modulates the stability of FAPP2 (and/or GLTP) may involve e.g. differential scanning calorimetry (DSC), circular dichroism (CD) spectra analyses.

Determining whether the potential binding compound modulates the intracellular trafficking of FAPP2 (and/or GLTP) may involve cell based assays.

The methods of the invention may further comprise the step of modifying the binding compound for administration as a pharmaceutical. The binding compound may have the required ability to bind to FAPP2 (and/or GLTP), as discussed above, but may still benefit from further optimisation. In such cases the binding compound's chemical structure is used as a starting point for chemical modifications. Such modifications may be designed to improve potency, selectivity, pharmacokinetic parameters or physicochemical properties (e.g. stability, solubility).

The methods of the invention may further comprise the step of formulating the binding compound, or the modified binding compound as a pharmaceutical. This will in general involve admixing the agent with a pharmaceutically acceptable carrier. The term "pharmaceutically acceptable carrier", as used herein, includes any agent that does not itself induce toxicity effects or cause the production of antibodies that are harmful to the individual receiving the pharmaceutical composition. Pharmaceutically acceptable carriers may additionally contain liquids such as water, saline, glycerol, ethanol or auxiliary substances such as wetting or emulsifying agents, pH buffering substances and the like. The pharmaceutical carrier employed will thus vary depending on the route of administration. Carriers may enable the pharmaceutical compositions to be formulated into tablets, pills, dragees, capsules, liquids, gels, syrups, slurries, suspensions to aid intake by the patient. A thorough discussion of pharmaceutically acceptable carriers is available in [38].

Computer Readable Media

The invention provides computer readable media comprising the atomic coordinates for the polypeptide of the invention, or a subset thereof. The computer readable medium may further comprise programming for displaying a molecular model of the polypeptide or a portion thereof. The computer readable medium may further comprise programming for identifying a binding molecule and to assist with this it may further comprise a database of structures of test compounds. Such test compounds may, for example be based on known inhibitors of FAPP2 and may for example be analogues of GlcCer.

The said atomic coordinates are set forth in Tables 1 to 3.

"Computer readable media" refers to any media which can be read and accessed directly by a computer. Such media include, but are not limited to: magnetic storage media such as floppy discs, hard disc storage medium and magnetic tape; optical storage media such as optical discs or CD-ROM; electrical storage media such as RAM and ROM; and hybrids of these categories such as magnetic/optical storage media.

A computer comprising the computer-readable medium of the invention is provided, as is a computer system comprising a memory unit comprising x-ray crystallographic structure coordinates defining the polypeptide of the invention as set forth in Table 1, or a subset thereof; and a processor in electrical communication with the memory unit; wherein the processor generates a molecular model having a three dimensional structure representative of at least a portion of said polypeptide.

A "computer system" refers to the hardware means, software means and data storage means used to analyse the atomic coordinate data of the present invention. The minimum hardware means of the computer-based systems of the present invention comprises a central processing unit (CPU), input means, output means and data storage means. Desirably a monitor is provided to visualise structure data. The data storage means may be RAM or means for accessing computer readable media of the invention. Examples of such systems are microcomputer workstations available from Silicon Graphics Incorporated and Sun Microsystems running Unix based, Windows.

It is another object of the invention to provide methods for solving the structures of other proteins. All or part of the structural coordinates provided herein can be used to determine the structure of another crystallized molecule more quickly and efficiently than attempting this process ab initio. This may be useful e.g. for solving the structures or partially solving the structure of other proteins which comprise protein domains of similar function, other homology domains, or proteins that comprise amino acid sequences of high homology or identity. Such protein structures may be solved using some or all of the structural information provided in the Tables. In some embodiments, molecular replacement methods may be employed to solve such structures using the structural information provided by the present invention.

Compounds and Pharmaceuticals

A compound identified, designed, selected and/or optimised by a method of the invention is provided in a further aspect of the invention, as are such compounds which have been modified for administration as a pharmaceutical, and/or which have been formulated as a pharmaceutical. Such compounds may be used as a medicament, e.g. in treating Fabry's disease. Methods of treating or preventing Fabry's disease comprising administering an effective amount of such a compound or pharmaceutical to a patient in need thereof are furthermore provided.

A further aspect of the invention provides a method of producing a pharmaceutical composition comprising designing, selecting and/or optimising a compound with the methods of the invention, modifying the identified compound for administration as a pharmaceutical and formulating the product obtained with a pharmaceutically acceptable carrier or diluent.

Any pharmaceutical may be delivered by any known route of administration. The pharmaceutical may be delivered locally or systemically. It may be delivered by a parenteral route (e.g. by injection, either subcutaneously, intraperitoneally, intravenously or intramuscularly or delivered to the interstitial space of a tissue), or into a lesion. Other modes of administration include oral and pulmonary administration, suppositories, and transdermal or transcutaneous applications, needles, and hyposprays.

The pharmaceutical may be administered alone or as part of a treatment regimen also involving the administration of other drugs currently used in the treatment of patients with Fabry disease. For example, it may be administered in combination with enzyme replacement therapy or with treatments associated with the treatment of the clinical manifestations of the disease, such as analgesics, anticonvulsants, and non-steroidal anti-inflammatory drugs (NSAIDs).

The agent may be administered simultaneously, sequentially or separately with the other drug(s).

For example, the agent may be administered before or after administration of the other drug(s).

The term "about" in relation to a numerical value x means, for example, x±10%.

EXAMPLES

Example 1—Crystallization Screening for FAPP2-C212

Figure 1:
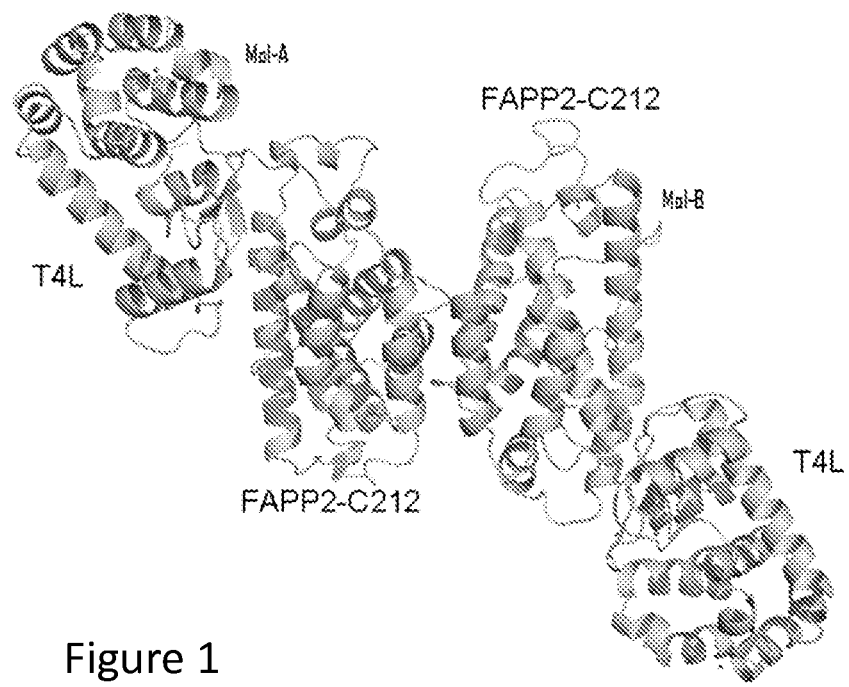
FIG. 1: Two molecules of T4L-FAPP2-C212 in crystallographic AU (Mol-A and Mol-B in cyan and green respectively)

C-terminal 212 amino acids, aa 308-519, of FAPP2 (FAPP2-C212) was expressed as SUMO or His fusions and purified as fusion proteins or as tag removed FAPP2-C212. These proteins were concentrated to 6-16 mg/ml for crystallization studies. Crystallization screening was carried out with purified FAPP2-C212 molecules using commercial crystallization screening kits from Qiagen (JCSG kits I-IV) by sitting drop vapour diffusion method. Crystallization screening was also carried out for FAPP2-C212 incubated with various ligands that are known to bind to FAPP2 or human GLTP proteins, including C8-ceramide, Phlorizin, disulfo or monosulfo galactosyl ceramides. These crystallization trials did not yield any promising crystallization hit.

Example 2—FAPP2-C212 Lysozyme Fusion

As an alternative strategy to crystallize FAPP2-C212, lysozyme (T4L) was chosen, as crystallisable fusion tag, to facilitate crystallization.

His-T4L-FAPP2-C212 (T4L-FAPP2-C212) was cloned into pRSET vector (Life Technologies), expressed in *E. coli* and purified by Ni-column and SEC column processes. Purified protein has a molecular weight of 47.2 kDa. T4L-FAPP2-C212 was concentrated to 6 mg/ml and crystallization trial was carried out using JCSG-I random matrix crystallization kit from Qiagen. All crystallization experiments were carried by sitting drop vapour diffusion method in 16° C. incubators. Initial crystallization hit was observed in condition# C6 JCSG kit-1 after three days.

Example 3—Crystallization Optimization for T4L-FAPP2-C212

The crystallization condition (JCSG-#C6) that produced T4L-FAPP2-C212 crystals was 0.2 M $MgCl_2$, 0.1 M Tris pH=7.0 and 2.5 M NaCl. Further optimization of crystallization was carried out by increasing the protein concentration up to 20 mg/ml, screening $MgCl_2$ and NaCl concentration in the crystallization solution and by microseeding crystallization drops. Crystal nucleation can be seen in 18-24 hours and crystals grow for about a week. Crystals of 50-100 micron size are reproducibly generated under this crystallization condition.

Example 4—Diffraction Data Collection

X-ray diffraction data were collected at BIDMC X-ray diffraction core facility using Rigaku X-ray diffractometer with Cu anode. Crystals of about 50-100 micron in size were used for data collection, after freezing them in liquid nitrogen using a cryo buffer of 0.2 M $MgCl_2$, 0.1 M Tris pH=7.0, 2.5 M NaCl, 10% glycerol and 5% xylitol. About 120 frames of X-ray diffraction data was collected with 1° oscillation and 10 min exposure. The X-ray diffraction data set was processed and scaled to P222 space group using HKL2000 at BIDMC. X-ray diffraction data set of 3.0 Å resolution, with a completeness of 95% and a I/sigma of >1.5 at the highest resolution shell, was used for initial structure determination. Subsequently a data set at 2.6 Å resolution was used.

Example 5—Structure Determination and Refinement

At 3.0 Å the unit cell dimensions are a=99.8 Å, b=130.6 Å, c=88.6 Å, $\alpha$=90°, $\beta$=90°, $\gamma$=90°. At 2.6 Å the unit cell dimensions are a=100.02 Å, b=130.87 Å, c=88.73 Å, $\alpha$=90°, $\beta$=90°, $\gamma$=90°. Molecular replacement (MR) was used to determine the structure of T4L-FAPP2-C212. T4L structure (PDB ID: 3G3V) and hGLTP structure (PDB ID: 1SWX) were used as search models. Molrep was used for MR, refmac5 was used for refinement and coot for used for model building.

Two molecules each of T4L and GLTP were identified in the asymmetric unit (AU) by the molecular replacement method under the space group of $P2_12_12$. Further model building and refinement were done iteratively using refmac and coot. The 3 Å structure was refined to a R=25.5% and Rfree=32.4%. The 2.6 Å structure has been refined to a final R factor of 20.5% and Rfree of 25.7%.

Example 6—Brief Description of Structure

Figure 2:
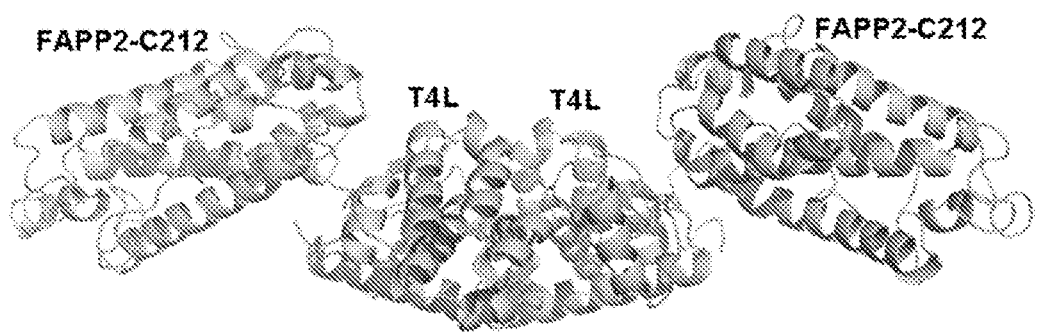
FIG. 2: Two adjacent T4L-FAPP2-C212 molecules in crystal lattice, showing extensive interaction between T4L
Figure 3:
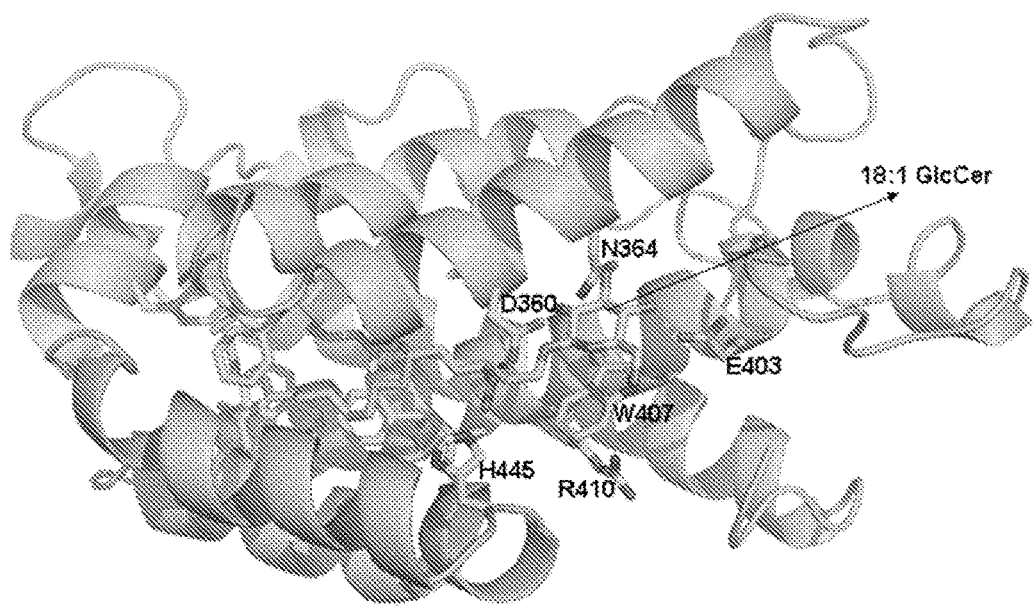
FIG. 3: 18:1 Glucosyl Ceramide (GlcCer, shown in green sticks) is docked into the structure of FAPP2-C212, without further energy minimization. Coordinates of GlcCer was taken from PDB ID: 3S0K. Hydrophobic residues of FAPP2 in close proximity of oleoyl and sphingosine chains are shown in stick model. Residues making contacts with glucosyl head group are shown in stick model and are labeled.
Figure 4:
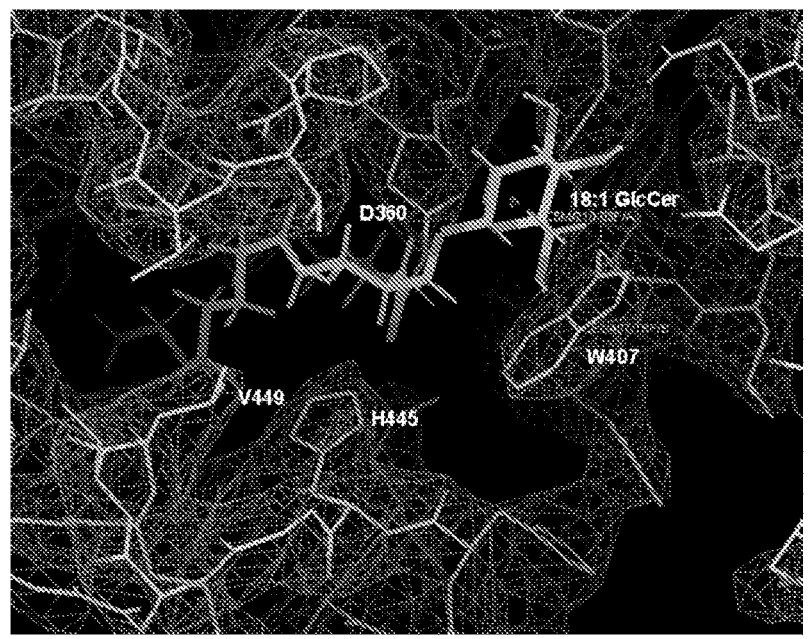
FIG. 4: Electron density map around W407 is shown here with docked 18:1 GlcCer (see FIG. 3). No energy minimization was done after docking.
Figure 5:
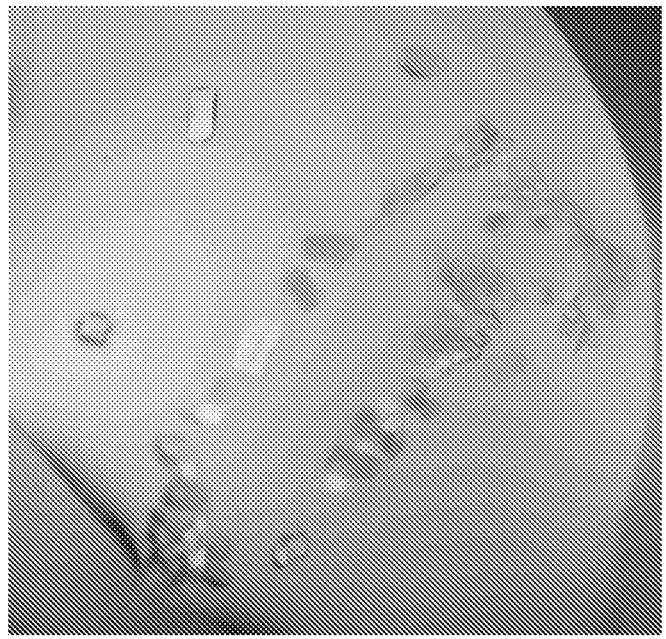
FIG. 5: T4L-FAPP2-C212 crystals.

There are two molecules of T4L-FAPP2-C212 in the asymmetric unit, referred as Mol-A and Mol-B (FIG. 1). T4L from adjacent molecules in the crystal lattice make extensive contacts that appear to have facilitated crystallization (FIG. 2). In the electron density map, aa 308-514 of FAPP2 for molecule-A and 308-515 of FAPP2 for molecule-B could be seen, without ambiguity. Electron densities are not clear for side chains of K190, 1322, E326, 5328, E333 and E509 of molecule-A and K190, L324, L325, E326, K377, E378 and R398 of molecule-B Residues involved ceramide binding, including W407, H445, D360 and other hydrophobic residues that interact with acyl sphingosine chains of ceramide are well refined in the electron density map. Glucosylceramide containing oleoyl acyl chain (18:1) from PDB ID: 3S0K was docked into the ligand binding pocket of our current FAPP2 structure (FIG. 3) and the corresponding electron density map is shown in FIG. 4. No energy minimization was done after docking.

Figure 6A:
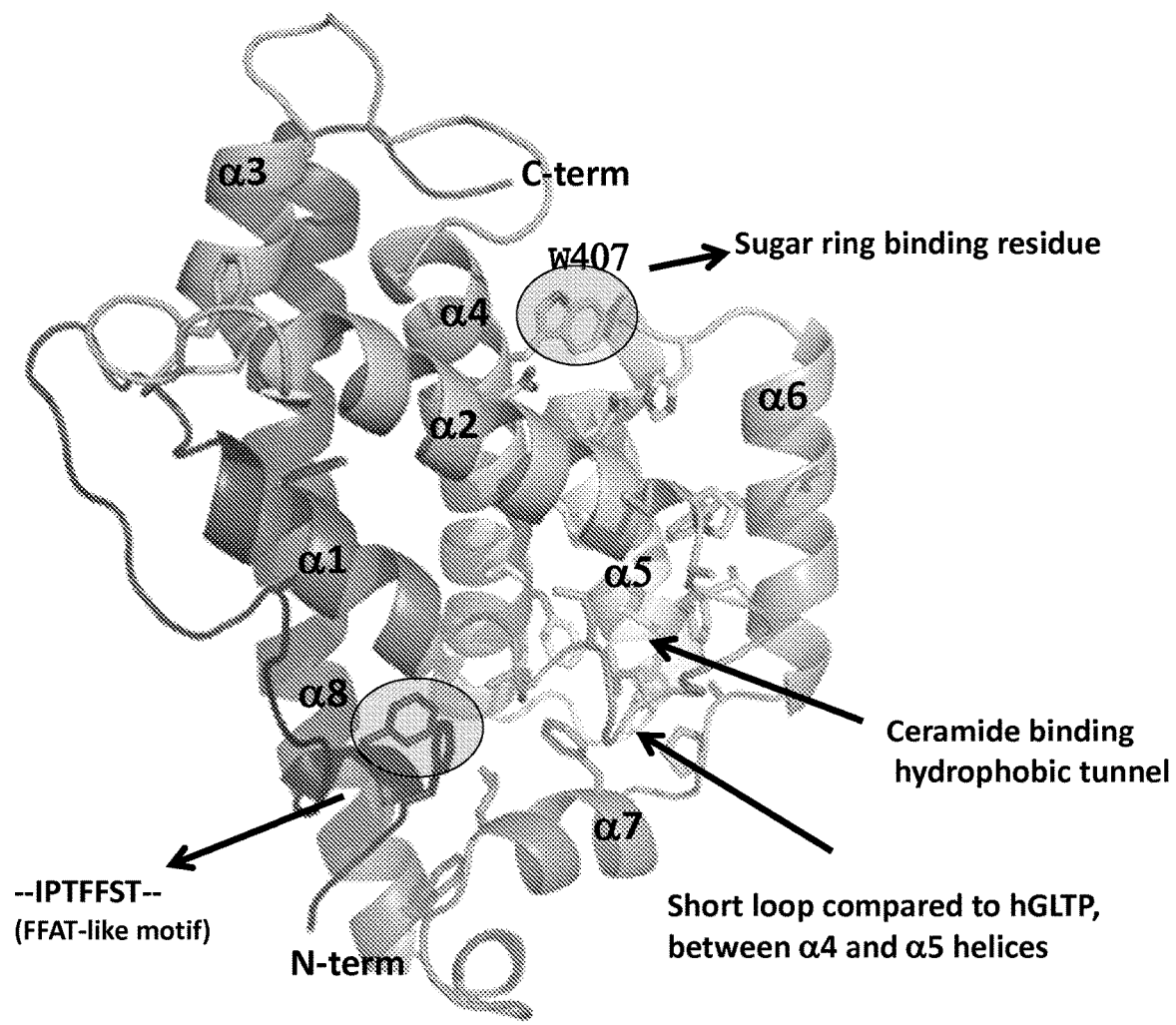
FIG. 6: FAPP2-C212 structure (T4L has been removed for clarity) (a) with hGLTP for comparison (b).
Figure 6B:
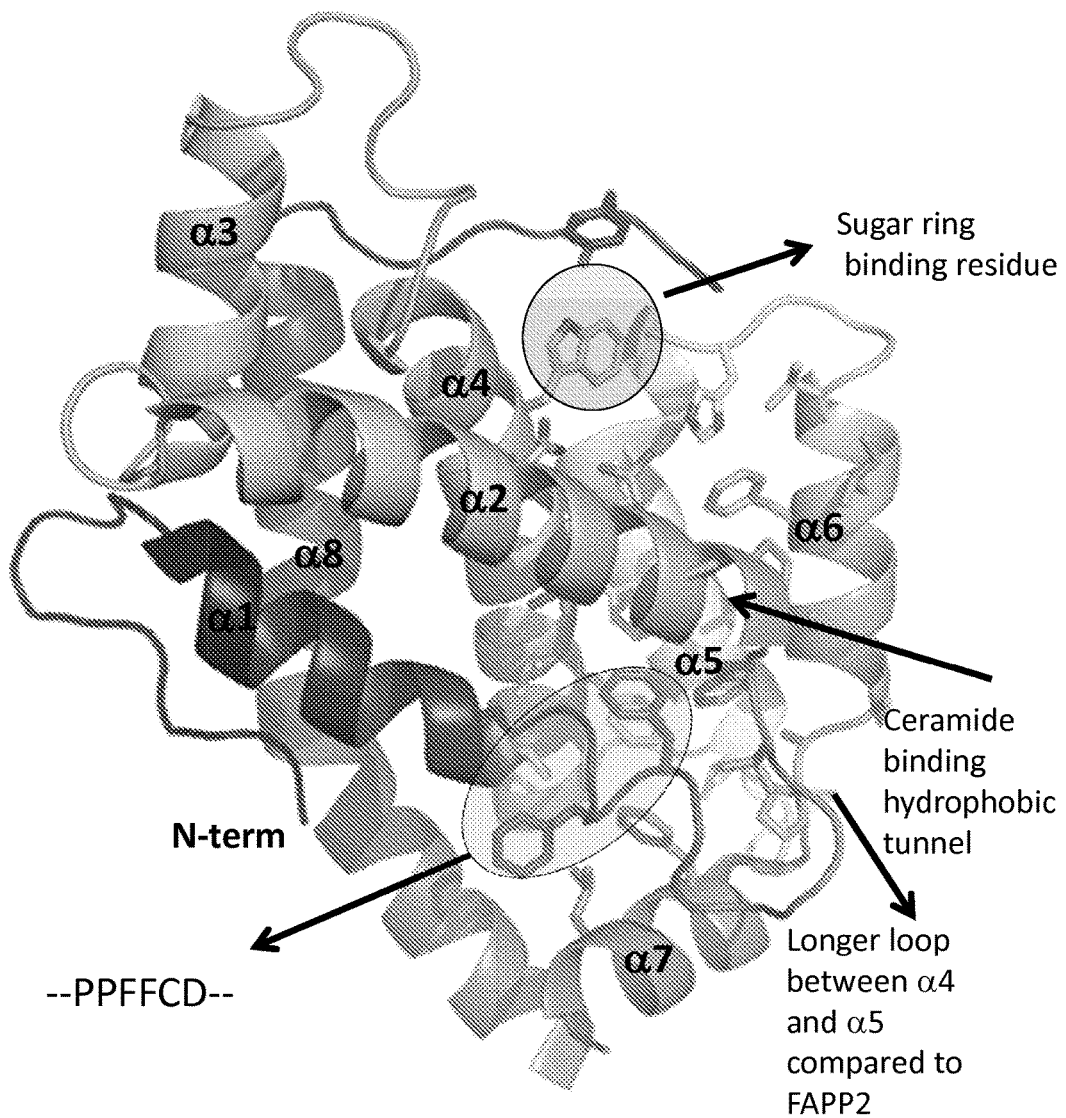
Figure 7:
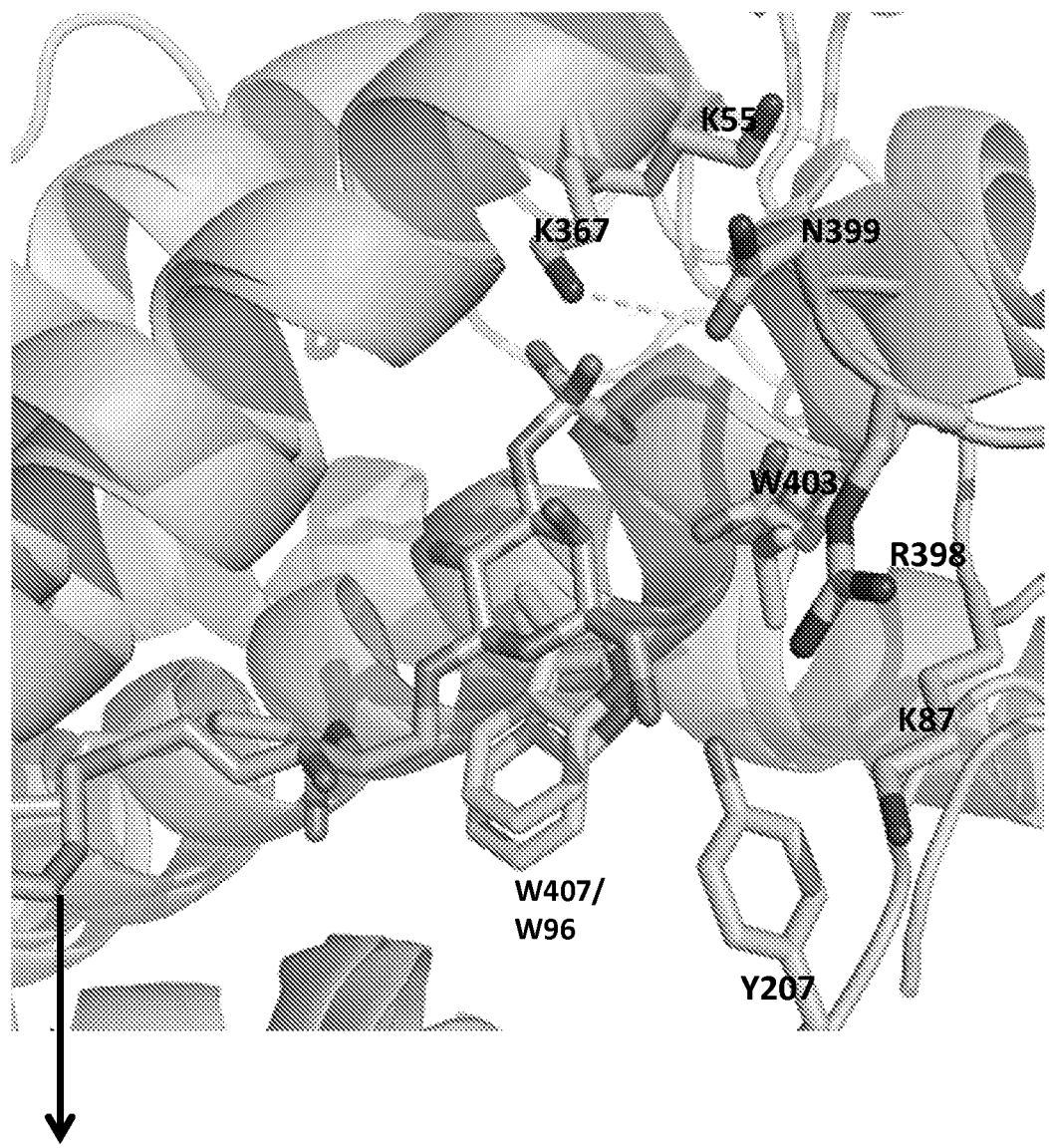
FIG. 7: Sugar head group binding: FAPP2-C212 (apo) versus hGLTP complex (PDB: 4H2Z). FAPP2 is shown in green and GLTP in cyan. Monosulfo-Galactosyl Ceramide bound to hGLTP is shown in pink. There is more negative charge near to the sugar binding pocket in FAPP2 and in FAPP2 the K367 is positioned and the positively charged loop around R398 is projected by the hydrogen bond.

FIG. 6 shows the FAPP2-C212 structure, compared to that of hGLTP (PDB ID 1SWX). The sugar headgroup binding residues of FAPP-C212 were compared to those of the hGLTP complex with monosulfo-galactosyl ceramide (PDB ID 4H2Z). It was observed that there is more negative charge near to the sugar headgroup in FAPP2, and further in FAPP2 the K367 is positioned and the positively charged loop around R398 is projected by a hydrogen bond between K367 and N399 (FIG. 7).

Figure 8:
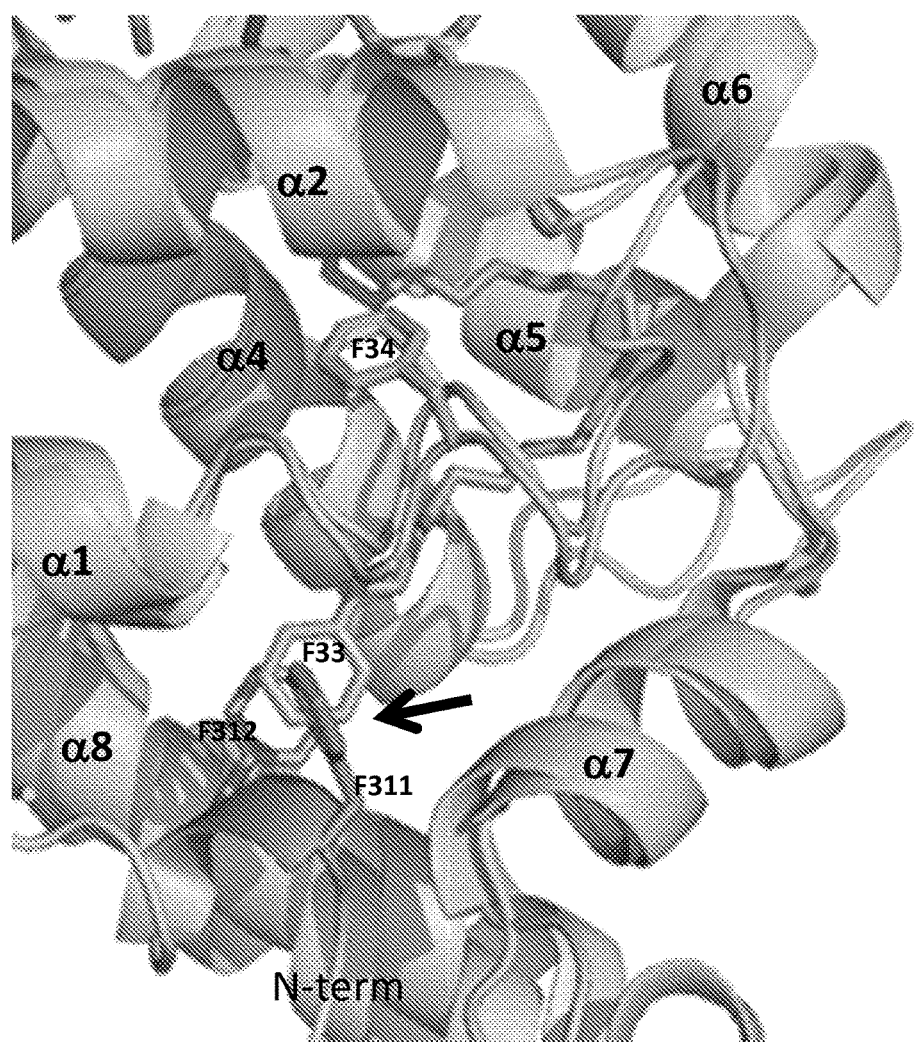
FIG. 8: FFAT-like motif in FAPP2 and GLTP (PDB ID: 2EUK). The FFAT motif (two Phe in acidic track) interacts with VAP proteins (vesicle-associated membrane protein associated proteins). F311 of FAPP2 and F33 of hGLTP take the same place (at the tail of ceramide 24:1). FAPP2 is shown in cyan and hGLTP in green. The 24:1 Galactosylceramide bound to hGLTP is in orange. The FFAT FAPP2-like motif is potentially involved in stability of the GLTP fold and ceramide release.

The comparison of the structure of hGLTP plus 24:1 galactosylceramide (PDB ID 2EUK) with that of FAPP2-C212 shows that the FFAT motif in FAPP2 is likely to be important in the stability of the GLTP fold and ceramide release (FIG. 8). F311 occupies the position of F33 of hGLTP (FIG. 8).

Sequences for Sequence Listing:

308-519 of human FAPP2
SEQ ID NO: 1
IPTFFSTMNTSFSDIELLEDSGIPTEAFLASCYAVVPVLDKLGPTVFAPV
KMDLVGNIKKVNQKYITNKEEFTTLQKIVLHEVEADVAQVRNSATEALLW
LKRGLKFLKGFLTEVKNGEKDIQTALNNAYGKTLRQHHGWVVRGVFALAL
RAAPSYEDFVAALTVKEGDHQKEAFSIGMQRDLSLYLPAMEKQLAILDTL
YEVHGLESDEVV T4L sequence (amino acids 2-164)
SEQ ID NO: 2
NIFEMLRIDEGLRLKIYKDTEGYYTIGIGHLLTKSPSLNAAKSELDKAIG
RNTNGVITKDEAEKLFNQDVDAAVRGILRNAKLKPVYDSLDAVRRAALIN
MVFQMGETGVAGFTNSLRMLQQKRWDEAAVNLAKSRWYNQTPNRAKRVIT
TFRTGTWDAYKNL T4L-C212-FAPP2
SEQ ID NO: 3
MRGSHHHHHHGMASMTGGQQMGRDLYDDDDKDRWGSENLYFQGNIFEMLR
IDEGLRLKIYKDTEGYYTIGIGHLLTKSPSLNAAKSELDKAIGRNTNGVI
TKDEAEKLFNQDVDAAVRGILRNAKLKPVYDSLDAVRRAALINMVFQMGE
TGVAGFTNSLRMLQQKRWDEAAVNLAKSRWYNQTPNRAKRVITTFRTGTW
DAYKNLGIPTFFSTMNTSFSDIELLEDSGIPTEAFLASCYAVVPVLDKLG
PTVFAPVKMDLVGNIKKVNQKYITNKEEFTTLQKIVLHEVEADVAQVRNS
ATEALLWLKRGLKFLKGFLTEVKNGEKDIQTALNNAYGKTLRQHHGWVVR
GVFALALRAAPSYEDFVAALTVKEGDHQKEAFSIGMQRDLSLYLPAMEKQ
LAILDTLYEVHGLESDEVV Full length human FAPP2
SEQ ID NO: 4
MEGVLYKWTN YLSGWQPRWF LLCGGILSYY DSPEDAWKGC
KGSIQMAVCE IQVHSVDNTR MDLIIPGEQY FYLKARSVAE
RQRWLVALGS AKACLTDSRT QKEKEFAENT ENLKTKMSEL
RLYCDLLVQQ VDKTKEVTTT GVSNSEEGID VGTLLKSTCN
TFLKTLEECM QIANAAFTSE LLYRTPPGSP QLAMLKSSKM
KHPIIPIHNS LERQMELSTC ENGSLNMEIN GEEEILMKNK
NSLYLKSAEI DCSISSEENT DDNITVQGEI RKEDGMENLK
NHDNNLTQSG SDSSCSPECL WEEGKEVIPT FFSTMNTSFS
DIELLEDSGI PTEAFLASCY AVVPVLDKLG PTVFAPVKMD
LVGNIKKVNQ KYITNKEEFT TLQKIVLHEV EADVAQV<u>RNS</u>
ATEALLWLKR GLKFLKGFLT EVKNGEKDIQ TALNNAYGKT
LRQHHGWVVR GVFALALRAA PSYEDFVAAL TVKEGDHQKE
AFSIGMQRDL SLYLPAMEKQ LAILDTLYEV HGLESDEVV nucleic acid sequence for T4L-C212-FAPP2
SEQ ID NO: 5
ATGCGGGGTTCTCATCATCATCATCATCATGGTATGGCTAGCATGACTGG
TGGACAGCAAATGGGTCGGGATCTGTACGACGATGACGATAAGGATCGAT
GGGGATCCGAGAACCTGTACTTCCAGGGCAATATATTTGAAATGTTACGT
ATAGATGAAGGTCTTAGACTTAAAATCTATAAAGACACAGAAGGCTATTA
CACTATTGGCATCGGTCATTTGCTTACAAAAAGTCCATCACTTAATGCTG
CTAAATCTGAATTAGATAAAGCTATTGGGCGTAATACCAATGGTGTAATT
ACAAAAGATGAGGCTGAAAAACTCTTTAATCAGGATGTTGATGCTGCTGT
TCGCGGTATTCTGAGAAATGCTAAATTAAAACCGGTTTATGATTCTCTTG
ATGCGGTTCGTCGCGCTGCATTGATTAATATGGTTTTCCAAATGGGAGAA
ACCGGTGTGGCAGGATTTACTAACTCTTTACGTATGCTTCAACAAAAACG
CTGGGATGAAGCAGCAGTTAACTTAGCTAAAAGTAGATGGTATAATCAAA
CACCTAATCGCGCAAAACGAGTCATTACAACGTTTAGAACTGGCACTTGG
GACGCGTATAAAAATCTAGGTATCCCAACTTTCTTTAGTACCATGAACAC
AAGCTTTAGTGACATTGAACTTCTGGAAGACAGTGGCATTCCCACAGAAG
CATTCTTGGCATCATGTTATGCTGTGGTTCCAGTATTAGACAAACTTGGC
CCTACAGTGTTTGCTCCTGTTAAGATGGATCTTGTTGGAAATATTAAGAA
AGTAAATCAGAAGTATATAACCAACAAAGAAGAGTTTACCACTCTCCAGA
AGATAGTGCTGCACGAAGTGGAGGCGGATGTAGCCCAGGTTAGGAACTCA
GCGACTGAAGCCCTCTTGTGGCTGAAGAGAGGTCTCAAATTTTTGAAGGG
ATTTTTGACAGAAGTGAAAAATGGGGAGAAGGATATCCAGACAGCCCTAA
ATAATGCATATGGTAAAACATTGCGGCAACACCATGGCTGGGTAGTTCGA
GGGGTTTTTGCGTTAGCTTTAAGGGCAGCTCCATCCTATGAAGATTTTGT
GGCCGCGTTAACCGTAAAGGAAGGTGACCACCAGAAAGAAGCTTTCAGTA
TTGGGATGCAGAGGGACCTCAGCCTTTACCTCCCTGCCATGGAGAAGCAG
CTGGCCATACTGGACACTTTATATGAGGTCCACGGGCTGGAATCTGATGA
GGTGGTATGA Tables

TABLE 1 structure data for residues 36-207 of SEQ ID NO: 3

| | | |
|---|---|---|
| REMARK | 3 | |
| REMARK | 3 | REFINEMENT. |
| REMARK | 3 | PROGRAM: REFMAC 5.8.0071 |
| REMARK | 3 | AUTHORS: MURSHUDOV, SKUBAK, LEBEDEV, PANNU, |
| REMARK | 3 | STEINER, NICHOLLS, WINN, LONG, VAGIN |
| REMARK | 3 | |
| REMARK | 3 | REFINEMENT TARGET: MAXIMUM LIKELIHOOD |
| REMARK | 3 | |
| REMARK | 3 | DATA USED IN REFINEMENT. |
| REMARK | 3 | RESOLUTION RANGE HIGH (ANGSTROMS): 2.60 |

TABLE 1-continued structure data for residues 36-207 of SEQ ID NO: 3

| | | |
|---|---|---|
| REMARK | 3 | RESOLUTION RANGE LOW (ANGSTROMS): 88.73 |
| REMARK | 3 | DATA CUTOFF (SIGMA (F)): NONE |
| REMARK | 3 | COMPLETENESS FOR RANGE (%): 99.37 |
| REMARK | 3 | NUMBER OF REFLECTIONS: 34535 |
| REMARK | 3 | |
| REMARK | 3 | FIT TO DATA USED IN REFINEMENT. |
| REMARK | 3 | CROSS-VALIDATION METHOD: THROUGHOUT |
| REMARK | 3 | FREE R VALUE TEST SET SELECTION: RANDOM |
| REMARK | 3 | R VALUE (WORKING + TEST SET): 0.20798 |
| REMARK | 3 | R VALUE (WORKING SET): 0.20541 |
| REMARK | 3 | FREE R VALUE: 0.25742 |
| REMARK | 3 | FREE R VALUE TEST SET SIZE (%): 4.9 |
| REMARK | 3 | FREE R VALUE TEST SET COUNT: 1782 |
| REMARK | 3 | |
| REMARK | 3 | FIT IN THE HIGHEST RESOLUTION BIN. |
| REMARK | 3 | TOTAL NUMBER OF BINS USED: 20 |
| REMARK | 3 | BIN RESOLUTION RANGE HIGH: 2.600 |
| REMARK | 3 | BIN RESOLUTION RANGE LOW: 2.667 |
| REMARK | 3 | REFLECTION IN BIN (WORKING SET): 2432 |
| REMARK | 3 | BIN COMPLETENESS (WORKING + TEST) (%): 96.13 |
| REMARK | 3 | BIN R VALUE (WORKING SET): 0.307 |
| REMARK | 3 | BIN FREE R VALUE SET COUNT: 127 |
| REMARK | 3 | BIN FREE R VALUE: 0.374 |
| REMARK | 3 | |
| REMARK | 3 | NUMBER OF NON-HYDROGEN ATOMS USED IN REFINEMENT. |
| REMARK | 3 | ALL ATOMS: 6104 |
| REMARK | 3 | |
| REMARK | 3 | B VALUES. |
| REMARK | 3 | FROM WILSON PLOT (A**2): NULL |
| REMARK | 3 | MEAN B VALUE (OVERALL, A**2): 29.581 |
| REMARK | 3 | OVERALL ANISOTROPIC B VALUE. |
| REMARK | 3 | B11 (A**2): 0.67 |
| REMARK | 3 | B22 (A**2): −0.88 |
| REMARK | 3 | B33 (A**2): 0.22 |
| REMARK | 3 | B12 (A**2): −0.00 |
| REMARK | 3 | B13 (A**2): 0.00 |
| REMARK | 3 | B23 (A**2): −0.00 |
| REMARK | 3 | |
| REMARK | 3 | ESTIMATED OVERALL COORDINATE ERROR. |
| REMARK | 3 | ESU BASED ON R VALUE (A): 0.423 |
| REMARK | 3 | ESU BASED ON FREE R VALUE (A): 0.287 |
| REMARK | 3 | ESU BASED ON MAXIMUM LIKELIHOOD (A): 0.265 |
| REMARK | 3 | ESU FOR B VALUES BASED ON MAXIMUM LIKELIHOOD (A**2): 26.465 |
| REMARK | 3 | |
| REMARK | 3 | CORRELATION COEFFICIENTS. |
| REMARK | 3 | CORRELATION COEFFICIENT FO-FC: 0.954 |
| REMARK | 3 | CORRELATION COEFFICIENT FO-FC FREE: 0.932 |
| REMARK | 3 | |
| REMARK | 3 | RMS DEVIATIONS FROM IDEAL VALUES COUNT RMS WEIGHT |
| REMARK | 3 | BOND LENGTHS REFINED ATOMS (A): 6117; 0.011; 0.019 |
| REMARK | 3 | BOND LENGTHS OTHERS (A): 5992; 0.001; 0.020 |
| REMARK | 3 | BOND ANGLES REFINED ATOMS (DEGREES): 8272; 1.519; 1.959 |
| REMARK | 3 | BOND ANGLES OTHERS (DEGREES): 13742; 0.863; 3.000 |
| REMARK | 3 | TORSION ANGLES, PERIOD 1 (DEGREES): 759; 6.922; 5.000 |
| REMARK | 3 | TORSION ANGLES, PERIOD 2 (DEGREES): 281; 35.820; 24.235 |
| REMARK | 3 | TORSION ANGLES, PERIOD 3 (DEGREES): 1104; 20.613; 15.000 |
| REMARK | 3 | TORSION ANGLES, PERIOD 4 (DEGREES): 40; 20.299; 15.000 |
| REMARK | 3 | CHIRAL-CENTER RESTRAINTS (A**3): 939; 0.089; 0.200 |
| REMARK | 3 | GENERAL PLANES REFINED ATOMS (A): 6913; 0.006; 0.020 |
| REMARK | 3 | GENERAL PLANES OTHERS (A): 1419; 0.001; 0.020 |
| REMARK | 3 | |
| REMARK | 3 | ISOTROPIC THERMAL FACTOR RESTRAINTS. COUNT RMS WEIGHT |
| REMARK | 3 | MAIN-CHAIN BOND REFINED ATOMS (A**2): 3030; 1.425; 2.844 |
| REMARK | 3 | MAIN-CHAIN BOND OTHER ATOMS (A**2): 3029; 1.420; 2.843 |
| REMARK | 3 | MAIN-CHAIN ANGLE REFINED ATOMS (A**2): 3785; 2.389; 4.262 |
| REMARK | 3 | MAIN-CHAIN ANGLE OTHER ATOMS (A**2): 3786; 2.389; 4.263 |
| REMARK | 3 | SIDE-CHAIN BOND REFINED ATOMS (A**2): 3087; 1.620; 3.033 |
| REMARK | 3 | SIDE-CHAIN BOND OTHER ATOMS (A**2): 3087; 1.619; 3.033 |
| REMARK | 3 | SIDE-CHAIN ANGLE OTHER ATOMS (A**2): 4486; 2.738; 4.474 |
| REMARK | 3 | LONG RANGE B REFINED ATOMS (A**2): 7219; 6.111; 22.969 |
| REMARK | 3 | LONG RANGE B OTHER ATOMS (A**2): 7205; 6.096; 22.924 |
| REMARK | 3 | |
| REMARK | 3 | NCS RESTRAINTS STATISTICS |
| REMARK | 3 | NUMBER OF NCS GROUPS: NULL |
| REMARK | 3 | |
| REMARK | 3 | TWIN DETAILS |
| REMARK | 3 | NUMBER OF TWIN DOMAINS: NULL |
| REMARK | 3 | |

TABLE 1-continued structure data for residues 36-207 of SEQ ID NO: 3

| | | |
|---|---|---|
| REMARK | 3 | |
| REMARK | 3 | TLS DETAILS |
| REMARK | 3 | NUMBER OF TLS GROUPS: 6 |
| REMARK | 3 | ATOM RECORD CONTAINS RESIDUAL B FACTORS ONLY |
| REMARK | 3 | |
| REMARK | 3 | TLS GROUP: 1 |
| REMARK | 3 | NUMBER OF COMPONENTS GROUP: 1 |
| REMARK | 3 | COMPONENTS C SSSEQI TO C SSSEQI |
| REMARK | 3 | RESIDUE RANGE: A 136 A 308 |
| REMARK | 3 | ORIGIN FOR THE GROUP (A): 13.9720 39.8720 6.3450 |
| REMARK | 3 | T TENSOR |
| REMARK | 3 | T11: 0.0197 T22: 0.6958 |
| REMARK | 3 | T33: 0.3017 T12: 0.0031 |
| REMARK | 3 | T13: −0.0059 T23: 0.0389 |
| REMARK | 3 | L TENSOR |
| REMARK | 3 | L11: 2.6201 L22: 1.5595 |
| REMARK | 3 | L33: 3.1519 L12: −0.1524 |
| REMARK | 3 | L13: −1.2544 L23: 0.7676 |
| REMARK | 3 | S TENSOR |
| REMARK | 3 | S11: 0.1939 S12: 0.0509 S13: 0.2063 |
| REMARK | 3 | S21: 0.0482 S22: −0.1039 S23: −0.0842 |
| REMARK | 3 | S31: −0.1338 S32: −0.1904 S33: −0.0900 |
| REMARK | 3 | |
| REMARK | 3 | TLS GROUP: 2 |
| REMARK | 3 | NUMBER OF COMPONENTS GROUP: 1 |
| REMARK | 3 | COMPONENTS C SSSEQI TO C SSSEQI |
| REMARK | 3 | RESIDUE RANGE: A 309 A 404 |
| REMARK | 3 | ORIGIN FOR THE GROUP (A): 27.3770 48.8170 47.3960 |
| REMARK | 3 | T TENSOR |
| REMARK | 3 | T11: 0.4887 T22: 1.3459 |
| REMARK | 3 | T33: 0.7008 T12: 0.2106 |
| REMARK | 3 | T13: −0.2091 T23: −0.3223 |
| REMARK | 3 | L TENSOR |
| REMARK | 3 | L11: 1.1503 L22: 3.8171 |
| REMARK | 3 | L33: 2.8069 L12: 0.1552 |
| REMARK | 3 | L13: 0.6241 L23: −1.6770 |
| REMARK | 3 | S TENSOR |
| REMARK | 3 | S11: −0.2055 S12: −0.1712 S13: −0.1711 |
| REMARK | 3 | S21: 0.7455 S22: 0.0994 S23: −0.4205 |
| REMARK | 3 | S31: −0.0178 S32: 0.9139 S33: 0.1061 |
| REMARK | 3 | |
| REMARK | 3 | TLS GROUP: 3 |
| REMARK | 3 | NUMBER OF COMPONENTS GROUP: 1 |
| REMARK | 3 | COMPONENTS C SSSEQI TO C SSSEQI |
| REMARK | 3 | RESIDUE RANGE: A 405 A 514 |
| REMARK | 3 | ORIGIN FOR THE GROUP (A): 15.8300 49.7400 36.1740 |
| REMARK | 3 | T TENSOR |
| REMARK | 3 | T11: 0.2421 T22: 0.9084 |
| REMARK | 3 | T33: 0.4825 T12: 0.0463 |
| REMARK | 3 | T13: −0.0785 T23: −0.2251 |
| REMARK | 3 | L TENSOR |
| REMARK | 3 | L11: 1.7466 L22: 3.2371 |
| REMARK | 3 | L33: 2.7640 L12: −1.5636 |
| REMARK | 3 | L13: −0.8225 L23: 1.3660 |
| REMARK | 3 | S TENSOR |
| REMARK | 3 | S11: −0.1057 S12: 0.0262 S13: −0.0987 |
| REMARK | 3 | S21: 0.2714 S22: 0.4784 S23: −0.4520 |
| REMARK | 3 | S31: 0.1187 S32: 0.5079 S33: −0.3728 |
| REMARK | 3 | |
| REMARK | 3 | TLS GROUP: 4 |
| REMARK | 3 | NUMBER OF COMPONENTS GROUP: 1 |
| REMARK | 3 | COMPONENTS C SSSEQI TO C SSSEQI |
| REMARK | 3 | RESIDUE RANGE: B 138 B 307 |
| REMARK | 3 | ORIGIN FOR THE GROUP (A): 9.6230 90.4590 83.2760 |
| REMARK | 3 | T TENSOR |
| REMARK | 3 | T11: 0.0295 T22: 0.7130 |
| REMARK | 3 | T33: 0.2574 T12: 0.0077 |
| REMARK | 3 | T13: 0.0097 T23: −0.0121 |
| REMARK | 3 | L TENSOR |
| REMARK | 3 | L11: 3.4402 L22: 2.1568 |
| REMARK | 3 | L33: 2.7018 L12: 0.7446 |
| REMARK | 3 | L13: 1.3474 L23: 1.1456 |
| REMARK | 3 | S TENSOR |
| REMARK | 3 | S11: 0.2841 S12: −0.1555 S13: −0.1300 |
| REMARK | 3 | S21: −0.0285 S22: −0.2823 S23: −0.0765 |
| REMARK | 3 | S31: 0.1077 S32: −0.2105 S33: −0.0018 |
| REMARK | 3 | |
| REMARK | 3 | TLS GROUP: 5 |

TABLE 1-continued structure data for residues 36-207 of SEQ ID NO: 3

| REMARK | 3 | NUMBER OF COMPONENTS GROUP: 1 |
| --- | --- | --- |
| REMARK | 3 | COMPONENTS C SSSEQI TO C SSSEQI |
| REMARK | 3 | RESIDUE RANGE: B 308 B 404 |
| REMARK | 3 | ORIGIN FOR THE GROUP (A): 28.7370 76.5020 47.0740 |
| REMARK | 3 | T TENSOR |
| REMARK | 3 | T11: 0.3844 T22: 1.1008 |
| REMARK | 3 | T33: 0.6263 T12: −0.0646 |
| REMARK | 3 | T13: 0.2005 T23: −0.1321 |
| REMARK | 3 | L TENSOR |
| REMARK | 3 | L11: 1.9523 L22: 1.5367 |
| REMARK | 3 | L33: 2.9604 L12: 0.3410 |
| REMARK | 3 | L13: −0.2554 L23: −0.5926 |
| REMARK | 3 | S TENSOR |
| REMARK | 3 | S11: −0.2083 S12: 0.5170 S13: −0.1482 |
| REMARK | 3 | S21: −0.5158 S22: 0.0811 S23: −0.7630 |
| REMARK | 3 | S31: −0.1371 S32: 0.7723 S33: 0.1272 |
| REMARK | 3 | |
| REMARK | 3 | TLS GROUP: 6 |
| REMARK | 3 | NUMBER OF COMPONENTS GROUP: 1 |
| REMARK | 3 | COMPONENTS C SSSEQI TO C SSSEQI |
| REMARK | 3 | RESIDUE RANGE: B 405 B 515 |
| REMARK | 3 | ORIGIN FOR THE GROUP (A): 15.4290 77.1950 55.5160 |
| REMARK | 3 | T TENSOR |
| REMARK | 3 | T11: 0.1903 T22: 0.6819 |
| REMARK | 3 | T33: 0.2755 T12: −0.0348 |
| REMARK | 3 | T13: 0.0926 T23: −0.0346 |
| REMARK | 3 | L TENSOR |
| REMARK | 3 | L11: 1.2810 L22: 1.6221 |
| REMARK | 3 | L33: 4.4432 L12: 0.2093 |
| REMARK | 3 | L13: 1.0288 L23: 1.7378 |
| REMARK | 3 | S TENSOR |
| REMARK | 3 | S11: 0.0478 S12: 0.1138 S13: 0.0559 |
| REMARK | 3 | S21: −0.1326 S22: 0.1501 S23: −0.1796 |
| REMARK | 3 | S31: −0.2987 S32: 0.2038 S33: −0.1979 |
| REMARK | 3 | |
| REMARK | 3 | |
| REMARK | 3 | BULK SOLVENT MODELLING. |
| REMARK | 3 | METHOD USED: MASK |
| REMARK | 3 | PARAMETERS FOR MASK CALCULATION |
| REMARK | 3 | VDW PROBE RADIUS: 1.20 |
| REMARK | 3 | ION PROBE RADIUS: 0.80 |
| REMARK | 3 | SHRINKAGE RADIUS: 0.80 |
| REMARK | 3 | |
| REMARK | 3 | OTHER REFINEMENT REMARKS: |
| REMARK | 3 | HYDROGENS HAVE BEEN ADDED IN THE RIDING POSITIONS |
| REMARK | 3 | U VALUES: RESIDUAL ONLY |
| REMARK | 3 | |
| CISPEP | 1 | GLU A 326 ASP A 327 0.00 |
| CISPEP | 2 | LYS B 304 ASN B 305 0.00 |
| CISPEP | 3 | ASP B 393 VAL B 394 0.00 |
| CISPEP | 4 | THR B 471 VAL B 472 0.00 |
| CRYST1 | | 100.020 130.872 88.733 90.00 90.00 90.00 P 21 21 2 |
| SCALE1 | | 0.009998 0.000000 0.000000 0.00000 |
| SCALE2 | | −0.000000 0.007641 0.000000 0.00000 |
| SCALE3 | | 0.000000 −0.000000 0.011270 0.00000 |

| ATOM | 1 | N | SER | A | 136 | 38.582 | 35.885 | 11.075 | 1.00 | 76.13 | N |
| --- | --- | --- | --- | --- | --- | --- | --- | --- | --- | --- | --- |
| ATOM | 2 | CA | SER | A | 136 | 38.485 | 36.758 | 12.292 | 1.00 | 80.60 | C |
| ATOM | 3 | CB | SER | A | 136 | 39.775 | 37.587 | 12.444 | 1.00 | 77.58 | C |
| ATOM | 4 | OG | SER | A | 136 | 39.741 | 38.452 | 13.569 | 1.00 | 70.83 | O |
| ATOM | 5 | C | SER | A | 136 | 37.245 | 37.662 | 12.216 | 1.00 | 84.58 | C |
| ATOM | 6 | O | SER | A | 136 | 36.318 | 37.381 | 11.448 | 1.00 | 90.66 | O |
| ATOM | 7 | N | GLU | A | 137 | 37.205 | 38.712 | 13.036 | 1.00 | 84.98 | N |
| ATOM | 8 | CA | GLU | A | 137 | 36.277 | 39.825 | 12.801 | 1.00 | 85.96 | C |
| ATOM | 9 | CB | GLU | A | 137 | 35.849 | 40.522 | 14.112 | 1.00 | 88.25 | C |
| ATOM | 10 | CG | GLU | A | 137 | 34.619 | 39.914 | 14.797 | 1.00 | 87.36 | C |
| ATOM | 11 | CD | GLU | A | 137 | 34.950 | 38.717 | 15.682 | 1.00 | 86.93 | C |
| ATOM | 12 | OE1 | GLU | A | 137 | 35.531 | 38.917 | 16.770 | 1.00 | 86.12 | O |
| ATOM | 13 | OE2 | GLU | A | 137 | 34.622 | 37.573 | 15.301 | 1.00 | 83.58 | O |
| ATOM | 14 | C | GLU | A | 137 | 36.917 | 40.821 | 11.818 | 1.00 | 80.47 | C |
| ATOM | 15 | O | GLU | A | 137 | 36.208 | 41.650 | 11.242 | 1.00 | 83.39 | O |
| ATOM | 16 | N | ASN | A | 138 | 38.244 | 40.725 | 11.633 | 1.00 | 66.74 | N |
| ATOM | 17 | CA | ASN | A | 138 | 38.996 | 41.531 | 10.648 | 1.00 | 57.60 | C |
| ATOM | 18 | CB | ASN | A | 138 | 40.514 | 41.300 | 10.797 | 1.00 | 56.69 | C |
| ATOM | 19 | CG | ASN | A | 138 | 41.076 | 41.841 | 12.098 | 1.00 | 57.89 | C |
| ATOM | 20 | OD1 | ASN | A | 138 | 40.330 | 42.254 | 12.987 | 1.00 | 60.82 | O |
| ATOM | 21 | ND2 | ASN | A | 138 | 42.403 | 41.832 | 12.219 | 1.00 | 54.56 | N |
| ATOM | 22 | C | ASN | A | 138 | 38.632 | 41.272 | 9.180 | 1.00 | 50.79 | C |

TABLE 1-continued structure data for residues 36-207 of SEQ ID NO: 3

| ATOM | 23 | O | ASN | A | 138 | 37.869 | 42.025 | 8.574 | 1.00 | 52.19 | O |
|---|---|---|---|---|---|---|---|---|---|---|---|
| ATOM | 24 | N | LEU | A | 139 | 39.167 | 40.183 | 8.632 | 1.00 | 43.81 | N |
| ATOM | 25 | CA | LEU | A | 139 | 39.362 | 40.026 | 7.188 | 1.00 | 37.79 | C |
| ATOM | 26 | CB | LEU | A | 139 | 40.758 | 39.461 | 6.932 | 1.00 | 38.16 | C |
| ATOM | 27 | CG | LEU | A | 139 | 41.907 | 40.452 | 7.136 | 1.00 | 36.33 | C |
| ATOM | 28 | CD1 | LEU | A | 139 | 43.101 | 39.813 | 7.816 | 1.00 | 36.25 | C |
| ATOM | 29 | CD2 | LEU | A | 139 | 42.311 | 41.029 | 5.794 | 1.00 | 36.10 | C |
| ATOM | 30 | C | LEU | A | 139 | 38.328 | 39.138 | 6.531 | 1.00 | 33.65 | C |
| ATOM | 31 | O | LEU | A | 139 | 37.847 | 39.449 | 5.447 | 1.00 | 33.28 | O |
| ATOM | 32 | N | TYR | A | 140 | 37.998 | 38.024 | 7.170 | 1.00 | 30.90 | N |
| ATOM | 33 | CA | TYR | A | 140 | 36.798 | 37.262 | 6.776 | 1.00 | 31.13 | C |
| ATOM | 34 | CB | TYR | A | 140 | 37.093 | 35.762 | 6.738 | 1.00 | 29.24 | C |
| ATOM | 35 | CG | TYR | A | 140 | 35.924 | 34.921 | 6.309 | 1.00 | 29.13 | C |
| ATOM | 36 | CD1 | TYR | A | 140 | 35.487 | 34.911 | 4.990 | 1.00 | 29.55 | C |
| ATOM | 37 | CE1 | TYR | A | 140 | 34.399 | 34.143 | 4.596 | 1.00 | 29.01 | C |
| ATOM | 38 | CZ | TYR | A | 140 | 33.740 | 33.375 | 5.527 | 1.00 | 28.48 | C |
| ATOM | 39 | OH | TYR | A | 140 | 32.667 | 32.611 | 5.168 | 1.00 | 28.61 | O |
| ATOM | 40 | CE2 | TYR | A | 140 | 34.142 | 33.381 | 6.838 | 1.00 | 29.02 | C |
| ATOM | 41 | CD2 | TYR | A | 140 | 35.237 | 34.139 | 7.223 | 1.00 | 29.72 | C |
| ATOM | 42 | C | TYR | A | 140 | 35.598 | 37.583 | 7.711 | 1.00 | 30.38 | C |
| ATOM | 43 | O | TYR | A | 140 | 35.735 | 37.572 | 8.942 | 1.00 | 28.31 | O |
| ATOM | 44 | N | PHE | A | 141 | 34.437 | 37.889 | 7.130 | 1.00 | 31.10 | N |
| ATOM | 45 | CA | PHE | A | 141 | 33.247 | 38.219 | 7.943 | 1.00 | 33.41 | C |
| ATOM | 46 | CB | PHE | A | 141 | 32.536 | 39.480 | 7.436 | 1.00 | 38.38 | C |
| ATOM | 47 | CG | PHE | A | 141 | 33.351 | 40.732 | 7.590 | 1.00 | 48.44 | C |
| ATOM | 48 | CD1 | PHE | A | 141 | 33.522 | 41.322 | 8.839 | 1.00 | 54.49 | C |
| ATOM | 49 | CE1 | PHE | A | 141 | 34.300 | 42.474 | 8.980 | 1.00 | 58.85 | C |
| ATOM | 50 | CZ | PHE | A | 141 | 34.926 | 43.045 | 7.874 | 1.00 | 59.05 | C |
| ATOM | 51 | CE2 | PHE | A | 141 | 34.768 | 42.467 | 6.627 | 1.00 | 58.88 | C |
| ATOM | 52 | CD2 | PHE | A | 141 | 33.982 | 41.320 | 6.487 | 1.00 | 55.59 | C |
| ATOM | 53 | C | PHE | A | 141 | 32.273 | 37.057 | 8.007 | 1.00 | 29.76 | C |
| ATOM | 54 | O | PHE | A | 141 | 31.612 | 36.732 | 7.018 | 1.00 | 29.63 | O |
| ATOM | 55 | N | GLN | A | 142 | 32.193 | 36.434 | 9.181 | 1.00 | 28.33 | N |
| ATOM | 56 | CA | GLN | A | 142 | 31.116 | 35.483 | 9.494 | 1.00 | 27.91 | C |
| ATOM | 57 | CB | GLN | A | 142 | 31.421 | 34.684 | 10.770 | 1.00 | 28.08 | C |
| ATOM | 58 | CG | GLN | A | 142 | 32.232 | 33.437 | 10.499 | 1.00 | 29.60 | C |
| ATOM | 59 | CD | GLN | A | 142 | 32.985 | 32.923 | 11.720 | 1.00 | 29.79 | C |
| ATOM | 60 | OE1 | GLN | A | 142 | 34.209 | 33.050 | 11.821 | 1.00 | 29.03 | O |
| ATOM | 61 | NE2 | GLN | A | 142 | 32.252 | 32.334 | 12.649 | 1.00 | 30.36 | N |
| ATOM | 62 | C | GLN | A | 142 | 29.798 | 36.232 | 9.658 | 1.00 | 26.04 | C |
| ATOM | 63 | O | GLN | A | 142 | 29.754 | 37.335 | 10.191 | 1.00 | 25.19 | O |
| ATOM | 64 | N | GLY | A | 143 | 28.712 | 35.647 | 9.195 | 1.00 | 24.28 | N |
| ATOM | 65 | CA | GLY | A | 143 | 27.425 | 36.263 | 9.447 | 1.00 | 23.44 | C |
| ATOM | 66 | C | GLY | A | 143 | 26.365 | 35.214 | 9.514 | 1.00 | 22.96 | C |
| ATOM | 67 | O | GLY | A | 143 | 26.664 | 34.005 | 9.458 | 1.00 | 23.65 | O |
| ATOM | 68 | N | ASN | A | 144 | 25.137 | 35.694 | 9.668 | 1.00 | 20.83 | N |
| ATOM | 69 | CA | ASN | A | 144 | 23.967 | 34.866 | 9.555 | 1.00 | 20.50 | C |
| ATOM | 70 | CB | ASN | A | 144 | 23.905 | 33.806 | 10.677 | 1.00 | 19.70 | C |
| ATOM | 71 | CG | ASN | A | 144 | 23.936 | 34.405 | 12.052 | 1.00 | 19.49 | C |
| ATOM | 72 | OD1 | ASN | A | 144 | 24.794 | 34.103 | 12.847 | 1.00 | 20.24 | O |
| ATOM | 73 | ND2 | ASN | A | 144 | 22.984 | 35.229 | 12.348 | 1.00 | 19.73 | N |
| ATOM | 74 | C | ASN | A | 144 | 22.661 | 35.691 | 9.481 | 1.00 | 20.85 | C |
| ATOM | 75 | O | ASN | A | 144 | 22.626 | 36.899 | 9.810 | 1.00 | 20.24 | O |
| ATOM | 76 | N | ILE | A | 145 | 21.598 | 35.013 | 9.044 | 1.00 | 20.38 | N |
| ATOM | 77 | CA | ILE | A | 145 | 20.301 | 35.650 | 8.829 | 1.00 | 19.82 | C |
| ATOM | 78 | CB | ILE | A | 145 | 19.317 | 34.673 | 8.197 | 1.00 | 19.45 | C |
| ATOM | 79 | CG1 | ILE | A | 145 | 18.122 | 35.436 | 7.651 | 1.00 | 20.89 | C |
| ATOM | 80 | CD1 | ILE | A | 145 | 17.237 | 34.601 | 6.747 | 1.00 | 21.27 | C |
| ATOM | 81 | CG2 | ILE | A | 145 | 18.880 | 33.613 | 9.183 | 1.00 | 19.46 | C |
| ATOM | 82 | C | ILE | A | 145 | 19.726 | 36.281 | 10.106 | 1.00 | 20.19 | C |
| ATOM | 83 | O | ILE | A | 145 | 19.135 | 37.357 | 10.048 | 1.00 | 20.02 | O |
| ATOM | 84 | N | PHE | A | 146 | 19.943 | 35.649 | 11.259 | 1.00 | 20.63 | N |
| ATOM | 85 | CA | PHE | A | 146 | 19.550 | 36.234 | 12.527 | 1.00 | 20.80 | C |
| ATOM | 86 | CB | PHE | A | 146 | 19.945 | 35.341 | 13.687 | 1.00 | 22.08 | C |
| ATOM | 87 | CG | PHE | A | 146 | 19.449 | 35.830 | 15.003 | 1.00 | 23.06 | C |
| ATOM | 88 | CD1 | PHE | A | 146 | 18.146 | 35.598 | 15.392 | 1.00 | 24.84 | C |
| ATOM | 89 | CE1 | PHE | A | 146 | 17.679 | 36.065 | 16.613 | 1.00 | 25.00 | C |
| ATOM | 90 | CZ | PHE | A | 146 | 18.517 | 36.772 | 17.447 | 1.00 | 22.83 | C |
| ATOM | 91 | CE2 | PHE | A | 146 | 19.809 | 37.009 | 17.061 | 1.00 | 22.83 | C |
| ATOM | 92 | CD2 | PHE | A | 146 | 20.265 | 36.540 | 15.845 | 1.00 | 23.66 | C |
| ATOM | 93 | C | PHE | A | 146 | 20.136 | 37.611 | 12.731 | 1.00 | 21.62 | C |
| ATOM | 94 | O | PHE | A | 146 | 19.392 | 38.564 | 12.826 | 1.00 | 22.98 | O |
| ATOM | 95 | N | GLU | A | 147 | 21.460 | 37.740 | 12.766 | 1.00 | 22.20 | N |
| ATOM | 96 | CA | GLU | A | 147 | 22.085 | 39.023 | 13.048 | 1.00 | 23.14 | C |
| ATOM | 97 | CB | GLU | A | 147 | 23.631 | 38.933 | 13.219 | 1.00 | 25.19 | C |
| ATOM | 98 | CG | GLU | A | 147 | 24.086 | 37.969 | 14.316 | 1.00 | 27.22 | C |
| ATOM | 99 | CD | GLU | A | 147 | 24.001 | 38.507 | 15.759 | 1.00 | 30.76 | C |
| ATOM | 100 | OE1 | GLU | A | 147 | 22.952 | 39.040 | 16.223 | 1.00 | 30.69 | O |

TABLE 1-continued structure data for residues 36-207 of SEQ ID NO: 3

| ATOM | 101 | OE2 | GLU | A | 147 | 25.026 | 38.370 | 16.478 | 1.00 | 36.46 | O |
|---|---|---|---|---|---|---|---|---|---|---|---|
| ATOM | 102 | C | GLU | A | 147 | 21.716 | 39.994 | 11.958 | 1.00 | 21.17 | C |
| ATOM | 103 | O | GLU | A | 147 | 21.547 | 41.169 | 12.222 | 1.00 | 22.09 | O |
| ATOM | 104 | N | MET | A | 148 | 21.572 | 39.508 | 10.738 | 1.00 | 20.28 | N |
| ATOM | 105 | CA | MET | A | 148 | 21.095 | 40.344 | 9.635 | 1.00 | 20.15 | C |
| ATOM | 106 | CB | MET | A | 148 | 21.110 | 39.489 | 8.352 | 1.00 | 20.63 | C |
| ATOM | 107 | CG | MET | A | 148 | 20.725 | 40.242 | 7.082 | 1.00 | 22.36 | C |
| ATOM | 108 | SD | MET | A | 148 | 20.056 | 39.308 | 5.676 | 1.00 | 22.81 | S |
| ATOM | 109 | CE | MET | A | 148 | 20.554 | 40.455 | 4.392 | 1.00 | 22.25 | C |
| ATOM | 110 | C | MET | A | 148 | 19.660 | 40.938 | 9.920 | 1.00 | 19.80 | C |
| ATOM | 111 | O | MET | A | 148 | 19.412 | 42.150 | 9.808 | 1.00 | 17.48 | O |
| ATOM | 112 | N | LEU | A | 149 | 18.715 | 40.092 | 10.294 | 1.00 | 19.77 | N |
| ATOM | 113 | CA | LEU | A | 149 | 17.359 | 40.591 | 10.513 | 1.00 | 21.40 | C |
| ATOM | 114 | CB | LEU | A | 149 | 16.351 | 39.491 | 10.329 | 1.00 | 21.96 | C |
| ATOM | 115 | CG | LEU | A | 149 | 16.047 | 39.400 | 8.848 | 1.00 | 22.95 | C |
| ATOM | 116 | CD1 | LEU | A | 149 | 15.281 | 38.146 | 8.511 | 1.00 | 23.84 | C |
| ATOM | 117 | CD2 | LEU | A | 149 | 15.253 | 40.617 | 8.410 | 1.00 | 23.97 | C |
| ATOM | 118 | C | LEU | A | 149 | 17.189 | 41.283 | 11.850 | 1.00 | 21.37 | C |
| ATOM | 119 | O | LEU | A | 149 | 16.466 | 42.263 | 11.960 | 1.00 | 20.45 | O |
| ATOM | 120 | N | ARG | A | 150 | 17.926 | 40.834 | 12.845 | 1.00 | 22.27 | N |
| ATOM | 121 | CA | ARG | A | 150 | 18.019 | 41.590 | 14.086 | 1.00 | 23.38 | C |
| ATOM | 122 | CB | ARG | A | 150 | 18.998 | 40.923 | 15.034 | 1.00 | 24.20 | C |
| ATOM | 123 | CG | ARG | A | 150 | 19.407 | 41.831 | 16.158 | 1.00 | 26.92 | C |
| ATOM | 124 | CD | ARG | A | 150 | 20.247 | 41.144 | 17.225 | 1.00 | 30.32 | C |
| ATOM | 125 | NE | ARG | A | 150 | 20.288 | 42.055 | 18.357 | 1.00 | 35.26 | N |
| ATOM | 126 | CZ | ARG | A | 150 | 20.998 | 43.185 | 18.399 | 1.00 | 39.30 | C |
| ATOM | 127 | NH1 | ARG | A | 150 | 21.829 | 43.535 | 17.401 | 1.00 | 39.37 | N |
| ATOM | 128 | NH2 | ARG | A | 150 | 20.891 | 43.958 | 19.474 | 1.00 | 41.12 | N |
| ATOM | 129 | C | ARG | A | 150 | 18.415 | 43.065 | 13.838 | 1.00 | 23.17 | C |
| ATOM | 130 | O | ARG | A | 150 | 17.905 | 43.973 | 14.506 | 1.00 | 23.04 | O |
| ATOM | 131 | N | ILE | A | 151 | 19.335 | 43.308 | 12.899 | 1.00 | 22.92 | N |
| ATOM | 132 | CA | ILE | A | 151 | 19.721 | 44.683 | 12.569 | 1.00 | 21.85 | C |
| ATOM | 133 | CB | ILE | A | 151 | 21.054 | 44.787 | 11.793 | 1.00 | 20.75 | C |
| ATOM | 134 | CG1 | ILE | A | 151 | 22.231 | 44.452 | 12.722 | 1.00 | 21.06 | C |
| ATOM | 135 | CD1 | ILE | A | 151 | 23.554 | 44.119 | 12.043 | 1.00 | 19.73 | C |
| ATOM | 136 | CG2 | ILE | A | 151 | 21.255 | 46.200 | 11.253 | 1.00 | 20.00 | C |
| ATOM | 137 | C | ILE | A | 151 | 18.624 | 45.373 | 11.781 | 1.00 | 22.65 | C |
| ATOM | 138 | O | ILE | A | 151 | 18.327 | 46.526 | 12.062 | 1.00 | 23.46 | O |
| ATOM | 139 | N | ASP | A | 152 | 18.033 | 44.692 | 10.805 | 1.00 | 22.40 | N |
| ATOM | 140 | CA | ASP | A | 152 | 17.134 | 45.373 | 9.890 | 1.00 | 24.17 | C |
| ATOM | 141 | CB | ASP | A | 152 | 16.993 | 44.608 | 8.559 | 1.00 | 25.02 | C |
| ATOM | 142 | CG | ASP | A | 152 | 18.181 | 44.839 | 7.625 | 1.00 | 25.90 | C |
| ATOM | 143 | OD1 | ASP | A | 152 | 18.863 | 45.857 | 7.821 | 1.00 | 25.40 | O |
| ATOM | 144 | OD2 | ASP | A | 152 | 18.436 | 44.031 | 6.692 | 1.00 | 26.63 | O |
| ATOM | 145 | C | ASP | A | 152 | 15.773 | 45.641 | 10.509 | 1.00 | 24.83 | C |
| ATOM | 146 | O | ASP | A | 152 | 15.257 | 46.741 | 10.381 | 1.00 | 25.26 | O |
| ATOM | 147 | N | GLU | A | 153 | 15.228 | 44.623 | 11.177 | 1.00 | 24.88 | N |
| ATOM | 148 | CA | GLU | A | 153 | 13.907 | 44.642 | 11.808 | 1.00 | 23.52 | C |
| ATOM | 149 | CB | GLU | A | 153 | 13.297 | 43.249 | 11.726 | 1.00 | 22.66 | C |
| ATOM | 150 | CG | GLU | A | 153 | 12.991 | 42.794 | 10.311 | 1.00 | 23.65 | C |
| ATOM | 151 | CD | GLU | A | 153 | 11.691 | 43.377 | 9.762 | 1.00 | 23.83 | C |
| ATOM | 152 | OE1 | GLU | A | 153 | 11.246 | 44.434 | 10.281 | 1.00 | 25.02 | O |
| ATOM | 153 | OE2 | GLU | A | 153 | 11.103 | 42.787 | 8.821 | 1.00 | 22.90 | O |
| ATOM | 154 | C | GLU | A | 153 | 13.887 | 45.044 | 13.282 | 1.00 | 23.98 | C |
| ATOM | 155 | O | GLU | A | 153 | 12.858 | 45.441 | 13.783 | 1.00 | 26.88 | O |
| ATOM | 156 | N | GLY | A | 154 | 15.004 | 44.918 | 13.985 | 1.00 | 24.39 | N |
| ATOM | 157 | CA | GLY | A | 154 | 15.043 | 45.094 | 15.446 | 1.00 | 23.43 | C |
| ATOM | 158 | C | GLY | A | 154 | 14.811 | 43.783 | 16.160 | 1.00 | 22.49 | C |
| ATOM | 159 | O | GLY | A | 154 | 14.350 | 42.825 | 15.561 | 1.00 | 25.62 | O |
| ATOM | 160 | N | LEU | A | 155 | 15.156 | 43.717 | 17.430 | 1.00 | 21.46 | N |
| ATOM | 161 | CA | LEU | A | 155 | 14.840 | 42.551 | 18.246 | 1.00 | 21.25 | C |
| ATOM | 162 | CB | LEU | A | 155 | 16.117 | 41.785 | 18.607 | 1.00 | 21.72 | C |
| ATOM | 163 | CG | LEU | A | 155 | 16.061 | 40.829 | 19.824 | 1.00 | 22.41 | C |
| ATOM | 164 | CD1 | LEU | A | 155 | 15.044 | 39.718 | 19.682 | 1.00 | 21.55 | C |
| ATOM | 165 | CD2 | LEU | A | 155 | 17.438 | 40.221 | 20.055 | 1.00 | 22.67 | C |
| ATOM | 166 | C | LEU | A | 155 | 14.164 | 43.096 | 19.486 | 1.00 | 20.30 | C |
| ATOM | 167 | O | LEU | A | 155 | 14.834 | 43.658 | 20.362 | 1.00 | 20.25 | O |
| ATOM | 168 | N | ARG | A | 156 | 12.836 | 42.983 | 19.548 | 1.00 | 19.25 | N |
| ATOM | 169 | CA | ARG | A | 156 | 12.076 | 43.553 | 20.669 | 1.00 | 18.25 | C |
| ATOM | 170 | CB | ARG | A | 156 | 11.103 | 44.539 | 20.135 | 1.00 | 18.18 | C |
| ATOM | 171 | CG | ARG | A | 156 | 11.741 | 45.627 | 19.323 | 1.00 | 17.92 | C |
| ATOM | 172 | CD | ARG | A | 156 | 11.834 | 46.887 | 20.139 | 1.00 | 17.94 | C |
| ATOM | 173 | NE | ARG | A | 156 | 11.485 | 48.009 | 19.293 | 1.00 | 18.47 | N |
| ATOM | 174 | CZ | ARG | A | 156 | 10.522 | 48.894 | 19.504 | 1.00 | 18.88 | C |
| ATOM | 175 | NH1 | ARG | A | 156 | 9.748 | 48.862 | 20.594 | 1.00 | 19.28 | N |
| ATOM | 176 | NH2 | ARG | A | 156 | 10.362 | 49.860 | 18.608 | 1.00 | 19.61 | N |
| ATOM | 177 | C | ARG | A | 156 | 11.323 | 42.498 | 21.427 | 1.00 | 17.78 | C |
| ATOM | 178 | O | ARG | A | 156 | 10.599 | 41.725 | 20.840 | 1.00 | 18.90 | O |

TABLE 1-continued structure data for residues 36-207 of SEQ ID NO: 3

| ATOM | 179 | N   | LEU | A | 157 | 11.484 | 42.449 | 22.734 | 1.00 | 17.64 | N |
|------|-----|-----|-----|---|-----|--------|--------|--------|------|-------|---|
| ATOM | 180 | CA  | LEU | A | 157 | 10.943 | 41.330 | 23.496 | 1.00 | 17.65 | C |
| ATOM | 181 | CB  | LEU | A | 157 | 11.945 | 40.926 | 24.577 | 1.00 | 17.56 | C |
| ATOM | 182 | CG  | LEU | A | 157 | 13.289 | 40.553 | 23.968 | 1.00 | 18.50 | C |
| ATOM | 183 | CD1 | LEU | A | 157 | 14.270 | 40.029 | 25.023 | 1.00 | 19.15 | C |
| ATOM | 184 | CD2 | LEU | A | 157 | 13.106 | 39.535 | 22.835 | 1.00 | 18.90 | C |
| ATOM | 185 | C   | LEU | A | 157 | 9.558  | 41.642 | 24.068 | 1.00 | 17.22 | C |
| ATOM | 186 | O   | LEU | A | 157 | 8.841  | 40.755 | 24.550 | 1.00 | 17.32 | O |
| ATOM | 187 | N   | LYS | A | 158 | 9.196  | 42.914 | 23.979 | 1.00 | 16.47 | N |
| ATOM | 188 | CA  | LYS | A | 158 | 7.912  | 43.390 | 24.386 | 1.00 | 15.77 | C |
| ATOM | 189 | CB  | LYS | A | 158 | 8.114  | 44.539 | 25.361 | 1.00 | 15.64 | C |
| ATOM | 190 | CG  | LYS | A | 158 | 6.824  | 45.182 | 25.772 | 1.00 | 15.68 | C |
| ATOM | 191 | CD  | LYS | A | 158 | 6.891  | 45.752 | 27.164 | 1.00 | 16.06 | C |
| ATOM | 192 | CE  | LYS | A | 158 | 5.655  | 46.576 | 27.470 | 1.00 | 16.39 | C |
| ATOM | 193 | NZ  | LYS | A | 158 | 6.028  | 47.600 | 28.478 | 1.00 | 17.35 | N |
| ATOM | 194 | C   | LYS | A | 158 | 7.163  | 43.876 | 23.159 | 1.00 | 15.07 | C |
| ATOM | 195 | O   | LYS | A | 158 | 7.755  | 44.497 | 22.288 | 1.00 | 15.00 | O |
| ATOM | 196 | N   | ILE | A | 159 | 5.860  | 43.622 | 23.116 | 1.00 | 14.48 | N |
| ATOM | 197 | CA  | ILE | A | 159 | 5.005  | 44.073 | 22.028 | 1.00 | 14.37 | C |
| ATOM | 198 | CB  | ILE | A | 159 | 3.518  | 43.864 | 22.351 | 1.00 | 14.22 | C |
| ATOM | 199 | CG1 | ILE | A | 159 | 3.148  | 42.394 | 22.264 | 1.00 | 14.47 | C |
| ATOM | 200 | CD1 | ILE | A | 159 | 1.725  | 42.107 | 22.696 | 1.00 | 14.82 | C |
| ATOM | 201 | CG2 | ILE | A | 159 | 2.643  | 44.633 | 21.380 | 1.00 | 14.03 | C |
| ATOM | 202 | C   | ILE | A | 159 | 5.187  | 45.548 | 21.785 | 1.00 | 14.60 | C |
| ATOM | 203 | O   | ILE | A | 159 | 5.354  | 46.297 | 22.723 | 1.00 | 15.07 | O |
| ATOM | 204 | N   | TYR | A | 160 | 5.106  | 45.962 | 20.528 | 1.00 | 15.03 | N |
| ATOM | 205 | CA  | TYR | A | 160 | 5.224  | 47.372 | 20.155 | 1.00 | 15.40 | C |
| ATOM | 206 | CB  | TYR | A | 160 | 6.710  | 47.755 | 20.006 | 1.00 | 14.73 | C |
| ATOM | 207 | CG  | TYR | A | 160 | 7.418  | 47.190 | 18.779 | 1.00 | 14.39 | C |
| ATOM | 208 | CD1 | TYR | A | 160 | 7.863  | 45.885 | 18.752 | 1.00 | 14.17 | C |
| ATOM | 209 | CE1 | TYR | A | 160 | 8.516  | 45.372 | 17.642 | 1.00 | 14.43 | C |
| ATOM | 210 | CZ  | TYR | A | 160 | 8.746  | 46.175 | 16.530 | 1.00 | 14.27 | C |
| ATOM | 211 | OH  | TYR | A | 160 | 9.418  | 45.655 | 15.449 | 1.00 | 14.05 | O |
| ATOM | 212 | CE2 | TYR | A | 160 | 8.335  | 47.485 | 16.530 | 1.00 | 14.13 | C |
| ATOM | 213 | CD2 | TYR | A | 160 | 7.673  | 47.987 | 17.651 | 1.00 | 14.70 | C |
| ATOM | 214 | C   | TYR | A | 160 | 4.515  | 47.643 | 18.832 | 1.00 | 16.21 | C |
| ATOM | 215 | O   | TYR | A | 160 | 4.195  | 46.710 | 18.102 | 1.00 | 15.56 | O |
| ATOM | 216 | N   | LYS | A | 161 | 4.352  | 48.918 | 18.502 | 1.00 | 17.63 | N |
| ATOM | 217 | CA  | LYS | A | 161 | 3.784  | 49.315 | 17.218 | 1.00 | 20.05 | C |
| ATOM | 218 | CB  | LYS | A | 161 | 2.873  | 50.527 | 17.405 | 1.00 | 20.46 | C |
| ATOM | 219 | CG  | LYS | A | 161 | 1.616  | 50.202 | 18.187 | 1.00 | 21.09 | C |
| ATOM | 220 | CD  | LYS | A | 161 | 0.735  | 51.419 | 18.427 | 1.00 | 21.28 | C |
| ATOM | 221 | CE  | LYS | A | 161 | −0.574 | 50.971 | 19.045 | 1.00 | 21.23 | C |
| ATOM | 222 | NZ  | LYS | A | 161 | −1.490 | 52.114 | 19.262 | 1.00 | 21.85 | N |
| ATOM | 223 | C   | LYS | A | 161 | 4.807  | 49.655 | 16.142 | 1.00 | 21.48 | C |
| ATOM | 224 | O   | LYS | A | 161 | 5.624  | 50.528 | 16.348 | 1.00 | 21.38 | O |
| ATOM | 225 | N   | ASP | A | 162 | 4.738  | 48.937 | 15.017 | 1.00 | 24.53 | N |
| ATOM | 226 | CA  | ASP | A | 162 | 5.200  | 49.365 | 13.663 | 1.00 | 26.25 | C |
| ATOM | 227 | CB  | ASP | A | 162 | 4.123  | 48.963 | 12.633 | 1.00 | 26.39 | C |
| ATOM | 228 | CG  | ASP | A | 162 | 4.382  | 47.677 | 11.931 | 1.00 | 25.65 | C |
| ATOM | 229 | CD1 | ASP | A | 162 | 5.270  | 46.893 | 12.275 | 1.00 | 24.89 | O |
| ATOM | 230 | OD2 | ASP | A | 162 | 3.608  | 47.424 | 11.011 | 1.00 | 28.34 | O |
| ATOM | 231 | C   | ASP | A | 162 | 5.265  | 50.863 | 13.401 | 1.00 | 27.83 | C |
| ATOM | 232 | O   | ASP | A | 162 | 4.550  | 51.667 | 14.031 | 1.00 | 27.25 | O |
| ATOM | 233 | N   | THR | A | 163 | 6.029  | 51.184 | 12.360 | 1.00 | 29.14 | N |
| ATOM | 234 | CA  | THR | A | 163 | 5.933  | 52.442 | 11.608 | 1.00 | 29.87 | C |
| ATOM | 235 | CB  | THR | A | 163 | 6.949  | 52.416 | 10.459 | 1.00 | 30.86 | C |
| ATOM | 236 | OG1 | THR | A | 163 | 8.246  | 52.693 | 11.009 | 1.00 | 30.69 | O |
| ATOM | 237 | CG2 | THR | A | 163 | 6.607  | 53.440 | 9.337  | 1.00 | 31.62 | C |
| ATOM | 238 | C   | THR | A | 163 | 4.566  | 52.728 | 11.002 | 1.00 | 30.36 | C |
| ATOM | 239 | O   | THR | A | 163 | 4.225  | 53.886 | 10.813 | 1.00 | 28.41 | O |
| ATOM | 240 | N   | GLU | A | 164 | 3.831  | 51.676 | 10.640 | 1.00 | 32.91 | N |
| ATOM | 241 | CA  | GLU | A | 164 | 2.431  | 51.784 | 10.192 | 1.00 | 35.65 | C |
| ATOM | 242 | CB  | GLU | A | 164 | 2.199  | 50.812 | 9.024  | 1.00 | 40.90 | C |
| ATOM | 243 | CG  | GLU | A | 164 | 3.011  | 51.184 | 7.787  | 1.00 | 45.60 | C |
| ATOM | 244 | CD  | GLU | A | 164 | 2.963  | 50.135 | 6.682  | 1.00 | 51.43 | C |
| ATOM | 245 | OE1 | GLU | A | 164 | 2.062  | 49.260 | 6.711  | 1.00 | 48.13 | O |
| ATOM | 246 | OE2 | GLU | A | 164 | 3.843  | 50.190 | 5.774  | 1.00 | 58.79 | O |
| ATOM | 247 | C   | GLU | A | 164 | 1.357  | 51.576 | 11.287 | 1.00 | 32.43 | C |
| ATOM | 248 | O   | GLU | A | 164 | 0.186  | 51.392 | 10.987 | 1.00 | 32.34 | O |
| ATOM | 249 | N   | GLY | A | 165 | 1.753  | 51.615 | 12.553 | 1.00 | 29.36 | N |
| ATOM | 250 | CA  | GLY | A | 165 | 0.816  | 51.487 | 13.649 | 1.00 | 26.37 | C |
| ATOM | 251 | C   | GLY | A | 165 | 0.371  | 50.094 | 14.075 | 1.00 | 24.97 | C |
| ATOM | 252 | O   | GLY | A | 165 | −0.451 | 49.995 | 14.963 | 1.00 | 27.26 | O |
| ATOM | 253 | N   | TYR | A | 166 | 0.884  | 49.024 | 13.477 | 1.00 | 24.09 | N |
| ATOM | 254 | CA  | TYR | A | 166 | 0.537  | 47.653 | 13.897 | 1.00 | 23.18 | C |
| ATOM | 255 | CB  | TYR | A | 166 | 0.446  | 46.726 | 12.694 | 1.00 | 24.48 | C |
| ATOM | 256 | CG  | TYR | A | 166 | −0.310 | 47.317 | 11.558 | 1.00 | 25.83 | C |

TABLE 1-continued structure data for residues 36-207 of SEQ ID NO: 3

| ATOM | 257 | CD1 | TYR | A | 166 | −1.566 | 47.848 | 11.757 | 1.00 | 25.06 | C |
|---|---|---|---|---|---|---|---|---|---|---|---|
| ATOM | 258 | CE1 | TYR | A | 166 | −2.251 | 48.410 | 10.727 | 1.00 | 25.49 | C |
| ATOM | 259 | CZ | TYR | A | 166 | −1.693 | 48.433 | 9.475 | 1.00 | 26.38 | C |
| ATOM | 260 | OH | TYR | A | 166 | −2.391 | 48.996 | 8.460 | 1.00 | 29.15 | O |
| ATOM | 261 | CE2 | TYR | A | 166 | −0.451 | 47.910 | 9.229 | 1.00 | 26.56 | C |
| ATOM | 262 | CD2 | TYR | A | 166 | 0.245 | 47.361 | 10.277 | 1.00 | 26.89 | C |
| ATOM | 263 | C | TYR | A | 166 | 1.445 | 46.940 | 14.901 | 1.00 | 21.92 | C |
| ATOM | 264 | O | TYR | A | 166 | 2.648 | 47.136 | 14.938 | 1.00 | 20.69 | O |
| ATOM | 265 | N | TYR | A | 167 | 0.815 | 45.988 | 15.584 | 1.00 | 20.91 | N |
| ATOM | 266 | CA | TYR | A | 167 | 1.329 | 45.292 | 16.746 | 1.00 | 20.62 | C |
| ATOM | 267 | CB | TYR | A | 167 | 0.156 | 44.738 | 17.601 | 1.00 | 20.63 | C |
| ATOM | 268 | CG | TYR | A | 167 | −0.553 | 45.791 | 18.460 | 1.00 | 19.66 | C |
| ATOM | 269 | CD1 | TYR | A | 167 | 0.161 | 46.532 | 19.399 | 1.00 | 19.28 | C |
| ATOM | 270 | CE1 | TYR | A | 167 | −0.448 | 47.493 | 20.165 | 1.00 | 19.13 | C |
| ATOM | 271 | CZ | TYR | A | 167 | −1.791 | 47.713 | 20.027 | 1.00 | 19.47 | C |
| ATOM | 272 | OH | TYR | A | 167 | −2.340 | 48.668 | 20.814 | 1.00 | 21.22 | O |
| ATOM | 273 | CE2 | TYR | A | 167 | −2.542 | 46.998 | 19.123 | 1.00 | 19.13 | C |
| ATOM | 274 | CD2 | TYR | A | 167 | −1.911 | 46.040 | 18.335 | 1.00 | 19.13 | C |
| ATOM | 275 | C | TYR | A | 167 | 2.260 | 44.164 | 16.349 | 1.00 | 20.50 | C |
| ATOM | 276 | O | TYR | A | 167 | 1.832 | 43.180 | 15.731 | 1.00 | 20.25 | O |
| ATOM | 277 | N | THR | A | 168 | 3.512 | 44.300 | 16.785 | 1.00 | 19.89 | N |
| ATOM | 278 | CA | THR | A | 168 | 4.643 | 43.500 | 16.318 | 1.00 | 19.71 | C |
| ATOM | 279 | CB | THR | A | 168 | 5.477 | 44.355 | 15.341 | 1.00 | 20.88 | C |
| ATOM | 280 | OG1 | THR | A | 168 | 4.672 | 44.664 | 14.196 | 1.00 | 22.43 | O |
| ATOM | 281 | CG2 | THR | A | 168 | 6.757 | 43.660 | 14.892 | 1.00 | 21.13 | C |
| ATOM | 282 | C | THR | A | 168 | 5.523 | 43.099 | 17.499 | 1.00 | 18.29 | C |
| ATOM | 283 | O | THR | A | 168 | 5.540 | 43.790 | 18.524 | 1.00 | 17.79 | O |
| ATOM | 284 | N | ILE | A | 169 | 6.247 | 41.991 | 17.359 | 1.00 | 16.80 | N |
| ATOM | 285 | CA | ILE | A | 169 | 7.189 | 41.551 | 18.389 | 1.00 | 16.21 | C |
| ATOM | 286 | CB | ILE | A | 169 | 6.446 | 40.750 | 19.492 | 1.00 | 16.11 | C |
| ATOM | 287 | CG1 | ILE | A | 169 | 7.166 | 40.906 | 20.844 | 1.00 | 16.23 | C |
| ATOM | 288 | CD1 | ILE | A | 169 | 6.566 | 40.082 | 21.944 | 1.00 | 16.42 | C |
| ATOM | 289 | CG2 | ILE | A | 169 | 6.272 | 39.289 | 19.107 | 1.00 | 15.84 | C |
| ATOM | 290 | C | ILE | A | 169 | 8.416 | 40.767 | 17.857 | 1.00 | 15.64 | C |
| ATOM | 291 | O | ILE | A | 169 | 8.434 | 40.304 | 16.726 | 1.00 | 15.20 | O |
| ATOM | 292 | N | GLY | A | 170 | 9.454 | 40.654 | 18.674 | 1.00 | 15.27 | N |
| ATOM | 293 | CA | GLY | A | 170 | 10.619 | 39.862 | 18.318 | 1.00 | 15.59 | C |
| ATOM | 294 | C | GLY | A | 170 | 11.358 | 40.481 | 17.160 | 1.00 | 15.81 | C |
| ATOM | 295 | O | GLY | A | 170 | 11.602 | 41.689 | 17.170 | 1.00 | 15.62 | O |
| ATOM | 296 | N | ILE | A | 171 | 11.677 | 39.662 | 16.146 | 1.00 | 16.26 | N |
| ATOM | 297 | CA | ILE | A | 171 | 12.402 | 40.151 | 14.973 | 1.00 | 16.42 | C |
| ATOM | 298 | CB | ILE | A | 171 | 13.612 | 39.237 | 14.608 | 1.00 | 17.17 | C |
| ATOM | 299 | CG1 | ILE | A | 171 | 14.597 | 39.246 | 15.783 | 1.00 | 18.43 | C |
| ATOM | 300 | CD1 | ILE | A | 171 | 15.977 | 38.695 | 15.471 | 1.00 | 19.67 | C |
| ATOM | 301 | CG2 | ILE | A | 171 | 14.325 | 39.698 | 13.352 | 1.00 | 16.64 | C |
| ATOM | 302 | C | ILE | A | 171 | 11.383 | 40.308 | 13.882 | 1.00 | 16.15 | C |
| ATOM | 303 | O | ILE | A | 171 | 11.105 | 39.385 | 13.110 | 1.00 | 15.34 | O |
| ATOM | 304 | N | GLY | A | 172 | 10.787 | 41.491 | 13.866 | 1.00 | 16.45 | N |
| ATOM | 305 | CA | GLY | A | 172 | 9.781 | 41.850 | 12.850 | 1.00 | 17.24 | C |
| ATOM | 306 | C | GLY | A | 172 | 8.574 | 40.925 | 12.674 | 1.00 | 17.70 | C |
| ATOM | 307 | O | GLY | A | 172 | 7.997 | 40.848 | 11.581 | 1.00 | 18.75 | O |
| ATOM | 308 | N | HIS | A | 173 | 8.180 | 40.229 | 13.730 | 1.00 | 17.55 | N |
| ATOM | 309 | CA | HIS | A | 173 | 7.035 | 39.336 | 13.643 | 1.00 | 18.51 | C |
| ATOM | 310 | CB | HIS | A | 173 | 7.142 | 38.202 | 14.655 | 1.00 | 18.89 | C |
| ATOM | 311 | CG | HIS | A | 173 | 6.022 | 37.231 | 14.558 | 1.00 | 19.53 | C |
| ATOM | 312 | ND1 | HIS | A | 173 | 4.824 | 37.416 | 15.211 | 1.00 | 20.51 | N |
| ATOM | 313 | CE1 | HIS | A | 173 | 4.015 | 36.408 | 14.931 | 1.00 | 20.95 | C |
| ATOM | 314 | NE2 | HIS | A | 173 | 4.648 | 35.589 | 14.107 | 1.00 | 21.49 | N |
| ATOM | 315 | CD2 | HIS | A | 173 | 5.901 | 36.082 | 13.856 | 1.00 | 19.62 | C |
| ATOM | 316 | C | HIS | A | 173 | 5.734 | 40.078 | 13.884 | 1.00 | 17.79 | C |
| ATOM | 317 | O | HIS | A | 173 | 5.405 | 40.409 | 15.013 | 1.00 | 17.24 | O |
| ATOM | 318 | N | LEU | A | 174 | 4.981 | 40.328 | 12.827 | 1.00 | 18.37 | N |
| ATOM | 319 | CA | LEU | A | 174 | 3.676 | 40.990 | 12.987 | 1.00 | 18.38 | C |
| ATOM | 320 | CB | LEU | A | 174 | 3.167 | 41.507 | 11.646 | 1.00 | 18.49 | C |
| ATOM | 321 | CG | LEU | A | 174 | 1.902 | 42.363 | 11.717 | 1.00 | 18.76 | C |
| ATOM | 322 | CD1 | LEU | A | 174 | 1.933 | 43.603 | 10.826 | 1.00 | 17.91 | C |
| ATOM | 323 | CD2 | LEU | A | 174 | 0.732 | 41.452 | 11.340 | 1.00 | 19.62 | C |
| ATOM | 324 | C | LEU | A | 174 | 2.664 | 40.032 | 13.611 | 1.00 | 18.52 | C |
| ATOM | 325 | O | LEU | A | 174 | 2.483 | 38.899 | 13.148 | 1.00 | 17.99 | O |
| ATOM | 326 | N | LEU | A | 175 | 2.012 | 40.499 | 14.670 | 1.00 | 18.61 | N |
| ATOM | 327 | CA | LEU | A | 175 | 1.013 | 39.714 | 15.367 | 1.00 | 18.96 | C |
| ATOM | 328 | CB | LEU | A | 175 | 1.050 | 40.064 | 16.848 | 1.00 | 18.91 | C |
| ATOM | 329 | CG | LEU | A | 175 | 2.273 | 39.609 | 17.637 | 1.00 | 18.46 | C |
| ATOM | 330 | CD1 | LEU | A | 175 | 2.549 | 40.587 | 18.758 | 1.00 | 18.69 | C |
| ATOM | 331 | CD2 | LEU | A | 175 | 2.065 | 38.215 | 18.198 | 1.00 | 18.53 | C |
| ATOM | 332 | C | LEU | A | 175 | −0.409 | 39.938 | 14.812 | 1.00 | 19.47 | C |
| ATOM | 333 | O | LEU | A | 175 | −1.147 | 38.964 | 14.652 | 1.00 | 20.05 | O |
| ATOM | 334 | N | THR | A | 176 | −0.784 | 41.203 | 14.557 | 1.00 | 19.41 | N |

TABLE 1-continued structure data for residues 36-207 of SEQ ID NO: 3

| ATOM | 335 | CA | THR | A | 176 | −2.116 | 41.568 | 14.046 | 1.00 | 19.83 | C |
|---|---|---|---|---|---|---|---|---|---|---|---|
| ATOM | 336 | CB | THR | A | 176 | −3.194 | 41.426 | 15.120 | 1.00 | 20.15 | C |
| ATOM | 337 | OG1 | THR | A | 176 | −4.489 | 41.417 | 14.509 | 1.00 | 20.64 | O |
| ATOM | 338 | CG2 | THR | A | 176 | −3.143 | 42.587 | 16.076 | 1.00 | 20.48 | C |
| ATOM | 339 | C | THR | A | 176 | −2.204 | 43.009 | 13.549 | 1.00 | 20.67 | C |
| ATOM | 340 | O | THR | A | 176 | −1.444 | 43.863 | 13.983 | 1.00 | 21.11 | O |
| ATOM | 341 | N | LYS | A | 177 | −3.162 | 43.273 | 12.660 | 1.00 | 21.56 | N |
| ATOM | 342 | CA | LYS | A | 177 | −3.448 | 44.636 | 12.184 | 1.00 | 22.00 | C |
| ATOM | 343 | CB | LYS | A | 177 | −3.900 | 44.627 | 10.719 | 1.00 | 23.77 | C |
| ATOM | 344 | CG | LYS | A | 177 | −2.792 | 44.496 | 9.672 | 1.00 | 26.56 | C |
| ATOM | 345 | CD | LYS | A | 177 | −3.422 | 44.271 | 8.294 | 1.00 | 27.74 | C |
| ATOM | 346 | CE | LYS | A | 177 | −2.506 | 44.568 | 7.097 | 1.00 | 27.22 | C |
| ATOM | 347 | NZ | LYS | A | 177 | −3.346 | 45.190 | 6.012 | 1.00 | 26.34 | N |
| ATOM | 348 | C | LYS | A | 177 | −4.544 | 45.261 | 13.041 | 1.00 | 20.97 | C |
| ATOM | 349 | O | LYS | A | 177 | −4.783 | 46.466 | 12.995 | 1.00 | 21.35 | O |
| ATOM | 350 | N | SER | A | 178 | −5.230 | 44.437 | 13.811 | 1.00 | 19.91 | N |
| ATOM | 351 | CA | SER | A | 178 | −6.247 | 44.919 | 14.715 | 1.00 | 20.11 | C |
| ATOM | 352 | CB | SER | A | 178 | −6.709 | 43.747 | 15.561 | 1.00 | 20.87 | C |
| ATOM | 353 | OG | SER | A | 178 | −7.305 | 44.215 | 16.761 | 1.00 | 22.69 | O |
| ATOM | 354 | C | SER | A | 178 | −5.726 | 45.993 | 15.664 | 1.00 | 19.74 | C |
| ATOM | 355 | O | SER | A | 178 | −4.684 | 45.800 | 16.245 | 1.00 | 19.78 | O |
| ATOM | 356 | N | PRO | A | 179 | −6.490 | 47.069 | 15.915 | 1.00 | 19.84 | N |
| ATOM | 357 | CA | PRO | A | 179 | −6.040 | 48.065 | 16.893 | 1.00 | 19.66 | C |
| ATOM | 358 | CB | PRO | A | 179 | −6.937 | 49.260 | 16.573 | 1.00 | 19.75 | C |
| ATOM | 359 | CG | PRO | A | 179 | −8.246 | 48.624 | 16.203 | 1.00 | 20.02 | C |
| ATOM | 360 | CD | PRO | A | 179 | −7.909 | 47.285 | 15.568 | 1.00 | 20.40 | C |
| ATOM | 361 | C | PRO | A | 179 | −6.225 | 47.662 | 18.380 | 1.00 | 19.61 | C |
| ATOM | 362 | O | PRO | A | 179 | −5.920 | 48.458 | 19.263 | 1.00 | 20.52 | O |
| ATOM | 363 | N | SER | A | 180 | −6.721 | 46.459 | 18.664 | 1.00 | 18.73 | N |
| ATOM | 364 | CA | SER | A | 180 | −6.868 | 46.004 | 20.041 | 1.00 | 18.38 | C |
| ATOM | 365 | CB | SER | A | 180 | −8.055 | 45.069 | 20.179 | 1.00 | 19.04 | C |
| ATOM | 366 | OG | SER | A | 180 | −7.667 | 43.917 | 20.897 | 1.00 | 19.54 | O |
| ATOM | 367 | C | SER | A | 180 | −5.648 | 45.261 | 20.527 | 1.00 | 18.67 | C |
| ATOM | 368 | O | SER | A | 180 | −5.335 | 44.187 | 20.015 | 1.00 | 18.64 | O |
| ATOM | 369 | N | LEU | A | 181 | −4.988 | 45.821 | 21.543 | 1.00 | 19.27 | N |
| ATOM | 370 | CA | LEU | A | 181 | −3.803 | 45.213 | 22.155 | 1.00 | 18.99 | C |
| ATOM | 371 | CB | LEU | A | 181 | −3.254 | 46.098 | 23.271 | 1.00 | 19.09 | C |
| ATOM | 372 | CG | LEU | A | 181 | −2.059 | 45.531 | 24.043 | 1.00 | 20.08 | C |
| ATOM | 373 | CD1 | LEU | A | 181 | −0.866 | 45.245 | 23.128 | 1.00 | 20.62 | C |
| ATOM | 374 | CD2 | LEU | A | 181 | −1.616 | 46.477 | 25.145 | 1.00 | 20.34 | C |
| ATOM | 375 | C | LEU | A | 181 | −4.089 | 43.833 | 22.727 | 1.00 | 19.29 | C |
| ATOM | 376 | O | LEU | A | 181 | −3.193 | 42.981 | 22.743 | 1.00 | 18.53 | O |
| ATOM | 377 | N | ASN | A | 182 | −5.320 | 43.602 | 23.199 | 1.00 | 19.09 | N |
| ATOM | 378 | CA | ASN | A | 182 | −5.655 | 42.293 | 23.729 | 1.00 | 19.39 | C |
| ATOM | 379 | CB | ASN | A | 182 | −7.014 | 42.282 | 24.400 | 1.00 | 20.72 | C |
| ATOM | 380 | CG | ASN | A | 182 | −6.957 | 42.798 | 25.820 | 1.00 | 21.97 | C |
| ATOM | 381 | OD1 | ASN | A | 182 | −6.011 | 42.531 | 26.582 | 1.00 | 23.21 | O |
| ATOM | 382 | ND2 | ASN | A | 182 | −7.961 | 43.551 | 26.186 | 1.00 | 22.57 | N |
| ATOM | 383 | C | ASN | A | 182 | −5.627 | 41.220 | 22.679 | 1.00 | 19.03 | C |
| ATOM | 384 | O | ASN | A | 182 | −5.233 | 40.098 | 22.976 | 1.00 | 20.18 | O |
| ATOM | 385 | N | ALA | A | 183 | −6.046 | 41.551 | 21.461 | 1.00 | 17.88 | N |
| ATOM | 386 | CA | ALA | A | 183 | −5.993 | 40.596 | 20.361 | 1.00 | 17.50 | C |
| ATOM | 387 | CB | ALA | A | 183 | −6.668 | 41.162 | 19.117 | 1.00 | 17.13 | C |
| ATOM | 388 | C | ALA | A | 183 | −4.534 | 40.267 | 20.060 | 1.00 | 17.73 | C |
| ATOM | 389 | O | ALA | A | 183 | −4.191 | 39.125 | 19.726 | 1.00 | 17.96 | O |
| ATOM | 390 | N | ALA | A | 184 | −3.675 | 41.276 | 20.179 | 1.00 | 17.22 | N |
| ATOM | 391 | CA | ALA | A | 184 | −2.260 | 41.078 | 19.932 | 1.00 | 16.70 | C |
| ATOM | 392 | CB | ALA | A | 184 | −1.516 | 42.397 | 19.983 | 1.00 | 16.36 | C |
| ATOM | 393 | C | ALA | A | 184 | −1.723 | 40.084 | 20.938 | 1.00 | 16.40 | C |
| ATOM | 394 | O | ALA | A | 184 | −1.044 | 39.134 | 20.580 | 1.00 | 15.35 | O |
| ATOM | 395 | N | LYS | A | 185 | −2.076 | 40.255 | 22.200 | 1.00 | 17.46 | N |
| ATOM | 396 | CA | LYS | A | 185 | −1.559 | 39.333 | 23.206 | 1.00 | 18.55 | C |
| ATOM | 397 | CB | LYS | A | 185 | −1.871 | 39.809 | 24.607 | 1.00 | 18.24 | C |
| ATOM | 398 | CG | LYS | A | 185 | −1.065 | 41.015 | 25.038 | 1.00 | 18.33 | C |
| ATOM | 399 | CD | LYS | A | 185 | −1.646 | 41.667 | 26.292 | 1.00 | 17.93 | C |
| ATOM | 400 | CE | LYS | A | 185 | −0.814 | 42.876 | 26.687 | 1.00 | 17.96 | C |
| ATOM | 401 | NZ | LYS | A | 185 | −1.444 | 43.625 | 27.793 | 1.00 | 18.18 | N |
| ATOM | 402 | C | LYS | A | 185 | −2.103 | 37.932 | 22.999 | 1.00 | 19.97 | C |
| ATOM | 403 | O | LYS | A | 185 | −1.428 | 36.961 | 23.314 | 1.00 | 20.54 | O |
| ATOM | 404 | N | SER | A | 186 | −3.317 | 37.822 | 22.469 | 1.00 | 21.24 | N |
| ATOM | 405 | CA | SER | A | 186 | −3.912 | 36.506 | 22.241 | 1.00 | 22.34 | C |
| ATOM | 406 | CB | SER | A | 186 | −5.414 | 36.591 | 21.947 | 1.00 | 22.53 | C |
| ATOM | 407 | OG | SER | A | 186 | −5.753 | 35.654 | 20.938 | 1.00 | 24.25 | O |
| ATOM | 408 | C | SER | A | 186 | −3.193 | 35.804 | 21.107 | 1.00 | 22.10 | C |
| ATOM | 409 | O | SER | A | 186 | −2.923 | 34.617 | 21.187 | 1.00 | 21.80 | O |
| ATOM | 410 | N | GLU | A | 187 | −2.891 | 36.529 | 20.046 | 1.00 | 23.43 | N |
| ATOM | 411 | CA | GLU | A | 187 | −2.094 | 35.946 | 18.959 | 1.00 | 25.41 | C |
| ATOM | 412 | CB | GLU | A | 187 | −1.913 | 36.928 | 17.801 | 1.00 | 26.48 | C |

TABLE 1-continued structure data for residues 36-207 of SEQ ID NO: 3

| ATOM | 413 | CG | GLU | A | 187 | −3.187 | 37.160 | 17.003 | 1.00 | 29.06 | C |
| ATOM | 414 | CD | GLU | A | 187 | −3.715 | 35.884 | 16.335 | 1.00 | 33.23 | C |
| ATOM | 415 | OE1 | GLU | A | 187 | −3.002 | 35.337 | 15.439 | 1.00 | 40.01 | O |
| ATOM | 416 | OE2 | GLU | A | 187 | −4.836 | 35.425 | 16.700 | 1.00 | 33.03 | O |
| ATOM | 417 | C | GLU | A | 187 | −0.749 | 35.477 | 19.500 | 1.00 | 24.48 | C |
| ATOM | 418 | O | GLU | A | 187 | −0.345 | 34.346 | 19.269 | 1.00 | 26.12 | O |
| ATOM | 419 | N | LEU | A | 188 | −0.094 | 36.336 | 20.264 | 1.00 | 22.78 | N |
| ATOM | 420 | CA | LEU | A | 188 | 1.196 | 36.030 | 20.839 | 1.00 | 21.66 | C |
| ATOM | 421 | CB | LEU | A | 188 | 1.658 | 37.238 | 21.629 | 1.00 | 21.13 | C |
| ATOM | 422 | CG | LEU | A | 188 | 3.016 | 37.109 | 22.288 | 1.00 | 20.46 | C |
| ATOM | 423 | CD1 | LEU | A | 188 | 4.098 | 36.771 | 21.270 | 1.00 | 19.65 | C |
| ATOM | 424 | CD2 | LEU | A | 188 | 3.332 | 38.410 | 23.002 | 1.00 | 20.70 | C |
| ATOM | 425 | C | LEU | A | 188 | 1.194 | 34.827 | 21.772 | 1.00 | 22.08 | C |
| ATOM | 426 | O | LEU | A | 188 | 2.128 | 34.032 | 21.786 | 1.00 | 20.38 | O |
| ATOM | 427 | N | ASP | A | 189 | 0.143 | 34.717 | 22.576 | 1.00 | 24.72 | N |
| ATOM | 428 | CA | ASP | A | 189 | 0.021 | 33.628 | 23.542 | 1.00 | 25.29 | C |
| ATOM | 429 | CB | ASP | A | 189 | −1.091 | 33.926 | 24.551 | 1.00 | 25.92 | C |
| ATOM | 430 | CG | ASP | A | 189 | −0.731 | 35.078 | 25.542 | 1.00 | 28.20 | C |
| ATOM | 431 | CD1 | ASP | A | 189 | 0.433 | 35.562 | 25.565 | 1.00 | 28.01 | O |
| ATOM | 432 | OD2 | ASP | A | 189 | −1.629 | 35.501 | 26.331 | 1.00 | 29.63 | O |
| ATOM | 433 | C | ASP | A | 189 | −0.200 | 32.294 | 22.818 | 1.00 | 26.01 | C |
| ATOM | 434 | O | ASP | A | 189 | 0.210 | 31.254 | 23.310 | 1.00 | 26.91 | O |
| ATOM | 435 | N | LYS | A | 190 | −0.814 | 32.337 | 21.639 | 1.00 | 26.91 | N |
| ATOM | 436 | CA | LYS | A | 190 | −0.956 | 31.167 | 20.780 | 1.00 | 28.76 | C |
| ATOM | 437 | CB | LYS | A | 190 | −2.005 | 31.451 | 19.693 | 1.00 | 32.16 | C |
| ATOM | 438 | CG | LYS | A | 190 | −2.576 | 30.203 | 19.005 | 1.00 | 36.17 | C |
| ATOM | 439 | CD | LYS | A | 190 | −2.754 | 30.362 | 17.491 | 1.00 | 38.31 | C |
| ATOM | 440 | CE | LYS | A | 190 | −3.890 | 31.320 | 17.127 | 1.00 | 39.88 | C |
| ATOM | 441 | NZ | LYS | A | 190 | −5.146 | 30.615 | 16.751 | 1.00 | 39.53 | N |
| ATOM | 442 | C | LYS | A | 190 | 0.377 | 30.817 | 20.099 | 1.00 | 28.86 | C |
| ATOM | 443 | O | LYS | A | 190 | 0.714 | 29.653 | 19.933 | 1.00 | 29.88 | O |
| ATOM | 444 | N | ALA | A | 191 | 1.121 | 31.834 | 19.684 | 1.00 | 27.48 | N |
| ATOM | 445 | CA | ALA | A | 191 | 2.357 | 31.630 | 18.957 | 1.00 | 26.90 | C |
| ATOM | 446 | CB | ALA | A | 191 | 2.886 | 32.959 | 18.466 | 1.00 | 25.64 | C |
| ATOM | 447 | C | ALA | A | 191 | 3.390 | 30.936 | 19.826 | 1.00 | 28.68 | C |
| ATOM | 448 | O | ALA | A | 191 | 4.096 | 30.019 | 19.383 | 1.00 | 28.71 | O |
| ATOM | 449 | N | ILE | A | 192 | 3.450 | 31.369 | 21.077 | 1.00 | 29.76 | N |
| ATOM | 450 | CA | ILE | A | 192 | 4.489 | 30.943 | 21.993 | 1.00 | 29.56 | C |
| ATOM | 451 | CB | ILE | A | 192 | 4.855 | 32.096 | 22.921 | 1.00 | 29.63 | C |
| ATOM | 452 | CG1 | ILE | A | 192 | 5.215 | 33.317 | 22.080 | 1.00 | 28.80 | C |
| ATOM | 453 | CD1 | ILE | A | 192 | 6.638 | 33.289 | 21.568 | 1.00 | 28.67 | C |
| ATOM | 454 | CG2 | ILE | A | 192 | 5.989 | 31.688 | 23.860 | 1.00 | 30.25 | C |
| ATOM | 455 | C | ILE | A | 192 | 4.035 | 29.773 | 22.848 | 1.00 | 30.43 | C |
| ATOM | 456 | O | ILE | A | 192 | 4.838 | 28.925 | 23.212 | 1.00 | 31.17 | O |
| ATOM | 457 | N | GLY | A | 193 | 2.754 | 29.737 | 23.191 | 1.00 | 30.06 | N |
| ATOM | 458 | CA | GLY | A | 193 | 2.219 | 28.614 | 23.947 | 1.00 | 29.82 | C |
| ATOM | 459 | C | GLY | A | 193 | 2.235 | 28.796 | 25.450 | 1.00 | 30.15 | C |
| ATOM | 460 | O | GLY | A | 193 | 2.446 | 27.834 | 26.192 | 1.00 | 31.27 | O |
| ATOM | 461 | N | ARG | A | 194 | 2.005 | 30.027 | 25.898 | 1.00 | 29.68 | N |
| ATOM | 462 | CA | ARG | A | 194 | 1.777 | 30.316 | 27.312 | 1.00 | 29.84 | C |
| ATOM | 463 | CB | ARG | A | 194 | 3.050 | 30.147 | 28.150 | 1.00 | 28.80 | C |
| ATOM | 464 | CG | ARG | A | 194 | 4.333 | 30.653 | 27.513 | 1.00 | 28.07 | C |
| ATOM | 465 | CD | ARG | A | 194 | 5.402 | 30.940 | 28.562 | 1.00 | 26.80 | C |
| ATOM | 466 | NE | ARG | A | 194 | 5.453 | 32.364 | 28.909 | 1.00 | 26.32 | N |
| ATOM | 467 | CZ | ARG | A | 194 | 6.424 | 33.214 | 28.565 | 1.00 | 25.93 | C |
| ATOM | 468 | NH1 | ARG | A | 194 | 7.475 | 32.810 | 27.877 | 1.00 | 25.76 | N |
| ATOM | 469 | NH2 | ARG | A | 194 | 6.358 | 34.491 | 28.935 | 1.00 | 26.04 | N |
| ATOM | 470 | C | ARG | A | 194 | 1.294 | 31.733 | 27.413 | 1.00 | 31.17 | C |
| ATOM | 471 | O | ARG | A | 194 | 1.470 | 32.497 | 26.489 | 1.00 | 34.43 | O |
| ATOM | 472 | N | ASN | A | 195 | 0.682 | 32.092 | 28.525 | 1.00 | 33.20 | N |
| ATOM | 473 | CA | ASN | A | 195 | 0.307 | 33.473 | 28.743 | 1.00 | 34.68 | C |
| ATOM | 474 | CB | ASN | A | 195 | −0.714 | 33.577 | 29.885 | 1.00 | 37.87 | C |
| ATOM | 475 | CG | ASN | A | 195 | −1.393 | 34.945 | 29.960 | 1.00 | 40.60 | C |
| ATOM | 476 | CD1 | ASN | A | 195 | −1.887 | 35.337 | 31.020 | 1.00 | 42.64 | O |
| ATOM | 477 | ND2 | ASN | A | 195 | −1.428 | 35.675 | 28.842 | 1.00 | 41.33 | N |
| ATOM | 478 | C | ASN | A | 195 | 1.574 | 34.282 | 29.032 | 1.00 | 32.42 | C |
| ATOM | 479 | O | ASN | A | 195 | 2.241 | 34.066 | 30.038 | 1.00 | 32.37 | O |
| ATOM | 480 | N | THR | A | 196 | 1.901 | 35.196 | 28.122 | 1.00 | 30.15 | N |
| ATOM | 481 | CA | THR | A | 196 | 3.138 | 35.972 | 28.172 | 1.00 | 27.91 | C |
| ATOM | 482 | CB | THR | A | 196 | 3.771 | 36.090 | 26.759 | 1.00 | 26.91 | C |
| ATOM | 483 | OG1 | THR | A | 196 | 2.950 | 36.924 | 25.945 | 1.00 | 26.87 | O |
| ATOM | 484 | CG2 | THR | A | 196 | 3.926 | 34.749 | 26.065 | 1.00 | 26.01 | C |
| ATOM | 485 | C | THR | A | 196 | 2.934 | 37.406 | 28.678 | 1.00 | 27.48 | C |
| ATOM | 486 | O | THR | A | 196 | 3.887 | 38.086 | 29.033 | 1.00 | 26.22 | O |
| ATOM | 487 | N | ASN | A | 197 | 1.688 | 37.865 | 28.677 | 1.00 | 29.41 | N |
| ATOM | 488 | CA | ASN | A | 197 | 1.341 | 39.283 | 28.880 | 1.00 | 30.00 | C |
| ATOM | 489 | CB | ASN | A | 197 | 1.351 | 39.646 | 30.363 | 1.00 | 31.81 | C |
| ATOM | 490 | CG | ASN | A | 197 | 0.436 | 40.818 | 30.678 | 1.00 | 34.00 | C |

TABLE 1-continued structure data for residues 36-207 of SEQ ID NO: 3

| ATOM | 491 | CD1 | ASN | A | 197 | 0.853 | 41.796 | 31.309 | 1.00 | 35.63 | O |
|------|-----|-----|-----|---|-----|-------|--------|--------|------|-------|---|
| ATOM | 492 | ND2 | ASN | A | 197 | −0.824 | 40.724 | 30.242 | 1.00 | 34.33 | N |
| ATOM | 493 | C | ASN | A | 197 | 2.198 | 40.270 | 28.070 | 1.00 | 28.30 | C |
| ATOM | 494 | O | ASN | A | 197 | 2.613 | 41.331 | 28.551 | 1.00 | 28.02 | O |
| ATOM | 495 | N | GLY | A | 198 | 2.456 | 39.906 | 26.825 | 1.00 | 25.71 | N |
| ATOM | 496 | CA | GLY | A | 198 | 3.111 | 40.813 | 25.899 | 1.00 | 24.29 | C |
| ATOM | 497 | C | GLY | A | 198 | 4.618 | 40.915 | 25.979 | 1.00 | 22.32 | C |
| ATOM | 498 | O | GLY | A | 198 | 5.185 | 41.776 | 25.335 | 1.00 | 21.92 | O |
| ATOM | 499 | N | VAL | A | 199 | 5.281 | 40.058 | 26.753 | 1.00 | 20.94 | N |
| ATOM | 500 | CA | VAL | A | 199 | 6.736 | 40.024 | 26.734 | 1.00 | 20.05 | C |
| ATOM | 501 | CB | VAL | A | 199 | 7.385 | 40.892 | 27.868 | 1.00 | 19.36 | C |
| ATOM | 502 | CG1 | VAL | A | 199 | 6.393 | 41.231 | 28.950 | 1.00 | 19.28 | C |
| ATOM | 503 | CG2 | VAL | A | 199 | 8.657 | 40.269 | 28.445 | 1.00 | 18.73 | C |
| ATOM | 504 | C | VAL | A | 199 | 7.264 | 38.596 | 26.656 | 1.00 | 20.18 | C |
| ATOM | 505 | O | VAL | A | 199 | 6.667 | 37.664 | 27.177 | 1.00 | 20.01 | O |
| ATOM | 506 | N | ILE | A | 200 | 8.406 | 38.457 | 26.001 | 1.00 | 20.76 | N |
| ATOM | 507 | CA | ILE | A | 200 | 8.885 | 37.187 | 25.554 | 1.00 | 21.98 | C |
| ATOM | 508 | CB | ILE | A | 200 | 8.539 | 37.077 | 24.055 | 1.00 | 24.28 | C |
| ATOM | 509 | CG1 | ILE | A | 200 | 8.086 | 35.689 | 23.741 | 1.00 | 26.33 | C |
| ATOM | 510 | CD1 | ILE | A | 200 | 6.630 | 35.550 | 24.076 | 1.00 | 27.63 | C |
| ATOM | 511 | CG2 | ILE | A | 200 | 9.640 | 37.485 | 23.090 | 1.00 | 24.68 | C |
| ATOM | 512 | C | ILE | A | 200 | 10.364 | 37.115 | 25.818 | 1.00 | 22.17 | C |
| ATOM | 513 | O | ILE | A | 200 | 11.009 | 38.147 | 25.954 | 1.00 | 23.26 | O |
| ATOM | 514 | N | THR | A | 201 | 10.920 | 35.913 | 25.901 | 1.00 | 22.43 | N |
| ATOM | 515 | CA | THR | A | 201 | 12.371 | 35.768 | 26.125 | 1.00 | 22.21 | C |
| ATOM | 516 | CB | THR | A | 201 | 12.733 | 34.430 | 26.768 | 1.00 | 21.32 | C |
| ATOM | 517 | OG1 | THR | A | 201 | 12.514 | 33.384 | 25.819 | 1.00 | 21.81 | O |
| ATOM | 518 | CG2 | THR | A | 201 | 11.936 | 34.193 | 28.015 | 1.00 | 20.10 | C |
| ATOM | 519 | C | THR | A | 201 | 13.119 | 35.833 | 24.817 | 1.00 | 23.37 | C |
| ATOM | 520 | O | THR | A | 201 | 12.521 | 35.747 | 23.757 | 1.00 | 23.95 | O |
| ATOM | 521 | N | LYS | A | 202 | 14.438 | 35.979 | 24.883 | 1.00 | 26.38 | N |
| ATOM | 522 | CA | LYS | A | 202 | 15.253 | 36.025 | 23.671 | 1.00 | 27.35 | C |
| ATOM | 523 | CB | LYS | A | 202 | 16.682 | 36.445 | 23.987 | 1.00 | 31.97 | C |
| ATOM | 524 | CG | LYS | A | 202 | 17.548 | 36.757 | 22.753 | 1.00 | 37.92 | C |
| ATOM | 525 | CD | LYS | A | 202 | 18.978 | 37.110 | 23.165 | 1.00 | 43.88 | C |
| ATOM | 526 | CE | LYS | A | 202 | 19.760 | 37.845 | 22.076 | 1.00 | 49.63 | C |
| ATOM | 527 | NZ | LYS | A | 202 | 20.595 | 38.926 | 22.695 | 1.00 | 52.23 | N |
| ATOM | 528 | C | LYS | A | 202 | 15.210 | 34.664 | 22.974 | 1.00 | 26.13 | C |
| ATOM | 529 | O | LYS | A | 202 | 15.191 | 34.586 | 21.762 | 1.00 | 24.49 | O |
| ATOM | 530 | N | ASP | A | 203 | 15.161 | 33.583 | 23.735 | 1.00 | 26.64 | N |
| ATOM | 531 | CA | ASP | A | 203 | 15.073 | 32.256 | 23.126 | 1.00 | 27.33 | C |
| ATOM | 532 | CB | ASP | A | 203 | 15.297 | 31.156 | 24.166 | 1.00 | 29.13 | C |
| ATOM | 533 | CG | ASP | A | 203 | 16.563 | 31.350 | 24.978 | 1.00 | 31.62 | C |
| ATOM | 534 | OD1 | ASP | A | 203 | 17.670 | 31.295 | 24.385 | 1.00 | 32.96 | O |
| ATOM | 535 | OD2 | ASP | A | 203 | 16.436 | 31.549 | 26.222 | 1.00 | 34.71 | O |
| ATOM | 536 | C | ASP | A | 203 | 13.700 | 32.043 | 22.462 | 1.00 | 25.46 | C |
| ATOM | 537 | O | ASP | A | 203 | 13.589 | 31.331 | 21.475 | 1.00 | 23.53 | O |
| ATOM | 538 | N | GLU | A | 204 | 12.659 | 32.641 | 23.022 | 1.00 | 23.80 | N |
| ATOM | 539 | CA | GLU | A | 204 | 11.355 | 32.590 | 22.386 | 1.00 | 24.30 | C |
| ATOM | 540 | CB | GLU | A | 204 | 10.262 | 32.979 | 23.366 | 1.00 | 24.03 | C |
| ATOM | 541 | CG | GLU | A | 204 | 10.017 | 31.860 | 24.347 | 1.00 | 24.92 | C |
| ATOM | 542 | CD | GLU | A | 204 | 9.190 | 32.270 | 25.543 | 1.00 | 27.08 | C |
| ATOM | 543 | OE1 | GLU | A | 204 | 9.205 | 33.468 | 25.929 | 1.00 | 27.21 | O |
| ATOM | 544 | OE2 | GLU | A | 204 | 8.525 | 31.368 | 26.119 | 1.00 | 29.49 | O |
| ATOM | 545 | C | GLU | A | 204 | 11.315 | 33.442 | 21.112 | 1.00 | 23.67 | C |
| ATOM | 546 | O | GLU | A | 204 | 10.786 | 33.010 | 20.094 | 1.00 | 22.45 | O |
| ATOM | 547 | N | ALA | A | 205 | 11.916 | 34.623 | 21.162 | 1.00 | 23.06 | N |
| ATOM | 548 | CA | ALA | A | 205 | 12.073 | 35.443 | 19.967 | 1.00 | 22.97 | C |
| ATOM | 549 | CB | ALA | A | 205 | 12.736 | 36.762 | 20.307 | 1.00 | 22.52 | C |
| ATOM | 550 | C | ALA | A | 205 | 12.838 | 34.736 | 18.851 | 1.00 | 22.68 | C |
| ATOM | 551 | O | ALA | A | 205 | 12.503 | 34.905 | 17.704 | 1.00 | 23.37 | O |
| ATOM | 552 | N | GLU | A | 206 | 13.839 | 33.934 | 19.177 | 1.00 | 23.98 | N |
| ATOM | 553 | CA | GLU | A | 206 | 14.609 | 33.222 | 18.158 | 1.00 | 26.18 | C |
| ATOM | 554 | CB | GLU | A | 206 | 15.980 | 32.770 | 18.709 | 1.00 | 27.49 | C |
| ATOM | 555 | CG | GLU | A | 206 | 16.825 | 31.974 | 17.709 | 1.00 | 29.61 | C |
| ATOM | 556 | CD | GLU | A | 206 | 18.331 | 32.000 | 17.999 | 1.00 | 32.63 | C |
| ATOM | 557 | OE1 | GLU | A | 206 | 18.693 | 31.892 | 19.214 | 1.00 | 32.79 | O |
| ATOM | 558 | OE2 | GLU | A | 206 | 19.138 | 32.124 | 17.012 | 1.00 | 31.63 | O |
| ATOM | 559 | C | GLU | A | 206 | 13.829 | 32.035 | 17.579 | 1.00 | 25.79 | C |
| ATOM | 560 | O | GLU | A | 206 | 13.856 | 31.811 | 16.380 | 1.00 | 26.03 | O |
| ATOM | 561 | N | LYS | A | 207 | 13.146 | 31.280 | 18.429 | 1.00 | 26.79 | N |
| ATOM | 562 | CA | LYS | A | 207 | 12.285 | 30.179 | 17.980 | 1.00 | 28.27 | C |
| ATOM | 563 | CB | LYS | A | 207 | 11.579 | 29.534 | 19.175 | 1.00 | 31.82 | C |
| ATOM | 564 | CG | LYS | A | 207 | 11.065 | 28.104 | 18.962 | 1.00 | 36.66 | C |
| ATOM | 565 | CD | LYS | A | 207 | 9.626 | 27.911 | 19.495 | 1.00 | 41.28 | C |
| ATOM | 566 | CE | LYS | A | 207 | 9.473 | 26.788 | 20.522 | 1.00 | 43.03 | C |
| ATOM | 567 | NZ | LYS | A | 207 | 9.906 | 25.448 | 20.034 | 1.00 | 43.26 | N |
| ATOM | 568 | C | LYS | A | 207 | 11.238 | 30.702 | 16.998 | 1.00 | 25.96 | C |

TABLE 1-continued structure data for residues 36-207 of SEQ ID NO: 3

| ATOM | 569 | O | LYS | A | 207 | 11.046 | 30.146 | 15.936 | 1.00 | 29.44 | O |
|---|---|---|---|---|---|---|---|---|---|---|---|
| ATOM | 570 | N | LEU | A | 208 | 10.592 | 31.790 | 17.364 | 1.00 | 22.79 | N |
| ATOM | 571 | CA | LEU | A | 208 | 9.614 | 32.451 | 16.539 | 1.00 | 22.70 | C |
| ATOM | 572 | CB | LEU | A | 208 | 9.140 | 33.678 | 17.297 | 1.00 | 24.46 | C |
| ATOM | 573 | CG | LEU | A | 208 | 7.935 | 34.483 | 16.824 | 1.00 | 25.67 | C |
| ATOM | 574 | CD1 | LEU | A | 208 | 6.709 | 33.589 | 16.704 | 1.00 | 27.21 | C |
| ATOM | 575 | CD2 | LEU | A | 208 | 7.664 | 35.614 | 17.813 | 1.00 | 24.18 | C |
| ATOM | 576 | C | LEU | A | 208 | 10.209 | 32.910 | 15.228 | 1.00 | 23.38 | C |
| ATOM | 577 | O | LEU | A | 208 | 9.582 | 32.809 | 14.166 | 1.00 | 22.17 | O |
| ATOM | 578 | N | PHE | A | 209 | 11.428 | 33.448 | 15.310 | 1.00 | 22.96 | N |
| ATOM | 579 | CA | PHE | A | 209 | 12.155 | 33.848 | 14.125 | 1.00 | 21.38 | C |
| ATOM | 580 | CB | PHE | A | 209 | 13.441 | 34.545 | 14.499 | 1.00 | 20.14 | C |
| ATOM | 581 | CG | PHE | A | 209 | 14.305 | 34.910 | 13.323 | 1.00 | 19.62 | C |
| ATOM | 582 | CD1 | PHE | A | 209 | 14.039 | 36.039 | 12.579 | 1.00 | 20.07 | C |
| ATOM | 583 | CE1 | PHE | A | 209 | 14.839 | 36.377 | 11.484 | 1.00 | 20.95 | C |
| ATOM | 584 | CZ | PHE | A | 209 | 15.963 | 35.614 | 11.180 | 1.00 | 20.18 | C |
| ATOM | 585 | CE2 | PHE | A | 209 | 16.252 | 34.491 | 11.942 | 1.00 | 19.63 | C |
| ATOM | 586 | CD2 | PHE | A | 209 | 15.421 | 34.143 | 12.993 | 1.00 | 19.25 | C |
| ATOM | 587 | C | PHE | A | 209 | 12.405 | 32.648 | 13.208 | 1.00 | 21.95 | C |
| ATOM | 588 | O | PHE | A | 209 | 12.086 | 32.707 | 12.017 | 1.00 | 21.67 | O |
| ATOM | 589 | N | ASN | A | 210 | 12.939 | 31.556 | 13.739 | 1.00 | 22.38 | N |
| ATOM | 590 | CA | ASN | A | 210 | 13.155 | 30.362 | 12.905 | 1.00 | 23.62 | C |
| ATOM | 591 | CB | ASN | A | 210 | 13.749 | 29.238 | 13.730 | 1.00 | 24.71 | C |
| ATOM | 592 | CG | ASN | A | 210 | 15.077 | 29.609 | 14.320 | 1.00 | 27.05 | C |
| ATOM | 593 | OD1 | ASN | A | 210 | 15.465 | 29.114 | 15.391 | 1.00 | 32.03 | O |
| ATOM | 594 | ND2 | ASN | A | 210 | 15.780 | 30.497 | 13.651 | 1.00 | 26.45 | N |
| ATOM | 595 | C | ASN | A | 210 | 11.886 | 29.841 | 12.232 | 1.00 | 23.36 | C |
| ATOM | 596 | O | ASN | A | 210 | 11.930 | 29.268 | 11.145 | 1.00 | 22.20 | O |
| ATOM | 597 | N | GLN | A | 211 | 10.760 | 30.007 | 12.909 | 1.00 | 23.40 | N |
| ATOM | 598 | CA | GLN | A | 211 | 9.502 | 29.619 | 12.340 | 1.00 | 23.37 | C |
| ATOM | 599 | CB | GLN | A | 211 | 8.430 | 29.597 | 13.412 | 1.00 | 24.77 | C |
| ATOM | 600 | CG | GLN | A | 211 | 8.474 | 28.335 | 14.247 | 1.00 | 26.40 | C |
| ATOM | 601 | CD | GLN | A | 211 | 7.545 | 28.395 | 15.448 | 1.00 | 29.75 | C |
| ATOM | 602 | OE1 | GLN | A | 211 | 6.555 | 29.151 | 15.474 | 1.00 | 32.61 | O |
| ATOM | 603 | NE2 | GLN | A | 211 | 7.853 | 27.594 | 16.453 | 1.00 | 31.32 | N |
| ATOM | 604 | C | GLN | A | 211 | 9.138 | 30.549 | 11.186 | 1.00 | 22.06 | C |
| ATOM | 605 | O | GLN | A | 211 | 8.727 | 30.084 | 10.129 | 1.00 | 22.00 | O |
| ATOM | 606 | N | ASP | A | 212 | 9.311 | 31.847 | 11.384 | 1.00 | 20.80 | N |
| ATOM | 607 | CA | ASP | A | 212 | 9.102 | 32.801 | 10.317 | 1.00 | 21.73 | C |
| ATOM | 608 | CB | ASP | A | 212 | 9.334 | 34.217 | 10.819 | 1.00 | 23.70 | C |
| ATOM | 609 | CG | ASP | A | 212 | 8.229 | 34.717 | 11.718 | 1.00 | 25.31 | C |
| ATOM | 610 | OD1 | ASP | A | 212 | 7.118 | 34.106 | 11.755 | 1.00 | 30.69 | O |
| ATOM | 611 | OD2 | ASP | A | 212 | 8.455 | 35.763 | 12.370 | 1.00 | 25.15 | O |
| ATOM | 612 | C | ASP | A | 212 | 10.013 | 32.577 | 9.111 | 1.00 | 21.79 | C |
| ATOM | 613 | O | ASP | A | 212 | 9.582 | 32.753 | 7.969 | 1.00 | 23.85 | O |
| ATOM | 614 | N | VAL | A | 213 | 11.270 | 32.215 | 9.349 | 1.00 | 20.29 | N |
| ATOM | 615 | CA | VAL | A | 213 | 12.187 | 31.933 | 8.255 | 1.00 | 19.12 | C |
| ATOM | 616 | CB | VAL | A | 213 | 13.645 | 31.770 | 8.753 | 1.00 | 18.94 | C |
| ATOM | 617 | CG1 | VAL | A | 213 | 14.548 | 31.130 | 7.690 | 1.00 | 18.87 | C |
| ATOM | 618 | CG2 | VAL | A | 213 | 14.194 | 33.114 | 9.191 | 1.00 | 18.74 | C |
| ATOM | 619 | C | VAL | A | 213 | 11.713 | 30.686 | 7.521 | 1.00 | 18.88 | C |
| ATOM | 620 | O | VAL | A | 213 | 11.707 | 30.660 | 6.302 | 1.00 | 18.55 | O |
| ATOM | 621 | N | ASP | A | 214 | 11.317 | 29.656 | 8.259 | 1.00 | 19.22 | N |
| ATOM | 622 | CA | ASP | A | 214 | 10.807 | 28.449 | 7.632 | 1.00 | 20.01 | C |
| ATOM | 623 | CB | ASP | A | 214 | 10.491 | 27.366 | 8.653 | 1.00 | 21.44 | C |
| ATOM | 624 | CG | ASP | A | 214 | 11.742 | 26.686 | 9.187 | 1.00 | 22.62 | C |
| ATOM | 625 | OD1 | ASP | A | 214 | 12.810 | 26.914 | 8.581 | 1.00 | 24.78 | O |
| ATOM | 626 | OD2 | ASP | A | 214 | 11.663 | 25.910 | 10.184 | 1.00 | 23.69 | O |
| ATOM | 627 | C | ASP | A | 214 | 9.569 | 28.714 | 6.818 | 1.00 | 19.61 | C |
| ATOM | 628 | O | ASP | A | 214 | 9.380 | 28.086 | 5.784 | 1.00 | 21.07 | O |
| ATOM | 629 | N | ALA | A | 215 | 8.726 | 29.632 | 7.267 | 1.00 | 18.15 | N |
| ATOM | 630 | CA | ALA | A | 215 | 7.518 | 29.968 | 6.509 | 1.00 | 17.43 | C |
| ATOM | 631 | CB | ALA | A | 215 | 6.548 | 30.763 | 7.373 | 1.00 | 16.47 | C |
| ATOM | 632 | C | ALA | A | 215 | 7.880 | 30.736 | 5.225 | 1.00 | 17.21 | C |
| ATOM | 633 | O | ALA | A | 215 | 7.392 | 30.431 | 4.147 | 1.00 | 17.31 | O |
| ATOM | 634 | N | ALA | A | 216 | 8.757 | 31.722 | 5.331 | 1.00 | 17.64 | N |
| ATOM | 635 | CA | ALA | A | 216 | 9.208 | 32.461 | 4.141 | 1.00 | 17.67 | C |
| ATOM | 636 | CB | ALA | A | 216 | 10.267 | 33.478 | 4.517 | 1.00 | 17.22 | C |
| ATOM | 637 | C | ALA | A | 216 | 9.739 | 31.525 | 3.059 | 1.00 | 18.03 | C |
| ATOM | 638 | O | ALA | A | 216 | 9.536 | 31.754 | 1.843 | 1.00 | 17.62 | O |
| ATOM | 639 | N | VAL | A | 217 | 10.418 | 30.466 | 3.498 | 1.00 | 18.12 | N |
| ATOM | 640 | CA | VAL | A | 217 | 11.022 | 29.532 | 2.562 | 1.00 | 18.68 | C |
| ATOM | 641 | CB | VAL | A | 217 | 12.208 | 28.780 | 3.216 | 1.00 | 19.18 | C |
| ATOM | 642 | CG1 | VAL | A | 217 | 12.810 | 27.755 | 2.272 | 1.00 | 19.87 | C |
| ATOM | 643 | CG2 | VAL | A | 217 | 13.296 | 29.773 | 3.588 | 1.00 | 19.03 | C |
| ATOM | 644 | C | VAL | A | 217 | 9.976 | 28.616 | 1.932 | 1.00 | 18.07 | C |
| ATOM | 645 | O | VAL | A | 217 | 10.023 | 28.350 | 0.752 | 1.00 | 17.53 | O |
| ATOM | 646 | N | ARG | A | 218 | 9.022 | 28.150 | 2.718 | 1.00 | 19.51 | N |

TABLE 1-continued structure data for residues 36-207 of SEQ ID NO: 3

| ATOM | 647 | CA | ARG | A | 218 | 7.973 | 27.286 | 2.201 | 1.00 | 20.44 | C |
|---|---|---|---|---|---|---|---|---|---|---|---|
| ATOM | 648 | CB | ARG | A | 218 | 7.045 | 26.763 | 3.319 | 1.00 | 22.11 | C |
| ATOM | 649 | CG | ARG | A | 218 | 7.513 | 25.415 | 3.878 | 1.00 | 24.33 | C |
| ATOM | 650 | CD | ARG | A | 218 | 6.582 | 24.813 | 4.914 | 1.00 | 25.73 | C |
| ATOM | 651 | NE | ARG | A | 218 | 6.349 | 25.803 | 5.951 | 1.00 | 27.95 | N |
| ATOM | 652 | CZ | ARG | A | 218 | 6.924 | 25.826 | 7.149 | 1.00 | 29.44 | C |
| ATOM | 653 | NH1 | ARG | A | 218 | 7.772 | 24.864 | 7.547 | 1.00 | 32.28 | N |
| ATOM | 654 | NH2 | ARG | A | 218 | 6.635 | 26.835 | 7.961 | 1.00 | 29.32 | N |
| ATOM | 655 | C | ARG | A | 218 | 7.211 | 28.079 | 1.166 | 1.00 | 19.81 | C |
| ATOM | 656 | O | ARG | A | 218 | 6.912 | 27.584 | 0.092 | 1.00 | 19.74 | O |
| ATOM | 657 | N | GLY | A | 219 | 6.964 | 29.338 | 1.475 | 1.00 | 19.34 | N |
| ATOM | 658 | CA | GLY | A | 219 | 6.295 | 30.211 | 0.557 | 1.00 | 19.42 | C |
| ATOM | 659 | C | GLY | A | 219 | 7.056 | 30.421 | −0.719 | 1.00 | 20.15 | C |
| ATOM | 660 | O | GLY | A | 219 | 6.503 | 30.278 | −1.790 | 1.00 | 23.87 | O |
| ATOM | 661 | N | ILE | A | 220 | 8.328 | 30.763 | −0.607 | 1.00 | 21.21 | N |
| ATOM | 662 | CA | ILE | A | 220 | 9.161 | 31.026 | −1.756 | 1.00 | 21.81 | C |
| ATOM | 663 | CB | ILE | A | 220 | 10.592 | 31.364 | −1.287 | 1.00 | 23.04 | C |
| ATOM | 664 | CG1 | ILE | A | 220 | 10.655 | 32.844 | −0.917 | 1.00 | 24.51 | C |
| ATOM | 665 | CD1 | ILE | A | 220 | 11.797 | 33.163 | 0.034 | 1.00 | 26.80 | C |
| ATOM | 666 | CG2 | ILE | A | 220 | 11.651 | 31.019 | −2.331 | 1.00 | 21.99 | C |
| ATOM | 667 | C | ILE | A | 220 | 9.164 | 29.854 | −2.731 | 1.00 | 22.39 | C |
| ATOM | 668 | O | ILE | A | 220 | 9.053 | 30.051 | −3.957 | 1.00 | 22.15 | O |
| ATOM | 669 | N | LEU | A | 221 | 9.272 | 28.638 | −2.197 | 1.00 | 22.45 | N |
| ATOM | 670 | CA | LEU | A | 221 | 9.362 | 27.447 | −3.054 | 1.00 | 23.16 | C |
| ATOM | 671 | CB | LEU | A | 221 | 9.898 | 26.261 | −2.255 | 1.00 | 23.21 | C |
| ATOM | 672 | CG | LEU | A | 221 | 11.253 | 26.355 | −1.590 | 1.00 | 23.23 | C |
| ATOM | 673 | CD1 | LEU | A | 221 | 11.431 | 25.155 | −0.686 | 1.00 | 23.08 | C |
| ATOM | 674 | CD2 | LEU | A | 221 | 12.355 | 26.425 | −2.625 | 1.00 | 23.33 | C |
| ATOM | 675 | C | LEU | A | 221 | 8.006 | 27.054 | −3.671 | 1.00 | 22.15 | C |
| ATOM | 676 | O | LEU | A | 221 | 7.938 | 26.192 | −4.541 | 1.00 | 19.88 | O |
| ATOM | 677 | N | ARG | A | 222 | 6.934 | 27.646 | −3.164 | 1.00 | 23.14 | N |
| ATOM | 678 | CA | ARG | A | 222 | 5.607 | 27.458 | −3.733 | 1.00 | 24.54 | C |
| ATOM | 679 | CB | ARG | A | 222 | 4.599 | 27.210 | −2.621 | 1.00 | 25.73 | C |
| ATOM | 680 | CG | ARG | A | 222 | 4.835 | 25.851 | −1.966 | 1.00 | 28.65 | C |
| ATOM | 681 | CD | ARG | A | 222 | 3.592 | 25.223 | −1.372 | 1.00 | 31.30 | C |
| ATOM | 682 | NE | ARG | A | 222 | 3.627 | 25.068 | 0.084 | 1.00 | 35.62 | N |
| ATOM | 683 | CZ | ARG | A | 222 | 3.528 | 26.058 | 0.986 | 1.00 | 41.07 | C |
| ATOM | 684 | NH1 | ARG | A | 222 | 3.430 | 27.345 | 0.615 | 1.00 | 42.76 | N |
| ATOM | 685 | NH2 | ARG | A | 222 | 3.545 | 25.762 | 2.291 | 1.00 | 40.43 | N |
| ATOM | 686 | C | ARG | A | 222 | 5.223 | 28.640 | −4.600 | 1.00 | 23.66 | C |
| ATOM | 687 | O | ARG | A | 222 | 4.068 | 28.802 | −4.969 | 1.00 | 26.31 | O |
| ATOM | 688 | N | ASN | A | 223 | 6.206 | 29.460 | −4.938 | 1.00 | 21.80 | N |
| ATOM | 689 | CA | ASN | A | 223 | 6.014 | 30.570 | −5.831 | 1.00 | 21.09 | C |
| ATOM | 690 | CB | ASN | A | 223 | 6.418 | 31.834 | −5.119 | 1.00 | 20.94 | C |
| ATOM | 691 | CG | ASN | A | 223 | 6.128 | 33.054 | −5.934 | 1.00 | 21.82 | C |
| ATOM | 692 | OD1 | ASN | A | 223 | 6.553 | 33.161 | −7.088 | 1.00 | 23.26 | O |
| ATOM | 693 | ND2 | ASN | A | 223 | 5.390 | 33.984 | −5.356 | 1.00 | 22.12 | N |
| ATOM | 694 | C | ASN | A | 223 | 6.838 | 30.385 | −7.113 | 1.00 | 21.61 | C |
| ATOM | 695 | O | ASN | A | 223 | 8.069 | 30.249 | −7.075 | 1.00 | 22.23 | O |
| ATOM | 696 | N | ALA | A | 224 | 6.172 | 30.371 | −8.251 | 1.00 | 21.19 | N |
| ATOM | 697 | CA | ALA | A | 224 | 6.839 | 29.996 | −9.472 | 1.00 | 22.05 | C |
| ATOM | 698 | CB | ALA | A | 224 | 5.832 | 29.662 | −10.565 | 1.00 | 21.08 | C |
| ATOM | 699 | C | ALA | A | 224 | 7.811 | 31.065 | −9.940 | 1.00 | 23.35 | C |
| ATOM | 700 | O | ALA | A | 224 | 8.700 | 30.755 | −10.738 | 1.00 | 23.35 | O |
| ATOM | 701 | N | LYS | A | 225 | 7.639 | 32.305 | −9.463 | 1.00 | 25.59 | N |
| ATOM | 702 | CA | LYS | A | 225 | 8.592 | 33.412 | −9.744 | 1.00 | 27.70 | C |
| ATOM | 703 | CB | LYS | A | 225 | 7.927 | 34.784 | −9.573 | 1.00 | 31.18 | C |
| ATOM | 704 | CG | LYS | A | 225 | 6.771 | 35.092 | −10.511 | 1.00 | 34.48 | C |
| ATOM | 705 | CD | LYS | A | 225 | 7.216 | 35.267 | −11.956 | 1.00 | 38.79 | C |
| ATOM | 706 | CE | LYS | A | 225 | 6.634 | 34.220 | −12.915 | 1.00 | 42.23 | C |
| ATOM | 707 | NZ | LYS | A | 225 | 7.508 | 34.048 | −14.129 | 1.00 | 44.21 | N |
| ATOM | 708 | C | LYS | A | 225 | 9.840 | 33.399 | −8.858 | 1.00 | 25.43 | C |
| ATOM | 709 | O | LYS | A | 225 | 10.913 | 33.717 | −9.329 | 1.00 | 28.80 | O |
| ATOM | 710 | N | LEU | A | 226 | 9.698 | 33.029 | −7.587 | 1.00 | 23.55 | N |
| ATOM | 711 | CA | LEU | A | 226 | 10.803 | 33.054 | −6.615 | 1.00 | 21.85 | C |
| ATOM | 712 | CB | LEU | A | 226 | 10.247 | 33.390 | −5.237 | 1.00 | 21.58 | C |
| ATOM | 713 | CG | LEU | A | 226 | 9.530 | 34.734 | −5.137 | 1.00 | 21.66 | C |
| ATOM | 714 | CD1 | LEU | A | 226 | 8.949 | 34.976 | −3.753 | 1.00 | 21.26 | C |
| ATOM | 715 | CD2 | LEU | A | 226 | 10.480 | 35.861 | −5.486 | 1.00 | 21.74 | C |
| ATOM | 716 | C | LEU | A | 226 | 11.611 | 31.771 | −6.487 | 1.00 | 20.55 | C |
| ATOM | 717 | O | LEU | A | 226 | 12.771 | 31.819 | −6.182 | 1.00 | 20.58 | O |
| ATOM | 718 | N | LYS | A | 227 | 10.982 | 30.630 | −6.686 | 1.00 | 20.44 | N |
| ATOM | 719 | CA | LYS | A | 227 | 11.617 | 29.333 | −6.511 | 1.00 | 20.42 | C |
| ATOM | 720 | CB | LYS | A | 227 | 10.590 | 28.231 | −6.789 | 1.00 | 21.43 | C |
| ATOM | 721 | CG | LYS | A | 227 | 11.144 | 26.841 | −7.059 | 1.00 | 22.66 | C |
| ATOM | 722 | CD | LYS | A | 227 | 10.192 | 25.749 | −6.563 | 1.00 | 23.81 | C |
| ATOM | 723 | CE | LYS | A | 227 | 10.560 | 24.354 | −7.066 | 1.00 | 24.76 | C |
| ATOM | 724 | NZ | LYS | A | 227 | 11.977 | 23.990 | −6.731 | 1.00 | 26.54 | N |

TABLE 1-continued structure data for residues 36-207 of SEQ ID NO: 3

| ATOM | 725 | C | LYS | A | 227 | 12.845 | 29.122 | −7.384 | 1.00 | 20.33 | C |
|---|---|---|---|---|---|---|---|---|---|---|---|
| ATOM | 726 | O | LYS | A | 227 | 13.845 | 28.625 | −6.929 | 1.00 | 19.19 | O |
| ATOM | 727 | N | PRO | A | 228 | 12.753 | 29.434 | −8.669 | 1.00 | 20.58 | N |
| ATOM | 728 | CA | PRO | A | 228 | 13.956 | 29.101 | −9.453 | 1.00 | 20.08 | C |
| ATOM | 729 | CB | PRO | A | 228 | 13.543 | 29.401 | −10.897 | 1.00 | 19.47 | C |
| ATOM | 730 | CG | PRO | A | 228 | 12.095 | 29.808 | −10.872 | 1.00 | 19.40 | C |
| ATOM | 731 | CD | PRO | A | 228 | 11.546 | 29.600 | −9.498 | 1.00 | 19.51 | C |
| ATOM | 732 | C | PRO | A | 228 | 15.168 | 29.940 | −9.053 | 1.00 | 21.31 | C |
| ATOM | 733 | O | PRO | A | 228 | 16.326 | 29.476 | −9.131 | 1.00 | 20.31 | O |
| ATOM | 734 | N | VAL | A | 229 | 14.882 | 31.168 | −8.624 | 1.00 | 21.71 | N |
| ATOM | 735 | CA | VAL | A | 229 | 15.903 | 32.137 | −8.230 | 1.00 | 21.49 | C |
| ATOM | 736 | CB | VAL | A | 229 | 15.282 | 33.527 | −8.048 | 1.00 | 21.49 | C |
| ATOM | 737 | CG1 | VAL | A | 229 | 16.293 | 34.558 | −7.627 | 1.00 | 21.22 | C |
| ATOM | 738 | CG2 | VAL | A | 229 | 14.648 | 33.964 | −9.343 | 1.00 | 23.12 | C |
| ATOM | 739 | C | VAL | A | 229 | 16.503 | 31.696 | −6.921 | 1.00 | 21.30 | C |
| ATOM | 740 | O | VAL | A | 229 | 17.733 | 31.570 | −6.789 | 1.00 | 23.59 | O |
| ATOM | 741 | N | TYR | A | 230 | 15.626 | 31.460 | −5.961 | 1.00 | 19.78 | N |
| ATOM | 742 | CA | TYR | A | 230 | 16.021 | 31.002 | −4.643 | 1.00 | 19.43 | C |
| ATOM | 743 | CB | TYR | A | 230 | 14.789 | 30.840 | −3.723 | 1.00 | 18.22 | C |
| ATOM | 744 | CG | TYR | A | 230 | 15.124 | 30.479 | −2.303 | 1.00 | 16.57 | C |
| ATOM | 745 | CD1 | TYR | A | 230 | 15.335 | 31.455 | −1.364 | 1.00 | 15.91 | C |
| ATOM | 746 | CE1 | TYR | A | 230 | 15.650 | 31.129 | −0.061 | 1.00 | 15.79 | C |
| ATOM | 747 | CZ | TYR | A | 230 | 15.750 | 29.809 | 0.319 | 1.00 | 16.39 | C |
| ATOM | 748 | OH | TYR | A | 230 | 16.094 | 29.506 | 1.634 | 1.00 | 17.44 | O |
| ATOM | 749 | CE2 | TYR | A | 230 | 15.541 | 28.806 | −0.604 | 1.00 | 16.17 | C |
| ATOM | 750 | CD2 | TYR | A | 230 | 15.229 | 29.151 | −1.908 | 1.00 | 16.27 | C |
| ATOM | 751 | C | TYR | A | 230 | 16.828 | 29.713 | −4.728 | 1.00 | 20.37 | C |
| ATOM | 752 | O | TYR | A | 230 | 17.847 | 29.610 | −4.072 | 1.00 | 20.80 | O |
| ATOM | 753 | N | ASP | A | 231 | 16.426 | 28.758 | −5.560 | 1.00 | 22.34 | N |
| ATOM | 754 | CA | ASP | A | 231 | 17.191 | 27.507 | −5.674 | 1.00 | 24.95 | C |
| ATOM | 755 | CB | ASP | A | 231 | 16.501 | 26.468 | −6.568 | 1.00 | 27.35 | C |
| ATOM | 756 | CG | ASP | A | 231 | 15.334 | 25.787 | −5.862 | 1.00 | 35.67 | C |
| ATOM | 757 | OD1 | ASP | A | 231 | 15.330 | 25.759 | −4.595 | 1.00 | 43.04 | O |
| ATOM | 758 | OD2 | ASP | A | 231 | 14.389 | 25.307 | −6.551 | 1.00 | 43.52 | O |
| ATOM | 759 | C | ASP | A | 231 | 18.613 | 27.743 | −6.166 | 1.00 | 23.94 | C |
| ATOM | 760 | O | ASP | A | 231 | 19.522 | 27.071 | −5.743 | 1.00 | 24.60 | O |
| ATOM | 761 | N | SER | A | 232 | 18.789 | 28.713 | −7.046 | 1.00 | 21.92 | N |
| ATOM | 762 | CA | SER | A | 232 | 20.045 | 28.953 | −7.691 | 1.00 | 20.30 | C |
| ATOM | 763 | CB | SER | A | 232 | 19.814 | 29.738 | −8.981 | 1.00 | 20.07 | C |
| ATOM | 764 | OG | SER | A | 232 | 19.496 | 31.094 | −8.687 | 1.00 | 20.05 | O |
| ATOM | 765 | C | SER | A | 232 | 20.951 | 29.803 | −6.843 | 1.00 | 19.81 | C |
| ATOM | 766 | O | SER | A | 232 | 22.035 | 30.106 | −7.253 | 1.00 | 21.11 | O |
| ATOM | 767 | N | LEU | A | 233 | 20.505 | 30.219 | −5.678 | 1.00 | 19.64 | N |
| ATOM | 768 | CA | LEU | A | 233 | 21.154 | 31.300 | −4.964 | 1.00 | 18.04 | C |
| ATOM | 769 | CB | LEU | A | 233 | 20.071 | 32.277 | −4.514 | 1.00 | 17.89 | C |
| ATOM | 770 | CG | LEU | A | 233 | 20.270 | 33.777 | −4.626 | 1.00 | 17.73 | C |
| ATOM | 771 | CD1 | LEU | A | 233 | 20.969 | 34.214 | −5.885 | 1.00 | 17.82 | C |
| ATOM | 772 | CD2 | LEU | A | 233 | 18.925 | 34.451 | −4.552 | 1.00 | 18.33 | C |
| ATOM | 773 | C | LEU | A | 233 | 21.888 | 30.696 | −3.783 | 1.00 | 17.45 | C |
| ATOM | 774 | O | LEU | A | 233 | 21.597 | 29.584 | −3.335 | 1.00 | 16.58 | O |
| ATOM | 775 | N | ASP | A | 234 | 22.863 | 31.443 | −3.307 | 1.00 | 17.73 | N |
| ATOM | 776 | CA | ASP | A | 234 | 23.737 | 31.007 | −2.229 | 1.00 | 18.42 | C |
| ATOM | 777 | CB | ASP | A | 234 | 25.136 | 31.653 | −2.350 | 1.00 | 18.89 | C |
| ATOM | 778 | CG | ASP | A | 234 | 25.067 | 33.168 | −2.472 | 1.00 | 20.33 | C |
| ATOM | 779 | OD1 | ASP | A | 234 | 24.908 | 33.851 | −1.425 | 1.00 | 20.21 | O |
| ATOM | 780 | OD2 | ASP | A | 234 | 25.112 | 33.671 | −3.635 | 1.00 | 21.91 | O |
| ATOM | 781 | C | ASP | A | 234 | 23.114 | 31.454 | −0.944 | 1.00 | 17.83 | C |
| ATOM | 782 | O | ASP | A | 234 | 22.394 | 32.422 | −0.935 | 1.00 | 19.99 | O |
| ATOM | 783 | N | ALA | A | 235 | 23.466 | 30.789 | 0.147 | 1.00 | 16.62 | N |
| ATOM | 784 | CA | ALA | A | 235 | 23.007 | 31.110 | 1.472 | 1.00 | 15.40 | C |
| ATOM | 785 | CB | ALA | A | 235 | 23.900 | 30.396 | 2.464 | 1.00 | 15.52 | C |
| ATOM | 786 | C | ALA | A | 235 | 22.927 | 32.590 | 1.814 | 1.00 | 15.22 | C |
| ATOM | 787 | O | ALA | A | 235 | 22.036 | 33.017 | 2.471 | 1.00 | 16.21 | O |
| ATOM | 788 | N | VAL | A | 236 | 23.871 | 33.393 | 1.397 | 1.00 | 15.84 | N |
| ATOM | 789 | CA | VAL | A | 236 | 23.885 | 34.773 | 1.822 | 1.00 | 15.56 | C |
| ATOM | 790 | CB | VAL | A | 236 | 25.265 | 35.419 | 1.594 | 1.00 | 15.35 | C |
| ATOM | 791 | CG1 | VAL | A | 236 | 25.269 | 36.913 | 1.943 | 1.00 | 14.95 | C |
| ATOM | 792 | CG2 | VAL | A | 236 | 26.277 | 34.670 | 2.418 | 1.00 | 15.43 | C |
| ATOM | 793 | C | VAL | A | 236 | 22.866 | 35.545 | 1.071 | 1.00 | 15.68 | C |
| ATOM | 794 | O | VAL | A | 236 | 22.210 | 36.379 | 1.652 | 1.00 | 16.30 | O |
| ATOM | 795 | N | ARG | A | 237 | 22.795 | 35.327 | −0.236 | 1.00 | 16.33 | N |
| ATOM | 796 | CA | ARG | A | 237 | 21.823 | 36.023 | −1.082 | 1.00 | 16.74 | C |
| ATOM | 797 | CB | ARG | A | 237 | 22.193 | 35.853 | −2.542 | 1.00 | 16.86 | C |
| ATOM | 798 | CG | ARG | A | 237 | 23.476 | 36.558 | −2.950 | 1.00 | 17.27 | C |
| ATOM | 799 | CD | ARG | A | 237 | 23.635 | 36.562 | −4.458 | 1.00 | 17.21 | C |
| ATOM | 800 | NE | ARG | A | 237 | 24.678 | 37.476 | −4.877 | 1.00 | 17.60 | N |
| ATOM | 801 | CZ | ARG | A | 237 | 25.988 | 37.191 | −4.865 | 1.00 | 17.24 | C |
| ATOM | 802 | NH1 | ARG | A | 237 | 26.426 | 36.017 | −4.446 | 1.00 | 17.01 | N |

TABLE 1-continued structure data for residues 36-207 of SEQ ID NO: 3

| ATOM | 803 | NH2 | ARG | A | 237 | 26.865 | 38.101 | −5.263 | 1.00 | 17.08 | N |
|---|---|---|---|---|---|---|---|---|---|---|---|
| ATOM | 804 | C | ARG | A | 237 | 20.376 | 35.507 | −0.843 | 1.00 | 16.82 | C |
| ATOM | 805 | O | ARG | A | 237 | 19.407 | 36.236 | −1.028 | 1.00 | 16.68 | O |
| ATOM | 806 | N | ARG | A | 238 | 20.268 | 34.256 | −0.430 | 1.00 | 16.23 | N |
| ATOM | 807 | CA | ARG | A | 238 | 19.019 | 33.686 | 0.046 | 1.00 | 17.23 | C |
| ATOM | 808 | CB | ARG | A | 238 | 19.194 | 32.206 | 0.421 | 1.00 | 16.74 | C |
| ATOM | 809 | CG | ARG | A | 238 | 19.219 | 31.335 | −0.810 | 1.00 | 16.16 | C |
| ATOM | 810 | CD | ARG | A | 238 | 19.209 | 29.894 | −0.426 | 1.00 | 16.33 | C |
| ATOM | 811 | NE | ARG | A | 238 | 19.300 | 29.051 | −1.613 | 1.00 | 16.27 | N |
| ATOM | 812 | CZ | ARG | A | 238 | 19.207 | 27.734 | −1.604 | 1.00 | 16.13 | C |
| ATOM | 813 | NH1 | ARG | A | 238 | 18.981 | 27.083 | −0.486 | 1.00 | 16.49 | N |
| ATOM | 814 | NH2 | ARG | A | 238 | 19.324 | 27.067 | −2.728 | 1.00 | 17.21 | N |
| ATOM | 815 | C | ARG | A | 238 | 18.519 | 34.407 | 1.248 | 1.00 | 17.52 | C |
| ATOM | 816 | O | ARG | A | 238 | 17.338 | 34.678 | 1.366 | 1.00 | 17.14 | O |
| ATOM | 817 | N | ALA | A | 239 | 19.432 | 34.697 | 2.149 | 1.00 | 18.06 | N |
| ATOM | 818 | CA | ALA | A | 239 | 19.108 | 35.460 | 3.323 | 1.00 | 18.51 | C |
| ATOM | 819 | CB | ALA | A | 239 | 20.317 | 35.626 | 4.203 | 1.00 | 18.76 | C |
| ATOM | 820 | C | ALA | A | 239 | 18.637 | 36.788 | 2.896 | 1.00 | 18.52 | C |
| ATOM | 821 | O | ALA | A | 239 | 17.634 | 37.265 | 3.371 | 1.00 | 19.59 | O |
| ATOM | 822 | N | ALA | A | 240 | 19.341 | 37.408 | 1.977 | 1.00 | 18.69 | N |
| ATOM | 823 | CA | ALA | A | 240 | 18.847 | 38.698 | 1.496 | 1.00 | 18.80 | C |
| ATOM | 824 | CB | ALA | A | 240 | 19.709 | 39.234 | 0.382 | 1.00 | 18.07 | C |
| ATOM | 825 | C | ALA | A | 240 | 17.390 | 38.616 | 1.038 | 1.00 | 17.92 | C |
| ATOM | 826 | O | ALA | A | 240 | 16.613 | 39.504 | 1.309 | 1.00 | 17.25 | O |
| ATOM | 827 | N | LEU | A | 241 | 17.045 | 37.546 | 0.342 | 1.00 | 17.70 | N |
| ATOM | 828 | CA | LEU | A | 241 | 15.740 | 37.430 | −0.270 | 1.00 | 18.29 | C |
| ATOM | 829 | CB | LEU | A | 241 | 15.749 | 36.272 | −1.257 | 1.00 | 18.09 | C |
| ATOM | 830 | CG | LEU | A | 241 | 14.600 | 36.324 | −2.239 | 1.00 | 18.56 | C |
| ATOM | 831 | CD1 | LEU | A | 241 | 14.818 | 37.419 | −3.252 | 1.00 | 18.24 | C |
| ATOM | 832 | CD2 | LEU | A | 241 | 14.467 | 34.989 | −2.935 | 1.00 | 19.14 | C |
| ATOM | 833 | C | LEU | A | 241 | 14.641 | 37.240 | 0.808 | 1.00 | 18.23 | C |
| ATOM | 834 | O | LEU | A | 241 | 13.602 | 37.885 | 0.782 | 1.00 | 17.04 | O |
| ATOM | 835 | N | ILE | A | 242 | 14.925 | 36.371 | 1.760 | 1.00 | 18.02 | N |
| ATOM | 836 | CA | ILE | A | 242 | 14.097 | 36.182 | 2.897 | 1.00 | 18.55 | C |
| ATOM | 837 | CB | ILE | A | 242 | 14.683 | 35.116 | 3.810 | 1.00 | 19.28 | C |
| ATOM | 838 | CG1 | ILE | A | 242 | 14.514 | 33.741 | 3.158 | 1.00 | 20.69 | C |
| ATOM | 839 | CD1 | ILE | A | 242 | 15.460 | 32.677 | 3.716 | 1.00 | 21.67 | C |
| ATOM | 840 | CG2 | ILE | A | 242 | 14.032 | 35.109 | 5.184 | 1.00 | 19.32 | C |
| ATOM | 841 | C | ILE | A | 242 | 13.915 | 37.511 | 3.601 | 1.00 | 19.62 | C |
| ATOM | 842 | O | ILE | A | 242 | 12.799 | 37.817 | 4.065 | 1.00 | 22.03 | O |
| ATOM | 843 | N | ASN | A | 243 | 14.941 | 38.347 | 3.610 | 1.00 | 19.43 | N |
| ATOM | 844 | CA | ASN | A | 243 | 14.860 | 39.636 | 4.313 | 1.00 | 20.23 | C |
| ATOM | 845 | CB | ASN | A | 243 | 16.223 | 40.338 | 4.339 | 1.00 | 20.95 | C |
| ATOM | 846 | CG | ASN | A | 243 | 16.219 | 41.658 | 5.082 | 1.00 | 20.65 | C |
| ATOM | 847 | OD1 | ASN | A | 243 | 15.392 | 42.518 | 4.850 | 1.00 | 21.45 | O |
| ATOM | 848 | ND2 | ASN | A | 243 | 17.216 | 41.855 | 5.902 | 1.00 | 21.18 | N |
| ATOM | 849 | C | ASN | A | 243 | 13.790 | 40.495 | 3.694 | 1.00 | 20.18 | C |
| ATOM | 850 | O | ASN | A | 243 | 12.927 | 41.050 | 4.397 | 1.00 | 20.98 | O |
| ATOM | 851 | N | MET | A | 244 | 13.784 | 40.534 | 2.381 | 1.00 | 20.54 | N |
| ATOM | 852 | CA | MET | A | 244 | 12.724 | 41.243 | 1.661 | 1.00 | 20.80 | C |
| ATOM | 853 | CB | MET | A | 244 | 13.018 | 41.252 | 0.161 | 1.00 | 21.36 | C |
| ATOM | 854 | CG | MET | A | 244 | 14.374 | 41.853 | −0.205 | 1.00 | 21.82 | C |
| ATOM | 855 | SD | MET | A | 244 | 14.578 | 42.056 | −1.977 | 1.00 | 24.76 | S |
| ATOM | 856 | CE | MET | A | 244 | 13.578 | 43.478 | −2.339 | 1.00 | 23.81 | C |
| ATOM | 857 | C | MET | A | 244 | 11.339 | 40.648 | 1.929 | 1.00 | 20.94 | C |
| ATOM | 858 | O | MET | A | 244 | 10.337 | 41.366 | 1.915 | 1.00 | 22.53 | O |
| ATOM | 859 | N | VAL | A | 245 | 11.247 | 39.350 | 2.184 | 1.00 | 20.09 | N |
| ATOM | 860 | CA | VAL | A | 245 | 9.927 | 38.752 | 2.366 | 1.00 | 19.93 | C |
| ATOM | 861 | CB | VAL | A | 245 | 9.962 | 37.233 | 2.167 | 1.00 | 18.97 | C |
| ATOM | 862 | CG1 | VAL | A | 245 | 8.621 | 36.636 | 2.573 | 1.00 | 18.56 | C |
| ATOM | 863 | CG2 | VAL | A | 245 | 10.278 | 36.894 | 0.734 | 1.00 | 18.18 | C |
| ATOM | 864 | C | VAL | A | 245 | 9.322 | 39.097 | 3.745 | 1.00 | 20.05 | C |
| ATOM | 865 | O | VAL | A | 245 | 8.140 | 39.304 | 3.870 | 1.00 | 19.28 | O |
| ATOM | 866 | N | PHE | A | 246 | 10.145 | 39.129 | 4.780 | 1.00 | 21.46 | N |
| ATOM | 867 | CA | PHE | A | 246 | 9.734 | 39.674 | 6.075 | 1.00 | 21.15 | C |
| ATOM | 868 | CB | PHE | A | 246 | 10.918 | 39.827 | 7.040 | 1.00 | 21.37 | C |
| ATOM | 869 | CG | PHE | A | 246 | 11.181 | 38.638 | 7.906 | 1.00 | 20.51 | C |
| ATOM | 870 | CD1 | PHE | A | 246 | 11.362 | 37.388 | 7.363 | 1.00 | 20.62 | C |
| ATOM | 871 | CE1 | PHE | A | 246 | 11.630 | 36.301 | 8.164 | 1.00 | 20.23 | C |
| ATOM | 872 | CZ | PHE | A | 246 | 11.725 | 36.461 | 9.522 | 1.00 | 20.13 | C |
| ATOM | 873 | CE2 | PHE | A | 246 | 11.562 | 37.702 | 10.076 | 1.00 | 20.65 | C |
| ATOM | 874 | CD2 | PHE | A | 246 | 11.290 | 38.790 | 9.268 | 1.00 | 20.53 | C |
| ATOM | 875 | C | PHE | A | 246 | 9.236 | 41.070 | 5.853 | 1.00 | 21.35 | C |
| ATOM | 876 | O | PHE | A | 246 | 8.276 | 41.480 | 6.481 | 1.00 | 27.53 | O |
| ATOM | 877 | N | GLN | A | 247 | 9.915 | 41.828 | 5.007 | 1.00 | 20.46 | N |
| ATOM | 878 | CA | GLN | A | 247 | 9.621 | 43.235 | 4.937 | 1.00 | 19.83 | C |
| ATOM | 879 | CB | GLN | A | 247 | 10.725 | 44.066 | 4.300 | 1.00 | 20.12 | C |
| ATOM | 880 | CG | GLN | A | 247 | 10.457 | 45.566 | 4.413 | 1.00 | 20.34 | C |

TABLE 1-continued structure data for residues 36-207 of SEQ ID NO: 3

| ATOM | 881 | CD | GLN | A | 247 | 11.588 | 46.441 | 3.900 | 1.00 | 21.53 | C |
|---|---|---|---|---|---|---|---|---|---|---|---|
| ATOM | 882 | OE1 | GLN | A | 247 | 12.716 | 45.980 | 3.672 | 1.00 | 23.11 | O |
| ATOM | 883 | NE2 | GLN | A | 247 | 11.290 | 47.716 | 3.697 | 1.00 | 21.56 | N |
| ATOM | 884 | C | GLN | A | 247 | 8.350 | 43.495 | 4.195 | 1.00 | 18.90 | C |
| ATOM | 885 | O | GLN | A | 247 | 7.626 | 44.361 | 4.612 | 1.00 | 17.95 | O |
| ATOM | 886 | N | MET | A | 248 | 8.107 | 42.795 | 3.090 | 1.00 | 18.67 | N |
| ATOM | 887 | CA | MET | A | 248 | 7.012 | 43.169 | 2.171 | 1.00 | 19.06 | C |
| ATOM | 888 | CB | MET | A | 248 | 7.542 | 44.005 | 0.988 | 1.00 | 19.09 | C |
| ATOM | 889 | CG | MET | A | 248 | 8.819 | 43.495 | 0.377 | 1.00 | 20.62 | C |
| ATOM | 890 | SD | MET | A | 248 | 9.401 | 44.436 | −1.055 | 1.00 | 20.66 | S |
| ATOM | 891 | CE | MET | A | 248 | 8.676 | 43.429 | −2.301 | 1.00 | 20.26 | C |
| ATOM | 892 | C | MET | A | 248 | 6.092 | 42.036 | 1.669 | 1.00 | 19.08 | C |
| ATOM | 893 | O | MET | A | 248 | 5.033 | 42.310 | 1.062 | 1.00 | 19.62 | O |
| ATOM | 894 | N | GLY | A | 249 | 6.469 | 40.793 | 1.943 | 1.00 | 18.93 | N |
| ATOM | 895 | CA | GLY | A | 249 | 5.649 | 39.642 | 1.628 | 1.00 | 19.79 | C |
| ATOM | 896 | C | GLY | A | 249 | 6.032 | 39.079 | 0.287 | 1.00 | 21.03 | C |
| ATOM | 897 | O | GLY | A | 249 | 6.517 | 39.801 | −0.584 | 1.00 | 22.31 | O |
| ATOM | 898 | N | GLU | A | 250 | 5.767 | 37.796 | 0.098 | 1.00 | 21.80 | N |
| ATOM | 899 | CA | GLU | A | 250 | 6.271 | 37.081 | −1.065 | 1.00 | 23.02 | C |
| ATOM | 900 | CB | GLU | A | 250 | 5.756 | 35.671 | −1.127 | 1.00 | 26.72 | C |
| ATOM | 901 | CG | GLU | A | 250 | 5.714 | 35.079 | 0.254 | 1.00 | 35.52 | C |
| ATOM | 902 | CD | GLU | A | 250 | 6.184 | 33.662 | 0.266 | 1.00 | 44.94 | C |
| ATOM | 903 | OE1 | GLU | A | 250 | 6.047 | 33.037 | −0.849 | 1.00 | 46.03 | O |
| ATOM | 904 | OE2 | GLU | A | 250 | 6.675 | 33.232 | 1.381 | 1.00 | 43.89 | O |
| ATOM | 905 | C | GLU | A | 250 | 5.812 | 37.730 | −2.291 | 1.00 | 21.27 | C |
| ATOM | 906 | O | GLU | A | 250 | 6.537 | 37.811 | −3.269 | 1.00 | 21.94 | O |
| ATOM | 907 | N | THR | A | 251 | 4.578 | 38.181 | −2.281 | 1.00 | 18.96 | N |
| ATOM | 908 | CA | THR | A | 251 | 4.055 | 38.612 | −3.546 | 1.00 | 17.99 | C |
| ATOM | 909 | CB | THR | A | 251 | 2.513 | 38.563 | −3.682 | 1.00 | 17.19 | C |
| ATOM | 910 | OG1 | THR | A | 251 | 2.096 | 39.717 | −4.380 | 1.00 | 16.04 | O |
| ATOM | 911 | CG2 | THR | A | 251 | 1.836 | 38.530 | −2.373 | 1.00 | 17.15 | C |
| ATOM | 912 | C | THR | A | 251 | 4.720 | 39.919 | −3.935 | 1.00 | 16.83 | C |
| ATOM | 913 | O | THR | A | 251 | 5.114 | 40.058 | −5.051 | 1.00 | 18.36 | O |
| ATOM | 914 | N | GLY | A | 252 | 4.926 | 40.832 | −3.008 | 1.00 | 16.05 | N |
| ATOM | 915 | CA | GLY | A | 252 | 5.666 | 42.050 | −3.295 | 1.00 | 15.68 | C |
| ATOM | 916 | C | GLY | A | 252 | 7.070 | 41.719 | −3.793 | 1.00 | 16.25 | C |
| ATOM | 917 | O | GLY | A | 252 | 7.526 | 42.255 | −4.796 | 1.00 | 15.71 | O |
| ATOM | 918 | N | VAL | A | 253 | 7.778 | 40.831 | −3.104 | 1.00 | 16.31 | N |
| ATOM | 919 | CA | VAL | A | 253 | 9.125 | 40.487 | −3.554 | 1.00 | 16.54 | C |
| ATOM | 920 | CB | VAL | A | 253 | 9.828 | 39.546 | −2.579 | 1.00 | 16.48 | C |
| ATOM | 921 | CG1 | VAL | A | 253 | 11.115 | 39.026 | −3.172 | 1.00 | 16.62 | C |
| ATOM | 922 | CG2 | VAL | A | 253 | 10.098 | 40.274 | −1.279 | 1.00 | 16.67 | C |
| ATOM | 923 | C | VAL | A | 253 | 9.079 | 39.885 | −4.950 | 1.00 | 16.45 | C |
| ATOM | 924 | O | VAL | A | 253 | 9.962 | 40.148 | −5.756 | 1.00 | 16.24 | O |
| ATOM | 925 | N | ALA | A | 254 | 8.027 | 39.133 | −5.251 | 1.00 | 16.79 | N |
| ATOM | 926 | CA | ALA | A | 254 | 7.918 | 38.466 | −6.548 | 1.00 | 16.85 | C |
| ATOM | 927 | CB | ALA | A | 254 | 6.845 | 37.391 | −6.530 | 1.00 | 16.50 | C |
| ATOM | 928 | C | ALA | A | 254 | 7.652 | 39.444 | −7.665 | 1.00 | 16.79 | C |
| ATOM | 929 | O | ALA | A | 254 | 7.812 | 39.091 | −8.842 | 1.00 | 18.68 | O |
| ATOM | 930 | N | GLY | A | 255 | 7.287 | 40.672 | −7.316 | 1.00 | 15.82 | N |
| ATOM | 931 | CA | GLY | A | 255 | 7.076 | 41.697 | −8.316 | 1.00 | 16.18 | C |
| ATOM | 932 | C | GLY | A | 255 | 8.290 | 42.116 | −9.126 | 1.00 | 17.33 | C |
| ATOM | 933 | O | GLY | A | 255 | 8.121 | 42.581 | −10.236 | 1.00 | 18.06 | O |
| ATOM | 934 | N | PHE | A | 256 | 9.505 | 41.941 | −8.594 | 1.00 | 17.97 | N |
| ATOM | 935 | CA | PHE | A | 256 | 10.719 | 42.455 | −9.208 | 1.00 | 18.24 | C |
| ATOM | 936 | CB | PHE | A | 256 | 11.808 | 42.721 | −8.163 | 1.00 | 17.76 | C |
| ATOM | 937 | CG | PHE | A | 256 | 11.476 | 43.823 | −7.188 | 1.00 | 17.26 | C |
| ATOM | 938 | CD1 | PHE | A | 256 | 11.433 | 45.145 | −7.605 | 1.00 | 17.00 | C |
| ATOM | 939 | CE1 | PHE | A | 256 | 11.130 | 46.166 | −6.725 | 1.00 | 16.32 | C |
| ATOM | 940 | CZ | PHE | A | 256 | 10.858 | 45.871 | −5.413 | 1.00 | 16.67 | C |
| ATOM | 941 | CE2 | PHE | A | 256 | 10.896 | 44.556 | −4.974 | 1.00 | 16.65 | C |
| ATOM | 942 | CD2 | PHE | A | 256 | 11.200 | 43.539 | −5.860 | 1.00 | 17.05 | C |
| ATOM | 943 | C | PHE | A | 256 | 11.216 | 41.447 | −10.217 | 1.00 | 20.07 | C |
| ATOM | 944 | O | PHE | A | 256 | 12.331 | 40.978 | −10.135 | 1.00 | 20.00 | O |
| ATOM | 945 | N | THR | A | 257 | 10.385 | 41.164 | −11.216 | 1.00 | 22.23 | N |
| ATOM | 946 | CA | THR | A | 257 | 10.626 | 40.057 | −12.145 | 1.00 | 22.31 | C |
| ATOM | 947 | CB | THR | A | 257 | 9.599 | 40.033 | −13.286 | 1.00 | 22.32 | C |
| ATOM | 948 | OG1 | THR | A | 257 | 9.683 | 41.254 | −14.025 | 1.00 | 22.96 | O |
| ATOM | 949 | CG2 | THR | A | 257 | 8.179 | 39.874 | −12.748 | 1.00 | 23.30 | C |
| ATOM | 950 | C | THR | A | 257 | 11.972 | 40.192 | −12.782 | 1.00 | 22.05 | C |
| ATOM | 951 | O | THR | A | 257 | 12.633 | 39.202 | −13.081 | 1.00 | 21.97 | O |
| ATOM | 952 | N | ASN | A | 258 | 12.365 | 41.430 | −13.010 | 1.00 | 21.62 | N |
| ATOM | 953 | CA | ASN | A | 258 | 13.534 | 41.673 | −13.796 | 1.00 | 23.43 | C |
| ATOM | 954 | CB | ASN | A | 258 | 13.403 | 43.041 | −14.411 | 1.00 | 24.08 | C |
| ATOM | 955 | CG | ASN | A | 258 | 14.337 | 43.237 | −15.549 | 1.00 | 25.18 | C |
| ATOM | 956 | OD1 | ASN | A | 258 | 14.182 | 42.647 | −16.624 | 1.00 | 24.71 | O |
| ATOM | 957 | ND2 | ASN | A | 258 | 15.336 | 44.054 | −15.318 | 1.00 | 27.31 | N |
| ATOM | 958 | C | ASN | A | 258 | 14.837 | 41.542 | −12.968 | 1.00 | 24.22 | C |

TABLE 1-continued structure data for residues 36-207 of SEQ ID NO: 3

| ATOM | 959 | O | ASN | A | 258 | 15.721 | 40.761 | −13.310 | 1.00 | 24.24 | O |
|---|---|---|---|---|---|---|---|---|---|---|---|
| ATOM | 960 | N | SER | A | 259 | 14.936 | 42.305 | −11.882 | 1.00 | 23.43 | N |
| ATOM | 961 | CA | SER | A | 259 | 15.964 | 42.095 | −10.895 | 1.00 | 23.46 | C |
| ATOM | 962 | CB | SER | A | 259 | 15.661 | 42.883 | −9.616 | 1.00 | 22.75 | C |
| ATOM | 963 | OG | SER | A | 259 | 15.548 | 44.274 | −9.894 | 1.00 | 22.24 | O |
| ATOM | 964 | C | SER | A | 259 | 16.080 | 40.610 | −10.582 | 1.00 | 24.13 | C |
| ATOM | 965 | O | SER | A | 259 | 17.183 | 40.095 | −10.495 | 1.00 | 25.38 | O |
| ATOM | 966 | N | LEU | A | 260 | 14.959 | 39.917 | −10.443 | 1.00 | 24.43 | N |
| ATOM | 967 | CA | LEU | A | 260 | 14.984 | 38.496 | −10.087 | 1.00 | 25.02 | C |
| ATOM | 968 | CB | LEU | A | 260 | 13.573 | 37.955 | −9.841 | 1.00 | 24.55 | C |
| ATOM | 969 | CG | LEU | A | 260 | 12.837 | 38.410 | −8.582 | 1.00 | 24.99 | C |
| ATOM | 970 | CD1 | LEU | A | 260 | 11.382 | 37.918 | −8.568 | 1.00 | 25.77 | C |
| ATOM | 971 | CD2 | LEU | A | 260 | 13.548 | 37.921 | −7.345 | 1.00 | 25.15 | C |
| ATOM | 972 | C | LEU | A | 260 | 15.631 | 37.637 | −11.147 | 1.00 | 25.73 | C |
| ATOM | 973 | O | LEU | A | 260 | 16.386 | 36.735 | −10.836 | 1.00 | 26.34 | O |
| ATOM | 974 | N | ARG | A | 261 | 15.332 | 37.880 | −12.405 | 1.00 | 27.95 | N |
| ATOM | 975 | CA | ARG | A | 261 | 15.899 | 37.026 | −13.423 | 1.00 | 30.51 | C |
| ATOM | 976 | CB | ARG | A | 261 | 15.218 | 37.208 | −14.776 | 1.00 | 36.29 | C |
| ATOM | 977 | CG | ARG | A | 261 | 15.935 | 38.134 | −15.749 | 1.00 | 43.10 | C |
| ATOM | 978 | CD | ARG | A | 261 | 15.557 | 37.798 | −17.181 | 1.00 | 49.47 | C |
| ATOM | 979 | NE | ARG | A | 261 | 14.099 | 37.758 | −17.344 | 1.00 | 52.44 | N |
| ATOM | 980 | CZ | ARG | A | 261 | 13.480 | 37.169 | −18.360 | 1.00 | 55.76 | C |
| ATOM | 981 | NH1 | ARG | A | 261 | 14.169 | 36.551 | −19.311 | 1.00 | 55.58 | N |
| ATOM | 982 | NH2 | ARG | A | 261 | 12.161 | 37.190 | −18.423 | 1.00 | 61.19 | N |
| ATOM | 983 | C | ARG | A | 261 | 17.395 | 37.309 | −13.498 | 1.00 | 28.40 | C |
| ATOM | 984 | O | ARG | A | 261 | 18.167 | 36.421 | −13.782 | 1.00 | 26.32 | O |
| ATOM | 985 | N | MET | A | 262 | 17.797 | 38.537 | −13.206 | 1.00 | 26.98 | N |
| ATOM | 986 | CA | MET | A | 262 | 19.196 | 38.878 | −13.226 | 1.00 | 27.80 | C |
| ATOM | 987 | CB | MET | A | 262 | 19.391 | 40.372 | −13.184 | 1.00 | 31.14 | C |
| ATOM | 988 | CG | MET | A | 262 | 19.390 | 40.947 | −14.584 | 1.00 | 35.95 | C |
| ATOM | 989 | SD | MET | A | 262 | 18.851 | 42.642 | −14.469 | 1.00 | 48.77 | S |
| ATOM | 990 | CE | MET | A | 262 | 18.574 | 43.054 | −16.208 | 1.00 | 49.05 | C |
| ATOM | 991 | C | MET | A | 262 | 19.988 | 38.198 | −12.134 | 1.00 | 25.96 | C |
| ATOM | 992 | O | MET | A | 262 | 21.102 | 37.760 | −12.384 | 1.00 | 27.56 | O |
| ATOM | 993 | N | LEU | A | 263 | 19.411 | 38.064 | −10.953 | 1.00 | 22.69 | N |
| ATOM | 994 | CA | LEU | A | 263 | 20.023 | 37.263 | −9.910 | 1.00 | 21.58 | C |
| ATOM | 995 | CB | LEU | A | 263 | 19.210 | 37.323 | −8.628 | 1.00 | 21.17 | C |
| ATOM | 996 | CG | LEU | A | 263 | 19.147 | 38.684 | −7.956 | 1.00 | 21.53 | C |
| ATOM | 997 | CD1 | LEU | A | 263 | 18.140 | 38.583 | −6.832 | 1.00 | 22.30 | C |
| ATOM | 998 | CD2 | LEU | A | 263 | 20.506 | 39.148 | −7.426 | 1.00 | 21.89 | C |
| ATOM | 999 | C | LEU | A | 263 | 20.145 | 35.813 | −10.287 | 1.00 | 21.63 | C |
| ATOM | 1000 | O | LEU | A | 263 | 21.100 | 35.155 | −9.875 | 1.00 | 19.83 | O |
| ATOM | 1001 | N | GLN | A | 264 | 19.160 | 35.295 | −11.019 | 1.00 | 22.61 | N |
| ATOM | 1002 | CA | GLN | A | 264 | 19.202 | 33.909 | −11.462 | 1.00 | 24.58 | C |
| ATOM | 1003 | CB | GLN | A | 264 | 17.882 | 33.513 | −12.077 | 1.00 | 29.08 | C |
| ATOM | 1004 | CG | GLN | A | 264 | 17.789 | 32.072 | −12.553 | 1.00 | 32.99 | C |
| ATOM | 1005 | CD | GLN | A | 264 | 16.338 | 31.629 | −12.750 | 1.00 | 40.07 | C |
| ATOM | 1006 | OE1 | GLN | A | 264 | 15.372 | 32.439 | −12.722 | 1.00 | 39.81 | O |
| ATOM | 1007 | NE2 | GLN | A | 264 | 16.168 | 30.335 | −12.963 | 1.00 | 44.90 | N |
| ATOM | 1008 | C | GLN | A | 264 | 20.322 | 33.685 | −12.463 | 1.00 | 23.48 | C |
| ATOM | 1009 | O | GLN | A | 264 | 20.837 | 32.576 | −12.579 | 1.00 | 22.96 | O |
| ATOM | 1010 | N | GLN | A | 265 | 20.718 | 34.741 | −13.165 | 1.00 | 22.96 | N |
| ATOM | 1011 | CA | GLN | A | 265 | 21.815 | 34.644 | −14.124 | 1.00 | 23.26 | C |
| ATOM | 1012 | CB | GLN | A | 265 | 21.514 | 35.389 | −15.431 | 1.00 | 23.05 | C |
| ATOM | 1013 | CG | GLN | A | 265 | 20.063 | 35.581 | −15.725 | 1.00 | 23.28 | C |
| ATOM | 1014 | CD | GLN | A | 265 | 19.770 | 36.119 | −17.105 | 1.00 | 24.44 | C |
| ATOM | 1015 | OE1 | GLN | A | 265 | 18.666 | 35.959 | −17.596 | 1.00 | 26.52 | O |
| ATOM | 1016 | NE2 | GLN | A | 265 | 20.731 | 36.800 | −17.719 | 1.00 | 25.97 | N |
| ATOM | 1017 | C | GLN | A | 265 | 23.094 | 35.196 | −13.552 | 1.00 | 22.09 | C |
| ATOM | 1018 | O | GLN | A | 265 | 24.035 | 35.411 | −14.282 | 1.00 | 23.13 | O |
| ATOM | 1019 | N | LYS | A | 266 | 23.140 | 35.407 | −12.246 | 1.00 | 21.65 | N |
| ATOM | 1020 | CA | LYS | A | 266 | 24.314 | 35.974 | −11.576 | 1.00 | 21.07 | C |
| ATOM | 1021 | CB | LYS | A | 266 | 25.507 | 34.992 | −11.504 | 1.00 | 21.29 | C |
| ATOM | 1022 | CG | LYS | A | 266 | 25.432 | 33.676 | −12.242 | 1.00 | 21.38 | C |
| ATOM | 1023 | CD | LYS | A | 266 | 24.731 | 32.620 | −11.411 | 1.00 | 21.72 | C |
| ATOM | 1024 | CE | LYS | A | 266 | 24.910 | 31.279 | −12.101 | 1.00 | 22.80 | C |
| ATOM | 1025 | NZ | LYS | A | 266 | 23.987 | 30.294 | −11.489 | 1.00 | 24.59 | N |
| ATOM | 1026 | C | LYS | A | 266 | 24.824 | 37.277 | −12.150 | 1.00 | 19.96 | C |
| ATOM | 1027 | O | LYS | A | 266 | 26.015 | 37.491 | −12.161 | 1.00 | 19.46 | O |
| ATOM | 1028 | N | ARG | A | 267 | 23.944 | 38.150 | −12.599 | 1.00 | 19.66 | N |
| ATOM | 1029 | CA | ARG | A | 267 | 24.360 | 39.468 | −13.002 | 1.00 | 20.68 | C |
| ATOM | 1030 | CB | ARG | A | 267 | 23.603 | 39.981 | −14.250 | 1.00 | 23.04 | C |
| ATOM | 1031 | CG | ARG | A | 267 | 23.248 | 38.901 | −15.268 | 1.00 | 24.71 | C |
| ATOM | 1032 | CD | ARG | A | 267 | 23.493 | 39.290 | −16.712 | 1.00 | 26.56 | C |
| ATOM | 1033 | NE | ARG | A | 267 | 22.456 | 40.103 | −17.364 | 1.00 | 29.50 | N |
| ATOM | 1034 | CZ | ARG | A | 267 | 22.534 | 41.424 | −17.572 | 1.00 | 32.34 | C |
| ATOM | 1035 | NH1 | ARG | A | 267 | 23.587 | 42.141 | −17.137 | 1.00 | 32.59 | N |
| ATOM | 1036 | NH2 | ARG | A | 267 | 21.534 | 42.046 | −18.199 | 1.00 | 32.65 | N |

TABLE 1-continued structure data for residues 36-207 of SEQ ID NO: 3

| ATOM | 1037 | C   | ARG | A | 267 | 24.124 | 40.331 | −11.792 | 1.00 | 19.91 | C |
| ATOM | 1038 | O   | ARG | A | 267 | 23.223 | 41.178 | −11.764 | 1.00 | 20.72 | O |
| ATOM | 1039 | N   | TRP | A | 268 | 24.949 | 40.110 | −10.784 | 1.00 | 18.80 | N |
| ATOM | 1040 | CA  | TRP | A | 268 | 24.806 | 40.808 | −9.508  | 1.00 | 18.52 | C |
| ATOM | 1041 | CB  | TRP | A | 268 | 25.933 | 40.446 | −8.526  | 1.00 | 16.77 | C |
| ATOM | 1042 | CG  | TRP | A | 268 | 26.325 | 39.031 | −8.481  | 1.00 | 15.52 | C |
| ATOM | 1043 | CD1 | TRP | A | 268 | 27.576 | 38.554 | −8.618  | 1.00 | 15.50 | C |
| ATOM | 1044 | NE1 | TRP | A | 268 | 27.579 | 37.193 | −8.514  | 1.00 | 15.46 | N |
| ATOM | 1045 | CE2 | TRP | A | 268 | 26.307 | 36.761 | −8.287  | 1.00 | 14.72 | C |
| ATOM | 1046 | CD2 | TRP | A | 268 | 25.484 | 37.896 | −8.260  | 1.00 | 15.16 | C |
| ATOM | 1047 | CE3 | TRP | A | 268 | 24.116 | 37.728 | −8.051  | 1.00 | 15.42 | C |
| ATOM | 1048 | CZ3 | TRP | A | 268 | 23.625 | 36.441 | −7.883  | 1.00 | 15.48 | C |
| ATOM | 1049 | CH2 | TRP | A | 268 | 24.477 | 35.331 | −7.932  | 1.00 | 15.07 | C |
| ATOM | 1050 | CZ2 | TRP | A | 268 | 25.821 | 35.479 | −8.122  | 1.00 | 14.67 | C |
| ATOM | 1051 | C   | TRP | A | 268 | 24.764 | 42.332 | −9.618  | 1.00 | 19.83 | C |
| ATOM | 1052 | O   | TRP | A | 268 | 23.912 | 42.956 | −9.027  | 1.00 | 18.87 | O |
| ATOM | 1053 | N   | ASP | A | 269 | 25.689 | 42.948 | −10.333 | 1.00 | 22.49 | N |
| ATOM | 1054 | CA  | ASP | A | 269 | 25.710 | 44.409 | −10.335 | 1.00 | 26.45 | C |
| ATOM | 1055 | CB  | ASP | A | 269 | 26.975 | 44.943 | −10.980 | 1.00 | 29.35 | C |
| ATOM | 1056 | CG  | ASP | A | 269 | 28.204 | 44.582 | −10.168 | 1.00 | 34.36 | C |
| ATOM | 1057 | OD1 | ASP | A | 269 | 28.727 | 43.458 | −10.386 | 1.00 | 38.55 | O |
| ATOM | 1058 | OD2 | ASP | A | 269 | 28.613 | 45.386 | −9.280  | 1.00 | 36.95 | O |
| ATOM | 1059 | C   | ASP | A | 269 | 24.491 | 44.983 | −11.002 | 1.00 | 26.06 | C |
| ATOM | 1060 | O   | ASP | A | 269 | 24.002 | 46.047 | −10.628 | 1.00 | 25.18 | O |
| ATOM | 1061 | N   | GLU | A | 270 | 23.994 | 44.251 | −11.980 | 1.00 | 26.66 | N |
| ATOM | 1062 | CA  | GLU | A | 270 | 22.819 | 44.647 | −12.711 | 1.00 | 27.52 | C |
| ATOM | 1063 | CB  | GLU | A | 270 | 22.675 | 43.700 | −13.886 | 1.00 | 31.90 | C |
| ATOM | 1064 | CG  | GLU | A | 270 | 21.614 | 44.097 | −14.891 | 1.00 | 37.76 | C |
| ATOM | 1065 | CD  | GLU | A | 270 | 22.099 | 45.053 | −15.952 | 1.00 | 41.79 | C |
| ATOM | 1066 | OE1 | GLU | A | 270 | 23.334 | 45.248 | −16.040 | 1.00 | 43.45 | O |
| ATOM | 1067 | OE2 | GLU | A | 270 | 21.228 | 45.580 | −16.701 | 1.00 | 46.67 | O |
| ATOM | 1068 | C   | GLU | A | 270 | 21.577 | 44.612 | −11.806 | 1.00 | 24.40 | C |
| ATOM | 1069 | O   | GLU | A | 270 | 20.797 | 45.573 | −11.736 | 1.00 | 24.47 | O |
| ATOM | 1070 | N   | ALA | A | 271 | 21.397 | 43.506 | −11.099 | 1.00 | 21.26 | N |
| ATOM | 1071 | CA  | ALA | A | 271 | 20.308 | 43.391 | −10.148 | 1.00 | 19.43 | C |
| ATOM | 1072 | CB  | ALA | A | 271 | 20.447 | 42.108 | −9.357  | 1.00 | 19.01 | C |
| ATOM | 1073 | C   | ALA | A | 271 | 20.271 | 44.582 | −9.201  | 1.00 | 19.09 | C |
| ATOM | 1074 | O   | ALA | A | 271 | 19.208 | 45.192 | −8.974  | 1.00 | 19.67 | O |
| ATOM | 1075 | N   | ALA | A | 272 | 21.440 | 44.903 | −8.657  | 1.00 | 17.53 | N |
| ATOM | 1076 | CA  | ALA | A | 272 | 21.595 | 45.920 | −7.636  | 1.00 | 17.46 | C |
| ATOM | 1077 | CB  | ALA | A | 272 | 23.033 | 45.956 | −7.148  | 1.00 | 17.78 | C |
| ATOM | 1078 | C   | ALA | A | 272 | 21.199 | 47.273 | −8.145  | 1.00 | 17.85 | C |
| ATOM | 1079 | O   | ALA | A | 272 | 20.409 | 47.974 | −7.524  | 1.00 | 18.84 | O |
| ATOM | 1080 | N   | VAL | A | 273 | 21.734 | 47.643 | −9.290  | 1.00 | 18.00 | N |
| ATOM | 1081 | CA  | VAL | A | 273 | 21.318 | 48.870 | −9.936  | 1.00 | 19.02 | C |
| ATOM | 1082 | CB  | VAL | A | 273 | 22.045 | 49.053 | −11.293 | 1.00 | 19.29 | C |
| ATOM | 1083 | CG1 | VAL | A | 273 | 21.316 | 50.025 | −12.224 | 1.00 | 19.00 | C |
| ATOM | 1084 | CG2 | VAL | A | 273 | 23.465 | 49.526 | −11.040 | 1.00 | 19.05 | C |
| ATOM | 1085 | C   | VAL | A | 273 | 19.796 | 48.892 | −10.108 | 1.00 | 20.18 | C |
| ATOM | 1086 | O   | VAL | A | 273 | 19.160 | 49.920 | −9.838  | 1.00 | 20.39 | O |
| ATOM | 1087 | N   | ASN | A | 274 | 19.214 | 47.769 | −10.534 | 1.00 | 21.12 | N |
| ATOM | 1088 | CA  | ASN | A | 274 | 17.761 | 47.721 | −10.762 | 1.00 | 22.02 | C |
| ATOM | 1089 | CB  | ASN | A | 274 | 17.346 | 46.439 | −11.476 | 1.00 | 22.56 | C |
| ATOM | 1090 | CG  | ASN | A | 274 | 17.523 | 46.537 | −12.978 | 1.00 | 23.13 | C |
| ATOM | 1091 | OD1 | ASN | A | 274 | 16.973 | 47.432 | −13.622 | 1.00 | 21.99 | O |
| ATOM | 1092 | ND2 | ASN | A | 274 | 18.292 | 45.613 | −13.546 | 1.00 | 23.82 | N |
| ATOM | 1093 | C   | ASN | A | 274 | 16.917 | 47.897 | −9.514  | 1.00 | 21.76 | C |
| ATOM | 1094 | O   | ASN | A | 274 | 15.980 | 48.688 | −9.539  | 1.00 | 23.09 | O |
| ATOM | 1095 | N   | LEU | A | 275 | 17.249 | 47.197 | −8.428  | 1.00 | 20.70 | N |
| ATOM | 1096 | CA  | LEU | A | 275 | 16.453 | 47.283 | −7.195  | 1.00 | 20.16 | C |
| ATOM | 1097 | CB  | LEU | A | 275 | 16.940 | 46.281 | −6.167  | 1.00 | 20.37 | C |
| ATOM | 1098 | CG  | LEU | A | 275 | 16.905 | 44.812 | −6.558  | 1.00 | 21.23 | C |
| ATOM | 1099 | CD1 | LEU | A | 275 | 17.556 | 43.997 | −5.476  | 1.00 | 20.63 | C |
| ATOM | 1100 | CD2 | LEU | A | 275 | 15.465 | 44.363 | −6.753  | 1.00 | 22.77 | C |
| ATOM | 1101 | C   | LEU | A | 275 | 16.480 | 48.641 | −6.522  | 1.00 | 20.74 | C |
| ATOM | 1102 | O   | LEU | A | 275 | 15.628 | 48.928 | −5.701  | 1.00 | 21.89 | O |
| ATOM | 1103 | N   | ALA | A | 276 | 17.482 | 49.462 | −6.826  | 1.00 | 22.28 | N |
| ATOM | 1104 | CA  | ALA | A | 276 | 17.594 | 50.796 | −6.242  | 1.00 | 22.42 | C |
| ATOM | 1105 | CB  | ALA | A | 276 | 19.010 | 51.320 | −6.352  | 1.00 | 22.05 | C |
| ATOM | 1106 | C   | ALA | A | 276 | 16.659 | 51.758 | −6.904  | 1.00 | 23.27 | C |
| ATOM | 1107 | O   | ALA | A | 276 | 16.458 | 52.850 | −6.395  | 1.00 | 24.20 | O |
| ATOM | 1108 | N   | LYS | A | 277 | 16.095 | 51.366 | −8.044  | 1.00 | 24.84 | N |
| ATOM | 1109 | CA  | LYS | A | 277 | 15.112 | 52.200 | −8.735  | 1.00 | 26.04 | C |
| ATOM | 1110 | CB  | LYS | A | 277 | 15.016 | 51.831 | −10.212 | 1.00 | 26.46 | C |
| ATOM | 1111 | CG  | LYS | A | 277 | 16.316 | 51.841 | −11.000 | 1.00 | 25.76 | C |
| ATOM | 1112 | CD  | LYS | A | 277 | 16.088 | 51.000 | −12.244 | 1.00 | 26.53 | C |
| ATOM | 1113 | CE  | LYS | A | 277 | 17.343 | 50.812 | −13.067 | 1.00 | 27.87 | C |
| ATOM | 1114 | NZ  | LYS | A | 277 | 17.546 | 51.917 | −14.034 | 1.00 | 28.01 | N |

TABLE 1-continued structure data for residues 36-207 of SEQ ID NO: 3

| ATOM | 1115 | C   | LYS | A | 277 | 13.730 | 52.051 | -8.138 | 1.00 | 25.63 | C |
| ---- | ---- | --- | --- | - | --- | ------ | ------ | ------ | ---- | ----- | - |
| ATOM | 1116 | O   | LYS | A | 277 | 12.831 | 52.747 | -8.538 | 1.00 | 29.63 | O |
| ATOM | 1117 | N   | SER | A | 278 | 13.561 | 51.148 | -7.185 | 1.00 | 25.60 | N |
| ATOM | 1118 | CA  | SER | A | 278 | 12.253 | 50.781 | -6.676 | 1.00 | 24.65 | C |
| ATOM | 1119 | CB  | SER | A | 278 | 12.371 | 49.408 | -6.038 | 1.00 | 23.51 | C |
| ATOM | 1120 | OG  | SER | A | 278 | 13.106 | 49.517 | -4.840 | 1.00 | 22.01 | O |
| ATOM | 1121 | C   | SER | A | 278 | 11.708 | 51.740 | -5.619 | 1.00 | 26.18 | C |
| ATOM | 1122 | O   | SER | A | 278 | 12.453 | 52.469 | -4.982 | 1.00 | 26.70 | O |
| ATOM | 1123 | N   | ARG | A | 279 | 10.395 | 51.698 | -5.419 | 1.00 | 27.57 | N |
| ATOM | 1124 | CA  | ARG | A | 279 | 9.748  | 52.367 | -4.295 | 1.00 | 28.26 | C |
| ATOM | 1125 | CB  | ARG | A | 279 | 8.244  | 52.085 | -4.341 | 1.00 | 30.50 | C |
| ATOM | 1126 | CG  | ARG | A | 279 | 7.362  | 53.134 | -3.682 | 1.00 | 33.21 | C |
| ATOM | 1127 | CD  | ARG | A | 279 | 5.958  | 53.140 | -4.305 | 1.00 | 35.85 | C |
| ATOM | 1128 | NE  | ARG | A | 279 | 5.963  | 53.596 | -5.709 | 1.00 | 36.04 | N |
| ATOM | 1129 | CZ  | ARG | A | 279 | 5.181  | 54.551 | -6.220 | 1.00 | 37.79 | C |
| ATOM | 1130 | NH1 | ARG | A | 279 | 4.259  | 55.165 | -5.480 | 1.00 | 40.07 | N |
| ATOM | 1131 | NH2 | ARG | A | 279 | 5.299  | 54.884 | -7.503 | 1.00 | 38.34 | N |
| ATOM | 1132 | C   | ARG | A | 279 | 10.331 | 51.870 | -2.960 | 1.00 | 27.11 | C |
| ATOM | 1133 | O   | ARG | A | 279 | 10.624 | 52.654 | -2.055 | 1.00 | 26.94 | O |
| ATOM | 1134 | N   | TRP | A | 280 | 10.493 | 50.562 | -2.831 | 1.00 | 25.54 | N |
| ATOM | 1135 | CA  | TRP | A | 280 | 11.100 | 49.988 | -1.631 | 1.00 | 24.89 | C |
| ATOM | 1136 | CB  | TRP | A | 280 | 11.410 | 48.519 | -1.889 | 1.00 | 24.08 | C |
| ATOM | 1137 | CG  | TRP | A | 280 | 12.295 | 47.870 | -0.904 | 1.00 | 24.34 | C |
| ATOM | 1138 | CD1 | TRP | A | 280 | 12.112 | 47.781 | 0.431  | 1.00 | 24.32 | C |
| ATOM | 1139 | NE1 | TRP | A | 280 | 13.134 | 47.078 | 1.006  | 1.00 | 23.81 | N |
| ATOM | 1140 | CE2 | TRP | A | 280 | 14.014 | 46.707 | 0.028  | 1.00 | 23.85 | C |
| ATOM | 1141 | CD2 | TRP | A | 280 | 13.521 | 47.184 | -1.184 | 1.00 | 24.87 | C |
| ATOM | 1142 | CE3 | TRP | A | 280 | 14.245 | 46.933 | -2.356 | 1.00 | 24.49 | C |
| ATOM | 1143 | CZ3 | TRP | A | 280 | 15.377 | 46.233 | -2.272 | 1.00 | 24.14 | C |
| ATOM | 1144 | CH2 | TRP | A | 280 | 15.844 | 45.770 | -1.050 | 1.00 | 25.34 | C |
| ATOM | 1145 | CZ2 | TRP | A | 280 | 15.176 | 46.004 | 0.111  | 1.00 | 24.16 | C |
| ATOM | 1146 | C   | TRP | A | 280 | 12.367 | 50.752 | -1.217 | 1.00 | 26.19 | C |
| ATOM | 1147 | O   | TRP | A | 280 | 12.586 | 51.025 | -0.033 | 1.00 | 27.34 | O |
| ATOM | 1148 | N   | TYR | A | 281 | 13.182 | 51.117 | -2.196 | 1.00 | 25.10 | N |
| ATOM | 1149 | CA  | TYR | A | 281 | 14.392 | 51.852 | -1.925 | 1.00 | 27.02 | C |
| ATOM | 1150 | CB  | TYR | A | 281 | 15.273 | 51.856 | -3.162 | 1.00 | 29.73 | C |
| ATOM | 1151 | CG  | TYR | A | 281 | 16.592 | 52.553 | -3.013 | 1.00 | 31.60 | C |
| ATOM | 1152 | CD1 | TYR | A | 281 | 16.706 | 53.910 | -3.275 | 1.00 | 33.25 | C |
| ATOM | 1153 | CE1 | TYR | A | 281 | 17.923 | 54.554 | -3.176 | 1.00 | 35.19 | C |
| ATOM | 1154 | CZ  | TYR | A | 281 | 19.053 | 53.837 | -2.817 | 1.00 | 36.13 | C |
| ATOM | 1155 | OH  | TYR | A | 281 | 20.255 | 54.506 | -2.719 | 1.00 | 40.80 | O |
| ATOM | 1156 | CE2 | TYR | A | 281 | 18.976 | 52.480 | -2.559 | 1.00 | 34.02 | C |
| ATOM | 1157 | CD2 | TYR | A | 281 | 17.746 | 51.845 | -2.662 | 1.00 | 34.24 | C |
| ATOM | 1158 | C   | TYR | A | 281 | 14.140 | 53.269 | -1.491 | 1.00 | 26.60 | C |
| ATOM | 1159 | O   | TYR | A | 281 | 14.875 | 53.805 | -0.672 | 1.00 | 27.61 | O |
| ATOM | 1160 | N   | ASN | A | 282 | 13.123 | 53.902 | -2.046 | 1.00 | 27.23 | N |
| ATOM | 1161 | CA  | ASN | A | 282 | 12.861 | 55.286 | -1.686 | 1.00 | 27.35 | C |
| ATOM | 1162 | CB  | ASN | A | 282 | 11.997 | 55.965 | -2.739 | 1.00 | 28.23 | C |
| ATOM | 1163 | CG  | ASN | A | 282 | 12.658 | 57.207 | -3.300 | 1.00 | 30.91 | C |
| ATOM | 1164 | OD1 | ASN | A | 282 | 13.482 | 57.135 | -4.245 | 1.00 | 31.77 | O |
| ATOM | 1165 | ND2 | ASN | A | 282 | 12.333 | 58.362 | -2.710 | 1.00 | 31.16 | N |
| ATOM | 1166 | C   | ASN | A | 282 | 12.256 | 55.429 | -0.286 | 1.00 | 27.09 | C |
| ATOM | 1167 | O   | ASN | A | 282 | 12.449 | 56.446 | 0.365  | 1.00 | 26.62 | O |
| ATOM | 1168 | N   | GLN | A | 283 | 11.559 | 54.399 | 0.185  | 1.00 | 26.60 | N |
| ATOM | 1169 | CA  | GLN | A | 283 | 10.887 | 54.458 | 1.474  | 1.00 | 27.12 | C |
| ATOM | 1170 | CB  | GLN | A | 283 | 9.701  | 53.475 | 1.520  | 1.00 | 28.86 | C |
| ATOM | 1171 | CG  | GLN | A | 283 | 8.629  | 53.674 | 0.450  | 1.00 | 30.05 | C |
| ATOM | 1172 | CD  | GLN | A | 283 | 8.270  | 55.140 | 0.218  | 1.00 | 32.11 | C |
| ATOM | 1173 | OE1 | GLN | A | 283 | 8.088  | 55.924 | 1.166  | 1.00 | 31.43 | O |
| ATOM | 1174 | NE2 | GLN | A | 283 | 8.168  | 55.521 | -1.054 | 1.00 | 35.23 | N |
| ATOM | 1175 | C   | GLN | A | 283 | 11.822 | 54.118 | 2.610  | 1.00 | 26.45 | C |
| ATOM | 1176 | O   | GLN | A | 283 | 11.901 | 54.858 | 3.594  | 1.00 | 27.45 | O |
| ATOM | 1177 | N   | THR | A | 284 | 12.492 | 52.973 | 2.478  | 1.00 | 25.01 | N |
| ATOM | 1178 | CA  | THR | A | 284 | 13.423 | 52.442 | 3.475  | 1.00 | 23.88 | C |
| ATOM | 1179 | CB  | THR | A | 284 | 12.966 | 51.040 | 3.920  | 1.00 | 23.35 | C |
| ATOM | 1180 | OG1 | THR | A | 284 | 12.652 | 50.248 | 2.763  | 1.00 | 24.29 | O |
| ATOM | 1181 | CG2 | THR | A | 284 | 11.753 | 51.134 | 4.777  | 1.00 | 22.52 | C |
| ATOM | 1182 | C   | THR | A | 284 | 14.838 | 52.322 | 2.874  | 1.00 | 23.41 | C |
| ATOM | 1183 | O   | THR | A | 284 | 15.307 | 51.220 | 2.609  | 1.00 | 24.02 | O |
| ATOM | 1184 | N   | PRO | A | 285 | 15.525 | 53.445 | 2.656  | 1.00 | 21.90 | N |
| ATOM | 1185 | CA  | PRO | A | 285 | 16.799 | 53.372 | 1.946  | 1.00 | 22.09 | C |
| ATOM | 1186 | CB  | PRO | A | 285 | 17.124 | 54.838 | 1.642  | 1.00 | 22.39 | C |
| ATOM | 1187 | CG  | PRO | A | 285 | 16.366 | 55.636 | 2.661  | 1.00 | 22.31 | C |
| ATOM | 1188 | CD  | PRO | A | 285 | 15.302 | 54.761 | 3.271  | 1.00 | 22.37 | C |
| ATOM | 1189 | C   | PRO | A | 285 | 17.936 | 52.719 | 2.745  | 1.00 | 22.14 | C |
| ATOM | 1190 | O   | PRO | A | 285 | 18.726 | 51.970 | 2.172  | 1.00 | 23.17 | O |
| ATOM | 1191 | N   | ASN | A | 286 | 18.015 | 52.981 | 4.045  | 1.00 | 21.07 | N |
| ATOM | 1192 | CA  | ASN | A | 286 | 19.048 | 52.378 | 4.863  | 1.00 | 20.91 | C |

TABLE 1-continued structure data for residues 36-207 of SEQ ID NO: 3

| ATOM | 1193 | CB | ASN | A | 286 | 19.017 | 52.911 | 6.296 | 1.00 | 20.37 | C |
|---|---|---|---|---|---|---|---|---|---|---|---|
| ATOM | 1194 | CG | ASN | A | 286 | 19.387 | 54.370 | 6.368 | 1.00 | 20.18 | C |
| ATOM | 1195 | OD1 | ASN | A | 286 | 18.847 | 55.107 | 7.154 | 1.00 | 20.53 | O |
| ATOM | 1196 | ND2 | ASN | A | 286 | 20.295 | 54.797 | 5.514 | 1.00 | 21.72 | N |
| ATOM | 1197 | C | ASN | A | 286 | 19.011 | 50.870 | 4.845 | 1.00 | 21.50 | C |
| ATOM | 1198 | O | ASN | A | 286 | 20.049 | 50.232 | 4.674 | 1.00 | 25.24 | O |
| ATOM | 1199 | N | ARG | A | 287 | 17.834 | 50.295 | 4.978 | 1.00 | 21.21 | N |
| ATOM | 1200 | CA | ARG | A | 287 | 17.687 | 48.845 | 4.909 | 1.00 | 21.78 | C |
| ATOM | 1201 | CB | ARG | A | 287 | 16.319 | 48.417 | 5.483 | 1.00 | 22.05 | C |
| ATOM | 1202 | CG | ARG | A | 287 | 16.026 | 46.936 | 5.334 | 1.00 | 22.22 | C |
| ATOM | 1203 | CD | ARG | A | 287 | 14.768 | 46.550 | 6.034 | 1.00 | 22.42 | C |
| ATOM | 1204 | NE | ARG | A | 287 | 14.478 | 45.113 | 5.991 | 1.00 | 23.63 | N |
| ATOM | 1205 | CZ | ARG | A | 287 | 13.446 | 44.547 | 6.639 | 1.00 | 23.31 | C |
| ATOM | 1206 | NH1 | ARG | A | 287 | 12.630 | 45.304 | 7.360 | 1.00 | 21.69 | N |
| ATOM | 1207 | NH2 | ARG | A | 287 | 13.233 | 43.225 | 6.577 | 1.00 | 23.11 | N |
| ATOM | 1208 | C | ARG | A | 287 | 17.834 | 48.366 | 3.465 | 1.00 | 21.64 | C |
| ATOM | 1209 | O | ARG | A | 287 | 18.502 | 47.379 | 3.183 | 1.00 | 23.69 | O |
| ATOM | 1210 | N | ALA | A | 288 | 17.209 | 49.056 | 2.538 | 1.00 | 21.65 | N |
| ATOM | 1211 | CA | ALA | A | 288 | 17.339 | 48.653 | 1.142 | 1.00 | 22.19 | C |
| ATOM | 1212 | CB | ALA | A | 288 | 16.397 | 49.460 | 0.233 | 1.00 | 21.97 | C |
| ATOM | 1213 | C | ALA | A | 288 | 18.805 | 48.687 | 0.628 | 1.00 | 20.50 | C |
| ATOM | 1214 | O | ALA | A | 288 | 19.223 | 47.738 | 0.003 | 1.00 | 19.73 | O |
| ATOM | 1215 | N | LYS | A | 289 | 19.568 | 49.749 | 0.882 | 1.00 | 20.37 | N |
| ATOM | 1216 | CA | LYS | A | 289 | 21.017 | 49.759 | 0.503 | 1.00 | 20.92 | C |
| ATOM | 1217 | CB | LYS | A | 289 | 21.764 | 51.030 | 0.923 | 1.00 | 21.84 | C |
| ATOM | 1218 | CG | LYS | A | 289 | 21.290 | 52.322 | 0.268 | 1.00 | 23.83 | C |
| ATOM | 1219 | CD | LYS | A | 289 | 22.084 | 53.510 | 0.817 | 1.00 | 25.87 | C |
| ATOM | 1220 | CE | LYS | A | 289 | 21.230 | 54.754 | 1.078 | 1.00 | 26.90 | C |
| ATOM | 1221 | NZ | LYS | A | 289 | 20.986 | 55.550 | −0.162 | 1.00 | 27.49 | N |
| ATOM | 1222 | C | LYS | A | 289 | 21.742 | 48.592 | 1.136 | 1.00 | 19.32 | C |
| ATOM | 1223 | O | LYS | A | 289 | 22.505 | 47.896 | 0.470 | 1.00 | 18.88 | O |
| ATOM | 1224 | N | ARG | A | 290 | 21.496 | 48.358 | 2.419 | 1.00 | 17.72 | N |
| ATOM | 1225 | CA | ARG | A | 290 | 22.090 | 47.190 | 3.039 | 1.00 | 16.89 | C |
| ATOM | 1226 | CB | ARG | A | 290 | 21.686 | 47.057 | 4.481 | 1.00 | 17.35 | C |
| ATOM | 1227 | CG | ARG | A | 290 | 22.751 | 47.503 | 5.455 | 1.00 | 17.36 | C |
| ATOM | 1228 | CD | ARG | A | 290 | 22.250 | 47.290 | 6.895 | 1.00 | 17.90 | C |
| ATOM | 1229 | NE | ARG | A | 290 | 21.835 | 48.571 | 7.433 | 1.00 | 18.00 | N |
| ATOM | 1230 | CZ | ARG | A | 290 | 20.644 | 48.866 | 7.915 | 1.00 | 18.13 | C |
| ATOM | 1231 | NH1 | ARG | A | 290 | 19.692 | 47.957 | 8.035 | 1.00 | 18.79 | N |
| ATOM | 1232 | NH2 | ARG | A | 290 | 20.428 | 50.094 | 8.327 | 1.00 | 18.55 | N |
| ATOM | 1233 | C | ARG | A | 290 | 21.750 | 45.904 | 2.299 | 1.00 | 15.91 | C |
| ATOM | 1234 | O | ARG | A | 290 | 22.653 | 45.199 | 1.885 | 1.00 | 15.62 | O |
| ATOM | 1235 | N | VAL | A | 291 | 20.469 | 45.599 | 2.120 | 1.00 | 14.38 | N |
| ATOM | 1236 | CA | VAL | A | 291 | 20.086 | 44.353 | 1.450 | 1.00 | 13.90 | C |
| ATOM | 1237 | CB | VAL | A | 291 | 18.550 | 44.206 | 1.439 | 1.00 | 13.94 | C |
| ATOM | 1238 | CG1 | VAL | A | 291 | 18.079 | 43.111 | 0.489 | 1.00 | 13.78 | C |
| ATOM | 1239 | CG2 | VAL | A | 291 | 18.088 | 43.871 | 2.843 | 1.00 | 14.14 | C |
| ATOM | 1240 | C | VAL | A | 291 | 20.629 | 44.219 | 0.020 | 1.00 | 13.74 | C |
| ATOM | 1241 | O | VAL | A | 291 | 20.961 | 43.142 | −0.424 | 1.00 | 13.31 | O |
| ATOM | 1242 | N | ILE | A | 292 | 20.720 | 45.333 | −0.683 | 1.00 | 13.88 | N |
| ATOM | 1243 | CA | ILE | A | 292 | 21.175 | 45.362 | −2.045 | 1.00 | 14.57 | C |
| ATOM | 1244 | CB | ILE | A | 292 | 20.787 | 46.710 | −2.659 | 1.00 | 14.88 | C |
| ATOM | 1245 | CG1 | ILE | A | 292 | 19.276 | 46.671 | −2.974 | 1.00 | 15.73 | C |
| ATOM | 1246 | CD1 | ILE | A | 292 | 18.642 | 48.029 | −3.167 | 1.00 | 15.96 | C |
| ATOM | 1247 | CG2 | ILE | A | 292 | 21.551 | 46.998 | −3.929 | 1.00 | 14.71 | C |
| ATOM | 1248 | C | ILE | A | 292 | 22.678 | 45.072 | −2.141 | 1.00 | 15.58 | C |
| ATOM | 1249 | O | ILE | A | 292 | 23.115 | 44.208 | −2.919 | 1.00 | 15.69 | O |
| ATOM | 1250 | N | THR | A | 293 | 23.460 | 45.780 | −1.324 | 1.00 | 15.70 | N |
| ATOM | 1251 | CA | THR | A | 293 | 24.863 | 45.522 | −1.209 | 1.00 | 15.08 | C |
| ATOM | 1252 | CB | THR | A | 293 | 25.498 | 46.248 | −0.018 | 1.00 | 14.65 | C |
| ATOM | 1253 | OG1 | THR | A | 293 | 25.495 | 47.661 | −0.243 | 1.00 | 14.26 | O |
| ATOM | 1254 | CG2 | THR | A | 293 | 26.907 | 45.816 | 0.151 | 1.00 | 14.51 | C |
| ATOM | 1255 | C | THR | A | 293 | 25.087 | 44.045 | −1.029 | 1.00 | 15.93 | C |
| ATOM | 1256 | O | THR | A | 293 | 26.075 | 43.516 | −1.540 | 1.00 | 17.16 | O |
| ATOM | 1257 | N | THR | A | 294 | 24.205 | 43.348 | −0.321 | 1.00 | 16.09 | N |
| ATOM | 1258 | CA | THR | A | 294 | 24.510 | 41.949 | −0.067 | 1.00 | 16.86 | C |
| ATOM | 1259 | CB | THR | A | 294 | 23.998 | 41.373 | 1.271 | 1.00 | 16.61 | C |
| ATOM | 1260 | OG1 | THR | A | 294 | 23.027 | 40.367 | 1.022 | 1.00 | 16.37 | O |
| ATOM | 1261 | CG2 | THR | A | 294 | 23.496 | 42.440 | 2.245 | 1.00 | 15.94 | C |
| ATOM | 1262 | C | THR | A | 294 | 24.097 | 41.100 | −1.248 | 1.00 | 18.08 | C |
| ATOM | 1263 | O | THR | A | 294 | 24.708 | 40.057 | −1.494 | 1.00 | 19.43 | O |
| ATOM | 1264 | N | PHE | A | 295 | 23.116 | 41.560 | −2.022 | 1.00 | 18.77 | N |
| ATOM | 1265 | CA | PHE | A | 295 | 22.894 | 40.962 | −3.349 | 1.00 | 18.57 | C |
| ATOM | 1266 | CB | PHE | A | 295 | 21.616 | 41.473 | −4.015 | 1.00 | 18.66 | C |
| ATOM | 1267 | CG | PHE | A | 295 | 20.365 | 40.809 | −3.545 | 1.00 | 19.48 | C |
| ATOM | 1268 | CD1 | PHE | A | 295 | 20.252 | 39.433 | −3.525 | 1.00 | 19.84 | C |
| ATOM | 1269 | CE1 | PHE | A | 295 | 19.063 | 38.833 | −3.106 | 1.00 | 20.01 | C |
| ATOM | 1270 | CZ | PHE | A | 295 | 17.978 | 39.611 | −2.733 | 1.00 | 19.25 | C |

TABLE 1-continued structure data for residues 36-207 of SEQ ID NO: 3

| ATOM | 1271 | CE2 | PHE | A | 295 | 18.077 | 40.984 | −2.761 | 1.00 | 19.33 | C |
|---|---|---|---|---|---|---|---|---|---|---|---|
| ATOM | 1272 | CD2 | PHE | A | 295 | 19.257 | 41.578 | −3.169 | 1.00 | 19.68 | C |
| ATOM | 1273 | C | PHE | A | 295 | 24.068 | 41.236 | −4.296 | 1.00 | 17.14 | C |
| ATOM | 1274 | O | PHE | A | 295 | 24.445 | 40.369 | −5.075 | 1.00 | 16.48 | O |
| ATOM | 1275 | N | ARG | A | 296 | 24.610 | 42.441 | −4.261 | 1.00 | 16.74 | N |
| ATOM | 1276 | CA | AARG | A | 296 | 25.733 | 42.809 | −5.125 | 0.50 | 17.43 | C |
| ATOM | 1277 | CA | BARG | A | 296 | 25.719 | 42.775 | −5.159 | 0.50 | 17.31 | C |
| ATOM | 1278 | CB | AARG | A | 296 | 26.176 | 44.248 | −4.821 | 0.50 | 17.07 | C |
| ATOM | 1279 | CB | BARG | A | 296 | 26.163 | 44.235 | −5.016 | 0.50 | 16.80 | C |
| ATOM | 1280 | CG | AARG | A | 296 | 26.873 | 44.963 | −5.962 | 0.50 | 16.85 | C |
| ATOM | 1281 | CG | BARG | A | 296 | 27.315 | 44.595 | −5.945 | 0.50 | 16.41 | C |
| ATOM | 1282 | CD | AARG | A | 296 | 27.291 | 46.371 | −5.554 | 0.50 | 16.90 | C |
| ATOM | 1283 | CD | BARG | A | 296 | 27.577 | 46.088 | −6.026 | 0.50 | 16.34 | C |
| ATOM | 1284 | NE | AARG | A | 296 | 26.376 | 47.005 | −4.592 | 0.50 | 16.67 | N |
| ATOM | 1285 | NE | BARG | A | 296 | 27.872 | 46.668 | −4.719 | 0.50 | 16.23 | N |
| ATOM | 1286 | CZ | AARG | A | 296 | 25.566 | 48.019 | −4.884 | 0.50 | 16.35 | C |
| ATOM | 1287 | CZ | BARG | A | 296 | 29.042 | 46.574 | −4.105 | 0.50 | 15.70 | C |
| ATOM | 1288 | NH1 | AARG | A | 296 | 25.543 | 48.532 | −6.115 | 0.50 | 16.46 | N |
| ATOM | 1289 | NH1 | BARG | A | 296 | 30.033 | 45.914 | −4.672 | 0.50 | 15.36 | N |
| ATOM | 1290 | NH2 | AARG | A | 296 | 24.790 | 48.527 | −3.946 | 0.50 | 15.89 | N |
| ATOM | 1291 | NH2 | BARG | A | 296 | 29.209 | 47.135 | −2.918 | 0.50 | 15.84 | N |
| ATOM | 1292 | C | ARG | A | 296 | 26.917 | 41.874 | −4.905 | 1.00 | 17.63 | C |
| ATOM | 1293 | O | ARG | A | 296 | 27.603 | 41.510 | −5.823 | 1.00 | 19.21 | O |
| ATOM | 1294 | N | THR | A | 297 | 27.097 | 41.468 | −3.654 | 1.00 | 17.90 | N |
| ATOM | 1295 | CA | THR | A | 297 | 28.369 | 41.022 | −3.098 | 1.00 | 16.56 | C |
| ATOM | 1296 | CB | THR | A | 297 | 28.635 | 42.052 | −1.988 | 1.00 | 16.70 | C |
| ATOM | 1297 | OG1 | THR | A | 297 | 29.551 | 43.027 | −2.471 | 1.00 | 15.78 | O |
| ATOM | 1298 | CG2 | THR | A | 297 | 29.071 | 41.470 | −0.701 | 1.00 | 16.77 | C |
| ATOM | 1299 | C | THR | A | 297 | 28.388 | 39.584 | −2.578 | 1.00 | 15.91 | C |
| ATOM | 1300 | O | THR | A | 297 | 29.365 | 38.877 | −2.747 | 1.00 | 14.56 | O |
| ATOM | 1301 | N | GLY | A | 298 | 27.290 | 39.139 | −1.979 | 1.00 | 16.23 | N |
| ATOM | 1302 | CA | GLY | A | 298 | 27.210 | 37.784 | −1.431 | 1.00 | 16.41 | C |
| ATOM | 1303 | C | GLY | A | 298 | 27.966 | 37.612 | −0.116 | 1.00 | 16.62 | C |
| ATOM | 1304 | O | GLY | A | 298 | 28.245 | 36.480 | 0.310 | 1.00 | 15.61 | O |
| ATOM | 1305 | N | THR | A | 299 | 28.242 | 38.746 | 0.536 | 1.00 | 17.10 | N |
| ATOM | 1306 | CA | THR | A | 299 | 28.933 | 38.811 | 1.808 | 1.00 | 17.93 | C |
| ATOM | 1307 | CB | THR | A | 299 | 30.343 | 39.458 | 1.708 | 1.00 | 18.54 | C |
| ATOM | 1308 | OG1 | THR | A | 299 | 30.213 | 40.855 | 1.438 | 1.00 | 19.28 | O |
| ATOM | 1309 | CG2 | THR | A | 299 | 31.182 | 38.812 | 0.648 | 1.00 | 18.70 | C |
| ATOM | 1310 | C | THR | A | 299 | 28.134 | 39.618 | 2.839 | 1.00 | 18.10 | C |
| ATOM | 1311 | O | THR | A | 299 | 27.190 | 40.360 | 2.513 | 1.00 | 17.00 | O |
| ATOM | 1312 | N | TRP | A | 300 | 28.574 | 39.498 | 4.091 | 1.00 | 18.62 | N |
| ATOM | 1313 | CA | TRP | A | 300 | 27.888 | 40.118 | 5.215 | 1.00 | 19.05 | C |
| ATOM | 1314 | CB | TRP | A | 300 | 28.034 | 39.201 | 6.400 | 1.00 | 18.79 | C |
| ATOM | 1315 | CG | TRP | A | 300 | 27.397 | 37.878 | 6.192 | 1.00 | 17.86 | C |
| ATOM | 1316 | CD1 | TRP | A | 300 | 28.021 | 36.691 | 6.049 | 1.00 | 18.14 | C |
| ATOM | 1317 | NE1 | TRP | A | 300 | 27.098 | 35.682 | 5.924 | 1.00 | 18.21 | N |
| ATOM | 1318 | CE2 | TRP | A | 300 | 25.847 | 36.228 | 5.973 | 1.00 | 18.08 | C |
| ATOM | 1319 | CD2 | TRP | A | 300 | 26.003 | 37.612 | 6.151 | 1.00 | 17.60 | C |
| ATOM | 1320 | CE3 | TRP | A | 300 | 24.865 | 38.414 | 6.211 | 1.00 | 17.25 | C |
| ATOM | 1321 | CZ3 | TRP | A | 300 | 23.642 | 37.819 | 6.096 | 1.00 | 17.17 | C |
| ATOM | 1322 | CH2 | TRP | A | 300 | 23.509 | 36.432 | 5.930 | 1.00 | 16.97 | C |
| ATOM | 1323 | CZ2 | TRP | A | 300 | 24.589 | 35.624 | 5.854 | 1.00 | 17.96 | C |
| ATOM | 1324 | C | TRP | A | 300 | 28.391 | 41.518 | 5.569 | 1.00 | 19.62 | C |
| ATOM | 1325 | O | TRP | A | 300 | 28.020 | 42.092 | 6.595 | 1.00 | 18.37 | O |
| ATOM | 1326 | N | ASP | A | 301 | 29.212 | 42.079 | 4.693 | 1.00 | 21.72 | N |
| ATOM | 1327 | CA | ASP | A | 301 | 29.901 | 43.330 | 4.981 | 1.00 | 22.99 | C |
| ATOM | 1328 | CB | ASP | A | 301 | 30.787 | 43.688 | 3.803 | 1.00 | 25.42 | C |
| ATOM | 1329 | CG | ASP | A | 301 | 32.087 | 42.919 | 3.824 | 1.00 | 27.44 | C |
| ATOM | 1330 | OD1 | ASP | A | 301 | 32.058 | 41.675 | 3.955 | 1.00 | 30.80 | O |
| ATOM | 1331 | OD2 | ASP | A | 301 | 33.135 | 43.568 | 3.740 | 1.00 | 29.83 | O |
| ATOM | 1332 | C | ASP | A | 301 | 29.038 | 44.520 | 5.347 | 1.00 | 21.64 | C |
| ATOM | 1333 | O | ASP | A | 301 | 29.456 | 45.364 | 6.159 | 1.00 | 21.37 | O |
| ATOM | 1334 | N | ALA | A | 302 | 27.846 | 44.596 | 4.765 | 1.00 | 20.10 | N |
| ATOM | 1335 | CA | ALA | A | 302 | 26.975 | 45.740 | 5.021 | 1.00 | 19.85 | C |
| ATOM | 1336 | CB | ALA | A | 302 | 25.892 | 45.822 | 3.963 | 1.00 | 19.75 | C |
| ATOM | 1337 | C | ALA | A | 302 | 26.390 | 45.704 | 6.439 | 1.00 | 19.67 | C |
| ATOM | 1338 | O | ALA | A | 302 | 25.921 | 46.715 | 6.935 | 1.00 | 18.10 | O |
| ATOM | 1339 | N | TYR | A | 303 | 26.475 | 44.544 | 7.088 | 1.00 | 20.84 | N |
| ATOM | 1340 | CA | TYR | A | 303 | 25.986 | 44.346 | 8.446 | 1.00 | 22.42 | C |
| ATOM | 1341 | CB | TYR | A | 303 | 25.168 | 43.062 | 8.507 | 1.00 | 22.47 | C |
| ATOM | 1342 | CG | TYR | A | 303 | 23.951 | 43.174 | 7.671 | 1.00 | 23.61 | C |
| ATOM | 1343 | CD1 | TYR | A | 303 | 22.818 | 43.828 | 8.152 | 1.00 | 23.91 | C |
| ATOM | 1344 | CE1 | TYR | A | 303 | 21.681 | 43.964 | 7.378 | 1.00 | 23.51 | C |
| ATOM | 1345 | CZ | TYR | A | 303 | 21.654 | 43.452 | 6.115 | 1.00 | 23.40 | C |
| ATOM | 1346 | OH | TYR | A | 303 | 20.527 | 43.603 | 5.341 | 1.00 | 24.50 | O |
| ATOM | 1347 | CE2 | TYR | A | 303 | 22.760 | 42.812 | 5.611 | 1.00 | 24.35 | C |
| ATOM | 1348 | CD2 | TYR | A | 303 | 23.917 | 42.682 | 6.382 | 1.00 | 24.07 | C |

TABLE 1-continued structure data for residues 36-207 of SEQ ID NO: 3

| ATOM | 1349 | C | TYR | A | 303 | 27.083 | 44.285 | 9.503 | 1.00 | 24.17 | C |
|---|---|---|---|---|---|---|---|---|---|---|---|
| ATOM | 1350 | O | TYR | A | 303 | 26.829 | 43.813 | 10.626 | 1.00 | 23.60 | O |
| ATOM | 1351 | N | LYS | A | 304 | 28.281 | 44.787 | 9.169 | 1.00 | 26.51 | N |
| ATOM | 1352 | CA | LYS | A | 304 | 29.412 | 44.800 | 10.102 | 1.00 | 27.32 | C |
| ATOM | 1353 | CB | LYS | A | 304 | 30.602 | 44.053 | 9.514 | 1.00 | 31.97 | C |
| ATOM | 1354 | CG | LYS | A | 304 | 30.355 | 42.580 | 9.234 | 1.00 | 35.85 | C |
| ATOM | 1355 | CD | LYS | A | 304 | 30.196 | 41.799 | 10.518 | 1.00 | 39.74 | C |
| ATOM | 1356 | CE | LYS | A | 304 | 29.929 | 40.327 | 10.250 | 1.00 | 44.42 | C |
| ATOM | 1357 | NZ | LYS | A | 304 | 30.209 | 39.522 | 11.483 | 1.00 | 47.87 | N |
| ATOM | 1358 | C | LYS | A | 304 | 29.828 | 46.215 | 10.409 | 1.00 | 26.36 | C |
| ATOM | 1359 | O | LYS | A | 304 | 29.602 | 47.122 | 9.611 | 1.00 | 22.82 | O |
| ATOM | 1360 | N | ASN | A | 305 | 30.447 | 46.378 | 11.578 | 1.00 | 28.44 | N |
| ATOM | 1361 | CA | ASN | A | 305 | 30.903 | 47.678 | 12.094 | 1.00 | 30.68 | C |
| ATOM | 1362 | CB | ASN | A | 305 | 32.049 | 48.265 | 11.256 | 1.00 | 32.63 | C |
| ATOM | 1363 | CG | ASN | A | 305 | 33.231 | 47.333 | 11.134 | 1.00 | 34.13 | C |
| ATOM | 1364 | OD1 | ASN | A | 305 | 33.980 | 47.405 | 10.158 | 1.00 | 36.05 | O |
| ATOM | 1365 | ND2 | ASN | A | 305 | 33.410 | 46.454 | 12.120 | 1.00 | 34.55 | N |
| ATOM | 1366 | C | ASN | A | 305 | 29.811 | 48.702 | 12.156 | 1.00 | 30.08 | C |
| ATOM | 1367 | O | ASN | A | 305 | 30.044 | 49.881 | 11.895 | 1.00 | 29.72 | O |
| ATOM | 1368 | N | LEU | A | 306 | 28.616 | 48.242 | 12.484 | 1.00 | 32.08 | N |
| ATOM | 1369 | CA | LEU | A | 306 | 27.496 | 49.128 | 12.697 | 1.00 | 33.51 | C |
| ATOM | 1370 | CB | LEU | A | 306 | 26.206 | 48.416 | 12.336 | 1.00 | 32.79 | C |
| ATOM | 1371 | CG | LEU | A | 306 | 26.112 | 47.991 | 10.880 | 1.00 | 32.69 | C |
| ATOM | 1372 | CD1 | LEU | A | 306 | 24.755 | 47.371 | 10.645 | 1.00 | 32.21 | C |
| ATOM | 1373 | CD2 | LEU | A | 306 | 26.325 | 49.164 | 9.933 | 1.00 | 32.06 | C |
| ATOM | 1374 | C | LEU | A | 306 | 27.465 | 49.575 | 14.158 | 1.00 | 36.34 | C |
| ATOM | 1375 | O | LEU | A | 306 | 26.829 | 50.578 | 14.472 | 1.00 | 38.63 | O |
| ATOM | 1376 | N | GLY | A | 307 | 28.169 | 48.841 | 15.029 | 1.00 | 37.02 | N |
| ATOM | 1377 | CA | GLY | A | 307 | 28.200 | 49.102 | 16.468 | 1.00 | 38.38 | C |
| ATOM | 1378 | C | GLY | A | 307 | 28.640 | 50.499 | 16.897 | 1.00 | 38.67 | C |
| ATOM | 1379 | O | GLY | A | 307 | 29.499 | 51.117 | 16.257 | 1.00 | 37.60 | O |

TABLE 2

Atomic coordinates for substrate binding pocket

Column 4-amino acid name
Column 5-chain id
Column 6-amino acid number
Columns 7, 8, 9 - x, y, z, coordinates
Column 10- occupancy
Column 11-B factor Identical to hGLTP

| ATOM | 1693 | N | LEU | A | 349 | 17.078 | 61.085 | 33.760 | 1.00 | 32.17 | N |
|---|---|---|---|---|---|---|---|---|---|---|---|
| ATOM | 1694 | CA | LEU | A | 349 | 15.613 | 61.133 | 33.683 | 1.00 | 31.89 | C |
| ATOM | 1695 | CB | LEU | A | 349 | 15.018 | 60.002 | 34.529 | 1.00 | 31.16 | C |
| ATOM | 1696 | CG | LEU | A | 349 | 15.387 | 58.576 | 34.127 | 1.00 | 30.62 | C |
| ATOM | 1697 | CD1 | LEU | A | 349 | 15.055 | 57.588 | 35.234 | 1.00 | 30.35 | C |
| ATOM | 1698 | CD2 | LEU | A | 349 | 14.661 | 58.203 | 32.847 | 1.00 | 31.02 | C |
| ATOM | 1699 | C | LEU | A | 349 | 15.005 | 62.437 | 34.189 | 1.00 | 32.16 | C |
| ATOM | 1700 | O | LEU | A | 349 | 13.908 | 62.809 | 33.782 | 1.00 | 32.34 | O |
| ATOM | 1773 | N | ASP | A | 360 | 18.506 | 57.831 | 47.954 | 1.00 | 38.15 | N |
| ATOM | 1774 | CA | ASP | A | 360 | 18.317 | 56.652 | 48.825 | 1.00 | 40.22 | C |
| ATOM | 1775 | CB | ASP | A | 360 | 16.885 | 56.070 | 48.744 | 1.00 | 40.94 | C |
| ATOM | 1776 | CG | ASP | A | 360 | 16.009 | 56.417 | 49.979 | 1.00 | 42.38 | C |
| ATOM | 1777 | OD1 | ASP | A | 360 | 16.483 | 57.111 | 50.913 | 1.00 | 43.03 | O |
| ATOM | 1778 | OD2 | ASP | A | 360 | 14.832 | 55.982 | 50.020 | 1.00 | 41.12 | O |
| ATOM | 1779 | C | ASP | A | 360 | 19.330 | 55.567 | 48.494 | 1.00 | 42.22 | C |
| ATOM | 1780 | O | ASP | A | 360 | 19.995 | 55.048 | 49.392 | 1.00 | 42.24 | O |
| ATOM | 1800 | N | ASN | A | 364 | 22.929 | 54.217 | 50.705 | 1.00 | 32.41 | N |
| ATOM | 1801 | CA | ASN | A | 364 | 23.263 | 52.850 | 51.106 | 1.00 | 34.01 | C |
| ATOM | 1802 | CB | ASN | A | 364 | 22.189 | 51.885 | 50.607 | 1.00 | 35.44 | C |
| ATOM | 1803 | CG | ASN | A | 364 | 20.810 | 52.196 | 51.172 | 1.00 | 35.65 | C |
| ATOM | 1804 | OD1 | ASN | A | 364 | 20.672 | 52.522 | 52.346 | 1.00 | 37.40 | O |
| ATOM | 1805 | ND2 | ASN | A | 364 | 19.785 | 52.086 | 50.339 | 1.00 | 34.54 | N |
| ATOM | 1806 | C | ASN | A | 364 | 24.616 | 52.406 | 50.555 | 1.00 | 34.42 | C |
| ATOM | 1807 | O | ASN | A | 364 | 25.119 | 51.342 | 50.906 | 1.00 | 34.10 | O |
| ATOM | 1825 | N | LYS | A | 367 | 27.203 | 54.062 | 53.116 | 1.00 | 42.74 | N |
| ATOM | 1826 | CA | LYS | A | 367 | 27.021 | 53.432 | 54.427 | 1.00 | 43.75 | C |
| ATOM | 1827 | CB | LYS | A | 367 | 25.549 | 53.584 | 54.809 | 1.00 | 43.56 | C |
| ATOM | 1828 | CG | LYS | A | 367 | 25.159 | 53.256 | 56.244 | 1.00 | 43.93 | C |
| ATOM | 1829 | CD | LYS | A | 367 | 23.730 | 53.728 | 56.554 | 1.00 | 43.91 | C |
| ATOM | 1830 | CE | LYS | A | 367 | 22.789 | 53.662 | 55.339 | 1.00 | 42.76 | C |
| ATOM | 1831 | NZ | LYS | A | 367 | 21.343 | 53.750 | 55.663 | 1.00 | 40.92 | N |

TABLE 2-continued

Atomic coordinates for substrate binding pocket

| ATOM | 1832 | C | LYS | A | 367 | 27.446 | 51.954 | 54.481 | 1.00 | 44.43 | C |
| --- | --- | --- | --- | --- | --- | --- | --- | --- | --- | --- | --- |
| ATOM | 1833 | O | LYS | A | 367 | 27.755 | 51.426 | 55.557 | 1.00 | 44.46 | O |
| ATOM | 2146 | N | TRP | A | 407 | 18.670 | 47.547 | 51.278 | 1.00 | 34.81 | N |
| ATOM | 2147 | CA | TRP | A | 407 | 17.963 | 48.614 | 50.565 | 1.00 | 36.69 | C |
| ATOM | 2148 | CB | TRP | A | 407 | 17.789 | 49.864 | 51.440 | 1.00 | 38.09 | C |
| ATOM | 2149 | CG | TRP | A | 407 | 16.670 | 49.696 | 52.404 | 1.00 | 39.08 | C |
| ATOM | 2150 | CD1 | TRP | A | 407 | 16.765 | 49.292 | 53.702 | 1.00 | 39.55 | C |
| ATOM | 2151 | NE1 | TRP | A | 407 | 15.519 | 49.224 | 54.269 | 1.00 | 40.32 | N |
| ATOM | 2152 | CE2 | TRP | A | 407 | 14.582 | 49.576 | 53.334 | 1.00 | 40.43 | C |
| ATOM | 2153 | CD2 | TRP | A | 407 | 15.275 | 49.871 | 52.137 | 1.00 | 40.09 | C |
| ATOM | 2154 | CE3 | TRP | A | 407 | 14.542 | 50.264 | 51.007 | 1.00 | 40.24 | C |
| ATOM | 2155 | CZ3 | TRP | A | 407 | 13.152 | 50.345 | 51.107 | 1.00 | 40.09 | C |
| ATOM | 2156 | CH2 | TRP | A | 407 | 12.490 | 50.049 | 52.322 | 1.00 | 40.28 | C |
| ATOM | 2157 | CZ2 | TRP | A | 407 | 13.184 | 49.657 | 53.439 | 1.00 | 40.12 | C |
| ATOM | 2158 | C | TRP | A | 407 | 18.682 | 48.931 | 49.265 | 1.00 | 35.35 | C |
| ATOM | 2159 | O | TRP | A | 407 | 18.034 | 49.233 | 48.256 | 1.00 | 33.58 | O |
| ATOM | 2177 | N | ARG | A | 410 | 17.530 | 46.308 | 46.837 | 1.00 | 29.69 | N |
| ATOM | 2178 | CA | ARG | A | 410 | 16.154 | 46.594 | 46.434 | 1.00 | 30.14 | C |
| ATOM | 2179 | CB | ARG | A | 410 | 15.264 | 46.894 | 47.631 | 1.00 | 31.24 | C |
| ATOM | 2180 | CG | ARG | A | 410 | 14.992 | 45.715 | 48.540 | 1.00 | 32.54 | C |
| ATOM | 2181 | CD | ARG | A | 410 | 14.472 | 46.248 | 49.866 | 1.00 | 33.77 | C |
| ATOM | 2182 | NE | ARG | A | 410 | 14.057 | 45.196 | 50.789 | 1.00 | 33.93 | N |
| ATOM | 2183 | CZ | ARG | A | 410 | 13.389 | 45.407 | 51.922 | 1.00 | 34.11 | C |
| ATOM | 2184 | NH1 | ARG | A | 410 | 13.042 | 46.641 | 52.292 | 1.00 | 34.51 | N |
| ATOM | 2185 | NH2 | ARG | A | 410 | 13.060 | 44.375 | 52.694 | 1.00 | 34.18 | N |
| ATOM | 2186 | C | ARG | A | 410 | 16.122 | 47.781 | 45.467 | 1.00 | 29.50 | C |
| ATOM | 2187 | O | ARG | A | 410 | 15.284 | 47.814 | 44.575 | 1.00 | 31.35 | O |
| ATOM | 2209 | N | PHE | A | 414 | 15.063 | 47.671 | 41.232 | 1.00 | 35.13 | N |
| ATOM | 2210 | CA | PHE | A | 414 | 14.210 | 48.631 | 40.533 | 1.00 | 34.62 | C |
| ATOM | 2211 | CB | PHE | A | 414 | 13.740 | 49.767 | 41.433 | 1.00 | 34.31 | C |
| ATOM | 2212 | CG | PHE | A | 414 | 13.182 | 50.924 | 40.662 | 1.00 | 34.71 | C |
| ATOM | 2213 | CD1 | PHE | A | 414 | 11.856 | 50.912 | 40.235 | 1.00 | 33.81 | C |
| ATOM | 2214 | CE1 | PHE | A | 414 | 11.347 | 51.960 | 39.495 | 1.00 | 33.60 | C |
| ATOM | 2215 | CZ | PHE | A | 414 | 12.162 | 53.031 | 39.159 | 1.00 | 35.52 | C |
| ATOM | 2216 | CE2 | PHE | A | 414 | 13.499 | 53.044 | 39.550 | 1.00 | 35.36 | C |
| ATOM | 2217 | CD2 | PHE | A | 414 | 14.004 | 51.990 | 40.290 | 1.00 | 34.78 | C |
| ATOM | 2218 | C | PHE | A | 414 | 14.892 | 49.213 | 39.285 | 1.00 | 34.68 | C |
| ATOM | 2219 | O | PHE | A | 414 | 14.259 | 49.296 | 38.224 | 1.00 | 35.11 | O |
| ATOM | 2330 | N | ILE | A | 429 | 8.965 | 55.858 | 28.594 | 1.00 | 31.75 | N |
| ATOM | 2331 | CA | ILE | A | 429 | 9.750 | 55.641 | 29.798 | 1.00 | 32.85 | C |
| ATOM | 2332 | CB | ILE | A | 429 | 11.026 | 56.489 | 29.857 | 1.00 | 34.71 | C |
| ATOM | 2333 | CG1 | ILE | A | 429 | 10.667 | 57.955 | 29.823 | 1.00 | 37.50 | C |
| ATOM | 2334 | CD1 | ILE | A | 429 | 11.813 | 58.797 | 30.305 | 1.00 | 40.52 | C |
| ATOM | 2335 | CG2 | ILE | A | 429 | 11.982 | 56.138 | 28.714 | 1.00 | 33.42 | C |
| ATOM | 2336 | C | ILE | A | 429 | 8.932 | 55.868 | 31.052 | 1.00 | 30.17 | C |
| ATOM | 2337 | O | ILE | A | 429 | 9.261 | 55.342 | 32.095 | 1.00 | 27.56 | O |
| ATOM | 2388 | N | TYR | A | 437 | 8.686 | 49.882 | 39.071 | 1.00 | 27.00 | N |
| ATOM | 2389 | CA | TYR | A | 437 | 8.338 | 50.239 | 40.448 | 1.00 | 27.42 | C |
| ATOM | 2390 | CB | TYR | A | 437 | 7.764 | 51.654 | 40.521 | 1.00 | 27.38 | C |
| ATOM | 2391 | CG | TYR | A | 437 | 7.713 | 52.262 | 41.914 | 1.00 | 27.32 | C |
| ATOM | 2392 | CD1 | TYR | A | 437 | 8.864 | 52.351 | 42.697 | 1.00 | 26.83 | C |
| ATOM | 2393 | CE1 | TYR | A | 437 | 8.837 | 52.924 | 43.961 | 1.00 | 27.10 | C |
| ATOM | 2394 | CZ | TYR | A | 437 | 7.641 | 53.412 | 44.466 | 1.00 | 28.13 | C |
| ATOM | 2395 | OH | TYR | A | 437 | 7.641 | 53.984 | 45.720 | 1.00 | 29.67 | O |
| ATOM | 2396 | CE2 | TYR | A | 437 | 6.470 | 53.332 | 43.717 | 1.00 | 27.32 | C |
| ATOM | 2397 | CD2 | TYR | A | 437 | 6.510 | 52.772 | 42.443 | 1.00 | 26.76 | C |
| ATOM | 2398 | C | TYR | A | 437 | 7.343 | 49.223 | 40.980 | 1.00 | 28.96 | C |
| ATOM | 2399 | O | TYR | A | 437 | 7.632 | 48.538 | 41.961 | 1.00 | 28.46 | O |
| ATOM | 2420 | N | LEU | A | 441 | 10.258 | 48.182 | 44.106 | 1.00 | 29.89 | N |
| ATOM | 2421 | CA | LEU | A | 441 | 10.312 | 48.939 | 45.358 | 1.00 | 28.91 | C |
| ATOM | 2422 | CB | LEU | A | 441 | 11.033 | 50.254 | 45.153 | 1.00 | 28.21 | C |
| ATOM | 2423 | CG | LEU | A | 441 | 12.537 | 50.163 | 45.163 | 1.00 | 28.77 | C |
| ATOM | 2424 | CD1 | LEU | A | 441 | 13.085 | 51.490 | 44.682 | 1.00 | 29.74 | C |
| ATOM | 2425 | CD2 | LEU | A | 441 | 13.039 | 49.842 | 46.555 | 1.00 | 28.82 | C |
| ATOM | 2426 | C | LEU | A | 441 | 8.960 | 49.258 | 45.965 | 1.00 | 30.20 | C |
| ATOM | 2427 | O | LEU | A | 441 | 8.856 | 49.371 | 47.185 | 1.00 | 28.88 | O |
| ATOM | 2458 | N | HIS | A | 445 | 7.995 | 50.618 | 49.983 | 1.00 | 30.01 | N |
| ATOM | 2459 | CA | HIS | A | 445 | 7.860 | 52.027 | 50.362 | 1.00 | 28.50 | C |
| ATOM | 2460 | CB | HIS | A | 445 | 7.958 | 52.933 | 49.128 | 1.00 | 28.90 | C |
| ATOM | 2461 | CG | HIS | A | 445 | 9.357 | 53.141 | 48.625 | 1.00 | 29.29 | C |
| ATOM | 2462 | ND1 | HIS | A | 445 | 9.629 | 53.533 | 47.329 | 1.00 | 28.66 | N |
| ATOM | 2463 | CE1 | HIS | A | 445 | 10.936 | 53.652 | 47.170 | 1.00 | 29.23 | C |
| ATOM | 2464 | NE2 | HIS | A | 445 | 11.525 | 53.332 | 48.310 | 1.00 | 29.16 | N |
| ATOM | 2465 | CD2 | HIS | A | 445 | 10.560 | 53.016 | 49.239 | 1.00 | 29.00 | C |
| ATOM | 2466 | C | HIS | A | 445 | 6.537 | 52.283 | 51.097 | 1.00 | 28.16 | C |
| ATOM | 2467 | O | HIS | A | 445 | 5.509 | 51.697 | 50.754 | 1.00 | 28.18 | O |
| ATOM | 2493 | N | VAL | A | 449 | 5.928 | 58.045 | 50.175 | 1.00 | 21.88 | N |
| ATOM | 2494 | CA | VAL | A | 449 | 6.979 | 57.901 | 49.185 | 1.00 | 21.38 | C |

TABLE 2-continued

Atomic coordinates for substrate binding pocket

| ATOM | 2495 | CB  | VAL | A | 449 | 8.125  | 56.996 | 49.700 | 1.00 | 21.01 | C |
|------|------|-----|-----|---|-----|--------|--------|--------|------|-------|---|
| ATOM | 2496 | CG1 | VAL | A | 449 | 9.095  | 56.681 | 48.593 | 1.00 | 21.35 | C |
| ATOM | 2497 | CG2 | VAL | A | 449 | 8.879  | 57.664 | 50.835 | 1.00 | 20.60 | C |
| ATOM | 2498 | C   | VAL | A | 449 | 6.393  | 57.357 | 47.885 | 1.00 | 21.93 | C |
| ATOM | 2499 | O   | VAL | A | 449 | 6.684  | 57.869 | 46.805 | 1.00 | 21.19 | O |
| ATOM | 2522 | N   | PHE | A | 453 | 6.829  | 59.248 | 44.352 | 1.00 | 32.95 | N |
| ATOM | 2523 | CA  | PHE | A | 453 | 7.250  | 58.590 | 43.137 | 1.00 | 36.27 | C |
| ATOM | 2524 | CB  | PHE | A | 453 | 7.674  | 57.173 | 43.446 | 1.00 | 38.78 | C |
| ATOM | 2525 | CG  | PHE | A | 453 | 8.302  | 56.496 | 42.289 | 1.00 | 43.00 | C |
| ATOM | 2526 | CD1 | PHE | A | 453 | 7.509  | 55.977 | 41.259 | 1.00 | 42.89 | C |
| ATOM | 2527 | CE1 | PHE | A | 453 | 8.081  | 55.353 | 40.167 | 1.00 | 44.04 | C |
| ATOM | 2528 | CZ  | PHE | A | 453 | 9.460  | 55.250 | 40.082 | 1.00 | 47.55 | C |
| ATOM | 2529 | CE2 | PHE | A | 453 | 10.266 | 55.764 | 41.102 | 1.00 | 49.11 | C |
| ATOM | 2530 | CD2 | PHE | A | 453 | 9.685  | 56.389 | 42.202 | 1.00 | 46.12 | C |
| ATOM | 2531 | C   | PHE | A | 453 | 6.165  | 58.578 | 42.052 | 1.00 | 37.23 | C |
| ATOM | 2532 | O   | PHE | A | 453 | 6.435  | 58.913 | 40.902 | 1.00 | 40.89 | O |
| ATOM | 2546 | N   | ALA | A | 456 | 6.280  | 61.840 | 40.500 | 1.00 | 36.16 | N |
| ATOM | 2547 | CA  | ALA | A | 456 | 7.532  | 62.027 | 39.778 | 1.00 | 36.34 | C |
| ATOM | 2548 | CB  | ALA | A | 456 | 8.692  | 61.470 | 40.584 | 1.00 | 36.40 | C |
| ATOM | 2549 | C   | ALA | A | 456 | 7.491  | 61.381 | 38.391 | 1.00 | 37.59 | C |
| ATOM | 2550 | O   | ALA | A | 456 | 8.125  | 61.867 | 37.458 | 1.00 | 37.39 | O |
| ATOM | 2630 | N   | PHE | A | 466 | 15.894 | 61.242 | 26.809 | 1.00 | 32.55 | N |
| ATOM | 2631 | CA  | PHE | A | 466 | 16.476 | 60.261 | 27.699 | 1.00 | 32.56 | C |
| ATOM | 2632 | CB  | PHE | A | 466 | 15.437 | 59.200 | 28.056 | 1.00 | 32.54 | C |
| ATOM | 2633 | CG  | PHE | A | 466 | 16.019 | 58.003 | 28.733 | 1.00 | 33.01 | C |
| ATOM | 2634 | CD1 | PHE | A | 466 | 16.608 | 58.122 | 29.982 | 1.00 | 34.52 | C |
| ATOM | 2635 | CE1 | PHE | A | 466 | 17.168 | 57.019 | 30.613 | 1.00 | 36.28 | C |
| ATOM | 2636 | CZ  | PHE | A | 466 | 17.142 | 55.781 | 29.989 | 1.00 | 36.66 | C |
| ATOM | 2637 | CE2 | PHE | A | 466 | 16.556 | 55.655 | 28.737 | 1.00 | 35.19 | C |
| ATOM | 2638 | CD2 | PHE | A | 466 | 15.995 | 56.762 | 28.120 | 1.00 | 33.41 | C |
| ATOM | 2639 | C   | PHE | A | 466 | 17.685 | 59.597 | 27.047 | 1.00 | 32.18 | C |
| ATOM | 2640 | O   | PHE | A | 466 | 18.743 | 59.449 | 27.651 | 1.00 | 32.48 | O |
| ATOM | 2658 | N   | LEU | A | 470 | 22.440 | 59.156 | 27.038 | 1.00 | 34.98 | N |
| ATOM | 2659 | CA  | LEU | A | 470 | 23.116 | 57.859 | 27.177 | 1.00 | 34.16 | C |
| ATOM | 2660 | CB  | LEU | A | 470 | 22.087 | 56.719 | 27.114 | 1.00 | 34.39 | C |
| ATOM | 2661 | CG  | LEU | A | 470 | 21.099 | 56.659 | 28.289 | 1.00 | 34.33 | C |
| ATOM | 2662 | CD1 | LEU | A | 470 | 20.108 | 55.523 | 28.108 | 1.00 | 35.58 | C |
| ATOM | 2663 | CD2 | LEU | A | 470 | 21.803 | 56.509 | 29.629 | 1.00 | 34.28 | C |
| ATOM | 2664 | C   | LEU | A | 470 | 24.210 | 57.644 | 26.130 | 1.00 | 33.60 | C |
| ATOM | 2665 | O   | LEU | A | 470 | 24.806 | 56.562 | 26.053 | 1.00 | 32.30 | O |

Residues that are similar to hGLTP

| ATOM | 1640 | N   | VAL | A | 342 | 26.295 | 53.397 | 37.424 | 1.00 | 30.41 | N |
|------|------|-----|-----|---|-----|--------|--------|--------|------|-------|---|
| ATOM | 1641 | CA  | VAL | A | 342 | 24.912 | 53.425 | 36.878 | 1.00 | 33.95 | C |
| ATOM | 1642 | CB  | VAL | A | 342 | 24.160 | 52.062 | 36.982 | 1.00 | 36.17 | C |
| ATOM | 1643 | CG1 | VAL | A | 342 | 24.390 | 51.216 | 35.737 | 1.00 | 37.22 | C |
| ATOM | 1644 | CG2 | VAL | A | 342 | 24.508 | 51.305 | 38.263 | 1.00 | 36.28 | C |
| ATOM | 1645 | C   | VAL | A | 342 | 23.947 | 54.457 | 37.473 | 1.00 | 34.21 | C |
| ATOM | 1646 | O   | VAL | A | 342 | 22.991 | 54.832 | 36.802 | 1.00 | 34.25 | O |
| ATOM | 1668 | N   | LEU | A | 346 | 19.404 | 57.674 | 36.816 | 1.00 | 36.05 | N |
| ATOM | 1669 | CA  | LEU | A | 346 | 18.301 | 58.397 | 37.449 | 1.00 | 36.42 | C |
| ATOM | 1670 | CB  | LEU | A | 346 | 18.142 | 58.008 | 38.922 | 1.00 | 38.49 | C |
| ATOM | 1671 | CG  | LEU | A | 346 | 17.699 | 56.585 | 39.328 | 1.00 | 40.20 | C |
| ATOM | 1672 | CD1 | LEU | A | 346 | 16.688 | 55.964 | 38.360 | 1.00 | 41.56 | C |
| ATOM | 1673 | CD2 | LEU | A | 346 | 18.896 | 55.660 | 39.508 | 1.00 | 40.73 | C |
| ATOM | 1674 | C   | LEU | A | 346 | 18.476 | 59.910 | 37.327 | 1.00 | 34.87 | C |
| ATOM | 1675 | O   | LEU | A | 346 | 17.504 | 60.653 | 37.392 | 1.00 | 34.48 | O |
| ATOM | 1749 | N   | VAL | A | 357 | 14.663 | 58.187 | 44.771 | 1.00 | 22.20 | N |
| ATOM | 1750 | CA  | VAL | A | 357 | 15.281 | 56.881 | 44.577 | 1.00 | 24.07 | C |
| ATOM | 1751 | CB  | VAL | A | 357 | 14.770 | 56.240 | 43.269 | 1.00 | 24.60 | C |
| ATOM | 1752 | CG1 | VAL | A | 357 | 15.472 | 54.913 | 43.007 | 1.00 | 24.52 | C |
| ATOM | 1753 | CG2 | VAL | A | 357 | 13.248 | 56.060 | 43.334 | 1.00 | 24.97 | C |
| ATOM | 1754 | C   | VAL | A | 357 | 16.828 | 56.967 | 44.588 | 1.00 | 25.22 | C |
| ATOM | 1755 | O   | VAL | A | 357 | 17.504 | 56.190 | 45.300 | 1.00 | 23.80 | O |
| ATOM | 1781 | N   | LEU | A | 361 | 19.447 | 55.236 | 47.208 | 1.00 | 44.04 | N |
| ATOM | 1782 | CA  | LEU | A | 361 | 20.454 | 54.276 | 46.753 | 1.00 | 44.79 | C |
| ATOM | 1783 | CB  | LEU | A | 361 | 20.358 | 54.065 | 45.239 | 1.00 | 49.90 | C |
| ATOM | 1784 | CG  | LEU | A | 361 | 21.102 | 52.845 | 44.671 | 1.00 | 54.97 | C |
| ATOM | 1785 | CD1 | LEU | A | 361 | 20.472 | 51.567 | 45.204 | 1.00 | 58.17 | C |
| ATOM | 1786 | CD2 | LEU | A | 361 | 21.102 | 52.829 | 43.146 | 1.00 | 55.60 | C |
| ATOM | 1787 | C   | LEU | A | 361 | 21.869 | 54.734 | 47.119 | 1.00 | 41.22 | C |
| ATOM | 1788 | O   | LEU | A | 361 | 22.624 | 53.975 | 47.734 | 1.00 | 40.12 | O |
| ATOM | 2359 | N   | LEU | A | 433 | 9.178  | 52.861 | 33.856 | 1.00 | 28.88 | N |
| ATOM | 2360 | CA  | LEU | A | 433 | 9.445  | 53.153 | 35.268 | 1.00 | 28.97 | C |
| ATOM | 2361 | CB  | LEU | A | 433 | 9.588  | 54.669 | 35.470 | 1.00 | 28.71 | C |
| ATOM | 2362 | CG  | LEU | A | 433 | 10.782 | 55.377 | 34.801 | 1.00 | 29.09 | C |
| ATOM | 2363 | CD1 | LEU | A | 433 | 10.665 | 56.897 | 34.882 | 1.00 | 28.81 | C |
| ATOM | 2364 | CD2 | LEU | A | 433 | 12.097 | 54.935 | 35.417 | 1.00 | 29.15 | C |

TABLE 2-continued

| | | | | | | | | | | |
|---|---|---|---|---|---|---|---|---|---|---|
| Atomic coordinates for substrate binding pocket | | | | | | | | | | |
| ATOM | 2365 | C | LEU | A | 433 | 8.330 | 52.633 | 36.167 | 1.00 | 29.17 C |
| ATOM | 2366 | O | LEU | A | 433 | 8.563 | 51.988 | 37.203 | 1.00 | 27.05 O |
| ATOM | 2515 | N | VAL | A | 452 | 4.910 | 60.198 | 46.235 | 1.00 | 27.19 N |
| ATOM | 2516 | CA | VAL | A | 452 | 5.947 | 61.054 | 45.686 | 1.00 | 28.22 C |
| ATOM | 2517 | CB | VAL | A | 452 | 7.140 | 61.167 | 46.662 | 1.00 | 27.69 C |
| ATOM | 2518 | CG1 | VAL | A | 452 | 8.411 | 61.668 | 45.972 | 1.00 | 27.47 C |
| ATOM | 2519 | CG2 | VAL | A | 452 | 6.769 | 62.084 | 47.801 | 1.00 | 26.92 C |
| ATOM | 2520 | C | VAL | A | 452 | 6.384 | 60.493 | 44.342 | 1.00 | 30.03 C |
| ATOM | 2521 | O | VAL | A | 452 | 6.295 | 61.164 | 43.321 | 1.00 | 29.95 O |
| ATOM | 2798 | N | ARG | A | 488 | 21.747 | 45.751 | 22.717 | 1.00 | 46.14 N |
| ATOM | 2799 | CA | ARG | A | 488 | 22.829 | 44.753 | 22.876 | 1.00 | 47.15 C |
| ATOM | 2800 | CB | ARG | A | 488 | 23.861 | 44.842 | 21.737 | 1.00 | 50.23 C |
| ATOM | 2801 | CG | ARG | A | 488 | 23.866 | 43.681 | 20.755 | 1.00 | 53.21 C |
| ATOM | 2802 | CD | ARG | A | 488 | 24.194 | 42.350 | 21.410 | 1.00 | 55.06 C |
| ATOM | 2803 | NE | ARG | A | 488 | 25.039 | 41.530 | 20.544 | 1.00 | 57.05 N |
| ATOM | 2804 | CZ | ARG | A | 488 | 24.652 | 40.957 | 19.405 | 1.00 | 60.48 C |
| ATOM | 2805 | NH1 | ARG | A | 488 | 23.408 | 41.094 | 18.949 | 1.00 | 62.17 N |
| ATOM | 2806 | NH2 | ARG | A | 488 | 25.527 | 40.231 | 18.711 | 1.00 | 61.80 N |
| ATOM | 2807 | C | ARG | A | 488 | 23.579 | 44.943 | 24.186 | 1.00 | 45.15 C |
| ATOM | 2808 | O | ARG | A | 488 | 23.582 | 44.059 | 25.041 | 1.00 | 43.32 O |
| ATOM | 2825 | N | SER | A | 491 | 21.495 | 43.694 | 27.179 | 1.00 | 30.94 N |
| ATOM | 2826 | CA | SER | A | 491 | 21.332 | 42.252 | 27.413 | 1.00 | 30.71 C |
| ATOM | 2827 | CB | SER | A | 491 | 20.762 | 41.550 | 26.177 | 1.00 | 30.02 C |
| ATOM | 2828 | OG | SER | A | 491 | 21.642 | 41.664 | 25.085 | 1.00 | 30.25 O |
| ATOM | 2829 | C | SER | A | 491 | 22.648 | 41.587 | 27.867 | 1.00 | 30.87 C |
| ATOM | 2830 | O | SER | A | 491 | 22.617 | 40.539 | 28.514 | 1.00 | 29.76 O |
| Residues that are different from hGLTP | | | | | | | | | | |
| ATOM | 1402 | N | PHE | A | 311 | 26.769 | 54.540 | 27.003 | 1.00 | 32.07 N |
| ATOM | 1403 | CA | PHE | A | 311 | 26.949 | 54.601 | 28.453 | 1.00 | 34.09 C |
| ATOM | 1404 | CB | PHE | A | 311 | 25.760 | 55.376 | 29.044 | 1.00 | 34.32 C |
| ATOM | 1405 | CG | PHE | A | 311 | 25.775 | 55.510 | 30.544 | 1.00 | 33.87 C |
| ATOM | 1406 | CD1 | PHE | A | 311 | 26.415 | 56.577 | 31.147 | 1.00 | 33.81 C |
| ATOM | 1407 | CE1 | PHE | A | 311 | 26.417 | 56.714 | 32.526 | 1.00 | 34.72 C |
| ATOM | 1408 | CZ | PHE | A | 311 | 25.758 | 55.788 | 33.318 | 1.00 | 34.67 C |
| ATOM | 1409 | CE2 | PHE | A | 311 | 25.100 | 54.722 | 32.724 | 1.00 | 34.28 C |
| ATOM | 1410 | CD2 | PHE | A | 311 | 25.108 | 54.591 | 31.345 | 1.00 | 33.99 C |
| ATOM | 1411 | C | PHE | A | 311 | 27.090 | 53.223 | 29.145 | 1.00 | 36.32 C |
| ATOM | 1412 | O | PHE | A | 311 | 27.765 | 53.128 | 30.192 | 1.00 | 37.54 O |
| ATOM | 1413 | N | PHE | A | 312 | 26.478 | 52.173 | 28.571 | 1.00 | 36.34 N |
| ATOM | 1414 | CA | PHE | A | 312 | 26.419 | 50.839 | 29.215 | 1.00 | 36.37 C |
| ATOM | 1415 | CB | PHE | A | 312 | 25.085 | 50.166 | 28.925 | 1.00 | 36.19 C |
| ATOM | 1416 | CG | PHE | A | 312 | 23.930 | 50.842 | 29.577 | 1.00 | 37.19 C |
| ATOM | 1417 | CD1 | PHE | A | 312 | 23.719 | 50.703 | 30.943 | 1.00 | 37.96 C |
| ATOM | 1418 | CE1 | PHE | A | 312 | 22.641 | 51.330 | 31.558 | 1.00 | 38.86 C |
| ATOM | 1419 | CZ | PHE | A | 312 | 21.773 | 52.112 | 30.807 | 1.00 | 38.12 C |
| ATOM | 1420 | CE2 | PHE | A | 312 | 21.990 | 52.270 | 29.443 | 1.00 | 37.60 C |
| ATOM | 1421 | CD2 | PHE | A | 312 | 23.059 | 51.636 | 28.835 | 1.00 | 36.59 C |
| ATOM | 1422 | C | PHE | A | 312 | 27.541 | 49.844 | 28.902 | 1.00 | 36.28 C |
| ATOM | 1423 | O | PHE | A | 312 | 27.575 | 48.767 | 29.505 | 1.00 | 36.76 O |
| ATOM | 1661 | N | VAL | A | 345 | 22.049 | 57.173 | 35.598 | 1.00 | 38.84 N |
| ATOM | 1662 | CA | VAL | A | 345 | 20.753 | 56.886 | 34.924 | 1.00 | 39.53 C |
| ATOM | 1663 | CB | VAL | A | 345 | 20.379 | 55.377 | 34.941 | 1.00 | 40.42 C |
| ATOM | 1664 | CG1 | VAL | A | 345 | 18.949 | 55.156 | 34.450 | 1.00 | 42.16 C |
| ATOM | 1665 | CG2 | VAL | A | 345 | 21.316 | 54.584 | 34.057 | 1.00 | 40.90 C |
| ATOM | 1666 | C | VAL | A | 345 | 19.572 | 57.691 | 35.497 | 1.00 | 37.21 C |
| ATOM | 1667 | O | VAL | A | 345 | 18.832 | 58.324 | 34.745 | 1.00 | 36.62 O |
| ATOM | 2079 | N | ARG | A | 398 | 19.896 | 48.606 | 63.328 | 1.00 | 54.38 N |
| ATOM | 2080 | CA | ARG | A | 398 | 19.679 | 49.892 | 62.623 | 1.00 | 53.73 C |
| ATOM | 2081 | CB | ARG | A | 398 | 19.486 | 51.058 | 63.613 | 1.00 | 54.59 C |
| ATOM | 2082 | CG | ARG | A | 398 | 18.039 | 51.275 | 64.036 | 1.00 | 55.66 C |
| ATOM | 2083 | CD | ARG | A | 398 | 17.533 | 50.165 | 64.939 | 1.00 | 56.49 C |
| ATOM | 2084 | NE | ARG | A | 398 | 18.208 | 50.178 | 66.236 | 1.00 | 58.33 N |
| ATOM | 2085 | CZ | ARG | A | 398 | 17.946 | 49.340 | 67.238 | 1.00 | 59.28 C |
| ATOM | 2086 | NH1 | ARG | A | 398 | 17.015 | 48.399 | 67.108 | 1.00 | 60.24 N |
| ATOM | 2087 | NH2 | ARG | A | 398 | 18.618 | 49.442 | 68.381 | 1.00 | 57.85 N |
| ATOM | 2088 | C | ARG | A | 398 | 20.741 | 50.220 | 61.552 | 1.00 | 51.17 C |
| ATOM | 2089 | O | ARG | A | 398 | 20.714 | 49.623 | 60.476 | 1.00 | 53.64 O |
| ATOM | 2090 | N | ASN | A | 399 | 21.681 | 51.129 | 61.826 | 1.00 | 47.16 N |
| ATOM | 2091 | CA | ASN | A | 399 | 22.566 | 51.657 | 60.761 | 1.00 | 43.46 C |
| ATOM | 2092 | CB | ASN | A | 399 | 23.240 | 52.973 | 61.198 | 1.00 | 43.11 C |
| ATOM | 2093 | CG | ASN | A | 399 | 22.665 | 54.187 | 60.486 | 1.00 | 42.49 C |
| ATOM | 2094 | OD1 | ASN | A | 399 | 22.237 | 54.104 | 59.330 | 1.00 | 40.36 O |
| ATOM | 2095 | ND2 | ASN | A | 399 | 22.660 | 55.325 | 61.169 | 1.00 | 41.76 N |
| ATOM | 2096 | C | ASN | A | 399 | 23.611 | 50.669 | 60.217 | 1.00 | 39.56 C |
| ATOM | 2097 | O | ASN | A | 399 | 24.570 | 51.067 | 59.539 | 1.00 | 36.76 O |
| ATOM | 2116 | N | GLU | A | 403 | 21.588 | 46.236 | 56.877 | 1.00 | 28.98 N |
| ATOM | 2117 | CA | GLU | A | 403 | 20.395 | 46.995 | 56.532 | 1.00 | 29.96 C |

TABLE 2-continued

Atomic coordinates for substrate binding pocket

| ATOM | 2118 | CB | GLU | A | 403 | 19.944 | 47.919 | 57.685 | 1.00 | 30.71 | C |
|---|---|---|---|---|---|---|---|---|---|---|---|
| ATOM | 2119 | CG | GLU | A | 403 | 18.422 | 48.071 | 57.806 | 1.00 | 31.61 | C |
| ATOM | 2120 | CD | GLU | A | 403 | 17.960 | 49.490 | 58.157 | 1.00 | 32.39 | C |
| ATOM | 2121 | OE1 | GLU | A | 403 | 18.250 | 49.964 | 59.280 | 1.00 | 30.96 | O |
| ATOM | 2122 | OE2 | GLU | A | 403 | 17.281 | 50.127 | 57.306 | 1.00 | 32.65 | O |
| ATOM | 2123 | C | GLU | A | 403 | 20.644 | 47.780 | 55.212 | 1.00 | 30.19 | C |
| ATOM | 2124 | O | GLU | A | 403 | 19.835 | 47.694 | 54.282 | 1.00 | 31.47 | O |

TABLE 3

GLTP domain of FAPP2 atomic coordinates

Column 4-amino acid name
Column 5-chain id
Column 6-amino acid number
Columns 7, 8, 9 - x, y, z, coordinates
Column 10- occupancy
Column 11-B factor

| ATOM | 1380 | N | ILE | A | 308 | 28.024 | 50.993 | 17.980 | 1.00 | 37.95 | N |
|---|---|---|---|---|---|---|---|---|---|---|---|
| ATOM | 1381 | CA | ILE | A | 308 | 28.275 | 52.337 | 18.506 | 1.00 | 36.49 | C |
| ATOM | 1382 | CB | ILE | A | 308 | 27.133 | 53.342 | 18.215 | 1.00 | 38.08 | C |
| ATOM | 1383 | CG1 | ILE | A | 308 | 26.627 | 53.231 | 16.767 | 1.00 | 39.48 | C |
| ATOM | 1384 | CD1 | ILE | A | 308 | 25.120 | 53.311 | 16.628 | 1.00 | 38.53 | C |
| ATOM | 1385 | CG2 | ILE | A | 308 | 27.604 | 54.769 | 18.484 | 1.00 | 37.75 | C |
| ATOM | 1386 | C | ILE | A | 308 | 28.376 | 52.238 | 20.008 | 1.00 | 34.41 | C |
| ATOM | 1387 | O | ILE | A | 308 | 27.599 | 51.517 | 20.632 | 1.00 | 34.21 | O |
| ATOM | 1388 | N | PRO | A | 309 | 29.323 | 52.980 | 20.598 | 1.00 | 33.94 | N |
| ATOM | 1389 | CA | PRO | A | 309 | 29.407 | 53.037 | 22.061 | 1.00 | 33.06 | C |
| ATOM | 1390 | CB | PRO | A | 309 | 30.648 | 53.897 | 22.309 | 1.00 | 33.08 | C |
| ATOM | 1391 | CG | PRO | A | 309 | 31.465 | 53.727 | 21.072 | 1.00 | 33.63 | C |
| ATOM | 1392 | CD | PRO | A | 309 | 30.482 | 53.624 | 19.953 | 1.00 | 33.19 | C |
| ATOM | 1393 | C | PRO | A | 309 | 28.188 | 53.648 | 22.770 | 1.00 | 31.66 | C |
| ATOM | 1394 | O | PRO | A | 309 | 27.537 | 54.587 | 22.282 | 1.00 | 29.71 | O |
| ATOM | 1395 | N | THR | A | 310 | 27.910 | 53.098 | 23.939 | 1.00 | 31.23 | N |
| ATOM | 1396 | CA | THR | A | 310 | 26.871 | 53.602 | 24.795 | 1.00 | 30.86 | C |
| ATOM | 1397 | CB | THR | A | 310 | 25.644 | 52.677 | 24.764 | 1.00 | 30.65 | C |
| ATOM | 1398 | OG1 | THR | A | 310 | 25.290 | 52.386 | 23.412 | 1.00 | 29.70 | O |
| ATOM | 1399 | CG2 | THR | A | 310 | 24.473 | 53.344 | 25.413 | 1.00 | 32.50 | C |
| ATOM | 1400 | C | THR | A | 310 | 27.403 | 53.687 | 26.213 | 1.00 | 30.45 | C |
| ATOM | 1401 | O | THR | A | 310 | 28.361 | 53.015 | 26.571 | 1.00 | 29.34 | O |
| ATOM | 1402 | N | PHE | A | 311 | 26.769 | 54.540 | 27.003 | 1.00 | 32.07 | N |
| ATOM | 1403 | CA | PHE | A | 311 | 26.949 | 54.601 | 28.453 | 1.00 | 34.09 | C |
| ATOM | 1404 | CB | PHE | A | 311 | 25.760 | 55.376 | 29.044 | 1.00 | 34.32 | C |
| ATOM | 1405 | CG | PHE | A | 311 | 25.775 | 55.510 | 30.544 | 1.00 | 33.87 | C |
| ATOM | 1406 | CD1 | PHE | A | 311 | 26.415 | 56.577 | 31.147 | 1.00 | 33.81 | C |
| ATOM | 1407 | CE1 | PHE | A | 311 | 26.417 | 56.714 | 32.526 | 1.00 | 34.72 | C |
| ATOM | 1408 | CZ | PHE | A | 311 | 25.758 | 55.788 | 33.318 | 1.00 | 34.67 | C |
| ATOM | 1409 | CE2 | PHE | A | 311 | 25.100 | 54.722 | 32.724 | 1.00 | 34.28 | C |
| ATOM | 1410 | CD2 | PHE | A | 311 | 25.108 | 54.591 | 31.345 | 1.00 | 33.99 | C |
| ATOM | 1411 | C | PHE | A | 311 | 27.090 | 53.223 | 29.145 | 1.00 | 36.32 | C |
| ATOM | 1412 | O | PHE | A | 311 | 27.765 | 53.128 | 30.192 | 1.00 | 37.54 | O |
| ATOM | 1413 | N | PHE | A | 312 | 26.478 | 52.173 | 28.571 | 1.00 | 36.34 | N |
| ATOM | 1414 | CA | PHE | A | 312 | 26.419 | 50.839 | 29.215 | 1.00 | 36.37 | C |
| ATOM | 1415 | CB | PHE | A | 312 | 25.085 | 50.166 | 28.925 | 1.00 | 36.19 | C |
| ATOM | 1416 | CG | PHE | A | 312 | 23.930 | 50.842 | 29.577 | 1.00 | 37.19 | C |
| ATOM | 1417 | CD1 | PHE | A | 312 | 23.719 | 50.703 | 30.943 | 1.00 | 37.96 | C |
| ATOM | 1418 | CE1 | PHE | A | 312 | 22.641 | 51.330 | 31.558 | 1.00 | 38.86 | C |
| ATOM | 1419 | CZ | PHE | A | 312 | 21.773 | 52.112 | 30.807 | 1.00 | 38.12 | C |
| ATOM | 1420 | CE2 | PHE | A | 312 | 21.990 | 52.270 | 29.443 | 1.00 | 37.60 | C |
| ATOM | 1421 | CD2 | PHE | A | 312 | 23.059 | 51.636 | 28.835 | 1.00 | 36.59 | C |
| ATOM | 1422 | C | PHE | A | 312 | 27.541 | 49.844 | 28.902 | 1.00 | 36.28 | C |
| ATOM | 1423 | O | PHE | A | 312 | 27.575 | 48.767 | 29.505 | 1.00 | 36.76 | O |
| ATOM | 1424 | N | SER | A | 313 | 28.422 | 50.165 | 27.955 | 1.00 | 35.23 | N |
| ATOM | 1425 | CA | SER | A | 313 | 29.682 | 49.418 | 27.800 | 1.00 | 34.91 | C |
| ATOM | 1426 | CB | SER | A | 313 | 29.738 | 48.714 | 26.435 | 1.00 | 33.62 | C |
| ATOM | 1427 | OG | SER | A | 313 | 29.267 | 49.547 | 25.399 | 1.00 | 32.91 | O |
| ATOM | 1428 | C | SER | A | 313 | 30.928 | 50.306 | 28.052 | 1.00 | 34.72 | C |
| ATOM | 1429 | O | SER | A | 313 | 32.052 | 49.809 | 28.028 | 1.00 | 33.15 | O |
| ATOM | 1430 | N | THR | A | 314 | 30.700 | 51.596 | 28.339 | 1.00 | 34.98 | N |
| ATOM | 1431 | CA | THR | A | 314 | 31.756 | 52.579 | 28.579 | 1.00 | 34.75 | C |
| ATOM | 1432 | CB | THR | A | 314 | 31.570 | 53.822 | 27.665 | 1.00 | 35.30 | C |
| ATOM | 1433 | OG1 | THR | A | 314 | 31.283 | 53.399 | 26.328 | 1.00 | 33.68 | O |
| ATOM | 1434 | CG2 | THR | A | 314 | 32.851 | 54.700 | 27.632 | 1.00 | 36.81 | C |
| ATOM | 1435 | C | THR | A | 314 | 31.821 | 52.993 | 30.074 | 1.00 | 34.54 | C |
| ATOM | 1436 | O | THR | A | 314 | 32.260 | 54.106 | 30.413 | 1.00 | 34.12 | O |

TABLE 3-continued

GLTP domain of FAPP2 atomic coordinates

| ATOM | 1437 | N   | MET | A | 315 | 31.406 | 52.084 | 30.963 | 1.00 | 33.23 | N |
|------|------|-----|-----|---|-----|--------|--------|--------|------|-------|---|
| ATOM | 1438 | CA  | MET | A | 315 | 31.482 | 52.321 | 32.409 | 1.00 | 32.33 | C |
| ATOM | 1439 | CB  | MET | A | 315 | 30.539 | 51.391 | 33.163 | 1.00 | 31.13 | C |
| ATOM | 1440 | CG  | MET | A | 315 | 29.065 | 51.710 | 33.017 | 1.00 | 30.63 | C |
| ATOM | 1441 | SD  | MET | A | 315 | 28.156 | 50.479 | 33.952 | 1.00 | 28.91 | S |
| ATOM | 1442 | CE  | MET | A | 315 | 26.532 | 50.647 | 33.231 | 1.00 | 30.00 | C |
| ATOM | 1443 | C   | MET | A | 315 | 32.889 | 52.058 | 32.914 | 1.00 | 32.40 | C |
| ATOM | 1444 | O   | MET | A | 315 | 33.503 | 51.070 | 32.521 | 1.00 | 32.35 | O |
| ATOM | 1445 | N   | ASN | A | 316 | 33.384 | 52.913 | 33.803 | 1.00 | 32.56 | N |
| ATOM | 1446 | CA  | ASN | A | 316 | 34.690 | 52.677 | 34.430 | 1.00 | 34.99 | C |
| ATOM | 1447 | CB  | ASN | A | 316 | 35.086 | 53.850 | 35.342 | 1.00 | 37.88 | C |
| ATOM | 1448 | CG  | ASN | A | 316 | 35.464 | 55.109 | 34.564 | 1.00 | 40.18 | C |
| ATOM | 1449 | OD1 | ASN | A | 316 | 35.766 | 55.065 | 33.359 | 1.00 | 42.66 | O |
| ATOM | 1450 | ND2 | ASN | A | 316 | 35.450 | 56.247 | 35.257 | 1.00 | 40.15 | N |
| ATOM | 1451 | C   | ASN | A | 316 | 34.779 | 51.348 | 35.202 | 1.00 | 32.94 | C |
| ATOM | 1452 | O   | ASN | A | 316 | 35.774 | 50.637 | 35.099 | 1.00 | 32.80 | O |
| ATOM | 1453 | N   | THR | A | 317 | 33.754 | 51.034 | 35.989 | 1.00 | 31.72 | N |
| ATOM | 1454 | CA  | THR | A | 317 | 33.600 | 49.699 | 36.580 | 1.00 | 30.44 | C |
| ATOM | 1455 | CB  | THR | A | 317 | 33.826 | 49.672 | 38.105 | 1.00 | 30.07 | C |
| ATOM | 1456 | OG1 | THR | A | 317 | 34.870 | 50.583 | 38.469 | 1.00 | 30.75 | O |
| ATOM | 1457 | CG2 | THR | A | 317 | 34.164 | 48.250 | 38.566 | 1.00 | 28.98 | C |
| ATOM | 1458 | C   | THR | A | 317 | 32.170 | 49.257 | 36.353 | 1.00 | 29.77 | C |
| ATOM | 1459 | O   | THR | A | 317 | 31.249 | 50.034 | 36.564 | 1.00 | 28.64 | O |
| ATOM | 1460 | N   | SER | A | 318 | 31.992 | 48.010 | 35.940 | 1.00 | 29.88 | N |
| ATOM | 1461 | CA  | SER | A | 318 | 30.672 | 47.450 | 35.726 | 1.00 | 31.24 | C |
| ATOM | 1462 | CB  | SER | A | 318 | 30.408 | 47.256 | 34.228 | 1.00 | 31.52 | C |
| ATOM | 1463 | OG  | SER | A | 318 | 29.128 | 46.690 | 34.006 | 1.00 | 31.35 | O |
| ATOM | 1464 | C   | SER | A | 318 | 30.553 | 46.123 | 36.470 | 1.00 | 31.66 | C |
| ATOM | 1465 | O   | SER | A | 318 | 31.562 | 45.548 | 36.890 | 1.00 | 30.91 | O |
| ATOM | 1466 | N   | PHE | A | 319 | 29.317 | 45.651 | 36.634 | 1.00 | 31.63 | N |
| ATOM | 1467 | CA  | PHE | A | 319 | 29.063 | 44.326 | 37.194 | 1.00 | 31.97 | C |
| ATOM | 1468 | CB  | PHE | A | 319 | 27.556 | 44.101 | 37.382 | 1.00 | 33.22 | C |
| ATOM | 1469 | CG  | PHE | A | 319 | 26.929 | 45.016 | 38.391 | 1.00 | 33.99 | C |
| ATOM | 1470 | CD1 | PHE | A | 319 | 27.065 | 44.772 | 39.750 | 1.00 | 33.84 | C |
| ATOM | 1471 | CE1 | PHE | A | 319 | 26.484 | 45.615 | 40.677 | 1.00 | 33.54 | C |
| ATOM | 1472 | CZ  | PHE | A | 319 | 25.761 | 46.719 | 40.256 | 1.00 | 33.91 | C |
| ATOM | 1473 | CE2 | PHE | A | 319 | 25.613 | 46.973 | 38.908 | 1.00 | 34.30 | C |
| ATOM | 1474 | CD2 | PHE | A | 319 | 26.196 | 46.124 | 37.983 | 1.00 | 34.95 | C |
| ATOM | 1475 | C   | PHE | A | 319 | 29.626 | 43.228 | 36.290 | 1.00 | 31.76 | C |
| ATOM | 1476 | O   | PHE | A | 319 | 29.923 | 42.135 | 36.760 | 1.00 | 30.90 | O |
| ATOM | 1477 | N   | SER | A | 320 | 29.739 | 43.521 | 34.991 | 1.00 | 32.44 | N |
| ATOM | 1478 | CA  | SER | A | 320 | 30.345 | 42.615 | 34.009 | 1.00 | 32.67 | C |
| ATOM | 1479 | CB  | SER | A | 320 | 30.137 | 43.155 | 32.583 | 1.00 | 32.38 | C |
| ATOM | 1480 | OG  | SER | A | 320 | 28.836 | 43.684 | 32.376 | 1.00 | 32.29 | O |
| ATOM | 1481 | C   | SER | A | 320 | 31.853 | 42.409 | 34.235 | 1.00 | 33.79 | C |
| ATOM | 1482 | O   | SER | A | 320 | 32.409 | 41.391 | 33.824 | 1.00 | 33.36 | O |
| ATOM | 1483 | N   | ASP | A | 321 | 32.512 | 43.381 | 34.866 | 1.00 | 35.59 | N |
| ATOM | 1484 | CA  | ASP | A | 321 | 33.970 | 43.353 | 35.052 | 1.00 | 36.97 | C |
| ATOM | 1485 | CB  | ASP | A | 321 | 34.557 | 44.772 | 34.900 | 1.00 | 35.46 | C |
| ATOM | 1486 | CG  | ASP | A | 321 | 34.262 | 45.392 | 33.542 | 1.00 | 35.83 | C |
| ATOM | 1487 | OD1 | ASP | A | 321 | 34.491 | 44.723 | 32.513 | 1.00 | 36.58 | O |
| ATOM | 1488 | OD2 | ASP | A | 321 | 33.799 | 46.552 | 33.495 | 1.00 | 35.21 | O |
| ATOM | 1489 | C   | ASP | A | 321 | 34.361 | 42.770 | 36.416 | 1.00 | 39.02 | C |
| ATOM | 1490 | O   | ASP | A | 321 | 35.408 | 43.126 | 36.953 | 1.00 | 40.96 | O |
| ATOM | 1491 | N   | ILE | A | 322 | 33.547 | 41.863 | 36.966 | 1.00 | 40.56 | N |
| ATOM | 1492 | CA  | ILE | A | 322 | 33.747 | 41.374 | 38.340 | 1.00 | 41.64 | C |
| ATOM | 1493 | CB  | ILE | A | 322 | 32.419 | 41.448 | 39.153 | 1.00 | 43.47 | C |
| ATOM | 1494 | CG1 | ILE | A | 322 | 32.347 | 42.788 | 39.914 | 1.00 | 45.20 | C |
| ATOM | 1495 | CD1 | ILE | A | 322 | 31.004 | 43.117 | 40.552 | 1.00 | 45.25 | C |
| ATOM | 1496 | CG2 | ILE | A | 322 | 32.269 | 40.289 | 40.140 | 1.00 | 43.51 | C |
| ATOM | 1497 | C   | ILE | A | 322 | 34.366 | 39.972 | 38.393 | 1.00 | 40.64 | C |
| ATOM | 1498 | O   | ILE | A | 322 | 33.937 | 39.078 | 37.671 | 1.00 | 41.20 | O |
| ATOM | 1499 | N   | GLU | A | 323 | 35.377 | 39.803 | 39.248 | 1.00 | 39.74 | N |
| ATOM | 1500 | CA  | GLU | A | 323 | 35.931 | 38.487 | 39.585 | 1.00 | 40.08 | C |
| ATOM | 1501 | CB  | GLU | A | 323 | 37.462 | 38.536 | 39.722 | 1.00 | 40.87 | C |
| ATOM | 1502 | CG  | GLU | A | 323 | 38.255 | 38.083 | 38.498 | 1.00 | 42.12 | C |
| ATOM | 1503 | CD  | GLU | A | 323 | 38.324 | 39.123 | 37.391 | 1.00 | 42.66 | C |
| ATOM | 1504 | OE1 | GLU | A | 323 | 37.885 | 40.271 | 37.613 | 1.00 | 43.00 | O |
| ATOM | 1505 | OE2 | GLU | A | 323 | 38.824 | 38.793 | 36.291 | 1.00 | 41.87 | O |
| ATOM | 1506 | C   | GLU | A | 323 | 35.335 | 38.040 | 40.918 | 1.00 | 39.71 | C |
| ATOM | 1507 | O   | GLU | A | 323 | 35.424 | 38.775 | 41.906 | 1.00 | 40.89 | O |
| ATOM | 1508 | N   | LEU | A | 324 | 34.737 | 36.845 | 40.943 | 1.00 | 38.13 | N |
| ATOM | 1509 | CA  | LEU | A | 324 | 34.199 | 36.257 | 42.178 | 1.00 | 36.74 | C |
| ATOM | 1510 | CB  | LEU | A | 324 | 32.949 | 35.400 | 41.908 | 1.00 | 36.30 | C |
| ATOM | 1511 | CG  | LEU | A | 324 | 31.690 | 36.095 | 41.355 | 1.00 | 35.96 | C |
| ATOM | 1512 | CD1 | LEU | A | 324 | 30.612 | 35.084 | 40.972 | 1.00 | 34.66 | C |
| ATOM | 1513 | CD2 | LEU | A | 324 | 31.140 | 37.113 | 42.346 | 1.00 | 36.11 | C |
| ATOM | 1514 | C   | LEU | A | 324 | 35.261 | 35.415 | 42.888 | 1.00 | 36.09 | C |

TABLE 3-continued

GLTP domain of FAPP2 atomic coordinates

| ATOM | 1515 | O | LEU | A | 324 | 36.165 | 34.862 | 42.263 | 1.00 | 35.63 | O |
|---|---|---|---|---|---|---|---|---|---|---|---|
| ATOM | 1516 | N | LEU | A | 325 | 35.123 | 35.342 | 44.206 | 1.00 | 35.99 | N |
| ATOM | 1517 | CA | LEU | A | 325 | 36.064 | 34.680 | 45.095 | 1.00 | 35.92 | C |
| ATOM | 1518 | CB | LEU | A | 325 | 36.517 | 35.682 | 46.173 | 1.00 | 35.58 | C |
| ATOM | 1519 | CG | LEU | A | 325 | 37.552 | 36.769 | 45.843 | 1.00 | 35.47 | C |
| ATOM | 1520 | CD1 | LEU | A | 325 | 37.408 | 37.356 | 44.443 | 1.00 | 35.66 | C |
| ATOM | 1521 | CD2 | LEU | A | 325 | 37.483 | 37.867 | 46.895 | 1.00 | 34.85 | C |
| ATOM | 1522 | C | LEU | A | 325 | 35.346 | 33.483 | 45.734 | 1.00 | 36.94 | C |
| ATOM | 1523 | O | LEU | A | 325 | 34.345 | 32.998 | 45.189 | 1.00 | 35.76 | O |
| ATOM | 1524 | N | GLU | A | 326 | 35.875 | 33.002 | 46.867 | 1.00 | 38.92 | N |
| ATOM | 1525 | CA | GLU | A | 326 | 35.145 | 32.132 | 47.827 | 1.00 | 39.57 | C |
| ATOM | 1526 | CB | GLU | A | 326 | 33.965 | 32.905 | 48.457 | 1.00 | 39.94 | C |
| ATOM | 1527 | CG | GLU | A | 326 | 34.414 | 34.112 | 49.299 | 1.00 | 39.89 | C |
| ATOM | 1528 | CD | GLU | A | 326 | 33.326 | 34.698 | 50.211 | 1.00 | 40.61 | C |
| ATOM | 1529 | OE1 | GLU | A | 326 | 32.137 | 34.777 | 49.808 | 1.00 | 40.37 | O |
| ATOM | 1530 | OE2 | GLU | A | 326 | 33.668 | 35.107 | 51.344 | 1.00 | 38.55 | O |
| ATOM | 1531 | C | GLU | A | 326 | 34.879 | 30.725 | 47.199 | 1.00 | 39.29 | C |
| ATOM | 1532 | O | GLU | A | 326 | 35.867 | 30.185 | 46.677 | 1.00 | 39.18 | O |
| ATOM | 1533 | N | ASP | A | 327 | 33.708 | 30.045 | 47.205 | 1.00 | 38.10 | N |
| ATOM | 1534 | CA | ASP | A | 327 | 32.372 | 30.274 | 47.856 | 1.00 | 36.07 | C |
| ATOM | 1535 | CB | ASP | A | 327 | 32.410 | 30.300 | 49.421 | 1.00 | 35.82 | C |
| ATOM | 1536 | CG | ASP | A | 327 | 33.573 | 29.483 | 50.036 | 1.00 | 35.87 | C |
| ATOM | 1537 | OD1 | ASP | A | 327 | 33.763 | 28.294 | 49.681 | 1.00 | 35.10 | O |
| ATOM | 1538 | OD2 | ASP | A | 327 | 34.279 | 30.035 | 50.916 | 1.00 | 35.41 | O |
| ATOM | 1539 | C | ASP | A | 327 | 31.461 | 31.388 | 47.258 | 1.00 | 34.58 | C |
| ATOM | 1540 | O | ASP | A | 327 | 30.537 | 31.857 | 47.926 | 1.00 | 34.00 | O |
| ATOM | 1541 | N | SER | A | 328 | 31.706 | 31.767 | 46.000 | 1.00 | 33.53 | N |
| ATOM | 1542 | CA | SER | A | 328 | 30.899 | 32.775 | 45.266 | 1.00 | 33.60 | C |
| ATOM | 1543 | CB | SER | A | 328 | 29.465 | 32.268 | 45.003 | 1.00 | 33.85 | C |
| ATOM | 1544 | OG | SER | A | 328 | 29.469 | 31.039 | 44.293 | 1.00 | 33.47 | O |
| ATOM | 1545 | C | SER | A | 328 | 30.853 | 34.153 | 45.945 | 1.00 | 32.67 | C |
| ATOM | 1546 | O | SER | A | 328 | 29.776 | 34.679 | 46.233 | 1.00 | 31.03 | O |
| ATOM | 1547 | N | GLY | A | 329 | 32.032 | 34.739 | 46.145 | 1.00 | 32.51 | N |
| ATOM | 1548 | CA | GLY | A | 329 | 32.201 | 35.957 | 46.959 | 1.00 | 32.51 | C |
| ATOM | 1549 | C | GLY | A | 329 | 32.349 | 37.262 | 46.187 | 1.00 | 31.65 | C |
| ATOM | 1550 | O | GLY | A | 329 | 33.280 | 37.425 | 45.401 | 1.00 | 32.16 | O |
| ATOM | 1551 | N | ILE | A | 330 | 31.455 | 38.212 | 46.449 | 1.00 | 29.95 | N |
| ATOM | 1552 | CA | ILE | A | 330 | 31.378 | 39.429 | 45.648 | 1.00 | 29.49 | C |
| ATOM | 1553 | CB | ILE | A | 330 | 29.939 | 40.021 | 45.641 | 1.00 | 30.50 | C |
| ATOM | 1554 | CG1 | ILE | A | 330 | 28.867 | 38.951 | 45.318 | 1.00 | 30.31 | C |
| ATOM | 1555 | CD1 | ILE | A | 330 | 27.441 | 39.354 | 45.645 | 1.00 | 29.36 | C |
| ATOM | 1556 | CG2 | ILE | A | 330 | 29.853 | 41.154 | 44.624 | 1.00 | 31.50 | C |
| ATOM | 1557 | C | ILE | A | 330 | 32.347 | 40.472 | 46.202 | 1.00 | 28.11 | C |
| ATOM | 1558 | O | ILE | A | 330 | 32.157 | 40.914 | 47.324 | 1.00 | 27.64 | O |
| ATOM | 1559 | N | PRO | A | 331 | 33.380 | 40.877 | 45.426 | 1.00 | 27.39 | N |
| ATOM | 1560 | CA | PRO | A | 331 | 34.346 | 41.819 | 46.017 | 1.00 | 27.10 | C |
| ATOM | 1561 | CB | PRO | A | 331 | 35.535 | 41.784 | 45.041 | 1.00 | 27.13 | C |
| ATOM | 1562 | CG | PRO | A | 331 | 34.955 | 41.349 | 43.739 | 1.00 | 27.67 | C |
| ATOM | 1563 | CD | PRO | A | 331 | 33.772 | 40.467 | 44.062 | 1.00 | 27.65 | C |
| ATOM | 1564 | C | PRO | A | 331 | 33.813 | 43.249 | 46.193 | 1.00 | 26.09 | C |
| ATOM | 1565 | O | PRO | A | 331 | 33.417 | 43.886 | 45.221 | 1.00 | 25.09 | O |
| ATOM | 1566 | N | THR | A | 332 | 33.827 | 43.718 | 47.442 | 1.00 | 26.43 | N |
| ATOM | 1567 | CA | THR | A | 332 | 33.481 | 45.091 | 47.834 | 1.00 | 27.17 | C |
| ATOM | 1568 | CB | THR | A | 332 | 33.948 | 45.378 | 49.287 | 1.00 | 27.33 | C |
| ATOM | 1569 | OG1 | THR | A | 332 | 33.742 | 44.234 | 50.125 | 1.00 | 27.50 | O |
| ATOM | 1570 | CG2 | THR | A | 332 | 33.215 | 46.560 | 49.879 | 1.00 | 27.48 | C |
| ATOM | 1571 | C | THR | A | 332 | 34.107 | 46.161 | 46.933 | 1.00 | 28.64 | C |
| ATOM | 1572 | O | THR | A | 332 | 33.396 | 46.892 | 46.253 | 1.00 | 29.46 | O |
| ATOM | 1573 | N | GLU | A | 333 | 35.439 | 46.242 | 46.937 | 1.00 | 31.22 | N |
| ATOM | 1574 | CA | GLU | A | 333 | 36.200 | 47.186 | 46.107 | 1.00 | 32.57 | C |
| ATOM | 1575 | CB | GLU | A | 333 | 37.658 | 47.228 | 46.601 | 1.00 | 35.03 | C |
| ATOM | 1576 | CG | GLU | A | 333 | 38.481 | 48.460 | 46.231 | 1.00 | 36.81 | C |
| ATOM | 1577 | CD | GLU | A | 333 | 39.761 | 48.569 | 47.066 | 1.00 | 38.67 | C |
| ATOM | 1578 | OE1 | GLU | A | 333 | 39.653 | 48.617 | 48.312 | 1.00 | 40.24 | O |
| ATOM | 1579 | OE2 | GLU | A | 333 | 40.877 | 48.603 | 46.489 | 1.00 | 38.27 | O |
| ATOM | 1580 | C | GLU | A | 333 | 36.103 | 46.748 | 44.625 | 1.00 | 32.00 | C |
| ATOM | 1581 | O | GLU | A | 333 | 37.077 | 46.204 | 44.048 | 1.00 | 31.18 | O |
| ATOM | 1582 | N | ALA | A | 334 | 34.912 | 46.999 | 44.051 | 1.00 | 28.75 | N |
| ATOM | 1583 | CA | ALA | A | 334 | 34.490 | 46.541 | 42.715 | 1.00 | 27.69 | C |
| ATOM | 1584 | CB | ALA | A | 334 | 34.939 | 45.110 | 42.435 | 1.00 | 27.56 | C |
| ATOM | 1585 | C | ALA | A | 334 | 32.958 | 46.645 | 42.574 | 1.00 | 27.32 | C |
| ATOM | 1586 | O | ALA | A | 334 | 32.462 | 47.295 | 41.646 | 1.00 | 26.29 | O |
| ATOM | 1587 | N | PHE | A | 335 | 32.225 | 46.006 | 43.496 | 1.00 | 26.71 | N |
| ATOM | 1588 | CA | PHE | A | 335 | 30.744 | 46.046 | 43.534 | 1.00 | 26.01 | C |
| ATOM | 1589 | CB | PHE | A | 335 | 30.202 | 45.140 | 44.664 | 1.00 | 25.43 | C |
| ATOM | 1590 | CG | PHE | A | 335 | 28.674 | 45.068 | 44.735 | 1.00 | 24.66 | C |
| ATOM | 1591 | CD1 | PHE | A | 335 | 27.943 | 46.010 | 45.455 | 1.00 | 24.18 | C |
| ATOM | 1592 | CE1 | PHE | A | 335 | 26.559 | 45.951 | 45.526 | 1.00 | 24.15 | C |

TABLE 3-continued

GLTP domain of FAPP2 atomic coordinates

| ATOM | 1593 | CZ | PHE | A | 335 | 25.880 | 44.935 | 44.888 | 1.00 | 24.11 | C |
|---|---|---|---|---|---|---|---|---|---|---|---|
| ATOM | 1594 | CE2 | PHE | A | 335 | 26.594 | 43.982 | 44.175 | 1.00 | 24.48 | C |
| ATOM | 1595 | CD2 | PHE | A | 335 | 27.980 | 44.046 | 44.108 | 1.00 | 23.83 | C |
| ATOM | 1596 | C | PHE | A | 335 | 30.186 | 47.465 | 43.719 | 1.00 | 26.45 | C |
| ATOM | 1597 | O | PHE | A | 335 | 29.211 | 47.857 | 43.074 | 1.00 | 26.11 | O |
| ATOM | 1598 | N | LEU | A | 336 | 30.798 | 48.211 | 44.630 | 1.00 | 27.34 | N |
| ATOM | 1599 | CA | LEU | A | 336 | 30.382 | 49.577 | 44.939 | 1.00 | 27.95 | C |
| ATOM | 1600 | CB | LEU | A | 336 | 30.999 | 50.018 | 46.283 | 1.00 | 29.19 | C |
| ATOM | 1601 | CG | LEU | A | 336 | 30.724 | 49.187 | 47.556 | 1.00 | 29.61 | C |
| ATOM | 1602 | CD1 | LEU | A | 336 | 31.220 | 49.934 | 48.783 | 1.00 | 29.32 | C |
| ATOM | 1603 | CD2 | LEU | A | 336 | 29.247 | 48.854 | 47.745 | 1.00 | 30.15 | C |
| ATOM | 1604 | C | LEU | A | 336 | 30.743 | 50.590 | 43.836 | 1.00 | 27.63 | C |
| ATOM | 1605 | O | LEU | A | 336 | 29.992 | 51.533 | 43.597 | 1.00 | 27.98 | O |
| ATOM | 1606 | N | ALA | A | 337 | 31.896 | 50.410 | 43.187 | 1.00 | 27.41 | N |
| ATOM | 1607 | CA | ALA | A | 337 | 32.309 | 51.277 | 42.077 | 1.00 | 25.98 | C |
| ATOM | 1608 | CB | ALA | A | 337 | 33.763 | 51.024 | 41.717 | 1.00 | 25.31 | C |
| ATOM | 1609 | C | ALA | A | 337 | 31.401 | 51.045 | 40.865 | 1.00 | 24.84 | C |
| ATOM | 1610 | O | ALA | A | 337 | 31.115 | 51.977 | 40.106 | 1.00 | 22.45 | O |
| ATOM | 1611 | N | SER | A | 338 | 30.970 | 49.793 | 40.709 | 1.00 | 25.28 | N |
| ATOM | 1612 | CA | SER | A | 338 | 29.971 | 49.402 | 39.703 | 1.00 | 26.59 | C |
| ATOM | 1613 | CB | SER | A | 338 | 29.781 | 47.877 | 39.659 | 1.00 | 26.24 | C |
| ATOM | 1614 | OG | SER | A | 338 | 30.968 | 47.198 | 39.310 | 1.00 | 26.55 | O |
| ATOM | 1615 | C | SER | A | 338 | 28.603 | 50.054 | 39.944 | 1.00 | 27.30 | C |
| ATOM | 1616 | O | SER | A | 338 | 27.949 | 50.470 | 38.989 | 1.00 | 26.61 | O |
| ATOM | 1617 | N | CYS | A | 339 | 28.180 | 50.130 | 41.209 | 1.00 | 27.92 | N |
| ATOM | 1618 | CA | CYS | A | 339 | 26.945 | 50.819 | 41.567 | 1.00 | 28.63 | C |
| ATOM | 1619 | CB | CYS | A | 339 | 26.647 | 50.705 | 43.070 | 1.00 | 29.61 | C |
| ATOM | 1620 | SG | CYS | A | 339 | 26.101 | 49.088 | 43.674 | 1.00 | 30.48 | S |
| ATOM | 1621 | C | CYS | A | 339 | 26.978 | 52.301 | 41.163 | 1.00 | 28.21 | C |
| ATOM | 1622 | O | CYS | A | 339 | 26.005 | 52.802 | 40.610 | 1.00 | 31.09 | O |
| ATOM | 1623 | N | TYR | A | 340 | 28.077 | 52.996 | 41.445 | 1.00 | 27.20 | N |
| ATOM | 1624 | CA | TYR | A | 340 | 28.201 | 54.430 | 41.123 | 1.00 | 26.80 | C |
| ATOM | 1625 | CB | TYR | A | 340 | 29.521 | 55.017 | 41.692 | 1.00 | 27.97 | C |
| ATOM | 1626 | CG | TYR | A | 340 | 29.493 | 55.455 | 43.170 | 1.00 | 28.67 | C |
| ATOM | 1627 | CD1 | TYR | A | 340 | 28.624 | 56.451 | 43.619 | 1.00 | 28.53 | C |
| ATOM | 1628 | CE1 | TYR | A | 340 | 28.606 | 56.852 | 44.942 | 1.00 | 28.59 | C |
| ATOM | 1629 | CZ | TYR | A | 340 | 29.476 | 56.276 | 45.838 | 1.00 | 29.89 | C |
| ATOM | 1630 | OH | TYR | A | 340 | 29.481 | 56.668 | 47.167 | 1.00 | 32.08 | O |
| ATOM | 1631 | CE2 | TYR | A | 340 | 30.362 | 55.303 | 45.420 | 1.00 | 29.96 | C |
| ATOM | 1632 | CD2 | TYR | A | 340 | 30.372 | 54.901 | 44.097 | 1.00 | 29.61 | C |
| ATOM | 1633 | C | TYR | A | 340 | 28.159 | 54.658 | 39.612 | 1.00 | 25.12 | C |
| ATOM | 1634 | O | TYR | A | 340 | 27.783 | 55.731 | 39.130 | 1.00 | 22.74 | O |
| ATOM | 1635 | N | ALA | A | 341 | 28.577 | 53.635 | 38.878 | 1.00 | 25.03 | N |
| ATOM | 1636 | CA | ALA | A | 341 | 28.727 | 53.724 | 37.452 | 1.00 | 25.74 | C |
| ATOM | 1637 | CB | ALA | A | 341 | 29.535 | 52.545 | 36.947 | 1.00 | 24.76 | C |
| ATOM | 1638 | C | ALA | A | 341 | 27.377 | 53.802 | 36.738 | 1.00 | 27.83 | C |
| ATOM | 1639 | O | ALA | A | 341 | 27.342 | 54.222 | 35.582 | 1.00 | 27.34 | O |
| ATOM | 1640 | N | VAL | A | 342 | 26.295 | 53.397 | 37.424 | 1.00 | 30.41 | N |
| ATOM | 1641 | CA | VAL | A | 342 | 24.912 | 53.425 | 36.878 | 1.00 | 33.95 | C |
| ATOM | 1642 | CB | VAL | A | 342 | 24.160 | 52.062 | 36.982 | 1.00 | 36.17 | C |
| ATOM | 1643 | CG1 | VAL | A | 342 | 24.390 | 51.216 | 35.737 | 1.00 | 37.22 | C |
| ATOM | 1644 | CG2 | VAL | A | 342 | 24.508 | 51.305 | 38.263 | 1.00 | 36.28 | C |
| ATOM | 1645 | C | VAL | A | 342 | 23.947 | 54.457 | 37.473 | 1.00 | 34.21 | C |
| ATOM | 1646 | O | VAL | A | 342 | 22.991 | 54.832 | 36.802 | 1.00 | 34.25 | O |
| ATOM | 1647 | N | VAL | A | 343 | 24.162 | 54.918 | 38.703 | 1.00 | 33.96 | N |
| ATOM | 1648 | CA | VAL | A | 343 | 23.212 | 55.871 | 39.289 | 1.00 | 34.86 | C |
| ATOM | 1649 | CB | VAL | A | 343 | 23.527 | 56.277 | 40.762 | 1.00 | 35.34 | C |
| ATOM | 1650 | CG1 | VAL | A | 343 | 23.543 | 55.048 | 41.665 | 1.00 | 35.35 | C |
| ATOM | 1651 | CG2 | VAL | A | 343 | 24.820 | 57.076 | 40.880 | 1.00 | 34.44 | C |
| ATOM | 1652 | C | VAL | A | 343 | 22.995 | 57.121 | 38.430 | 1.00 | 34.80 | C |
| ATOM | 1653 | O | VAL | A | 343 | 21.890 | 57.682 | 38.483 | 1.00 | 32.43 | O |
| ATOM | 1654 | N | PRO | A | 344 | 24.022 | 57.556 | 37.640 | 1.00 | 35.54 | N |
| ATOM | 1655 | CA | PRO | A | 344 | 23.725 | 58.611 | 36.680 | 1.00 | 36.45 | C |
| ATOM | 1656 | CB | PRO | A | 344 | 24.923 | 58.564 | 35.744 | 1.00 | 35.73 | C |
| ATOM | 1657 | CG | PRO | A | 344 | 26.046 | 58.268 | 36.668 | 1.00 | 35.28 | C |
| ATOM | 1658 | CD | PRO | A | 344 | 25.480 | 57.295 | 37.672 | 1.00 | 35.26 | C |
| ATOM | 1659 | C | PRO | A | 344 | 22.423 | 58.415 | 35.916 | 1.00 | 37.77 | C |
| ATOM | 1660 | O | PRO | A | 344 | 21.750 | 59.396 | 35.656 | 1.00 | 40.26 | O |
| ATOM | 1661 | N | VAL | A | 345 | 22.049 | 57.173 | 35.598 | 1.00 | 38.84 | N |
| ATOM | 1662 | CA | VAL | A | 345 | 20.753 | 56.886 | 34.924 | 1.00 | 39.53 | C |
| ATOM | 1663 | CB | VAL | A | 345 | 20.379 | 55.377 | 34.941 | 1.00 | 40.42 | C |
| ATOM | 1664 | CG1 | VAL | A | 345 | 18.949 | 55.156 | 34.450 | 1.00 | 42.16 | C |
| ATOM | 1665 | CG2 | VAL | A | 345 | 21.316 | 54.584 | 34.057 | 1.00 | 40.90 | C |
| ATOM | 1666 | C | VAL | A | 345 | 19.572 | 57.691 | 35.497 | 1.00 | 37.21 | C |
| ATOM | 1667 | O | VAL | A | 345 | 18.832 | 58.324 | 34.745 | 1.00 | 36.62 | O |
| ATOM | 1668 | N | LEU | A | 346 | 19.404 | 57.674 | 36.816 | 1.00 | 36.05 | N |
| ATOM | 1669 | CA | LEU | A | 346 | 18.301 | 58.397 | 37.449 | 1.00 | 36.42 | C |
| ATOM | 1670 | CB | LEU | A | 346 | 18.142 | 58.008 | 38.922 | 1.00 | 38.49 | C |

TABLE 3-continued

GLTP domain of FAPP2 atomic coordinates

| ATOM | 1671 | CG | LEU | A | 346 | 17.699 | 56.585 | 39.328 | 1.00 | 40.20 | C |
|---|---|---|---|---|---|---|---|---|---|---|---|
| ATOM | 1672 | CD1 | LEU | A | 346 | 16.688 | 55.964 | 38.360 | 1.00 | 41.56 | C |
| ATOM | 1673 | CD2 | LEU | A | 346 | 18.896 | 55.660 | 39.508 | 1.00 | 40.73 | C |
| ATOM | 1674 | C | LEU | A | 346 | 18.476 | 59.910 | 37.327 | 1.00 | 34.87 | C |
| ATOM | 1675 | O | LEU | A | 346 | 17.504 | 60.653 | 37.392 | 1.00 | 34.48 | O |
| ATOM | 1676 | N | ASP | A | 347 | 19.720 | 60.349 | 37.164 | 1.00 | 33.90 | N |
| ATOM | 1677 | CA | ASP | A | 347 | 20.044 | 61.747 | 36.882 | 1.00 | 34.29 | C |
| ATOM | 1678 | CB | ASP | A | 347 | 21.573 | 61.940 | 36.974 | 1.00 | 36.13 | C |
| ATOM | 1679 | CG | ASP | A | 347 | 22.026 | 63.367 | 36.691 | 1.00 | 38.09 | C |
| ATOM | 1680 | OD1 | ASP | A | 347 | 21.453 | 64.036 | 35.790 | 1.00 | 38.80 | O |
| ATOM | 1681 | OD2 | ASP | A | 347 | 22.999 | 63.801 | 37.356 | 1.00 | 39.27 | O |
| ATOM | 1682 | C | ASP | A | 347 | 19.540 | 62.160 | 35.506 | 1.00 | 31.85 | C |
| ATOM | 1683 | O | ASP | A | 347 | 19.119 | 63.290 | 35.302 | 1.00 | 31.17 | O |
| ATOM | 1684 | N | LYS | A | 348 | 19.568 | 61.227 | 34.571 | 1.00 | 31.65 | N |
| ATOM | 1685 | CA | LYS | A | 348 | 19.357 | 61.541 | 33.166 | 1.00 | 31.33 | C |
| ATOM | 1686 | CB | LYS | A | 348 | 20.022 | 60.491 | 32.287 | 1.00 | 30.65 | C |
| ATOM | 1687 | CG | LYS | A | 348 | 21.321 | 59.993 | 32.881 | 1.00 | 29.82 | C |
| ATOM | 1688 | CD | LYS | A | 348 | 22.375 | 59.687 | 31.848 | 1.00 | 30.94 | C |
| ATOM | 1689 | CE | LYS | A | 348 | 23.772 | 59.778 | 32.458 | 1.00 | 31.12 | C |
| ATOM | 1690 | NZ | LYS | A | 348 | 24.669 | 60.604 | 31.605 | 1.00 | 30.90 | N |
| ATOM | 1691 | C | LYS | A | 348 | 17.891 | 61.631 | 32.856 | 1.00 | 31.36 | C |
| ATOM | 1692 | O | LYS | A | 348 | 17.515 | 62.176 | 31.825 | 1.00 | 32.62 | O |
| ATOM | 1693 | N | LEU | A | 349 | 17.078 | 61.085 | 33.760 | 1.00 | 32.17 | N |
| ATOM | 1694 | CA | LEU | A | 349 | 15.613 | 61.133 | 33.683 | 1.00 | 31.89 | C |
| ATOM | 1695 | CB | LEU | A | 349 | 15.018 | 60.002 | 34.529 | 1.00 | 31.16 | C |
| ATOM | 1696 | CG | LEU | A | 349 | 15.387 | 58.576 | 34.127 | 1.00 | 30.62 | C |
| ATOM | 1697 | CD1 | LEU | A | 349 | 15.055 | 57.588 | 35.234 | 1.00 | 30.35 | C |
| ATOM | 1698 | CD2 | LEU | A | 349 | 14.661 | 58.203 | 32.847 | 1.00 | 31.02 | C |
| ATOM | 1699 | C | LEU | A | 349 | 15.005 | 62.437 | 34.189 | 1.00 | 32.16 | C |
| ATOM | 1700 | O | LEU | A | 349 | 13.908 | 62.809 | 33.782 | 1.00 | 32.34 | O |
| ATOM | 1701 | N | GLY | A | 350 | 15.688 | 63.110 | 35.107 | 1.00 | 32.34 | N |
| ATOM | 1702 | CA | GLY | A | 350 | 15.066 | 64.210 | 35.856 | 1.00 | 34.01 | C |
| ATOM | 1703 | C | GLY | A | 350 | 15.741 | 64.349 | 37.207 | 1.00 | 34.30 | C |
| ATOM | 1704 | O | GLY | A | 350 | 15.259 | 63.832 | 38.219 | 1.00 | 33.20 | O |
| ATOM | 1705 | N | PRO | A | 351 | 16.868 | 65.060 | 37.227 | 1.00 | 35.08 | N |
| ATOM | 1706 | CA | PRO | A | 351 | 17.781 | 65.014 | 38.354 | 1.00 | 35.76 | C |
| ATOM | 1707 | CB | PRO | A | 351 | 18.987 | 65.808 | 37.848 | 1.00 | 36.75 | C |
| ATOM | 1708 | CG | PRO | A | 351 | 18.419 | 66.757 | 36.849 | 1.00 | 35.94 | C |
| ATOM | 1709 | CD | PRO | A | 351 | 17.261 | 66.060 | 36.220 | 1.00 | 35.23 | C |
| ATOM | 1710 | C | PRO | A | 351 | 17.218 | 65.605 | 39.654 | 1.00 | 35.02 | C |
| ATOM | 1711 | O | PRO | A | 351 | 17.731 | 65.290 | 40.738 | 1.00 | 35.18 | O |
| ATOM | 1712 | N | THR | A | 352 | 16.196 | 66.452 | 39.549 | 1.00 | 34.13 | N |
| ATOM | 1713 | CA | THR | A | 352 | 15.471 | 66.932 | 40.726 | 1.00 | 35.12 | C |
| ATOM | 1714 | CB | THR | A | 352 | 14.685 | 68.232 | 40.446 | 1.00 | 36.74 | C |
| ATOM | 1715 | OG1 | THR | A | 352 | 13.760 | 68.012 | 39.363 | 1.00 | 40.61 | O |
| ATOM | 1716 | CG2 | THR | A | 352 | 15.619 | 69.373 | 40.105 | 1.00 | 36.37 | C |
| ATOM | 1717 | C | THR | A | 352 | 14.441 | 65.907 | 41.186 | 1.00 | 32.82 | C |
| ATOM | 1718 | O | THR | A | 352 | 14.427 | 65.490 | 42.342 | 1.00 | 33.41 | O |
| ATOM | 1719 | N | VAL | A | 353 | 13.569 | 65.517 | 40.270 | 1.00 | 30.06 | N |
| ATOM | 1720 | CA | VAL | A | 353 | 12.331 | 64.875 | 40.656 | 1.00 | 28.62 | C |
| ATOM | 1721 | CB | VAL | A | 353 | 11.231 | 65.176 | 39.623 | 1.00 | 28.97 | C |
| ATOM | 1722 | CG1 | VAL | A | 353 | 11.334 | 64.253 | 38.414 | 1.00 | 29.69 | C |
| ATOM | 1723 | CG2 | VAL | A | 353 | 9.869 | 65.072 | 40.279 | 1.00 | 29.21 | C |
| ATOM | 1724 | C | VAL | A | 353 | 12.461 | 63.371 | 40.928 | 1.00 | 26.72 | C |
| ATOM | 1725 | O | VAL | A | 353 | 11.632 | 62.811 | 41.647 | 1.00 | 27.55 | O |
| ATOM | 1726 | N | PHE | A | 354 | 13.483 | 62.724 | 40.363 | 1.00 | 24.13 | N |
| ATOM | 1727 | CA | PHE | A | 354 | 13.811 | 61.338 | 40.712 | 1.00 | 22.48 | C |
| ATOM | 1728 | CB | PHE | A | 354 | 14.099 | 60.526 | 39.451 | 1.00 | 22.38 | C |
| ATOM | 1729 | CG | PHE | A | 354 | 12.949 | 60.478 | 38.493 | 1.00 | 22.82 | C |
| ATOM | 1730 | CD1 | PHE | A | 354 | 11.919 | 59.559 | 38.669 | 1.00 | 23.14 | C |
| ATOM | 1731 | CE1 | PHE | A | 354 | 10.844 | 59.529 | 37.800 | 1.00 | 22.91 | C |
| ATOM | 1732 | CZ | PHE | A | 354 | 10.795 | 60.415 | 36.738 | 1.00 | 22.87 | C |
| ATOM | 1733 | CE2 | PHE | A | 354 | 11.814 | 61.332 | 36.548 | 1.00 | 22.47 | C |
| ATOM | 1734 | CD2 | PHE | A | 354 | 12.882 | 61.360 | 37.422 | 1.00 | 22.73 | C |
| ATOM | 1735 | C | PHE | A | 354 | 14.986 | 61.250 | 41.706 | 1.00 | 21.23 | C |
| ATOM | 1736 | O | PHE | A | 354 | 15.601 | 60.197 | 41.879 | 1.00 | 21.29 | O |
| ATOM | 1737 | N | ALA | A | 355 | 15.286 | 62.353 | 42.378 | 1.00 | 20.01 | N |
| ATOM | 1738 | CA | ALA | A | 355 | 16.215 | 62.321 | 43.491 | 1.00 | 19.26 | C |
| ATOM | 1739 | CB | ALA | A | 355 | 16.284 | 63.676 | 44.177 | 1.00 | 19.09 | C |
| ATOM | 1740 | C | ALA | A | 355 | 15.846 | 61.228 | 44.492 | 1.00 | 19.21 | C |
| ATOM | 1741 | O | ALA | A | 355 | 16.718 | 60.455 | 44.856 | 1.00 | 19.93 | O |
| ATOM | 1742 | N | PRO | A | 356 | 14.556 | 61.133 | 44.909 | 1.00 | 19.06 | N |
| ATOM | 1743 | CA | PRO | A | 356 | 14.166 | 60.215 | 45.974 | 1.00 | 19.34 | C |
| ATOM | 1744 | CB | PRO | A | 356 | 12.649 | 60.131 | 45.798 | 1.00 | 19.09 | C |
| ATOM | 1745 | CG | PRO | A | 356 | 12.284 | 61.510 | 45.398 | 1.00 | 18.79 | C |
| ATOM | 1746 | CD | PRO | A | 356 | 13.376 | 61.890 | 44.434 | 1.00 | 19.01 | C |
| ATOM | 1747 | C | PRO | A | 356 | 14.791 | 58.835 | 45.912 | 1.00 | 20.16 | C |
| ATOM | 1748 | O | PRO | A | 356 | 15.390 | 58.372 | 46.879 | 1.00 | 19.31 | O |

TABLE 3-continued

GLTP domain of FAPP2 atomic coordinates

| ATOM | 1749 | N   | VAL | A | 357 | 14.663 | 58.187 | 44.771 | 1.00 | 22.20 | N |
|------|------|-----|-----|---|-----|--------|--------|--------|------|-------|---|
| ATOM | 1750 | CA  | VAL | A | 357 | 15.281 | 56.881 | 44.577 | 1.00 | 24.07 | C |
| ATOM | 1751 | CB  | VAL | A | 357 | 14.770 | 56.240 | 43.269 | 1.00 | 24.60 | C |
| ATOM | 1752 | CG1 | VAL | A | 357 | 15.472 | 54.913 | 43.007 | 1.00 | 24.52 | C |
| ATOM | 1753 | CG2 | VAL | A | 357 | 13.248 | 56.060 | 43.334 | 1.00 | 24.97 | C |
| ATOM | 1754 | C   | VAL | A | 357 | 16.828 | 56.967 | 44.588 | 1.00 | 25.22 | C |
| ATOM | 1755 | O   | VAL | A | 357 | 17.504 | 56.190 | 45.300 | 1.00 | 23.80 | O |
| ATOM | 1756 | N   | LYS | A | 358 | 17.365 | 57.924 | 43.825 | 1.00 | 26.57 | N |
| ATOM | 1757 | CA  | LYS | A | 358 | 18.811 | 58.074 | 43.653 | 1.00 | 29.23 | C |
| ATOM | 1758 | CB  | LYS | A | 358 | 19.134 | 59.233 | 42.718 | 1.00 | 29.81 | C |
| ATOM | 1759 | CG  | LYS | A | 358 | 20.594 | 59.634 | 42.798 | 1.00 | 30.79 | C |
| ATOM | 1760 | CD  | LYS | A | 358 | 20.955 | 60.706 | 41.801 | 1.00 | 32.22 | C |
| ATOM | 1761 | CE  | LYS | A | 358 | 22.369 | 61.188 | 42.073 | 1.00 | 33.10 | C |
| ATOM | 1762 | NZ  | LYS | A | 358 | 22.766 | 62.218 | 41.082 | 1.00 | 34.47 | N |
| ATOM | 1763 | C   | LYS | A | 358 | 19.555 | 58.304 | 44.959 | 1.00 | 31.56 | C |
| ATOM | 1764 | O   | LYS | A | 358 | 20.479 | 57.570 | 45.290 | 1.00 | 32.09 | O |
| ATOM | 1765 | N   | MET | A | 359 | 19.178 | 59.366 | 45.658 | 1.00 | 34.06 | N |
| ATOM | 1766 | CA  | MET | A | 359 | 19.737 | 59.680 | 46.950 | 1.00 | 35.89 | C |
| ATOM | 1767 | CB  | MET | A | 359 | 18.942 | 60.814 | 47.587 | 1.00 | 39.91 | C |
| ATOM | 1768 | CG  | MET | A | 359 | 19.254 | 62.200 | 47.032 | 1.00 | 42.17 | C |
| ATOM | 1769 | SD  | MET | A | 359 | 20.606 | 63.104 | 47.823 | 1.00 | 46.88 | S |
| ATOM | 1770 | CE  | MET | A | 359 | 20.755 | 62.325 | 49.439 | 1.00 | 45.36 | C |
| ATOM | 1771 | C   | MET | A | 359 | 19.686 | 58.451 | 47.843 | 1.00 | 36.43 | C |
| ATOM | 1772 | O   | MET | A | 359 | 20.708 | 58.064 | 48.400 | 1.00 | 36.41 | O |
| ATOM | 1773 | N   | ASP | A | 360 | 18.506 | 57.831 | 47.954 | 1.00 | 38.15 | N |
| ATOM | 1774 | CA  | ASP | A | 360 | 18.317 | 56.652 | 48.825 | 1.00 | 40.22 | C |
| ATOM | 1775 | CB  | ASP | A | 360 | 16.885 | 56.070 | 48.744 | 1.00 | 40.94 | C |
| ATOM | 1776 | CG  | ASP | A | 360 | 16.009 | 56.417 | 49.979 | 1.00 | 42.38 | C |
| ATOM | 1777 | OD1 | ASP | A | 360 | 16.483 | 57.111 | 50.913 | 1.00 | 43.03 | O |
| ATOM | 1778 | OD2 | ASP | A | 360 | 14.832 | 55.982 | 50.020 | 1.00 | 41.12 | O |
| ATOM | 1779 | C   | ASP | A | 360 | 19.330 | 55.567 | 48.494 | 1.00 | 42.22 | C |
| ATOM | 1780 | O   | ASP | A | 360 | 19.995 | 55.048 | 49.392 | 1.00 | 42.24 | O |
| ATOM | 1781 | N   | LEU | A | 361 | 19.447 | 55.236 | 47.208 | 1.00 | 44.04 | N |
| ATOM | 1782 | CA  | LEU | A | 361 | 20.454 | 54.276 | 46.753 | 1.00 | 44.79 | C |
| ATOM | 1783 | CB  | LEU | A | 361 | 20.358 | 54.065 | 45.239 | 1.00 | 49.90 | C |
| ATOM | 1784 | CG  | LEU | A | 361 | 21.102 | 52.845 | 44.671 | 1.00 | 54.97 | C |
| ATOM | 1785 | CD1 | LEU | A | 361 | 20.472 | 51.567 | 45.204 | 1.00 | 58.17 | C |
| ATOM | 1786 | CD2 | LEU | A | 361 | 21.102 | 52.829 | 43.146 | 1.00 | 55.60 | C |
| ATOM | 1787 | C   | LEU | A | 361 | 21.869 | 54.734 | 47.119 | 1.00 | 41.22 | C |
| ATOM | 1788 | O   | LEU | A | 361 | 22.624 | 53.975 | 47.734 | 1.00 | 40.12 | O |
| ATOM | 1789 | N   | VAL | A | 362 | 22.205 | 55.977 | 46.759 | 1.00 | 37.16 | N |
| ATOM | 1790 | CA  | VAL | A | 362 | 23.543 | 56.538 | 46.984 | 1.00 | 34.59 | C |
| ATOM | 1791 | CB  | VAL | A | 362 | 23.670 | 57.970 | 46.406 | 1.00 | 33.88 | C |
| ATOM | 1792 | CG1 | VAL | A | 362 | 24.968 | 58.634 | 46.854 | 1.00 | 33.98 | C |
| ATOM | 1793 | CG2 | VAL | A | 362 | 23.616 | 57.939 | 44.889 | 1.00 | 33.19 | C |
| ATOM | 1794 | C   | VAL | A | 362 | 23.898 | 56.539 | 48.470 | 1.00 | 33.66 | C |
| ATOM | 1795 | O   | VAL | A | 362 | 25.070 | 56.414 | 48.832 | 1.00 | 31.00 | O |
| ATOM | 1796 | N   | GLY | A | 363 | 22.877 | 56.676 | 49.316 | 1.00 | 33.12 | N |
| ATOM | 1797 | CA  | GLY | A | 363 | 23.033 | 56.640 | 50.771 | 1.00 | 32.57 | C |
| ATOM | 1798 | C   | GLY | A | 363 | 23.375 | 55.281 | 51.360 | 1.00 | 32.04 | C |
| ATOM | 1799 | O   | GLY | A | 363 | 24.019 | 55.201 | 52.404 | 1.00 | 31.47 | O |
| ATOM | 1800 | N   | ASN | A | 364 | 22.929 | 54.217 | 50.705 | 1.00 | 32.41 | N |
| ATOM | 1801 | CA  | ASN | A | 364 | 23.263 | 52.850 | 51.106 | 1.00 | 34.01 | C |
| ATOM | 1802 | CB  | ASN | A | 364 | 22.189 | 51.885 | 50.607 | 1.00 | 35.44 | C |
| ATOM | 1803 | CG  | ASN | A | 364 | 20.810 | 52.196 | 51.172 | 1.00 | 35.65 | C |
| ATOM | 1804 | OD1 | ASN | A | 364 | 20.672 | 52.522 | 52.346 | 1.00 | 37.40 | O |
| ATOM | 1805 | ND2 | ASN | A | 364 | 19.785 | 52.086 | 50.339 | 1.00 | 34.54 | N |
| ATOM | 1806 | C   | ASN | A | 364 | 24.616 | 52.406 | 50.555 | 1.00 | 34.42 | C |
| ATOM | 1807 | O   | ASN | A | 364 | 25.119 | 51.342 | 50.906 | 1.00 | 34.10 | O |
| ATOM | 1808 | N   | ILE | A | 365 | 25.177 | 53.221 | 49.667 | 1.00 | 35.11 | N |
| ATOM | 1809 | CA  | ILE | A | 365 | 26.498 | 52.995 | 49.095 | 1.00 | 35.70 | C |
| ATOM | 1810 | CB  | ILE | A | 365 | 26.552 | 53.534 | 47.647 | 1.00 | 35.09 | C |
| ATOM | 1811 | CG1 | ILE | A | 365 | 25.707 | 52.627 | 46.735 | 1.00 | 34.99 | C |
| ATOM | 1812 | CD1 | ILE | A | 365 | 25.442 | 53.173 | 45.345 | 1.00 | 34.45 | C |
| ATOM | 1813 | CG2 | ILE | A | 365 | 27.984 | 53.621 | 47.145 | 1.00 | 34.16 | C |
| ATOM | 1814 | C   | ILE | A | 365 | 27.583 | 53.627 | 49.972 | 1.00 | 37.03 | C |
| ATOM | 1815 | O   | ILE | A | 365 | 28.633 | 53.014 | 50.199 | 1.00 | 36.95 | O |
| ATOM | 1816 | N   | LYS | A | 366 | 27.329 | 54.844 | 50.458 | 1.00 | 39.31 | N |
| ATOM | 1817 | CA  | LYS | A | 366 | 28.202 | 55.478 | 51.462 | 1.00 | 41.90 | C |
| ATOM | 1818 | CB  | LYS | A | 366 | 27.618 | 56.781 | 52.036 | 1.00 | 43.01 | C |
| ATOM | 1819 | CG  | LYS | A | 366 | 27.049 | 57.804 | 51.071 | 1.00 | 44.48 | C |
| ATOM | 1820 | CD  | LYS | A | 366 | 28.042 | 58.269 | 50.029 | 1.00 | 45.57 | C |
| ATOM | 1821 | CE  | LYS | A | 366 | 27.500 | 59.511 | 49.342 | 1.00 | 47.78 | C |
| ATOM | 1822 | NZ  | LYS | A | 366 | 27.857 | 59.556 | 47.898 | 1.00 | 50.62 | N |
| ATOM | 1823 | C   | LYS | A | 366 | 28.358 | 54.537 | 52.647 | 1.00 | 42.13 | C |
| ATOM | 1824 | O   | LYS | A | 366 | 29.473 | 54.249 | 53.093 | 1.00 | 40.25 | O |
| ATOM | 1825 | N   | LYS | A | 367 | 27.203 | 54.062 | 53.116 | 1.00 | 42.74 | N |
| ATOM | 1826 | CA  | LYS | A | 367 | 27.021 | 53.432 | 54.427 | 1.00 | 43.75 | C |

TABLE 3-continued

| | | | | GLTP domain of FAPP2 atomic coordinates | | | | | |
|---|---|---|---|---|---|---|---|---|---|
| ATOM | 1827 | CB | LYS | A | 367 | 25.549 | 53.584 | 54.809 | 1.00 | 43.56 C |
| ATOM | 1828 | CG | LYS | A | 367 | 25.159 | 53.256 | 56.244 | 1.00 | 43.93 C |
| ATOM | 1829 | CD | LYS | A | 367 | 23.730 | 53.728 | 56.554 | 1.00 | 43.91 C |
| ATOM | 1830 | CE | LYS | A | 367 | 22.789 | 53.662 | 55.339 | 1.00 | 42.76 C |
| ATOM | 1831 | NZ | LYS | A | 367 | 21.343 | 53.750 | 55.663 | 1.00 | 40.92 N |
| ATOM | 1832 | C | LYS | A | 367 | 27.446 | 51.954 | 54.481 | 1.00 | 44.43 C |
| ATOM | 1833 | O | LYS | A | 367 | 27.755 | 51.426 | 55.557 | 1.00 | 44.46 O |
| ATOM | 1834 | N | VAL | A | 368 | 27.446 | 51.284 | 53.331 | 1.00 | 44.02 N |
| ATOM | 1835 | CA | VAL | A | 368 | 28.125 | 49.996 | 53.213 | 1.00 | 43.07 C |
| ATOM | 1836 | CB | VAL | A | 368 | 27.558 | 49.149 | 52.050 | 1.00 | 43.55 C |
| ATOM | 1837 | CG1 | VAL | A | 368 | 28.450 | 47.953 | 51.745 | 1.00 | 43.46 C |
| ATOM | 1838 | CG2 | VAL | A | 368 | 26.155 | 48.675 | 52.392 | 1.00 | 43.74 C |
| ATOM | 1839 | C | VAL | A | 368 | 29.632 | 50.246 | 53.054 | 1.00 | 41.73 C |
| ATOM | 1840 | O | VAL | A | 368 | 30.438 | 49.468 | 53.565 | 1.00 | 40.10 O |
| ATOM | 1841 | N | ASN | A | 369 | 29.999 | 51.332 | 52.363 | 1.00 | 41.05 N |
| ATOM | 1842 | CA | ASN | A | 369 | 31.411 | 51.709 | 52.172 | 1.00 | 40.25 C |
| ATOM | 1843 | CB | ASN | A | 369 | 31.562 | 52.732 | 51.033 | 1.00 | 38.67 C |
| ATOM | 1844 | CG | ASN | A | 369 | 33.020 | 53.011 | 50.688 | 1.00 | 36.99 C |
| ATOM | 1845 | OD1 | ASN | A | 369 | 33.885 | 52.143 | 50.824 | 1.00 | 34.18 O |
| ATOM | 1846 | ND2 | ASN | A | 369 | 33.297 | 54.227 | 50.240 | 1.00 | 36.42 N |
| ATOM | 1847 | C | ASN | A | 369 | 32.079 | 52.260 | 53.441 | 1.00 | 40.54 C |
| ATOM | 1848 | O | ASN | A | 369 | 33.238 | 51.954 | 53.728 | 1.00 | 39.08 O |
| ATOM | 1849 | N | GLN | A | 370 | 31.342 | 53.074 | 54.188 | 1.00 | 40.73 N |
| ATOM | 1850 | CA | GLN | A | 370 | 31.819 | 53.605 | 55.459 | 1.00 | 41.72 C |
| ATOM | 1851 | CB | GLN | A | 370 | 30.752 | 54.535 | 56.064 | 1.00 | 42.12 C |
| ATOM | 1852 | CG | GLN | A | 370 | 31.274 | 55.521 | 57.105 | 1.00 | 42.70 C |
| ATOM | 1853 | CD | GLN | A | 370 | 32.002 | 56.711 | 56.494 | 1.00 | 41.73 C |
| ATOM | 1854 | OE1 | GLN | A | 370 | 32.320 | 56.720 | 55.298 | 1.00 | 39.98 O |
| ATOM | 1855 | NE2 | GLN | A | 370 | 32.273 | 57.723 | 57.319 | 1.00 | 40.06 N |
| ATOM | 1856 | C | GLN | A | 370 | 32.169 | 52.453 | 56.432 | 1.00 | 42.62 C |
| ATOM | 1857 | O | GLN | A | 370 | 33.042 | 52.598 | 57.295 | 1.00 | 42.07 O |
| ATOM | 1858 | N | LYS | A | 371 | 31.477 | 51.321 | 56.280 | 1.00 | 43.25 N |
| ATOM | 1859 | CA | LYS | A | 371 | 31.758 | 50.090 | 57.035 | 1.00 | 41.98 C |
| ATOM | 1860 | CB | LYS | A | 371 | 30.531 | 49.155 | 56.973 | 1.00 | 41.46 C |
| ATOM | 1861 | CG | LYS | A | 371 | 30.684 | 47.782 | 57.613 | 1.00 | 40.88 C |
| ATOM | 1862 | CD | LYS | A | 371 | 30.760 | 47.842 | 59.129 | 1.00 | 40.91 C |
| ATOM | 1863 | CE | LYS | A | 371 | 30.846 | 46.437 | 59.713 | 1.00 | 41.07 C |
| ATOM | 1864 | NZ | LYS | A | 371 | 30.849 | 46.391 | 61.204 | 1.00 | 40.50 N |
| ATOM | 1865 | C | LYS | A | 371 | 33.023 | 49.386 | 56.511 | 1.00 | 41.54 C |
| ATOM | 1866 | O | LYS | A | 371 | 33.833 | 48.903 | 57.303 | 1.00 | 40.97 O |
| ATOM | 1867 | N | TYR | A | 372 | 33.186 | 49.331 | 55.185 | 1.00 | 40.56 N |
| ATOM | 1868 | CA | TYR | A | 372 | 34.356 | 48.690 | 54.556 | 1.00 | 40.18 C |
| ATOM | 1869 | CB | TYR | A | 372 | 34.176 | 48.617 | 53.028 | 1.00 | 38.88 C |
| ATOM | 1870 | CG | TYR | A | 372 | 35.415 | 48.164 | 52.261 | 1.00 | 38.18 C |
| ATOM | 1871 | CD1 | TYR | A | 372 | 35.875 | 46.855 | 52.351 | 1.00 | 37.41 C |
| ATOM | 1872 | CE1 | TYR | A | 372 | 37.006 | 46.438 | 51.659 | 1.00 | 37.47 C |
| ATOM | 1873 | CZ | TYR | A | 372 | 37.693 | 47.336 | 50.848 | 1.00 | 37.36 C |
| ATOM | 1874 | OH | TYR | A | 372 | 38.815 | 46.922 | 50.157 | 1.00 | 36.28 O |
| ATOM | 1875 | CE2 | TYR | A | 372 | 37.253 | 48.643 | 50.736 | 1.00 | 37.29 C |
| ATOM | 1876 | CD2 | TYR | A | 372 | 36.124 | 49.051 | 51.439 | 1.00 | 37.98 C |
| ATOM | 1877 | C | TYR | A | 372 | 35.692 | 49.381 | 54.889 | 1.00 | 41.28 C |
| ATOM | 1878 | O | TYR | A | 372 | 36.667 | 48.717 | 55.254 | 1.00 | 39.56 O |
| ATOM | 1879 | N | ILE | A | 373 | 35.728 | 50.707 | 54.759 | 1.00 | 43.08 N |
| ATOM | 1880 | CA | ILE | A | 373 | 36.966 | 51.475 | 54.949 | 1.00 | 44.94 C |
| ATOM | 1881 | CB | ILE | A | 373 | 36.757 | 53.002 | 54.715 | 1.00 | 46.01 C |
| ATOM | 1882 | CG1 | ILE | A | 373 | 36.444 | 53.306 | 53.233 | 1.00 | 46.09 C |
| ATOM | 1883 | CD1 | ILE | A | 373 | 37.641 | 53.297 | 52.292 | 1.00 | 46.31 C |
| ATOM | 1884 | CG2 | ILE | A | 373 | 37.978 | 53.808 | 55.174 | 1.00 | 46.11 C |
| ATOM | 1885 | C | ILE | A | 373 | 37.582 | 51.220 | 56.332 | 1.00 | 44.80 C |
| ATOM | 1886 | O | ILE | A | 373 | 38.810 | 51.223 | 56.466 | 1.00 | 44.68 O |
| ATOM | 1887 | N | THR | A | 374 | 36.741 | 50.990 | 57.344 | 1.00 | 45.02 N |
| ATOM | 1888 | CA | THR | A | 374 | 37.230 | 50.643 | 58.687 | 1.00 | 46.29 C |
| ATOM | 1889 | CB | THR | A | 374 | 36.203 | 50.965 | 59.804 | 1.00 | 45.10 C |
| ATOM | 1890 | OG1 | THR | A | 374 | 35.069 | 50.094 | 59.711 | 1.00 | 43.00 O |
| ATOM | 1891 | CG2 | THR | A | 374 | 35.741 | 52.414 | 59.719 | 1.00 | 44.66 C |
| ATOM | 1892 | C | THR | A | 374 | 37.624 | 49.161 | 58.733 | 1.00 | 48.10 C |
| ATOM | 1893 | O | THR | A | 374 | 36.834 | 48.311 | 59.147 | 1.00 | 48.49 O |
| ATOM | 1894 | N | ASN | A | 375 | 38.853 | 48.879 | 58.293 | 1.00 | 49.72 N |
| ATOM | 1895 | CA | ASN | A | 375 | 39.425 | 47.516 | 58.215 | 1.00 | 50.03 C |
| ATOM | 1896 | CB | ASN | A | 375 | 39.303 | 46.770 | 59.571 | 1.00 | 50.44 C |
| ATOM | 1897 | CG | ASN | A | 375 | 38.953 | 45.301 | 59.423 | 1.00 | 50.32 C |
| ATOM | 1898 | OD1 | ASN | A | 375 | 39.831 | 44.435 | 59.442 | 1.00 | 51.21 O |
| ATOM | 1899 | ND2 | ASN | A | 375 | 37.662 | 45.012 | 59.292 | 1.00 | 49.01 N |
| ATOM | 1900 | C | ASN | A | 375 | 38.947 | 46.693 | 56.986 | 1.00 | 48.85 C |
| ATOM | 1901 | O | ASN | A | 375 | 37.837 | 46.154 | 56.954 | 1.00 | 48.66 O |
| ATOM | 1902 | N | LYS | A | 376 | 39.819 | 46.617 | 55.981 | 1.00 | 47.47 N |
| ATOM | 1903 | CA | LYS | A | 376 | 39.533 | 45.939 | 54.719 | 1.00 | 46.06 C |
| ATOM | 1904 | CB | LYS | A | 376 | 40.153 | 46.724 | 53.560 | 1.00 | 46.34 C |

TABLE 3-continued

GLTP domain of FAPP2 atomic coordinates

| ATOM | 1905 | CG | LYS | A | 376 | 39.806 | 48.203 | 53.544 | 1.00 | 46.78 | C |
|---|---|---|---|---|---|---|---|---|---|---|---|
| ATOM | 1906 | CD | LYS | A | 376 | 40.605 | 48.938 | 52.485 | 1.00 | 47.29 | C |
| ATOM | 1907 | CE | LYS | A | 376 | 40.323 | 50.428 | 52.527 | 1.00 | 48.10 | C |
| ATOM | 1908 | NZ | LYS | A | 376 | 41.032 | 51.152 | 51.438 | 1.00 | 48.86 | N |
| ATOM | 1909 | C | LYS | A | 376 | 40.057 | 44.501 | 54.674 | 1.00 | 44.77 | C |
| ATOM | 1910 | O | LYS | A | 376 | 39.629 | 43.724 | 53.824 | 1.00 | 45.01 | O |
| ATOM | 1911 | N | GLU | A | 377 | 40.986 | 44.151 | 55.568 | 1.00 | 43.86 | N |
| ATOM | 1912 | CA | GLU | A | 377 | 41.598 | 42.810 | 55.582 | 1.00 | 42.35 | C |
| ATOM | 1913 | CB | GLU | A | 377 | 42.504 | 42.628 | 56.806 | 1.00 | 41.60 | C |
| ATOM | 1914 | CG | GLU | A | 377 | 43.241 | 41.287 | 56.845 | 1.00 | 40.90 | C |
| ATOM | 1915 | CD | GLU | A | 377 | 43.760 | 40.912 | 58.225 | 1.00 | 40.31 | C |
| ATOM | 1916 | OE1 | GLU | A | 377 | 43.704 | 41.752 | 59.150 | 1.00 | 39.64 | O |
| ATOM | 1917 | OE2 | GLU | A | 377 | 44.231 | 39.765 | 58.384 | 1.00 | 39.19 | O |
| ATOM | 1918 | C | GLU | A | 377 | 40.554 | 41.699 | 55.583 | 1.00 | 41.45 | C |
| ATOM | 1919 | O | GLU | A | 377 | 40.671 | 40.738 | 54.819 | 1.00 | 41.01 | O |
| ATOM | 1920 | N | GLU | A | 378 | 39.551 | 41.830 | 56.454 | 1.00 | 40.13 | N |
| ATOM | 1921 | CA | GLU | A | 378 | 38.512 | 40.801 | 56.602 | 1.00 | 38.87 | C |
| ATOM | 1922 | CB | GLU | A | 378 | 38.264 | 40.440 | 58.087 | 1.00 | 38.77 | C |
| ATOM | 1923 | CG | GLU | A | 378 | 37.769 | 41.557 | 59.002 | 1.00 | 38.87 | C |
| ATOM | 1924 | CD | GLU | A | 378 | 37.920 | 41.227 | 60.491 | 1.00 | 39.17 | C |
| ATOM | 1925 | OE1 | GLU | A | 378 | 36.887 | 41.214 | 61.197 | 1.00 | 40.05 | O |
| ATOM | 1926 | OE2 | GLU | A | 378 | 39.061 | 40.986 | 60.964 | 1.00 | 36.76 | O |
| ATOM | 1927 | C | GLU | A | 378 | 37.202 | 41.128 | 55.867 | 1.00 | 37.48 | C |
| ATOM | 1928 | O | GLU | A | 378 | 36.438 | 40.215 | 55.570 | 1.00 | 37.05 | O |
| ATOM | 1929 | N | PHE | A | 379 | 36.959 | 42.401 | 55.542 | 1.00 | 35.87 | N |
| ATOM | 1930 | CA | PHE | A | 379 | 35.749 | 42.793 | 54.800 | 1.00 | 34.69 | C |
| ATOM | 1931 | CB | PHE | A | 379 | 35.180 | 44.109 | 55.359 | 1.00 | 34.65 | C |
| ATOM | 1932 | CG | PHE | A | 379 | 34.720 | 44.031 | 56.795 | 1.00 | 34.19 | C |
| ATOM | 1933 | CD1 | PHE | A | 379 | 34.272 | 42.838 | 57.357 | 1.00 | 33.97 | C |
| ATOM | 1934 | CE1 | PHE | A | 379 | 33.843 | 42.791 | 58.670 | 1.00 | 33.77 | C |
| ATOM | 1935 | CZ | PHE | A | 379 | 33.836 | 43.939 | 59.441 | 1.00 | 33.64 | C |
| ATOM | 1936 | CE2 | PHE | A | 379 | 34.262 | 45.132 | 58.891 | 1.00 | 33.87 | C |
| ATOM | 1937 | CD2 | PHE | A | 379 | 34.692 | 45.176 | 57.574 | 1.00 | 33.92 | C |
| ATOM | 1938 | C | PHE | A | 379 | 35.979 | 42.933 | 53.286 | 1.00 | 33.55 | C |
| ATOM | 1939 | O | PHE | A | 379 | 35.426 | 43.836 | 52.654 | 1.00 | 33.10 | O |
| ATOM | 1940 | N | THR | A | 380 | 36.752 | 42.014 | 52.702 | 1.00 | 32.02 | N |
| ATOM | 1941 | CA | THR | A | 380 | 37.126 | 42.093 | 51.281 | 1.00 | 30.65 | C |
| ATOM | 1942 | CB | THR | A | 380 | 38.205 | 41.056 | 50.894 | 1.00 | 29.97 | C |
| ATOM | 1943 | OG1 | THR | A | 380 | 37.650 | 39.737 | 50.960 | 1.00 | 28.90 | O |
| ATOM | 1944 | CG2 | THR | A | 380 | 39.444 | 41.156 | 51.796 | 1.00 | 29.86 | C |
| ATOM | 1945 | C | THR | A | 380 | 35.956 | 41.859 | 50.325 | 1.00 | 30.17 | C |
| ATOM | 1946 | O | THR | A | 380 | 35.996 | 42.311 | 49.173 | 1.00 | 28.69 | O |
| ATOM | 1947 | N | THR | A | 381 | 34.937 | 41.136 | 50.789 | 1.00 | 30.33 | N |
| ATOM | 1948 | CA | THR | A | 381 | 33.839 | 40.732 | 49.916 | 1.00 | 31.37 | C |
| ATOM | 1949 | CB | THR | A | 381 | 33.434 | 39.260 | 50.120 | 1.00 | 30.76 | C |
| ATOM | 1950 | OG1 | THR | A | 381 | 32.911 | 39.084 | 51.440 | 1.00 | 30.15 | O |
| ATOM | 1951 | CG2 | THR | A | 381 | 34.610 | 38.342 | 49.886 | 1.00 | 30.62 | C |
| ATOM | 1952 | C | THR | A | 381 | 32.586 | 41.598 | 50.050 | 1.00 | 32.57 | C |
| ATOM | 1953 | O | THR | A | 381 | 32.415 | 42.555 | 49.290 | 1.00 | 34.17 | O |
| ATOM | 1954 | N | LEU | A | 382 | 31.725 | 41.263 | 51.010 | 1.00 | 32.45 | N |
| ATOM | 1955 | CA | LEU | A | 382 | 30.309 | 41.706 | 51.030 | 1.00 | 32.54 | C |
| ATOM | 1956 | CB | LEU | A | 382 | 29.672 | 41.749 | 49.624 | 1.00 | 31.34 | C |
| ATOM | 1957 | CG | LEU | A | 382 | 28.545 | 42.751 | 49.373 | 1.00 | 30.81 | C |
| ATOM | 1958 | CD1 | LEU | A | 382 | 29.009 | 44.182 | 49.592 | 1.00 | 30.71 | C |
| ATOM | 1959 | CD2 | LEU | A | 382 | 28.018 | 42.594 | 47.954 | 1.00 | 31.02 | C |
| ATOM | 1960 | C | LEU | A | 382 | 29.550 | 40.708 | 51.889 | 1.00 | 32.56 | C |
| ATOM | 1961 | O | LEU | A | 382 | 28.816 | 41.082 | 52.806 | 1.00 | 33.00 | O |
| ATOM | 1962 | N | GLN | A | 383 | 29.749 | 39.431 | 51.569 | 1.00 | 32.22 | N |
| ATOM | 1963 | CA | GLN | A | 383 | 29.363 | 38.330 | 52.444 | 1.00 | 31.25 | C |
| ATOM | 1964 | CB | GLN | A | 383 | 29.566 | 36.975 | 51.736 | 1.00 | 30.72 | C |
| ATOM | 1965 | CG | GLN | A | 383 | 28.597 | 36.718 | 50.575 | 1.00 | 29.75 | C |
| ATOM | 1966 | CD | GLN | A | 383 | 29.217 | 36.867 | 49.188 | 1.00 | 27.96 | C |
| ATOM | 1967 | OE1 | GLN | A | 383 | 30.069 | 37.729 | 48.949 | 1.00 | 26.22 | O |
| ATOM | 1968 | NE2 | GLN | A | 383 | 28.777 | 36.026 | 48.262 | 1.00 | 27.14 | N |
| ATOM | 1969 | C | GLN | A | 383 | 30.159 | 38.386 | 53.761 | 1.00 | 30.51 | C |
| ATOM | 1970 | O | GLN | A | 383 | 29.606 | 38.110 | 54.829 | 1.00 | 29.95 | O |
| ATOM | 1971 | N | LYS | A | 384 | 31.442 | 38.756 | 53.677 | 1.00 | 29.62 | N |
| ATOM | 1972 | CA | LYS | A | 384 | 32.298 | 38.941 | 54.871 | 1.00 | 29.39 | C |
| ATOM | 1973 | CB | LYS | A | 384 | 33.768 | 39.088 | 54.479 | 1.00 | 29.07 | C |
| ATOM | 1974 | CG | LYS | A | 384 | 34.370 | 37.872 | 53.782 | 1.00 | 29.18 | C |
| ATOM | 1975 | CD | LYS | A | 384 | 34.762 | 36.764 | 54.746 | 1.00 | 29.26 | C |
| ATOM | 1976 | CE | LYS | A | 384 | 35.549 | 35.673 | 54.032 | 1.00 | 29.29 | C |
| ATOM | 1977 | NZ | LYS | A | 384 | 36.394 | 34.890 | 54.974 | 1.00 | 29.70 | N |
| ATOM | 1978 | C | LYS | A | 384 | 31.888 | 40.142 | 55.726 | 1.00 | 29.14 | C |
| ATOM | 1979 | O | LYS | A | 384 | 32.109 | 40.152 | 56.937 | 1.00 | 28.47 | O |
| ATOM | 1980 | N | ILE | A | 385 | 31.300 | 41.153 | 55.091 | 1.00 | 29.47 | N |
| ATOM | 1981 | CA | ILE | A | 385 | 30.692 | 42.269 | 55.821 | 1.00 | 28.97 | C |
| ATOM | 1982 | CB | ILE | A | 385 | 30.434 | 43.477 | 54.881 | 1.00 | 28.98 | C |

TABLE 3-continued

GLTP domain of FAPP2 atomic coordinates

| ATOM | 1983 | CG1 | ILE | A | 385 | 31.781 | 44.086 | 54.461 | 1.00 | 29.24 | C |
|------|------|-----|-----|---|-----|--------|--------|--------|------|-------|---|
| ATOM | 1984 | CD1 | ILE | A | 385 | 31.693 | 45.126 | 53.364 | 1.00 | 29.27 | C |
| ATOM | 1985 | CG2 | ILE | A | 385 | 29.584 | 44.544 | 55.563 | 1.00 | 29.04 | C |
| ATOM | 1986 | C | ILE | A | 385 | 29.419 | 41.821 | 56.573 | 1.00 | 27.62 | C |
| ATOM | 1987 | O | ILE | A | 385 | 29.231 | 42.180 | 57.744 | 1.00 | 27.44 | O |
| ATOM | 1988 | N | VAL | A | 386 | 28.577 | 41.018 | 55.915 | 1.00 | 26.35 | N |
| ATOM | 1989 | CA | VAL | A | 386 | 27.278 | 40.595 | 56.480 | 1.00 | 25.71 | C |
| ATOM | 1990 | CB | VAL | A | 386 | 26.280 | 40.118 | 55.376 | 1.00 | 24.91 | C |
| ATOM | 1991 | CG1 | VAL | A | 386 | 25.073 | 39.391 | 55.964 | 1.00 | 24.57 | C |
| ATOM | 1992 | CG2 | VAL | A | 386 | 25.832 | 41.299 | 54.524 | 1.00 | 24.56 | C |
| ATOM | 1993 | C | VAL | A | 386 | 27.467 | 39.531 | 57.562 | 1.00 | 25.50 | C |
| ATOM | 1994 | O | VAL | A | 386 | 26.990 | 39.699 | 58.682 | 1.00 | 25.52 | O |
| ATOM | 1995 | N | LEU | A | 387 | 28.173 | 38.452 | 57.241 | 1.00 | 25.79 | N |
| ATOM | 1996 | CA | LEU | A | 387 | 28.443 | 37.400 | 58.229 | 1.00 | 25.91 | C |
| ATOM | 1997 | CB | LEU | A | 387 | 29.261 | 36.249 | 57.611 | 1.00 | 25.66 | C |
| ATOM | 1998 | CG | LEU | A | 387 | 28.568 | 35.147 | 56.784 | 1.00 | 25.38 | C |
| ATOM | 1999 | CD1 | LEU | A | 387 | 27.086 | 35.033 | 57.106 | 1.00 | 25.23 | C |
| ATOM | 2000 | CD2 | LEU | A | 387 | 28.754 | 35.305 | 55.283 | 1.00 | 25.13 | C |
| ATOM | 2001 | C | LEU | A | 387 | 29.141 | 37.912 | 59.504 | 1.00 | 26.00 | C |
| ATOM | 2002 | O | LEU | A | 387 | 29.028 | 37.289 | 60.558 | 1.00 | 25.93 | O |
| ATOM | 2003 | N | HIS | A | 388 | 29.855 | 39.033 | 59.407 | 1.00 | 26.32 | N |
| ATOM | 2004 | CA | HIS | A | 388 | 30.447 | 39.680 | 60.585 | 1.00 | 26.60 | C |
| ATOM | 2005 | CB | HIS | A | 388 | 31.507 | 40.690 | 60.152 | 1.00 | 26.44 | C |
| ATOM | 2006 | CG | HIS | A | 388 | 32.286 | 41.265 | 61.290 | 1.00 | 26.59 | C |
| ATOM | 2007 | ND1 | HIS | A | 388 | 33.351 | 40.608 | 61.868 | 1.00 | 26.44 | N |
| ATOM | 2008 | CE1 | HIS | A | 388 | 33.839 | 41.346 | 62.848 | 1.00 | 26.47 | C |
| ATOM | 2009 | NE2 | HIS | A | 388 | 33.127 | 42.456 | 62.928 | 1.00 | 26.56 | N |
| ATOM | 2010 | CD2 | HIS | A | 388 | 32.147 | 42.430 | 61.966 | 1.00 | 26.56 | C |
| ATOM | 2011 | C | HIS | A | 388 | 29.405 | 40.365 | 61.487 | 1.00 | 27.10 | C |
| ATOM | 2012 | O | HIS | A | 388 | 29.585 | 40.419 | 62.711 | 1.00 | 26.45 | O |
| ATOM | 2013 | N | GLU | A | 389 | 28.341 | 40.899 | 60.880 | 1.00 | 28.12 | N |
| ATOM | 2014 | CA | GLU | A | 389 | 27.197 | 41.442 | 61.630 | 1.00 | 29.20 | C |
| ATOM | 2015 | CB | GLU | A | 389 | 26.200 | 42.191 | 60.719 | 1.00 | 30.17 | C |
| ATOM | 2016 | CG | GLU | A | 389 | 26.000 | 43.684 | 61.022 | 1.00 | 30.80 | C |
| ATOM | 2017 | CD | GLU | A | 389 | 26.873 | 44.613 | 60.177 | 1.00 | 31.25 | C |
| ATOM | 2018 | OE1 | GLU | A | 389 | 28.004 | 44.921 | 60.606 | 1.00 | 31.92 | O |
| ATOM | 2019 | OE2 | GLU | A | 389 | 26.426 | 45.061 | 59.095 | 1.00 | 29.79 | O |
| ATOM | 2020 | C | GLU | A | 389 | 26.468 | 40.347 | 62.425 | 1.00 | 29.64 | C |
| ATOM | 2021 | O | GLU | A | 389 | 26.255 | 40.512 | 63.629 | 1.00 | 30.97 | O |
| ATOM | 2022 | N | VAL | A | 390 | 26.116 | 39.231 | 61.778 | 1.00 | 29.29 | N |
| ATOM | 2023 | CA | VAL | A | 390 | 25.407 | 38.131 | 62.471 | 1.00 | 29.48 | C |
| ATOM | 2024 | CB | VAL | A | 390 | 24.922 | 37.022 | 61.498 | 1.00 | 29.00 | C |
| ATOM | 2025 | CG1 | VAL | A | 390 | 24.132 | 35.946 | 62.243 | 1.00 | 28.84 | C |
| ATOM | 2026 | CG2 | VAL | A | 390 | 24.059 | 37.615 | 60.392 | 1.00 | 28.94 | C |
| ATOM | 2027 | C | VAL | A | 390 | 26.256 | 37.527 | 63.621 | 1.00 | 29.87 | C |
| ATOM | 2028 | O | VAL | A | 390 | 25.707 | 36.994 | 64.592 | 1.00 | 29.69 | O |
| ATOM | 2029 | N | GLU | A | 391 | 27.582 | 37.627 | 63.519 | 1.00 | 30.16 | N |
| ATOM | 2030 | CA | GLU | A | 391 | 28.463 | 37.253 | 64.624 | 1.00 | 30.90 | C |
| ATOM | 2031 | CB | GLU | A | 391 | 29.931 | 37.254 | 64.192 | 1.00 | 30.85 | C |
| ATOM | 2032 | CG | GLU | A | 391 | 30.881 | 36.659 | 65.230 | 1.00 | 30.81 | C |
| ATOM | 2033 | CD | GLU | A | 391 | 32.353 | 36.918 | 64.925 | 1.00 | 31.10 | C |
| ATOM | 2034 | OE1 | GLU | A | 391 | 32.677 | 37.409 | 63.815 | 1.00 | 30.52 | O |
| ATOM | 2035 | OE2 | GLU | A | 391 | 33.195 | 36.626 | 65.808 | 1.00 | 30.55 | O |
| ATOM | 2036 | C | GLU | A | 391 | 28.274 | 38.182 | 65.831 | 1.00 | 31.24 | C |
| ATOM | 2037 | O | GLU | A | 391 | 28.370 | 37.732 | 66.965 | 1.00 | 29.37 | O |
| ATOM | 2038 | N | ALA | A | 392 | 28.010 | 39.466 | 65.582 | 1.00 | 32.58 | N |
| ATOM | 2039 | CA | ALA | A | 392 | 27.749 | 40.426 | 66.660 | 1.00 | 34.27 | C |
| ATOM | 2040 | CB | ALA | A | 392 | 28.500 | 41.728 | 66.404 | 1.00 | 33.90 | C |
| ATOM | 2041 | C | ALA | A | 392 | 26.240 | 40.676 | 66.900 | 1.00 | 36.08 | C |
| ATOM | 2042 | O | ALA | A | 392 | 25.638 | 40.017 | 67.752 | 1.00 | 36.07 | O |
| ATOM | 2043 | N | ASP | A | 393 | 25.624 | 41.600 | 66.157 | 1.00 | 39.28 | N |
| ATOM | 2044 | CA | ASP | A | 393 | 24.229 | 42.017 | 66.453 | 1.00 | 42.55 | C |
| ATOM | 2045 | CB | ASP | A | 393 | 23.820 | 43.361 | 65.771 | 1.00 | 41.64 | C |
| ATOM | 2046 | CG | ASP | A | 393 | 24.595 | 43.673 | 64.484 | 1.00 | 40.83 | C |
| ATOM | 2047 | OD1 | ASP | A | 393 | 25.833 | 43.817 | 64.572 | 1.00 | 40.21 | O |
| ATOM | 2048 | OD2 | ASP | A | 393 | 23.965 | 43.828 | 63.405 | 1.00 | 38.28 | O |
| ATOM | 2049 | C | ASP | A | 393 | 23.128 | 40.933 | 66.254 | 1.00 | 47.81 | C |
| ATOM | 2050 | O | ASP | A | 393 | 22.179 | 40.884 | 67.045 | 1.00 | 47.92 | O |
| ATOM | 2051 | N | VAL | A | 394 | 23.261 | 40.083 | 65.224 | 1.00 | 53.09 | N |
| ATOM | 2052 | CA | VAL | A | 394 | 22.312 | 38.965 | 64.925 | 1.00 | 55.65 | C |
| ATOM | 2053 | CB | VAL | A | 394 | 22.035 | 38.030 | 66.154 | 1.00 | 54.84 | C |
| ATOM | 2054 | CG1 | VAL | A | 394 | 21.202 | 36.817 | 65.741 | 1.00 | 53.81 | C |
| ATOM | 2055 | CG2 | VAL | A | 394 | 23.330 | 37.566 | 66.818 | 1.00 | 54.29 | C |
| ATOM | 2056 | C | VAL | A | 394 | 20.964 | 39.452 | 64.345 | 1.00 | 57.09 | C |
| ATOM | 2057 | O | VAL | A | 394 | 20.098 | 39.915 | 65.087 | 1.00 | 57.66 | O |
| ATOM | 2058 | N | ALA | A | 395 | 20.803 | 39.334 | 63.024 | 1.00 | 58.19 | N |
| ATOM | 2059 | CA | ALA | A | 395 | 19.532 | 39.633 | 62.319 | 1.00 | 58.40 | C |
| ATOM | 2060 | CB | ALA | A | 395 | 18.430 | 38.675 | 62.772 | 1.00 | 57.94 | C |

TABLE 3-continued

GLTP domain of FAPP2 atomic coordinates

| ATOM | 2061 | C   | ALA | A | 395 | 19.042 | 41.099 | 62.393 | 1.00 | 58.30 | C |
| ATOM | 2062 | O   | ALA | A | 395 | 18.328 | 41.478 | 63.320 | 1.00 | 57.31 | O |
| ATOM | 2063 | N   | GLN | A | 396 | 19.444 | 41.895 | 61.399 | 1.00 | 59.77 | N |
| ATOM | 2064 | CA  | GLN | A | 396 | 18.932 | 43.264 | 61.126 | 1.00 | 62.84 | C |
| ATOM | 2065 | CB  | GLN | A | 396 | 17.632 | 43.192 | 60.278 | 1.00 | 66.00 | C |
| ATOM | 2066 | CG  | GLN | A | 396 | 16.354 | 42.780 | 61.017 | 1.00 | 66.81 | C |
| ATOM | 2067 | CD  | GLN | A | 396 | 15.321 | 42.117 | 60.118 | 1.00 | 66.35 | C |
| ATOM | 2068 | OE1 | GLN | A | 396 | 14.923 | 40.974 | 60.359 | 1.00 | 65.67 | O |
| ATOM | 2069 | NE2 | GLN | A | 396 | 14.879 | 42.831 | 59.080 | 1.00 | 64.73 | N |
| ATOM | 2070 | C   | GLN | A | 396 | 18.772 | 44.250 | 62.317 | 1.00 | 60.08 | C |
| ATOM | 2071 | O   | GLN | A | 396 | 17.708 | 44.339 | 62.932 | 1.00 | 57.72 | O |
| ATOM | 2072 | N   | VAL | A | 397 | 19.839 | 44.998 | 62.609 | 1.00 | 57.79 | N |
| ATOM | 2073 | CA  | VAL | A | 397 | 19.790 | 46.127 | 63.555 | 1.00 | 55.77 | C |
| ATOM | 2074 | CB  | VAL | A | 397 | 20.989 | 46.075 | 64.542 | 1.00 | 54.13 | C |
| ATOM | 2075 | CG1 | VAL | A | 397 | 22.222 | 46.782 | 63.990 | 1.00 | 54.50 | C |
| ATOM | 2076 | CG2 | VAL | A | 397 | 20.596 | 46.616 | 65.912 | 1.00 | 52.53 | C |
| ATOM | 2077 | C   | VAL | A | 397 | 19.698 | 47.428 | 62.721 | 1.00 | 55.32 | C |
| ATOM | 2078 | O   | VAL | A | 397 | 19.425 | 47.346 | 61.519 | 1.00 | 54.09 | O |
| ATOM | 2079 | N   | ARG | A | 398 | 19.896 | 48.606 | 63.328 | 1.00 | 54.38 | N |
| ATOM | 2080 | CA  | ARG | A | 398 | 19.679 | 49.892 | 62.623 | 1.00 | 53.73 | C |
| ATOM | 2081 | CB  | ARG | A | 398 | 19.486 | 51.058 | 63.613 | 1.00 | 54.59 | C |
| ATOM | 2082 | CG  | ARG | A | 398 | 18.039 | 51.275 | 64.036 | 1.00 | 55.66 | C |
| ATOM | 2083 | CD  | ARG | A | 398 | 17.533 | 50.165 | 64.939 | 1.00 | 56.49 | C |
| ATOM | 2084 | NE  | ARG | A | 398 | 18.208 | 50.178 | 66.236 | 1.00 | 58.33 | N |
| ATOM | 2085 | CZ  | ARG | A | 398 | 17.946 | 49.340 | 67.238 | 1.00 | 59.28 | C |
| ATOM | 2086 | NH1 | ARG | A | 398 | 17.015 | 48.399 | 67.108 | 1.00 | 60.24 | N |
| ATOM | 2087 | NH2 | ARG | A | 398 | 18.618 | 49.442 | 68.381 | 1.00 | 57.85 | N |
| ATOM | 2088 | C   | ARG | A | 398 | 20.741 | 50.220 | 61.552 | 1.00 | 51.17 | C |
| ATOM | 2089 | O   | ARG | A | 398 | 20.714 | 49.623 | 60.476 | 1.00 | 53.64 | O |
| ATOM | 2090 | N   | ASN | A | 399 | 21.681 | 51.129 | 61.826 | 1.00 | 47.16 | N |
| ATOM | 2091 | CA  | ASN | A | 399 | 22.566 | 51.657 | 60.761 | 1.00 | 43.46 | C |
| ATOM | 2092 | CB  | ASN | A | 399 | 23.240 | 52.973 | 61.198 | 1.00 | 43.11 | C |
| ATOM | 2093 | CG  | ASN | A | 399 | 22.665 | 54.187 | 60.486 | 1.00 | 42.49 | C |
| ATOM | 2094 | OD1 | ASN | A | 399 | 22.237 | 54.104 | 59.330 | 1.00 | 40.36 | O |
| ATOM | 2095 | ND2 | ASN | A | 399 | 22.660 | 55.325 | 61.169 | 1.00 | 41.76 | N |
| ATOM | 2096 | C   | ASN | A | 399 | 23.611 | 50.669 | 60.217 | 1.00 | 39.56 | C |
| ATOM | 2097 | O   | ASN | A | 399 | 24.570 | 51.067 | 59.539 | 1.00 | 36.76 | O |
| ATOM | 2098 | N   | SER | A | 400 | 23.399 | 49.385 | 60.497 | 1.00 | 36.08 | N |
| ATOM | 2099 | CA  | SER | A | 400 | 24.229 | 48.330 | 59.968 | 1.00 | 34.36 | C |
| ATOM | 2100 | CB  | SER | A | 400 | 23.697 | 46.960 | 60.405 | 1.00 | 33.83 | C |
| ATOM | 2101 | OG  | SER | A | 400 | 22.375 | 46.738 | 59.945 | 1.00 | 32.18 | O |
| ATOM | 2102 | C   | SER | A | 400 | 24.302 | 48.397 | 58.451 | 1.00 | 33.40 | C |
| ATOM | 2103 | O   | SER | A | 400 | 23.413 | 48.937 | 57.792 | 1.00 | 32.88 | O |
| ATOM | 2104 | N   | ALA | A | 401 | 25.392 | 47.853 | 57.918 | 1.00 | 33.16 | N |
| ATOM | 2105 | CA  | ALA | A | 401 | 25.589 | 47.713 | 56.478 | 1.00 | 32.13 | C |
| ATOM | 2106 | CB  | ALA | A | 401 | 27.071 | 47.523 | 56.163 | 1.00 | 32.42 | C |
| ATOM | 2107 | C   | ALA | A | 401 | 24.764 | 46.548 | 55.919 | 1.00 | 30.46 | C |
| ATOM | 2108 | O   | ALA | A | 401 | 24.578 | 46.466 | 54.716 | 1.00 | 30.36 | O |
| ATOM | 2109 | N   | THR | A | 402 | 24.302 | 45.647 | 56.792 | 1.00 | 29.79 | N |
| ATOM | 2110 | CA  | THR | A | 402 | 23.337 | 44.598 | 56.436 | 1.00 | 29.15 | C |
| ATOM | 2111 | CB  | THR | A | 402 | 23.166 | 43.528 | 57.547 | 1.00 | 29.09 | C |
| ATOM | 2112 | OG1 | THR | A | 402 | 23.399 | 44.107 | 58.838 | 1.00 | 30.74 | O |
| ATOM | 2113 | CG2 | THR | A | 402 | 24.120 | 42.384 | 57.346 | 1.00 | 28.99 | C |
| ATOM | 2114 | C   | THR | A | 402 | 21.965 | 45.193 | 56.139 | 1.00 | 28.93 | C |
| ATOM | 2115 | O   | THR | A | 402 | 21.255 | 44.703 | 55.257 | 1.00 | 28.25 | O |
| ATOM | 2116 | N   | GLU | A | 403 | 21.588 | 46.236 | 56.877 | 1.00 | 28.98 | N |
| ATOM | 2117 | CA  | GLU | A | 403 | 20.395 | 46.995 | 56.532 | 1.00 | 29.96 | C |
| ATOM | 2118 | CB  | GLU | A | 403 | 19.944 | 47.919 | 57.685 | 1.00 | 30.71 | C |
| ATOM | 2119 | CG  | GLU | A | 403 | 18.422 | 48.071 | 57.806 | 1.00 | 31.61 | C |
| ATOM | 2120 | CD  | GLU | A | 403 | 17.960 | 49.490 | 58.157 | 1.00 | 32.39 | C |
| ATOM | 2121 | OE1 | GLU | A | 403 | 18.250 | 49.964 | 59.280 | 1.00 | 30.96 | O |
| ATOM | 2122 | OE2 | GLU | A | 403 | 17.281 | 50.127 | 57.306 | 1.00 | 32.65 | O |
| ATOM | 2123 | C   | GLU | A | 403 | 20.644 | 47.780 | 55.212 | 1.00 | 30.19 | C |
| ATOM | 2124 | O   | GLU | A | 403 | 19.835 | 47.694 | 54.282 | 1.00 | 31.47 | O |
| ATOM | 2125 | N   | ALA | A | 404 | 21.768 | 48.499 | 55.114 | 1.00 | 29.78 | N |
| ATOM | 2126 | CA  | ALA | A | 404 | 22.121 | 49.273 | 53.895 | 1.00 | 29.51 | C |
| ATOM | 2127 | CB  | ALA | A | 404 | 23.434 | 50.011 | 54.106 | 1.00 | 30.08 | C |
| ATOM | 2128 | C   | ALA | A | 404 | 22.214 | 48.424 | 52.620 | 1.00 | 29.04 | C |
| ATOM | 2129 | O   | ALA | A | 404 | 21.750 | 48.827 | 51.556 | 1.00 | 28.62 | O |
| ATOM | 2130 | N   | LEU | A | 405 | 22.820 | 47.247 | 52.738 | 1.00 | 28.76 | N |
| ATOM | 2131 | CA  | LEU | A | 405 | 22.976 | 46.344 | 51.610 | 1.00 | 28.05 | C |
| ATOM | 2132 | CB  | LEU | A | 405 | 23.918 | 45.194 | 51.973 | 1.00 | 26.66 | C |
| ATOM | 2133 | CG  | LEU | A | 405 | 24.445 | 44.365 | 50.809 | 1.00 | 26.18 | C |
| ATOM | 2134 | CD1 | LEU | A | 405 | 25.325 | 45.227 | 49.919 | 1.00 | 26.01 | C |
| ATOM | 2135 | CD2 | LEU | A | 405 | 25.203 | 43.139 | 51.296 | 1.00 | 25.64 | C |
| ATOM | 2136 | C   | LEU | A | 405 | 21.625 | 45.805 | 51.143 | 1.00 | 29.16 | C |
| ATOM | 2137 | O   | LEU | A | 405 | 21.474 | 45.476 | 49.979 | 1.00 | 30.40 | O |
| ATOM | 2138 | N   | LEU | A | 406 | 20.645 | 45.720 | 52.039 | 1.00 | 30.38 | N |

TABLE 3-continued

| | | | | | | | | | | |
|---|---|---|---|---|---|---|---|---|---|---|
| ATOM | 2139 | CA | LEU | A | 406 | 19.313 | 45.231 | 51.671 | 1.00 | 31.89 C |
| ATOM | 2140 | CB | LEU | A | 406 | 18.531 | 44.776 | 52.917 | 1.00 | 32.91 C |
| ATOM | 2141 | CG | LEU | A | 406 | 17.060 | 44.315 | 52.780 | 1.00 | 32.90 C |
| ATOM | 2142 | CD1 | LEU | A | 406 | 16.882 | 43.223 | 51.727 | 1.00 | 32.41 C |
| ATOM | 2143 | CD2 | LEU | A | 406 | 16.515 | 43.848 | 54.128 | 1.00 | 32.59 C |
| ATOM | 2144 | C | LEU | A | 406 | 18.514 | 46.282 | 50.905 | 1.00 | 32.93 C |
| ATOM | 2145 | O | LEU | A | 406 | 17.745 | 45.951 | 49.999 | 1.00 | 31.88 O |
| ATOM | 2146 | N | TRP | A | 407 | 18.670 | 47.547 | 51.278 | 1.00 | 34.81 N |
| ATOM | 2147 | CA | TRP | A | 407 | 17.963 | 48.614 | 50.565 | 1.00 | 36.69 C |
| ATOM | 2148 | CB | TRP | A | 407 | 17.789 | 49.864 | 51.440 | 1.00 | 38.09 C |
| ATOM | 2149 | CG | TRP | A | 407 | 16.670 | 49.696 | 52.404 | 1.00 | 39.08 C |
| ATOM | 2150 | CD1 | TRP | A | 407 | 16.765 | 49.292 | 53.702 | 1.00 | 39.55 C |
| ATOM | 2151 | NE1 | TRP | A | 407 | 15.519 | 49.224 | 54.269 | 1.00 | 40.32 N |
| ATOM | 2152 | CE2 | TRP | A | 407 | 14.582 | 49.576 | 53.334 | 1.00 | 40.43 C |
| ATOM | 2153 | CD2 | TRP | A | 407 | 15.275 | 49.871 | 52.137 | 1.00 | 40.09 C |
| ATOM | 2154 | CE3 | TRP | A | 407 | 14.542 | 50.264 | 51.007 | 1.00 | 40.24 C |
| ATOM | 2155 | CZ3 | TRP | A | 407 | 13.152 | 50.345 | 51.107 | 1.00 | 40.09 C |
| ATOM | 2156 | CH2 | TRP | A | 407 | 12.490 | 50.049 | 52.322 | 1.00 | 40.28 C |
| ATOM | 2157 | CZ2 | TRP | A | 407 | 13.184 | 49.657 | 53.439 | 1.00 | 40.12 C |
| ATOM | 2158 | C | TRP | A | 407 | 18.682 | 48.931 | 49.265 | 1.00 | 35.35 C |
| ATOM | 2159 | O | TRP | A | 407 | 18.034 | 49.233 | 48.256 | 1.00 | 33.58 O |
| ATOM | 2160 | N | LEU | A | 408 | 20.014 | 48.849 | 49.301 | 1.00 | 33.64 N |
| ATOM | 2161 | CA | LEU | A | 408 | 20.836 | 48.962 | 48.100 | 1.00 | 33.80 C |
| ATOM | 2162 | CB | LEU | A | 408 | 22.314 | 48.724 | 48.451 | 1.00 | 34.32 C |
| ATOM | 2163 | CG | LEU | A | 408 | 23.347 | 48.685 | 47.321 | 1.00 | 34.55 C |
| ATOM | 2164 | CD1 | LEU | A | 408 | 23.245 | 49.890 | 46.401 | 1.00 | 34.91 C |
| ATOM | 2165 | CD2 | LEU | A | 408 | 24.729 | 48.608 | 47.932 | 1.00 | 35.12 C |
| ATOM | 2166 | C | LEU | A | 408 | 20.363 | 47.991 | 46.994 | 1.00 | 32.57 C |
| ATOM | 2167 | O | LEU | A | 408 | 20.084 | 48.418 | 45.865 | 1.00 | 31.75 O |
| ATOM | 2168 | N | LYS | A | 409 | 20.236 | 46.705 | 47.331 | 1.00 | 30.95 N |
| ATOM | 2169 | CA | LYS | A | 409 | 19.850 | 45.699 | 46.342 | 1.00 | 29.68 C |
| ATOM | 2170 | CB | LYS | A | 409 | 20.267 | 44.281 | 46.752 | 1.00 | 29.26 C |
| ATOM | 2171 | CG | LYS | A | 409 | 19.355 | 43.560 | 47.733 | 1.00 | 28.67 C |
| ATOM | 2172 | CD | LYS | A | 409 | 19.251 | 42.072 | 47.409 | 1.00 | 28.51 C |
| ATOM | 2173 | CE | LYS | A | 409 | 19.461 | 41.193 | 48.637 | 1.00 | 28.94 C |
| ATOM | 2174 | NZ | LYS | A | 409 | 18.267 | 41.082 | 49.523 | 1.00 | 29.27 N |
| ATOM | 2175 | C | LYS | A | 409 | 18.373 | 45.740 | 45.984 | 1.00 | 28.81 C |
| ATOM | 2176 | O | LYS | A | 409 | 18.000 | 45.235 | 44.945 | 1.00 | 28.11 O |
| ATOM | 2177 | N | ARG | A | 410 | 17.530 | 46.308 | 46.837 | 1.00 | 29.69 N |
| ATOM | 2178 | CA | ARG | A | 410 | 16.154 | 46.594 | 46.434 | 1.00 | 30.14 C |
| ATOM | 2179 | CB | ARG | A | 410 | 15.264 | 46.894 | 47.631 | 1.00 | 31.24 C |
| ATOM | 2180 | CG | ARG | A | 410 | 14.992 | 45.715 | 48.540 | 1.00 | 32.54 C |
| ATOM | 2181 | CD | ARG | A | 410 | 14.472 | 46.248 | 49.866 | 1.00 | 33.77 C |
| ATOM | 2182 | NE | ARG | A | 410 | 14.057 | 45.196 | 50.789 | 1.00 | 33.93 N |
| ATOM | 2183 | CZ | ARG | A | 410 | 13.389 | 45.407 | 51.922 | 1.00 | 34.11 C |
| ATOM | 2184 | NH1 | ARG | A | 410 | 13.042 | 46.641 | 52.292 | 1.00 | 34.51 N |
| ATOM | 2185 | NH2 | ARG | A | 410 | 13.060 | 44.375 | 52.694 | 1.00 | 34.18 N |
| ATOM | 2186 | C | ARG | A | 410 | 16.122 | 47.781 | 45.467 | 1.00 | 29.50 C |
| ATOM | 2187 | O | ARG | A | 410 | 15.284 | 47.814 | 44.575 | 1.00 | 31.35 O |
| ATOM | 2188 | N | GLY | A | 411 | 17.017 | 48.753 | 45.660 | 1.00 | 28.32 N |
| ATOM | 2189 | CA | GLY | A | 411 | 17.184 | 49.859 | 44.722 | 1.00 | 27.52 C |
| ATOM | 2190 | C | GLY | A | 411 | 17.668 | 49.390 | 43.360 | 1.00 | 27.83 C |
| ATOM | 2191 | O | GLY | A | 411 | 17.067 | 49.734 | 42.334 | 1.00 | 26.61 O |
| ATOM | 2192 | N | LEU | A | 412 | 18.751 | 48.606 | 43.359 | 1.00 | 27.91 N |
| ATOM | 2193 | CA | LEU | A | 412 | 19.275 | 47.980 | 42.138 | 1.00 | 29.04 C |
| ATOM | 2194 | CB | LEU | A | 412 | 20.436 | 47.018 | 42.468 | 1.00 | 29.21 C |
| ATOM | 2195 | CG | LEU | A | 412 | 21.911 | 47.480 | 42.581 | 1.00 | 29.32 C |
| ATOM | 2196 | CD1 | LEU | A | 412 | 22.176 | 48.785 | 41.830 | 1.00 | 29.54 C |
| ATOM | 2197 | CD2 | LEU | A | 412 | 22.384 | 47.597 | 44.023 | 1.00 | 28.54 C |
| ATOM | 2198 | C | LEU | A | 412 | 18.193 | 47.221 | 41.331 | 1.00 | 30.20 C |
| ATOM | 2199 | O | LEU | A | 412 | 18.070 | 47.413 | 40.115 | 1.00 | 28.47 O |
| ATOM | 2200 | N | LYS | A | 413 | 17.419 | 46.371 | 42.015 | 1.00 | 32.44 N |
| ATOM | 2201 | CA | LYS | A | 413 | 16.340 | 45.587 | 41.383 | 1.00 | 33.39 C |
| ATOM | 2202 | CB | LYS | A | 413 | 15.602 | 44.679 | 42.384 | 1.00 | 33.78 C |
| ATOM | 2203 | CG | LYS | A | 413 | 16.337 | 43.387 | 42.761 | 1.00 | 35.28 C |
| ATOM | 2204 | CD | LYS | A | 413 | 15.409 | 42.356 | 43.423 | 1.00 | 36.32 C |
| ATOM | 2205 | CE | LYS | A | 413 | 16.064 | 41.518 | 44.533 | 1.00 | 36.04 C |
| ATOM | 2206 | NZ | LYS | A | 413 | 15.686 | 41.985 | 45.913 | 1.00 | 36.27 N |
| ATOM | 2207 | C | LYS | A | 413 | 15.327 | 46.485 | 40.686 | 1.00 | 34.70 C |
| ATOM | 2208 | O | LYS | A | 413 | 14.787 | 46.103 | 39.654 | 1.00 | 37.88 O |
| ATOM | 2209 | N | PHE | A | 414 | 15.063 | 47.671 | 41.232 | 1.00 | 35.13 N |
| ATOM | 2210 | CA | PHE | A | 414 | 14.210 | 48.631 | 40.533 | 1.00 | 34.62 C |
| ATOM | 2211 | CB | PHE | A | 414 | 13.740 | 49.767 | 41.433 | 1.00 | 34.31 C |
| ATOM | 2212 | CG | PHE | A | 414 | 13.182 | 50.924 | 40.662 | 1.00 | 34.71 C |
| ATOM | 2213 | CD1 | PHE | A | 414 | 11.856 | 50.912 | 40.235 | 1.00 | 33.81 C |
| ATOM | 2214 | CE1 | PHE | A | 414 | 11.347 | 51.960 | 39.495 | 1.00 | 33.60 C |
| ATOM | 2215 | CZ | PHE | A | 414 | 12.162 | 53.031 | 39.159 | 1.00 | 35.52 C |
| ATOM | 2216 | CE2 | PHE | A | 414 | 13.499 | 53.044 | 39.550 | 1.00 | 35.36 C |

TABLE 3-continued

| GLTP domain of FAPP2 atomic coordinates | | | | | | | | | |
|---|---|---|---|---|---|---|---|---|---|
| ATOM | 2217 | CD2 | PHE | A | 414 | 14.004 | 51.990 | 40.290 | 1.00 | 34.78 | C |
| ATOM | 2218 | C | PHE | A | 414 | 14.892 | 49.213 | 39.285 | 1.00 | 34.68 | C |
| ATOM | 2219 | O | PHE | A | 414 | 14.259 | 49.296 | 38.224 | 1.00 | 35.11 | O |
| ATOM | 2220 | N | LEU | A | 415 | 16.147 | 49.640 | 39.408 | 1.00 | 32.41 | N |
| ATOM | 2221 | CA | LEU | A | 415 | 16.911 | 50.071 | 38.234 | 1.00 | 33.02 | C |
| ATOM | 2222 | CB | LEU | A | 415 | 18.333 | 50.377 | 38.633 | 1.00 | 34.13 | C |
| ATOM | 2223 | CG | LEU | A | 415 | 18.562 | 51.854 | 38.850 | 1.00 | 35.36 | C |
| ATOM | 2224 | CD1 | LEU | A | 415 | 19.561 | 52.053 | 39.974 | 1.00 | 35.16 | C |
| ATOM | 2225 | CD2 | LEU | A | 415 | 19.037 | 52.458 | 37.538 | 1.00 | 36.38 | C |
| ATOM | 2226 | C | LEU | A | 415 | 16.971 | 48.998 | 37.155 | 1.00 | 33.89 | C |
| ATOM | 2227 | O | LEU | A | 415 | 16.787 | 49.259 | 35.950 | 1.00 | 31.91 | O |
| ATOM | 2228 | N | LYS | A | 416 | 17.261 | 47.785 | 37.608 | 1.00 | 34.82 | N |
| ATOM | 2229 | CA | LYS | A | 416 | 17.429 | 46.650 | 36.721 | 1.00 | 34.75 | C |
| ATOM | 2230 | CB | LYS | A | 416 | 17.839 | 45.414 | 37.526 | 1.00 | 34.13 | C |
| ATOM | 2231 | CG | LYS | A | 416 | 18.132 | 44.186 | 36.690 | 1.00 | 34.77 | C |
| ATOM | 2232 | CD | LYS | A | 416 | 18.370 | 42.979 | 37.578 | 1.00 | 36.67 | C |
| ATOM | 2233 | CE | LYS | A | 416 | 18.015 | 41.683 | 36.869 | 1.00 | 38.72 | C |
| ATOM | 2234 | NZ | LYS | A | 416 | 16.553 | 41.394 | 36.932 | 1.00 | 39.80 | N |
| ATOM | 2235 | C | LYS | A | 416 | 16.124 | 46.413 | 35.965 | 1.00 | 33.29 | C |
| ATOM | 2236 | O | LYS | A | 416 | 16.120 | 46.388 | 34.735 | 1.00 | 33.82 | O |
| ATOM | 2237 | N | GLY | A | 417 | 15.030 | 46.255 | 36.710 | 1.00 | 31.59 | N |
| ATOM | 2238 | CA | GLY | A | 417 | 13.683 | 46.100 | 36.138 | 1.00 | 30.22 | C |
| ATOM | 2239 | C | GLY | A | 417 | 13.271 | 47.182 | 35.144 | 1.00 | 28.65 | C |
| ATOM | 2240 | O | GLY | A | 417 | 12.513 | 46.903 | 34.223 | 1.00 | 28.55 | O |
| ATOM | 2241 | N | PHE | A | 418 | 13.762 | 48.408 | 35.347 | 1.00 | 28.09 | N |
| ATOM | 2242 | CA | PHE | A | 418 | 13.547 | 49.550 | 34.437 | 1.00 | 27.72 | C |
| ATOM | 2243 | CB | PHE | A | 418 | 13.987 | 50.882 | 35.092 | 1.00 | 27.54 | C |
| ATOM | 2244 | CG | PHE | A | 418 | 14.171 | 52.032 | 34.112 | 1.00 | 26.99 | C |
| ATOM | 2245 | CD1 | PHE | A | 418 | 13.108 | 52.468 | 33.303 | 1.00 | 27.72 | C |
| ATOM | 2246 | CE1 | PHE | A | 418 | 13.268 | 53.528 | 32.414 | 1.00 | 26.31 | C |
| ATOM | 2247 | CZ | PHE | A | 418 | 14.492 | 54.157 | 32.326 | 1.00 | 25.57 | C |
| ATOM | 2248 | CE2 | PHE | A | 418 | 15.545 | 53.741 | 33.125 | 1.00 | 25.55 | C |
| ATOM | 2249 | CD2 | PHE | A | 418 | 15.385 | 52.691 | 34.012 | 1.00 | 25.87 | C |
| ATOM | 2250 | C | PHE | A | 418 | 14.321 | 49.372 | 33.164 | 1.00 | 28.71 | C |
| ATOM | 2251 | O | PHE | A | 418 | 13.783 | 49.530 | 32.081 | 1.00 | 28.71 | O |
| ATOM | 2252 | N | LEU | A | 419 | 15.608 | 49.081 | 33.309 | 1.00 | 30.89 | N |
| ATOM | 2253 | CA | LEU | A | 419 | 16.483 | 48.883 | 32.160 | 1.00 | 31.32 | C |
| ATOM | 2254 | CB | LEU | A | 419 | 17.915 | 48.779 | 32.644 | 1.00 | 32.07 | C |
| ATOM | 2255 | CG | LEU | A | 419 | 18.414 | 50.088 | 33.217 | 1.00 | 33.07 | C |
| ATOM | 2256 | CD1 | LEU | A | 419 | 19.723 | 49.813 | 33.949 | 1.00 | 33.35 | C |
| ATOM | 2257 | CD2 | LEU | A | 419 | 18.568 | 51.130 | 32.111 | 1.00 | 32.96 | C |
| ATOM | 2258 | C | LEU | A | 419 | 16.116 | 47.638 | 31.346 | 1.00 | 30.02 | C |
| ATOM | 2259 | O | LEU | A | 419 | 16.218 | 47.641 | 30.130 | 1.00 | 29.20 | O |
| ATOM | 2260 | N | THR | A | 420 | 15.704 | 46.582 | 32.042 | 1.00 | 29.80 | N |
| ATOM | 2261 | CA | THR | A | 420 | 15.195 | 45.368 | 31.420 | 1.00 | 29.75 | C |
| ATOM | 2262 | CB | THR | A | 420 | 14.655 | 44.357 | 32.477 | 1.00 | 30.36 | C |
| ATOM | 2263 | OG1 | THR | A | 420 | 15.758 | 43.646 | 33.048 | 1.00 | 32.98 | O |
| ATOM | 2264 | CG2 | THR | A | 420 | 13.696 | 43.324 | 31.872 | 1.00 | 29.63 | C |
| ATOM | 2265 | C | THR | A | 420 | 14.099 | 45.755 | 30.470 | 1.00 | 28.48 | C |
| ATOM | 2266 | O | THR | A | 420 | 14.028 | 45.255 | 29.365 | 1.00 | 29.24 | O |
| ATOM | 2267 | N | GLU | A | 421 | 13.241 | 46.652 | 30.930 | 1.00 | 28.13 | N |
| ATOM | 2268 | CA | GLU | A | 421 | 12.092 | 47.117 | 30.167 | 1.00 | 25.83 | C |
| ATOM | 2269 | CB | GLU | A | 421 | 11.123 | 47.838 | 31.109 | 1.00 | 25.80 | C |
| ATOM | 2270 | CG | GLU | A | 421 | 9.744 | 48.070 | 30.525 | 1.00 | 26.95 | C |
| ATOM | 2271 | CD | GLU | A | 421 | 8.618 | 47.316 | 31.214 | 1.00 | 27.72 | C |
| ATOM | 2272 | OE1 | GLU | A | 421 | 8.665 | 47.081 | 32.441 | 1.00 | 27.53 | O |
| ATOM | 2273 | OE2 | GLU | A | 421 | 7.637 | 46.992 | 30.514 | 1.00 | 29.78 | O |
| ATOM | 2274 | C | GLU | A | 421 | 12.547 | 48.026 | 29.015 | 1.00 | 23.60 | C |
| ATOM | 2275 | O | GLU | A | 421 | 11.894 | 48.099 | 27.987 | 1.00 | 22.44 | O |
| ATOM | 2276 | N | VAL | A | 422 | 13.674 | 48.706 | 29.180 | 1.00 | 22.64 | N |
| ATOM | 2277 | CA | VAL | A | 422 | 14.219 | 49.538 | 28.109 | 1.00 | 22.55 | C |
| ATOM | 2278 | CB | VAL | A | 422 | 15.229 | 50.576 | 28.640 | 1.00 | 22.19 | C |
| ATOM | 2279 | CG1 | VAL | A | 422 | 15.978 | 51.242 | 27.489 | 1.00 | 21.69 | C |
| ATOM | 2280 | CG2 | VAL | A | 422 | 14.518 | 51.621 | 29.493 | 1.00 | 21.80 | C |
| ATOM | 2281 | C | VAL | A | 422 | 14.868 | 48.686 | 27.012 | 1.00 | 22.41 | C |
| ATOM | 2282 | O | VAL | A | 422 | 14.717 | 48.984 | 25.815 | 1.00 | 22.33 | O |
| ATOM | 2283 | N | LYS | A | 423 | 15.551 | 47.619 | 27.410 | 1.00 | 22.42 | N |
| ATOM | 2284 | CA | LYS | A | 423 | 16.237 | 46.768 | 26.440 | 1.00 | 24.14 | C |
| ATOM | 2285 | CB | LYS | A | 423 | 17.387 | 45.986 | 27.096 | 1.00 | 25.56 | C |
| ATOM | 2286 | CG | LYS | A | 423 | 16.980 | 44.744 | 27.872 | 1.00 | 26.31 | C |
| ATOM | 2287 | CD | LYS | A | 423 | 17.317 | 43.445 | 27.160 | 1.00 | 26.66 | C |
| ATOM | 2288 | CE | LYS | A | 423 | 16.614 | 42.282 | 27.860 | 1.00 | 27.69 | C |
| ATOM | 2289 | NZ | LYS | A | 423 | 16.880 | 40.977 | 27.184 | 1.00 | 29.43 | N |
| ATOM | 2290 | C | LYS | A | 423 | 15.286 | 45.819 | 25.768 | 1.00 | 22.80 | C |
| ATOM | 2291 | O | LYS | A | 423 | 15.645 | 45.201 | 24.793 | 1.00 | 22.68 | O |
| ATOM | 2292 | N | ASN | A | 424 | 14.095 | 45.679 | 26.339 | 1.00 | 22.75 | N |
| ATOM | 2293 | CA | ASN | A | 424 | 12.962 | 45.017 | 25.696 | 1.00 | 22.67 | C |
| ATOM | 2294 | CB | ASN | A | 424 | 11.981 | 44.491 | 26.758 | 1.00 | 23.20 | C |

TABLE 3-continued

GLTP domain of FAPP2 atomic coordinates

| ATOM | 2295 | CG | ASN | A | 424 | 12.486 | 43.238 | 27.461 | 1.00 | 23.98 | C |
|---|---|---|---|---|---|---|---|---|---|---|---|
| ATOM | 2296 | OD1 | ASN | A | 424 | 13.550 | 42.706 | 27.139 | 1.00 | 24.65 | O |
| ATOM | 2297 | ND2 | ASN | A | 424 | 11.714 | 42.752 | 28.420 | 1.00 | 24.05 | N |
| ATOM | 2298 | C | ASN | A | 424 | 12.221 | 45.950 | 24.739 | 1.00 | 22.58 | C |
| ATOM | 2299 | O | ASN | A | 424 | 11.191 | 45.572 | 24.175 | 1.00 | 22.43 | O |
| ATOM | 2300 | N | GLY | A | 425 | 12.714 | 47.178 | 24.591 | 1.00 | 22.66 | N |
| ATOM | 2301 | CA | GLY | A | 425 | 12.229 | 48.092 | 23.566 | 1.00 | 23.35 | C |
| ATOM | 2302 | C | GLY | A | 425 | 10.981 | 48.879 | 23.891 | 1.00 | 24.03 | C |
| ATOM | 2303 | O | GLY | A | 425 | 10.245 | 49.263 | 23.011 | 1.00 | 22.88 | O |
| ATOM | 2304 | N | GLU | A | 426 | 10.763 | 49.144 | 25.167 | 1.00 | 27.56 | N |
| ATOM | 2305 | CA | GLU | A | 426 | 9.633 | 49.941 | 25.612 | 1.00 | 29.24 | C |
| ATOM | 2306 | CB | GLU | A | 426 | 9.303 | 49.597 | 27.071 | 1.00 | 29.96 | C |
| ATOM | 2307 | CG | GLU | A | 426 | 8.296 | 50.503 | 27.756 | 1.00 | 30.23 | C |
| ATOM | 2308 | CD | GLU | A | 426 | 7.019 | 50.689 | 26.955 | 1.00 | 30.45 | C |
| ATOM | 2309 | OE1 | GLU | A | 426 | 6.382 | 49.689 | 26.555 | 1.00 | 29.81 | O |
| ATOM | 2310 | OE2 | GLU | A | 426 | 6.643 | 51.856 | 26.740 | 1.00 | 32.11 | O |
| ATOM | 2311 | C | GLU | A | 426 | 10.020 | 51.397 | 25.480 | 1.00 | 30.14 | C |
| ATOM | 2312 | O | GLU | A | 426 | 10.977 | 51.826 | 26.099 | 1.00 | 28.27 | O |
| ATOM | 2313 | N | LYS | A | 427 | 9.263 | 52.156 | 24.696 | 1.00 | 32.84 | N |
| ATOM | 2314 | CA | LYS | A | 427 | 9.639 | 53.530 | 24.377 | 1.00 | 36.04 | C |
| ATOM | 2315 | CB | LYS | A | 427 | 9.249 | 53.880 | 22.943 | 1.00 | 38.20 | C |
| ATOM | 2316 | CG | LYS | A | 427 | 10.053 | 53.132 | 21.892 | 1.00 | 39.50 | C |
| ATOM | 2317 | CD | LYS | A | 427 | 11.462 | 53.677 | 21.769 | 1.00 | 41.32 | C |
| ATOM | 2318 | CE | LYS | A | 427 | 12.253 | 52.984 | 20.654 | 1.00 | 43.46 | C |
| ATOM | 2319 | NZ | LYS | A | 427 | 13.107 | 51.866 | 21.157 | 1.00 | 43.47 | N |
| ATOM | 2320 | C | LYS | A | 427 | 9.047 | 54.558 | 25.304 | 1.00 | 35.27 | C |
| ATOM | 2321 | O | LYS | A | 427 | 9.582 | 55.651 | 25.410 | 1.00 | 38.91 | O |
| ATOM | 2322 | N | ASP | A | 428 | 7.943 | 54.235 | 25.961 | 1.00 | 34.36 | N |
| ATOM | 2323 | CA | ASP | A | 428 | 7.334 | 55.160 | 26.925 | 1.00 | 35.50 | C |
| ATOM | 2324 | CB | ASP | A | 428 | 5.808 | 54.925 | 27.040 | 1.00 | 36.24 | C |
| ATOM | 2325 | CG | ASP | A | 428 | 5.091 | 56.022 | 27.816 | 1.00 | 38.88 | C |
| ATOM | 2326 | OD1 | ASP | A | 428 | 5.653 | 56.512 | 28.822 | 1.00 | 42.01 | O |
| ATOM | 2327 | OD2 | ASP | A | 428 | 3.951 | 56.382 | 27.440 | 1.00 | 39.68 | O |
| ATOM | 2328 | C | ASP | A | 428 | 8.056 | 54.952 | 28.257 | 1.00 | 34.40 | C |
| ATOM | 2329 | O | ASP | A | 428 | 7.807 | 53.969 | 28.969 | 1.00 | 35.04 | O |
| ATOM | 2330 | N | ILE | A | 429 | 8.965 | 55.858 | 28.594 | 1.00 | 31.75 | N |
| ATOM | 2331 | CA | ILE | A | 429 | 9.750 | 55.641 | 29.798 | 1.00 | 32.85 | C |
| ATOM | 2332 | CB | ILE | A | 429 | 11.026 | 56.489 | 29.857 | 1.00 | 34.71 | C |
| ATOM | 2333 | CG1 | ILE | A | 429 | 10.667 | 57.955 | 29.823 | 1.00 | 37.50 | C |
| ATOM | 2334 | CD1 | ILE | A | 429 | 11.813 | 58.797 | 30.305 | 1.00 | 40.52 | C |
| ATOM | 2335 | CG2 | ILE | A | 429 | 11.982 | 56.138 | 28.714 | 1.00 | 33.42 | C |
| ATOM | 2336 | C | ILE | A | 429 | 8.932 | 55.868 | 31.052 | 1.00 | 30.17 | C |
| ATOM | 2337 | O | ILE | A | 429 | 9.261 | 55.342 | 32.095 | 1.00 | 27.56 | O |
| ATOM | 2338 | N | GLN | A | 430 | 7.858 | 56.639 | 30.946 | 1.00 | 30.81 | N |
| ATOM | 2339 | CA | GLN | A | 430 | 6.910 | 56.751 | 32.060 | 1.00 | 31.67 | C |
| ATOM | 2340 | CB | GLN | A | 430 | 5.811 | 57.765 | 31.771 | 1.00 | 32.79 | C |
| ATOM | 2341 | CG | GLN | A | 430 | 4.742 | 57.824 | 32.839 | 1.00 | 34.55 | C |
| ATOM | 2342 | CD | GLN | A | 430 | 3.691 | 58.881 | 32.545 | 1.00 | 37.04 | C |
| ATOM | 2343 | OE1 | GLN | A | 430 | 3.906 | 59.793 | 31.747 | 1.00 | 39.74 | O |
| ATOM | 2344 | NE2 | GLN | A | 430 | 2.550 | 58.765 | 33.197 | 1.00 | 38.38 | N |
| ATOM | 2345 | C | GLN | A | 430 | 6.309 | 55.389 | 32.351 | 1.00 | 29.43 | C |
| ATOM | 2346 | O | GLN | A | 430 | 6.121 | 55.026 | 33.497 | 1.00 | 29.04 | O |
| ATOM | 2347 | N | THR | A | 431 | 6.042 | 54.627 | 31.305 | 1.00 | 28.14 | N |
| ATOM | 2348 | CA | THR | A | 431 | 5.532 | 53.288 | 31.477 | 1.00 | 27.73 | C |
| ATOM | 2349 | CB | THR | A | 431 | 4.876 | 52.769 | 30.184 | 1.00 | 28.20 | C |
| ATOM | 2350 | OG1 | THR | A | 431 | 3.724 | 53.584 | 29.876 | 1.00 | 28.13 | O |
| ATOM | 2351 | CG2 | THR | A | 431 | 4.432 | 51.322 | 30.357 | 1.00 | 27.80 | C |
| ATOM | 2352 | C | THR | A | 431 | 6.603 | 52.334 | 31.993 | 1.00 | 28.01 | C |
| ATOM | 2353 | O | THR | A | 431 | 6.322 | 51.545 | 32.897 | 1.00 | 29.47 | O |
| ATOM | 2354 | N | ALA | A | 432 | 7.823 | 52.426 | 31.458 | 1.00 | 27.28 | N |
| ATOM | 2355 | CA | ALA | A | 432 | 8.924 | 51.552 | 31.868 | 1.00 | 26.38 | C |
| ATOM | 2356 | CB | ALA | A | 432 | 10.198 | 51.901 | 31.109 | 1.00 | 27.39 | C |
| ATOM | 2357 | C | ALA | A | 432 | 9.198 | 51.633 | 33.343 | 1.00 | 27.34 | C |
| ATOM | 2358 | O | ALA | A | 432 | 9.449 | 50.616 | 33.989 | 1.00 | 27.15 | O |
| ATOM | 2359 | N | LEU | A | 433 | 9.178 | 52.861 | 33.856 | 1.00 | 28.88 | N |
| ATOM | 2360 | CA | LEU | A | 433 | 9.445 | 53.153 | 35.268 | 1.00 | 28.97 | C |
| ATOM | 2361 | CB | LEU | A | 433 | 9.588 | 54.669 | 35.470 | 1.00 | 28.71 | C |
| ATOM | 2362 | CG | LEU | A | 433 | 10.782 | 55.377 | 34.801 | 1.00 | 29.09 | C |
| ATOM | 2363 | CD1 | LEU | A | 433 | 10.665 | 56.897 | 34.882 | 1.00 | 28.81 | C |
| ATOM | 2364 | CD2 | LEU | A | 433 | 12.097 | 54.935 | 35.417 | 1.00 | 29.15 | C |
| ATOM | 2365 | C | LEU | A | 433 | 8.330 | 52.633 | 36.167 | 1.00 | 29.17 | C |
| ATOM | 2366 | O | LEU | A | 433 | 8.563 | 51.988 | 37.203 | 1.00 | 27.05 | O |
| ATOM | 2367 | N | ASN | A | 434 | 7.107 | 52.945 | 35.767 | 1.00 | 30.44 | N |
| ATOM | 2368 | CA | ASN | A | 434 | 5.945 | 52.580 | 36.553 | 1.00 | 30.87 | C |
| ATOM | 2369 | CB | ASN | A | 434 | 4.673 | 53.039 | 35.836 | 1.00 | 32.64 | C |
| ATOM | 2370 | CG | ASN | A | 434 | 3.458 | 53.017 | 36.732 | 1.00 | 34.21 | C |
| ATOM | 2371 | OD1 | ASN | A | 434 | 3.558 | 53.118 | 37.953 | 1.00 | 33.72 | O |
| ATOM | 2372 | ND2 | ASN | A | 434 | 2.301 | 52.893 | 36.125 | 1.00 | 38.20 | N |

TABLE 3-continued

| GLTP domain of FAPP2 atomic coordinates | | | | | | | | | |
|---|---|---|---|---|---|---|---|---|---|
| ATOM | 2373 | C | ASN | A | 434 | 5.918 | 51.070 | 36.769 | 1.00 30.15 C |
| ATOM | 2374 | O | ASN | A | 434 | 5.730 | 50.595 | 37.895 | 1.00 29.04 O |
| ATOM | 2375 | N | ASN | A | 435 | 6.117 | 50.333 | 35.674 | 1.00 29.40 N |
| ATOM | 2376 | CA | ASN | A | 435 | 6.126 | 48.877 | 35.703 | 1.00 28.52 C |
| ATOM | 2377 | CB | ASN | A | 435 | 6.343 | 48.306 | 34.311 | 1.00 28.49 C |
| ATOM | 2378 | CG | ASN | A | 435 | 5.153 | 48.501 | 33.394 | 1.00 29.48 C |
| ATOM | 2379 | OD1 | ASN | A | 435 | 4.135 | 49.116 | 33.756 | 1.00 30.45 O |
| ATOM | 2380 | ND2 | ASN | A | 435 | 5.274 | 47.965 | 32.183 | 1.00 29.07 N |
| ATOM | 2381 | C | ASN | A | 435 | 7.217 | 48.343 | 36.603 | 1.00 28.16 C |
| ATOM | 2382 | O | ASN | A | 435 | 6.973 | 47.478 | 37.430 | 1.00 29.58 O |
| ATOM | 2383 | N | ALA | A | 436 | 8.426 | 48.847 | 36.446 | 1.00 27.39 N |
| ATOM | 2384 | CA | ALA | A | 436 | 9.496 | 48.412 | 37.309 | 1.00 27.52 C |
| ATOM | 2385 | CB | ALA | A | 436 | 10.786 | 49.175 | 37.006 | 1.00 27.20 C |
| ATOM | 2386 | C | ALA | A | 436 | 9.037 | 48.639 | 38.757 | 1.00 27.19 C |
| ATOM | 2387 | O | ALA | A | 436 | 8.961 | 47.695 | 39.562 | 1.00 26.15 O |
| ATOM | 2388 | N | TYR | A | 437 | 8.686 | 49.882 | 39.071 | 1.00 27.00 N |
| ATOM | 2389 | CA | TYR | A | 437 | 8.338 | 50.239 | 40.448 | 1.00 27.42 C |
| ATOM | 2390 | CB | TYR | A | 437 | 7.764 | 51.654 | 40.521 | 1.00 27.38 C |
| ATOM | 2391 | CG | TYR | A | 437 | 7.713 | 52.262 | 41.914 | 1.00 27.32 C |
| ATOM | 2392 | CD1 | TYR | A | 437 | 8.864 | 52.351 | 42.697 | 1.00 26.83 C |
| ATOM | 2393 | CE1 | TYR | A | 437 | 8.837 | 52.924 | 43.961 | 1.00 27.10 C |
| ATOM | 2394 | CZ | TYR | A | 437 | 7.641 | 53.412 | 44.466 | 1.00 28.13 C |
| ATOM | 2395 | OH | TYR | A | 437 | 7.641 | 53.984 | 45.720 | 1.00 29.67 O |
| ATOM | 2396 | CE2 | TYR | A | 437 | 6.470 | 53.332 | 43.717 | 1.00 27.32 C |
| ATOM | 2397 | CD2 | TYR | A | 437 | 6.510 | 52.772 | 42.443 | 1.00 26.76 C |
| ATOM | 2398 | C | TYR | A | 437 | 7.343 | 49.223 | 40.980 | 1.00 28.96 C |
| ATOM | 2399 | O | TYR | A | 437 | 7.632 | 48.538 | 41.961 | 1.00 28.46 O |
| ATOM | 2400 | N | GLY | A | 438 | 6.200 | 49.092 | 40.300 | 1.00 30.39 N |
| ATOM | 2401 | CA | GLY | A | 438 | 5.161 | 48.135 | 40.687 | 1.00 31.87 C |
| ATOM | 2402 | C | GLY | A | 438 | 5.688 | 46.760 | 41.068 | 1.00 33.05 C |
| ATOM | 2403 | O | GLY | A | 438 | 5.306 | 46.212 | 42.094 | 1.00 32.22 O |
| ATOM | 2404 | N | LYS | A | 439 | 6.574 | 46.216 | 40.237 | 1.00 35.34 N |
| ATOM | 2405 | CA | LYS | A | 439 | 7.177 | 44.912 | 40.478 | 1.00 35.77 C |
| ATOM | 2406 | CB | LYS | A | 439 | 7.773 | 44.356 | 39.185 | 1.00 37.96 C |
| ATOM | 2407 | CG | LYS | A | 439 | 6.828 | 44.011 | 38.035 | 1.00 39.21 C |
| ATOM | 2408 | CD | LYS | A | 439 | 7.661 | 43.984 | 36.736 | 1.00 41.04 C |
| ATOM | 2409 | CE | LYS | A | 439 | 7.291 | 42.877 | 35.760 | 1.00 42.34 C |
| ATOM | 2410 | NZ | LYS | A | 439 | 6.041 | 43.179 | 35.011 | 1.00 42.55 N |
| ATOM | 2411 | C | LYS | A | 439 | 8.317 | 44.920 | 41.514 | 1.00 34.98 C |
| ATOM | 2412 | O | LYS | A | 439 | 8.721 | 43.849 | 41.966 | 1.00 35.35 O |
| ATOM | 2413 | N | THR | A | 440 | 8.872 | 46.083 | 41.864 | 1.00 33.58 N |
| ATOM | 2414 | CA | THR | A | 440 | 10.055 | 46.117 | 42.766 | 1.00 31.98 C |
| ATOM | 2415 | CB | THR | A | 440 | 11.330 | 46.564 | 42.013 | 1.00 30.55 C |
| ATOM | 2416 | OG1 | THR | A | 440 | 11.068 | 47.770 | 41.279 | 1.00 30.02 O |
| ATOM | 2417 | CG2 | THR | A | 440 | 11.775 | 45.467 | 41.054 | 1.00 29.53 C |
| ATOM | 2418 | C | THR | A | 440 | 9.869 | 46.909 | 44.081 | 1.00 31.42 C |
| ATOM | 2419 | O | THR | A | 440 | 9.377 | 46.351 | 45.064 | 1.00 32.13 O |
| ATOM | 2420 | N | LEU | A | 441 | 10.258 | 48.182 | 44.106 | 1.00 29.89 N |
| ATOM | 2421 | CA | LEU | A | 441 | 10.312 | 48.939 | 45.358 | 1.00 28.91 C |
| ATOM | 2422 | CB | LEU | A | 441 | 11.033 | 50.254 | 45.153 | 1.00 28.21 C |
| ATOM | 2423 | CG | LEU | A | 441 | 12.537 | 50.163 | 45.163 | 1.00 28.77 C |
| ATOM | 2424 | CD1 | LEU | A | 441 | 13.085 | 51.490 | 44.682 | 1.00 29.74 C |
| ATOM | 2425 | CD2 | LEU | A | 441 | 13.039 | 49.842 | 46.555 | 1.00 28.82 C |
| ATOM | 2426 | C | LEU | A | 441 | 8.960 | 49.258 | 45.965 | 1.00 30.20 C |
| ATOM | 2427 | O | LEU | A | 441 | 8.856 | 49.371 | 47.185 | 1.00 28.88 O |
| ATOM | 2428 | N | ARG | A | 442 | 7.942 | 49.423 | 45.124 | 1.00 31.62 N |
| ATOM | 2429 | CA | ARG | A | 442 | 6.616 | 49.814 | 45.580 | 1.00 34.02 C |
| ATOM | 2430 | CB | ARG | A | 442 | 5.549 | 49.586 | 44.494 | 1.00 36.26 C |
| ATOM | 2431 | CG | ARG | A | 442 | 4.283 | 50.377 | 44.767 | 1.00 39.24 C |
| ATOM | 2432 | CD | ARG | A | 442 | 3.077 | 50.037 | 43.898 | 1.00 43.17 C |
| ATOM | 2433 | NE | ARG | A | 442 | 1.906 | 50.830 | 44.319 | 1.00 46.78 N |
| ATOM | 2434 | CZ | ARG | A | 442 | 1.153 | 50.587 | 45.403 | 1.00 48.22 C |
| ATOM | 2435 | NH1 | ARG | A | 442 | 1.415 | 49.565 | 46.213 | 1.00 49.00 N |
| ATOM | 2436 | NH2 | ARG | A | 442 | 0.127 | 51.379 | 45.694 | 1.00 48.13 N |
| ATOM | 2437 | C | ARG | A | 442 | 6.235 | 49.063 | 46.859 | 1.00 35.62 C |
| ATOM | 2438 | O | ARG | A | 442 | 5.886 | 49.675 | 47.872 | 1.00 35.31 O |
| ATOM | 2439 | N | GLN | A | 443 | 6.338 | 47.740 | 46.833 | 1.00 37.12 N |
| ATOM | 2440 | CA | GLN | A | 443 | 5.966 | 46.940 | 48.007 | 1.00 37.57 C |
| ATOM | 2441 | CB | GLN | A | 443 | 6.143 | 45.438 | 47.721 | 1.00 40.12 C |
| ATOM | 2442 | CG | GLN | A | 443 | 7.569 | 44.943 | 47.926 | 1.00 42.53 C |
| ATOM | 2443 | CD | GLN | A | 443 | 7.820 | 43.571 | 47.320 | 1.00 44.85 C |
| ATOM | 2444 | OE1 | GLN | A | 443 | 7.442 | 42.547 | 47.903 | 1.00 44.44 O |
| ATOM | 2445 | NE2 | GLN | A | 443 | 8.487 | 43.542 | 46.152 | 1.00 43.69 N |
| ATOM | 2446 | C | GLN | A | 443 | 6.723 | 47.337 | 49.300 | 1.00 34.82 C |
| ATOM | 2447 | O | GLN | A | 443 | 6.192 | 47.145 | 50.399 | 1.00 32.46 O |
| ATOM | 2448 | N | HIS | A | 444 | 7.941 | 47.882 | 49.168 | 1.00 32.59 N |
| ATOM | 2449 | CA | HIS | A | 444 | 8.753 | 48.293 | 50.334 | 1.00 31.30 C |
| ATOM | 2450 | CB | HIS | A | 444 | 10.230 | 47.975 | 50.105 | 1.00 30.47 C |

TABLE 3-continued

| | | | | GLTP domain of FAPP2 atomic coordinates | | | | | |
|---|---|---|---|---|---|---|---|---|---|
| ATOM | 2451 | CG | HIS | A | 444 | 10.466 | 46.573 | 49.662 | 1.00 | 30.35 C |
| ATOM | 2452 | ND1 | HIS | A | 444 | 10.069 | 45.486 | 50.407 | 1.00 | 30.21 N |
| ATOM | 2453 | CE1 | HIS | A | 444 | 10.376 | 44.377 | 49.759 | 1.00 | 30.21 C |
| ATOM | 2454 | NE2 | HIS | A | 444 | 10.962 | 44.708 | 48.622 | 1.00 | 30.48 N |
| ATOM | 2455 | CD2 | HIS | A | 444 | 11.032 | 46.076 | 48.537 | 1.00 | 30.39 C |
| ATOM | 2456 | C | HIS | A | 444 | 8.645 | 49.755 | 50.765 | 1.00 | 31.26 C |
| ATOM | 2457 | O | HIS | A | 444 | 9.164 | 50.100 | 51.816 | 1.00 | 32.52 O |
| ATOM | 2458 | N | HIS | A | 445 | 7.995 | 50.618 | 49.983 | 1.00 | 30.01 N |
| ATOM | 2459 | CA | HIS | A | 445 | 7.860 | 52.027 | 50.362 | 1.00 | 28.50 C |
| ATOM | 2460 | CB | HIS | A | 445 | 7.958 | 52.933 | 49.128 | 1.00 | 28.90 C |
| ATOM | 2461 | CG | HIS | A | 445 | 9.357 | 53.141 | 48.625 | 1.00 | 29.29 C |
| ATOM | 2462 | ND1 | HIS | A | 445 | 9.629 | 53.533 | 47.329 | 1.00 | 28.66 N |
| ATOM | 2463 | CE1 | HIS | A | 445 | 10.936 | 53.652 | 47.170 | 1.00 | 29.23 C |
| ATOM | 2464 | NE2 | HIS | A | 445 | 11.525 | 53.332 | 48.310 | 1.00 | 29.16 N |
| ATOM | 2465 | CD2 | HIS | A | 445 | 10.560 | 53.016 | 49.239 | 1.00 | 29.00 C |
| ATOM | 2466 | C | HIS | A | 445 | 6.537 | 52.283 | 51.097 | 1.00 | 28.16 C |
| ATOM | 2467 | O | HIS | A | 445 | 5.509 | 51.697 | 50.754 | 1.00 | 28.18 O |
| ATOM | 2468 | N | GLY | A | 446 | 6.567 | 53.169 | 52.095 | 1.00 | 27.16 N |
| ATOM | 2469 | CA | GLY | A | 446 | 5.352 | 53.617 | 52.781 | 1.00 | 26.86 C |
| ATOM | 2470 | C | GLY | A | 446 | 4.480 | 54.484 | 51.899 | 1.00 | 26.93 C |
| ATOM | 2471 | O | GLY | A | 446 | 4.872 | 54.815 | 50.792 | 1.00 | 27.62 O |
| ATOM | 2472 | N | TRP | A | 447 | 3.311 | 54.886 | 52.380 | 1.00 | 27.50 N |
| ATOM | 2473 | CA | TRP | A | 447 | 2.329 | 55.535 | 51.494 | 1.00 | 29.44 C |
| ATOM | 2474 | CB | TRP | A | 447 | 0.980 | 55.718 | 52.215 | 1.00 | 32.63 C |
| ATOM | 2475 | CG | TRP | A | 447 | 0.090 | 54.485 | 52.178 | 1.00 | 36.28 C |
| ATOM | 2476 | CD1 | TRP | A | 447 | −0.355 | 53.752 | 53.250 | 1.00 | 38.75 C |
| ATOM | 2477 | NE1 | TRP | A | 447 | −1.145 | 52.712 | 52.816 | 1.00 | 40.14 N |
| ATOM | 2478 | CE2 | TRP | A | 447 | −1.218 | 52.746 | 51.446 | 1.00 | 40.39 C |
| ATOM | 2479 | CD2 | TRP | A | 447 | −0.457 | 53.855 | 51.007 | 1.00 | 38.97 C |
| ATOM | 2480 | CE3 | TRP | A | 447 | −0.375 | 54.119 | 49.630 | 1.00 | 39.28 C |
| ATOM | 2481 | CZ3 | TRP | A | 447 | −1.051 | 53.270 | 48.738 | 1.00 | 39.52 C |
| ATOM | 2482 | CH2 | TRP | A | 447 | −1.802 | 52.180 | 49.205 | 1.00 | 40.29 C |
| ATOM | 2483 | CZ2 | TRP | A | 447 | −1.901 | 51.901 | 50.551 | 1.00 | 41.30 C |
| ATOM | 2484 | C | TRP | A | 447 | 2.778 | 56.874 | 50.858 | 1.00 | 27.55 C |
| ATOM | 2485 | O | TRP | A | 447 | 2.438 | 57.178 | 49.696 | 1.00 | 26.27 O |
| ATOM | 2486 | N | VAL | A | 448 | 3.542 | 57.658 | 51.615 | 1.00 | 25.57 N |
| ATOM | 2487 | CA | VAL | A | 448 | 3.930 | 59.011 | 51.192 | 1.00 | 23.48 C |
| ATOM | 2488 | CB | VAL | A | 448 | 4.511 | 59.838 | 52.365 | 1.00 | 22.61 C |
| ATOM | 2489 | CG1 | VAL | A | 448 | 4.703 | 61.292 | 51.953 | 1.00 | 21.92 C |
| ATOM | 2490 | CG2 | VAL | A | 448 | 3.629 | 59.723 | 53.605 | 1.00 | 22.43 C |
| ATOM | 2491 | C | VAL | A | 448 | 4.974 | 58.974 | 50.080 | 1.00 | 23.03 C |
| ATOM | 2492 | O | VAL | A | 448 | 4.922 | 59.789 | 49.172 | 1.00 | 23.59 O |
| ATOM | 2493 | N | VAL | A | 449 | 5.928 | 58.045 | 50.175 | 1.00 | 21.88 N |
| ATOM | 2494 | CA | VAL | A | 449 | 6.979 | 57.901 | 49.185 | 1.00 | 21.38 C |
| ATOM | 2495 | CB | VAL | A | 449 | 8.125 | 56.996 | 49.700 | 1.00 | 21.01 C |
| ATOM | 2496 | CG1 | VAL | A | 449 | 9.095 | 56.681 | 48.593 | 1.00 | 21.35 C |
| ATOM | 2497 | CG2 | VAL | A | 449 | 8.879 | 57.664 | 50.835 | 1.00 | 20.60 C |
| ATOM | 2498 | C | VAL | A | 449 | 6.393 | 57.357 | 47.885 | 1.00 | 21.93 C |
| ATOM | 2499 | O | VAL | A | 449 | 6.684 | 57.869 | 46.805 | 1.00 | 21.19 O |
| ATOM | 2500 | N | ARG | A | 450 | 5.549 | 56.336 | 47.984 | 1.00 | 23.72 N |
| ATOM | 2501 | CA | ARG | A | 450 | 4.865 | 55.797 | 46.797 | 1.00 | 24.81 C |
| ATOM | 2502 | CB | ARG | A | 450 | 3.847 | 54.725 | 47.176 | 1.00 | 26.97 C |
| ATOM | 2503 | CG | ARG | A | 450 | 4.430 | 53.500 | 47.875 | 1.00 | 29.67 C |
| ATOM | 2504 | CD | ARG | A | 450 | 3.729 | 52.208 | 47.459 | 1.00 | 32.40 C |
| ATOM | 2505 | NE | ARG | A | 450 | 2.621 | 51.821 | 48.331 | 1.00 | 34.54 N |
| ATOM | 2506 | CZ | ARG | A | 450 | 2.629 | 50.808 | 49.199 | 1.00 | 37.95 C |
| ATOM | 2507 | NH1 | ARG | A | 450 | 3.694 | 50.029 | 49.349 | 1.00 | 39.20 N |
| ATOM | 2508 | NH2 | ARG | A | 450 | 1.549 | 50.576 | 49.945 | 1.00 | 41.40 N |
| ATOM | 2509 | C | ARG | A | 450 | 4.155 | 56.902 | 46.045 | 1.00 | 24.17 C |
| ATOM | 2510 | O | ARG | A | 450 | 4.189 | 56.954 | 44.814 | 1.00 | 25.30 O |
| ATOM | 2511 | N | GLY | A | 451 | 3.507 | 57.787 | 46.794 | 1.00 | 23.36 N |
| ATOM | 2512 | CA | GLY | A | 451 | 2.855 | 58.941 | 46.214 | 1.00 | 23.61 C |
| ATOM | 2513 | C | GLY | A | 451 | 3.842 | 59.846 | 45.527 | 1.00 | 24.50 C |
| ATOM | 2514 | O | GLY | A | 451 | 3.652 | 60.218 | 44.387 | 1.00 | 24.46 O |
| ATOM | 2515 | N | VAL | A | 452 | 4.910 | 60.198 | 46.235 | 1.00 | 27.19 N |
| ATOM | 2516 | CA | VAL | A | 452 | 5.947 | 61.054 | 45.686 | 1.00 | 28.22 C |
| ATOM | 2517 | CB | VAL | A | 452 | 7.140 | 61.167 | 46.662 | 1.00 | 27.69 C |
| ATOM | 2518 | CG1 | VAL | A | 452 | 8.411 | 61.668 | 45.972 | 1.00 | 27.47 C |
| ATOM | 2519 | CG2 | VAL | A | 452 | 6.769 | 62.084 | 47.801 | 1.00 | 26.92 C |
| ATOM | 2520 | C | VAL | A | 452 | 6.384 | 60.493 | 44.342 | 1.00 | 30.03 C |
| ATOM | 2521 | O | VAL | A | 452 | 6.295 | 61.164 | 43.321 | 1.00 | 29.95 O |
| ATOM | 2522 | N | PHE | A | 453 | 6.829 | 59.248 | 44.352 | 1.00 | 32.95 N |
| ATOM | 2523 | CA | PHE | A | 453 | 7.250 | 58.590 | 43.137 | 1.00 | 36.27 C |
| ATOM | 2524 | CB | PHE | A | 453 | 7.674 | 57.173 | 43.446 | 1.00 | 38.78 C |
| ATOM | 2525 | CG | PHE | A | 453 | 8.302 | 56.496 | 42.289 | 1.00 | 43.00 C |
| ATOM | 2526 | CD1 | PHE | A | 453 | 7.509 | 55.977 | 41.259 | 1.00 | 42.89 C |
| ATOM | 2527 | CE1 | PHE | A | 453 | 8.081 | 55.353 | 40.167 | 1.00 | 44.04 C |
| ATOM | 2528 | CZ | PHE | A | 453 | 9.460 | 55.250 | 40.082 | 1.00 | 47.55 C |

TABLE 3-continued

GLTP domain of FAPP2 atomic coordinates

| ATOM | 2529 | CE2 | PHE | A | 453 | 10.266 | 55.764 | 41.102 | 1.00 | 49.11 | C |
|---|---|---|---|---|---|---|---|---|---|---|---|
| ATOM | 2530 | CD2 | PHE | A | 453 | 9.685 | 56.389 | 42.202 | 1.00 | 46.12 | C |
| ATOM | 2531 | C | PHE | A | 453 | 6.165 | 58.578 | 42.052 | 1.00 | 37.23 | C |
| ATOM | 2532 | O | PHE | A | 453 | 6.435 | 58.913 | 40.902 | 1.00 | 40.89 | O |
| ATOM | 2533 | N | ALA | A | 454 | 4.943 | 58.191 | 42.397 | 1.00 | 36.45 | N |
| ATOM | 2534 | CA | ALA | A | 454 | 3.849 | 58.197 | 41.411 | 1.00 | 38.15 | C |
| ATOM | 2535 | CB | ALA | A | 454 | 2.532 | 57.839 | 42.067 | 1.00 | 38.11 | C |
| ATOM | 2536 | C | ALA | A | 454 | 3.699 | 59.534 | 40.685 | 1.00 | 37.75 | C |
| ATOM | 2537 | O | ALA | A | 454 | 3.381 | 59.578 | 39.503 | 1.00 | 41.66 | O |
| ATOM | 2538 | N | LEU | A | 455 | 3.920 | 60.624 | 41.399 | 1.00 | 35.38 | N |
| ATOM | 2539 | CA | LEU | A | 455 | 3.849 | 61.932 | 40.796 | 1.00 | 34.88 | C |
| ATOM | 2540 | CB | LEU | A | 455 | 3.639 | 62.973 | 41.878 | 1.00 | 34.54 | C |
| ATOM | 2541 | CG | LEU | A | 455 | 2.705 | 64.103 | 41.488 | 1.00 | 35.83 | C |
| ATOM | 2542 | CD1 | LEU | A | 455 | 1.271 | 63.620 | 41.319 | 1.00 | 36.99 | C |
| ATOM | 2543 | CD2 | LEU | A | 455 | 2.775 | 65.162 | 42.567 | 1.00 | 36.75 | C |
| ATOM | 2544 | C | LEU | A | 455 | 5.119 | 62.227 | 39.985 | 1.00 | 35.65 | C |
| ATOM | 2545 | O | LEU | A | 455 | 5.050 | 62.789 | 38.902 | 1.00 | 36.33 | O |
| ATOM | 2546 | N | ALA | A | 456 | 6.280 | 61.840 | 40.500 | 1.00 | 36.16 | N |
| ATOM | 2547 | CA | ALA | A | 456 | 7.532 | 62.027 | 39.778 | 1.00 | 36.34 | C |
| ATOM | 2548 | CB | ALA | A | 456 | 8.692 | 61.470 | 40.584 | 1.00 | 36.40 | C |
| ATOM | 2549 | C | ALA | A | 456 | 7.491 | 61.381 | 38.391 | 1.00 | 37.59 | C |
| ATOM | 2550 | O | ALA | A | 456 | 8.125 | 61.867 | 37.458 | 1.00 | 37.39 | O |
| ATOM | 2551 | N | LEU | A | 457 | 6.745 | 60.286 | 38.255 | 1.00 | 39.09 | N |
| ATOM | 2552 | CA | LEU | A | 457 | 6.576 | 59.631 | 36.953 | 1.00 | 39.47 | C |
| ATOM | 2553 | CB | LEU | A | 457 | 5.524 | 58.521 | 37.039 | 1.00 | 41.98 | C |
| ATOM | 2554 | CG | LEU | A | 457 | 5.853 | 57.243 | 37.813 | 1.00 | 43.78 | C |
| ATOM | 2555 | CD1 | LEU | A | 457 | 4.612 | 56.358 | 37.944 | 1.00 | 44.45 | C |
| ATOM | 2556 | CD2 | LEU | A | 457 | 6.997 | 56.499 | 37.136 | 1.00 | 43.85 | C |
| ATOM | 2557 | C | LEU | A | 457 | 6.125 | 60.606 | 35.875 | 1.00 | 36.30 | C |
| ATOM | 2558 | O | LEU | A | 457 | 6.606 | 60.553 | 34.740 | 1.00 | 39.88 | O |
| ATOM | 2559 | N | ARG | A | 458 | 5.225 | 61.515 | 36.246 | 1.00 | 32.77 | N |
| ATOM | 2560 | CA | AARG | A | 458 | 4.588 | 62.381 | 35.259 | 0.50 | 31.92 | C |
| ATOM | 2561 | CA | BARG | A | 458 | 4.563 | 62.413 | 35.293 | 0.50 | 32.34 | C |
| ATOM | 2562 | CB | AARG | A | 458 | 3.360 | 63.054 | 35.854 | 0.50 | 30.10 | C |
| ATOM | 2563 | CB | BARG | A | 458 | 3.406 | 63.193 | 35.952 | 0.50 | 31.20 | C |
| ATOM | 2564 | CG | AARG | A | 458 | 2.352 | 62.043 | 36.336 | 0.50 | 28.75 | C |
| ATOM | 2565 | CG | BARG | A | 458 | 2.342 | 62.366 | 36.662 | 0.50 | 30.43 | C |
| ATOM | 2566 | CD | AARG | A | 458 | 0.985 | 62.329 | 35.777 | 0.50 | 27.44 | C |
| ATOM | 2567 | CD | BARG | A | 458 | 1.638 | 61.359 | 35.763 | 0.50 | 29.52 | C |
| ATOM | 2568 | NE | AARG | A | 458 | 0.648 | 61.529 | 34.604 | 0.50 | 25.79 | N |
| ATOM | 2569 | NE | BARG | A | 458 | 1.278 | 60.169 | 36.529 | 0.50 | 28.46 | N |
| ATOM | 2570 | CZ | AARG | A | 458 | 0.367 | 62.032 | 33.409 | 0.50 | 24.01 | C |
| ATOM | 2571 | CZ | BARG | A | 458 | 0.564 | 59.160 | 36.062 | 0.50 | 27.16 | C |
| ATOM | 2572 | NH1 | AARG | A | 458 | 0.392 | 63.341 | 33.201 | 0.50 | 23.04 | N |
| ATOM | 2573 | NH1 | BARG | A | 458 | 0.097 | 59.196 | 34.830 | 0.50 | 27.22 | N |
| ATOM | 2574 | NH2 | AARG | A | 458 | 0.058 | 61.214 | 32.423 | 0.50 | 23.59 | N |
| ATOM | 2575 | NH2 | BARG | A | 458 | 0.303 | 58.127 | 36.842 | 0.50 | 27.07 | N |
| ATOM | 2576 | C | ARG | A | 458 | 5.521 | 63.420 | 34.664 | 1.00 | 32.28 | C |
| ATOM | 2577 | O | ARG | A | 458 | 5.109 | 64.197 | 33.805 | 1.00 | 31.62 | O |
| ATOM | 2578 | N | ALA | A | 459 | 6.776 | 63.428 | 35.123 | 1.00 | 32.71 | N |
| ATOM | 2579 | CA | ALA | A | 459 | 7.827 | 64.252 | 34.521 | 1.00 | 32.71 | C |
| ATOM | 2580 | CB | ALA | A | 459 | 8.414 | 65.209 | 35.548 | 1.00 | 33.03 | C |
| ATOM | 2581 | C | ALA | A | 459 | 8.929 | 63.382 | 33.926 | 1.00 | 32.30 | C |
| ATOM | 2582 | O | ALA | A | 459 | 10.081 | 63.815 | 33.826 | 1.00 | 33.06 | O |
| ATOM | 2583 | N | ALA | A | 460 | 8.584 | 62.162 | 33.522 | 1.00 | 32.38 | N |
| ATOM | 2584 | CA | ALA | A | 460 | 9.527 | 61.320 | 32.800 | 1.00 | 32.17 | C |
| ATOM | 2585 | CB | ALA | A | 460 | 8.962 | 59.924 | 32.638 | 1.00 | 32.22 | C |
| ATOM | 2586 | C | ALA | A | 460 | 9.791 | 61.967 | 31.437 | 1.00 | 32.29 | C |
| ATOM | 2587 | O | ALA | A | 460 | 8.878 | 62.490 | 30.812 | 1.00 | 31.07 | O |
| ATOM | 2588 | N | PRO | A | 461 | 11.046 | 61.971 | 30.977 | 1.00 | 33.95 | N |
| ATOM | 2589 | CA | PRO | A | 461 | 11.298 | 62.669 | 29.706 | 1.00 | 34.56 | C |
| ATOM | 2590 | CB | PRO | A | 461 | 12.821 | 62.823 | 29.689 | 1.00 | 33.48 | C |
| ATOM | 2591 | CG | PRO | A | 461 | 13.313 | 61.714 | 30.555 | 1.00 | 33.46 | C |
| ATOM | 2592 | CD | PRO | A | 461 | 12.297 | 61.593 | 31.649 | 1.00 | 33.77 | C |
| ATOM | 2593 | C | PRO | A | 461 | 10.816 | 61.961 | 28.424 | 1.00 | 34.39 | C |
| ATOM | 2594 | O | PRO | A | 461 | 10.390 | 60.803 | 28.438 | 1.00 | 33.09 | O |
| ATOM | 2595 | N | SER | A | 462 | 10.856 | 62.703 | 27.327 | 1.00 | 34.17 | N |
| ATOM | 2596 | CA | SER | A | 462 | 10.770 | 62.128 | 26.010 | 1.00 | 34.35 | C |
| ATOM | 2597 | CB | SER | A | 462 | 10.990 | 63.241 | 24.987 | 1.00 | 35.99 | C |
| ATOM | 2598 | OG | SER | A | 462 | 11.246 | 62.730 | 23.696 | 1.00 | 40.00 | O |
| ATOM | 2599 | C | SER | A | 462 | 11.862 | 61.060 | 25.865 | 1.00 | 35.13 | C |
| ATOM | 2600 | O | SER | A | 462 | 13.021 | 61.272 | 26.254 | 1.00 | 33.09 | O |
| ATOM | 2601 | N | TYR | A | 463 | 11.493 | 59.910 | 25.308 | 1.00 | 35.97 | N |
| ATOM | 2602 | CA | TYR | A | 463 | 12.473 | 58.896 | 24.928 | 1.00 | 36.00 | C |
| ATOM | 2603 | CB | TYR | A | 463 | 11.835 | 57.840 | 24.020 | 1.00 | 35.52 | C |
| ATOM | 2604 | CG | TYR | A | 463 | 12.799 | 56.730 | 23.678 | 1.00 | 36.78 | C |
| ATOM | 2605 | CD1 | TYR | A | 463 | 13.000 | 55.668 | 24.553 | 1.00 | 36.80 | C |
| ATOM | 2606 | CE1 | TYR | A | 463 | 13.905 | 54.660 | 24.264 | 1.00 | 37.32 | C |

TABLE 3-continued

GLTP domain of FAPP2 atomic coordinates

| ATOM | 2607 | CZ  | TYR | A | 463 | 14.624 | 54.707 | 23.080 | 1.00 | 38.32 | C |
| --- | --- | --- | --- | --- | --- | --- | --- | --- | --- | --- | --- |
| ATOM | 2608 | OH  | TYR | A | 463 | 15.515 | 53.699 | 22.798 | 1.00 | 40.26 | O |
| ATOM | 2609 | CE2 | TYR | A | 463 | 14.449 | 55.756 | 22.192 | 1.00 | 37.13 | C |
| ATOM | 2610 | CD2 | TYR | A | 463 | 13.549 | 56.764 | 22.499 | 1.00 | 37.04 | C |
| ATOM | 2611 | C   | TYR | A | 463 | 13.702 | 59.529 | 24.230 | 1.00 | 36.37 | C |
| ATOM | 2612 | O   | TYR | A | 463 | 14.843 | 59.205 | 24.556 | 1.00 | 33.63 | O |
| ATOM | 2613 | N   | GLU | A | 464 | 13.445 | 60.436 | 23.284 | 1.00 | 37.03 | N |
| ATOM | 2614 | CA  | GLU | A | 464 | 14.493 | 61.193 | 22.588 | 1.00 | 38.04 | C |
| ATOM | 2615 | CB  | GLU | A | 464 | 13.868 | 62.283 | 21.697 | 1.00 | 41.09 | C |
| ATOM | 2616 | CG  | GLU | A | 464 | 14.824 | 62.902 | 20.668 | 1.00 | 44.47 | C |
| ATOM | 2617 | CD  | GLU | A | 464 | 14.378 | 64.274 | 20.134 | 1.00 | 47.63 | C |
| ATOM | 2618 | OE1 | GLU | A | 464 | 13.251 | 64.736 | 20.468 | 1.00 | 50.07 | O |
| ATOM | 2619 | OE2 | GLU | A | 464 | 15.166 | 64.903 | 19.379 | 1.00 | 45.62 | O |
| ATOM | 2620 | C   | GLU | A | 464 | 15.481 | 61.849 | 23.554 | 1.00 | 36.67 | C |
| ATOM | 2621 | O   | GLU | A | 464 | 16.698 | 61.758 | 23.357 | 1.00 | 36.56 | O |
| ATOM | 2622 | N   | ASP | A | 465 | 14.961 | 62.525 | 24.579 | 1.00 | 34.48 | N |
| ATOM | 2623 | CA  | ASP | A | 465 | 15.811 | 63.270 | 25.509 | 1.00 | 34.34 | C |
| ATOM | 2624 | CB  | ASP | A | 465 | 14.988 | 64.254 | 26.341 | 1.00 | 35.60 | C |
| ATOM | 2625 | CG  | ASP | A | 465 | 14.345 | 65.344 | 25.506 | 1.00 | 37.14 | C |
| ATOM | 2626 | OD1 | ASP | A | 465 | 14.252 | 65.194 | 24.272 | 1.00 | 38.95 | O |
| ATOM | 2627 | OD2 | ASP | A | 465 | 13.915 | 66.355 | 26.096 | 1.00 | 38.54 | O |
| ATOM | 2628 | C   | ASP | A | 465 | 16.561 | 62.326 | 26.442 | 1.00 | 33.06 | C |
| ATOM | 2629 | O   | ASP | A | 465 | 17.707 | 62.582 | 26.831 | 1.00 | 31.16 | O |
| ATOM | 2630 | N   | PHE | A | 466 | 15.894 | 61.242 | 26.809 | 1.00 | 32.55 | N |
| ATOM | 2631 | CA  | PHE | A | 466 | 16.476 | 60.261 | 27.699 | 1.00 | 32.56 | C |
| ATOM | 2632 | CB  | PHE | A | 466 | 15.437 | 59.200 | 28.056 | 1.00 | 32.54 | C |
| ATOM | 2633 | CG  | PHE | A | 466 | 16.019 | 58.003 | 28.733 | 1.00 | 33.01 | C |
| ATOM | 2634 | CD1 | PHE | A | 466 | 16.608 | 58.122 | 29.982 | 1.00 | 34.52 | C |
| ATOM | 2635 | CE1 | PHE | A | 466 | 17.168 | 57.019 | 30.613 | 1.00 | 36.28 | C |
| ATOM | 2636 | CZ  | PHE | A | 466 | 17.142 | 55.781 | 29.989 | 1.00 | 36.66 | C |
| ATOM | 2637 | CE2 | PHE | A | 466 | 16.556 | 55.655 | 28.737 | 1.00 | 35.19 | C |
| ATOM | 2638 | CD2 | PHE | A | 466 | 15.995 | 56.762 | 28.120 | 1.00 | 33.41 | C |
| ATOM | 2639 | C   | PHE | A | 466 | 17.685 | 59.597 | 27.047 | 1.00 | 32.18 | C |
| ATOM | 2640 | O   | PHE | A | 466 | 18.743 | 59.449 | 27.651 | 1.00 | 32.48 | O |
| ATOM | 2641 | N   | VAL | A | 467 | 17.512 | 59.198 | 25.801 | 1.00 | 31.76 | N |
| ATOM | 2642 | CA  | VAL | A | 467 | 18.511 | 58.420 | 25.099 | 1.00 | 31.57 | C |
| ATOM | 2643 | CB  | VAL | A | 467 | 17.842 | 57.706 | 23.907 | 1.00 | 32.30 | C |
| ATOM | 2644 | CG1 | VAL | A | 467 | 17.615 | 58.649 | 22.731 | 1.00 | 32.17 | C |
| ATOM | 2645 | CG2 | VAL | A | 467 | 18.657 | 56.509 | 23.492 | 1.00 | 32.91 | C |
| ATOM | 2646 | C   | VAL | A | 467 | 19.702 | 59.298 | 24.671 | 1.00 | 32.47 | C |
| ATOM | 2647 | O   | VAL | A | 467 | 20.853 | 58.842 | 24.624 | 1.00 | 30.79 | O |
| ATOM | 2648 | N   | ALA | A | 468 | 19.413 | 60.564 | 24.372 | 1.00 | 33.67 | N |
| ATOM | 2649 | CA  | ALA | A | 468 | 20.443 | 61.565 | 24.123 | 1.00 | 33.77 | C |
| ATOM | 2650 | CB  | ALA | A | 468 | 19.830 | 62.957 | 24.100 | 1.00 | 33.56 | C |
| ATOM | 2651 | C   | ALA | A | 468 | 21.511 | 61.491 | 25.195 | 1.00 | 34.23 | C |
| ATOM | 2652 | O   | ALA | A | 468 | 22.696 | 61.381 | 24.888 | 1.00 | 36.89 | O |
| ATOM | 2653 | N   | ALA | A | 469 | 21.075 | 61.511 | 26.451 | 1.00 | 33.85 | N |
| ATOM | 2654 | CA  | ALA | A | 469 | 21.981 | 61.511 | 27.599 | 1.00 | 34.63 | C |
| ATOM | 2655 | CB  | ALA | A | 469 | 21.246 | 61.986 | 28.847 | 1.00 | 35.21 | C |
| ATOM | 2656 | C   | ALA | A | 469 | 22.659 | 60.167 | 27.888 | 1.00 | 36.01 | C |
| ATOM | 2657 | O   | ALA | A | 469 | 23.381 | 60.059 | 28.890 | 1.00 | 37.30 | O |
| ATOM | 2658 | N   | LEU | A | 470 | 22.440 | 59.156 | 27.038 | 1.00 | 34.98 | N |
| ATOM | 2659 | CA  | LEU | A | 470 | 23.116 | 57.859 | 27.177 | 1.00 | 34.16 | C |
| ATOM | 2660 | CB  | LEU | A | 470 | 22.087 | 56.719 | 27.114 | 1.00 | 34.39 | C |
| ATOM | 2661 | CG  | LEU | A | 470 | 21.099 | 56.659 | 28.289 | 1.00 | 34.33 | C |
| ATOM | 2662 | CD1 | LEU | A | 470 | 20.108 | 55.523 | 28.108 | 1.00 | 35.58 | C |
| ATOM | 2663 | CD2 | LEU | A | 470 | 21.803 | 56.509 | 29.629 | 1.00 | 34.28 | C |
| ATOM | 2664 | C   | LEU | A | 470 | 24.210 | 57.644 | 26.130 | 1.00 | 33.60 | C |
| ATOM | 2665 | O   | LEU | A | 470 | 24.806 | 56.562 | 26.053 | 1.00 | 32.30 | O |
| ATOM | 2666 | N   | THR | A | 471 | 24.488 | 58.681 | 25.342 | 1.00 | 33.53 | N |
| ATOM | 2667 | CA  | THR | A | 471 | 25.446 | 58.591 | 24.248 | 1.00 | 32.24 | C |
| ATOM | 2668 | CB  | THR | A | 471 | 25.230 | 59.730 | 23.231 | 1.00 | 30.99 | C |
| ATOM | 2669 | OG1 | THR | A | 471 | 25.277 | 60.994 | 23.896 | 1.00 | 29.65 | O |
| ATOM | 2670 | CG2 | THR | A | 471 | 23.893 | 59.605 | 22.572 | 1.00 | 31.81 | C |
| ATOM | 2671 | C   | THR | A | 471 | 26.855 | 58.694 | 24.786 | 1.00 | 33.86 | C |
| ATOM | 2672 | O   | THR | A | 471 | 27.069 | 58.899 | 25.989 | 1.00 | 32.98 | O |
| ATOM | 2673 | N   | VAL | A | 472 | 27.814 | 58.528 | 23.884 | 1.00 | 36.15 | N |
| ATOM | 2674 | CA  | VAL | A | 472 | 29.202 | 58.923 | 24.141 | 1.00 | 36.70 | C |
| ATOM | 2675 | CB  | VAL | A | 472 | 30.154 | 57.696 | 24.163 | 1.00 | 37.11 | C |
| ATOM | 2676 | CG1 | VAL | A | 472 | 31.288 | 57.922 | 25.151 | 1.00 | 36.83 | C |
| ATOM | 2677 | CG2 | VAL | A | 472 | 29.399 | 56.425 | 24.551 | 1.00 | 37.76 | C |
| ATOM | 2678 | C   | VAL | A | 472 | 29.695 | 59.990 | 23.134 | 1.00 | 36.78 | C |
| ATOM | 2679 | O   | VAL | A | 472 | 30.856 | 60.354 | 23.172 | 1.00 | 37.73 | O |
| ATOM | 2680 | N   | LYS | A | 473 | 28.822 | 60.477 | 22.243 | 1.00 | 37.86 | N |
| ATOM | 2681 | CA  | LYS | A | 473 | 29.070 | 61.689 | 21.436 | 1.00 | 39.20 | C |
| ATOM | 2682 | CB  | LYS | A | 473 | 29.795 | 61.356 | 20.127 | 1.00 | 41.89 | C |
| ATOM | 2683 | CG  | LYS | A | 473 | 31.302 | 61.141 | 20.250 | 1.00 | 43.49 | C |
| ATOM | 2684 | CD  | LYS | A | 473 | 32.115 | 61.839 | 19.154 | 1.00 | 44.53 | C |

TABLE 3-continued

| | | | | | | | | | | |
|---|---|---|---|---|---|---|---|---|---|---|
| GLTP domain of FAPP2 atomic coordinates | | | | | | | | | | |
| ATOM | 2685 | CE | LYS | A | 473 | 31.672 | 61.494 | 17.739 | 1.00 | 44.74 C |
| ATOM | 2686 | NZ | LYS | A | 473 | 31.584 | 60.026 | 17.522 | 1.00 | 45.40 N |
| ATOM | 2687 | C | LYS | A | 473 | 27.761 | 62.416 | 21.103 | 1.00 | 39.98 C |
| ATOM | 2688 | O | LYS | A | 473 | 26.677 | 61.862 | 21.280 | 1.00 | 41.01 O |
| ATOM | 2689 | N | GLU | A | 474 | 27.865 | 63.649 | 20.606 | 1.00 | 40.72 N |
| ATOM | 2690 | CA | GLU | A | 474 | 26.685 | 64.469 | 20.265 | 1.00 | 42.23 C |
| ATOM | 2691 | CB | GLU | A | 474 | 27.050 | 65.959 | 20.268 | 1.00 | 43.97 C |
| ATOM | 2692 | CG | GLU | A | 474 | 25.870 | 66.924 | 20.150 | 1.00 | 45.22 C |
| ATOM | 2693 | CD | GLU | A | 474 | 25.291 | 67.357 | 21.493 | 1.00 | 47.06 C |
| ATOM | 2694 | OE1 | GLU | A | 474 | 26.024 | 67.352 | 22.510 | 1.00 | 49.01 O |
| ATOM | 2695 | OE2 | GLU | A | 474 | 24.095 | 67.726 | 21.531 | 1.00 | 46.92 O |
| ATOM | 2696 | C | GLU | A | 474 | 26.114 | 64.092 | 18.895 | 1.00 | 41.38 C |
| ATOM | 2697 | O | GLU | A | 474 | 26.839 | 64.069 | 17.901 | 1.00 | 39.95 O |
| ATOM | 2698 | N | GLY | A | 475 | 24.809 | 63.814 | 18.855 | 1.00 | 41.53 N |
| ATOM | 2699 | CA | GLY | A | 475 | 24.129 | 63.350 | 17.636 | 1.00 | 40.88 C |
| ATOM | 2700 | C | GLY | A | 475 | 23.932 | 61.838 | 17.569 | 1.00 | 39.55 C |
| ATOM | 2701 | O | GLY | A | 475 | 23.038 | 61.357 | 16.857 | 1.00 | 38.47 O |
| ATOM | 2702 | N | ASP | A | 476 | 24.766 | 61.096 | 18.312 | 1.00 | 38.07 N |
| ATOM | 2703 | CA | ASP | A | 476 | 24.742 | 59.615 | 18.361 | 1.00 | 37.20 C |
| ATOM | 2704 | CB | ASP | A | 476 | 25.630 | 59.087 | 19.526 | 1.00 | 36.72 C |
| ATOM | 2705 | CG | ASP | A | 476 | 27.037 | 58.615 | 19.074 | 1.00 | 36.83 C |
| ATOM | 2706 | OD1 | ASP | A | 476 | 27.522 | 58.984 | 17.978 | 1.00 | 35.59 O |
| ATOM | 2707 | OD2 | ASP | A | 476 | 27.668 | 57.857 | 19.845 | 1.00 | 36.75 O |
| ATOM | 2708 | C | ASP | A | 476 | 23.327 | 59.004 | 18.470 | 1.00 | 36.13 C |
| ATOM | 2709 | O | ASP | A | 476 | 23.046 | 57.960 | 17.868 | 1.00 | 34.40 O |
| ATOM | 2710 | N | HIS | A | 477 | 22.446 | 59.646 | 19.235 | 1.00 | 34.66 N |
| ATOM | 2711 | CA | HIS | A | 477 | 21.086 | 59.136 | 19.400 | 1.00 | 34.51 C |
| ATOM | 2712 | CB | HIS | A | 477 | 20.338 | 59.870 | 20.535 | 1.00 | 35.43 C |
| ATOM | 2713 | CG | HIS | A | 477 | 20.163 | 61.343 | 20.317 | 1.00 | 35.99 C |
| ATOM | 2714 | ND1 | HIS | A | 477 | 21.070 | 62.277 | 20.770 | 1.00 | 36.07 N |
| ATOM | 2715 | CE1 | HIS | A | 477 | 20.650 | 63.487 | 20.448 | 1.00 | 36.45 C |
| ATOM | 2716 | NE2 | HIS | A | 477 | 19.500 | 63.372 | 19.807 | 1.00 | 36.67 N |
| ATOM | 2717 | CD2 | HIS | A | 477 | 19.169 | 62.042 | 19.720 | 1.00 | 36.32 C |
| ATOM | 2718 | C | HIS | A | 477 | 20.258 | 59.124 | 18.102 | 1.00 | 32.69 C |
| ATOM | 2719 | O | HIS | A | 477 | 19.363 | 58.300 | 17.958 | 1.00 | 30.28 O |
| ATOM | 2720 | N | GLN | A | 478 | 20.562 | 60.009 | 17.157 | 1.00 | 33.01 N |
| ATOM | 2721 | CA | GLN | A | 478 | 19.832 | 60.041 | 15.883 | 1.00 | 33.24 C |
| ATOM | 2722 | CB | GLN | A | 478 | 19.836 | 61.444 | 15.304 | 1.00 | 34.21 C |
| ATOM | 2723 | CG | GLN | A | 478 | 19.285 | 62.517 | 16.216 | 1.00 | 35.53 C |
| ATOM | 2724 | CD | GLN | A | 478 | 19.736 | 63.903 | 15.786 | 1.00 | 37.54 C |
| ATOM | 2725 | OE1 | GLN | A | 478 | 20.867 | 64.091 | 15.318 | 1.00 | 36.02 O |
| ATOM | 2726 | NE2 | GLN | A | 478 | 18.854 | 64.888 | 15.948 | 1.00 | 39.01 N |
| ATOM | 2727 | C | GLN | A | 478 | 20.388 | 59.080 | 14.820 | 1.00 | 32.68 C |
| ATOM | 2728 | O | GLN | A | 478 | 19.743 | 58.869 | 13.791 | 1.00 | 32.36 O |
| ATOM | 2729 | N | LYS | A | 479 | 21.590 | 58.539 | 15.042 | 1.00 | 31.68 N |
| ATOM | 2730 | CA | LYS | A | 479 | 22.154 | 57.500 | 14.161 | 1.00 | 30.40 C |
| ATOM | 2731 | CB | LYS | A | 479 | 23.568 | 57.088 | 14.593 | 1.00 | 30.99 C |
| ATOM | 2732 | CG | LYS | A | 479 | 24.714 | 57.746 | 13.842 | 1.00 | 31.25 C |
| ATOM | 2733 | CD | LYS | A | 479 | 25.995 | 57.624 | 14.660 | 1.00 | 32.27 C |
| ATOM | 2734 | CE | LYS | A | 479 | 27.242 | 57.420 | 13.812 | 1.00 | 33.39 C |
| ATOM | 2735 | NZ | LYS | A | 479 | 28.340 | 56.864 | 14.655 | 1.00 | 33.77 N |
| ATOM | 2736 | C | LYS | A | 479 | 21.287 | 56.271 | 14.222 | 1.00 | 28.65 C |
| ATOM | 2737 | O | LYS | A | 479 | 20.732 | 55.963 | 15.271 | 1.00 | 27.88 O |
| ATOM | 2738 | N | GLU | A | 480 | 21.210 | 55.542 | 13.117 | 1.00 | 27.90 N |
| ATOM | 2739 | CA | GLU | A | 480 | 20.278 | 54.432 | 13.032 | 1.00 | 27.70 C |
| ATOM | 2740 | CB | GLU | A | 480 | 20.249 | 53.846 | 11.632 | 1.00 | 26.36 C |
| ATOM | 2741 | CG | GLU | A | 480 | 18.915 | 53.184 | 11.322 | 1.00 | 26.03 C |
| ATOM | 2742 | CD | GLU | A | 480 | 18.986 | 52.182 | 10.192 | 1.00 | 24.49 C |
| ATOM | 2743 | OE1 | GLU | A | 480 | 17.936 | 51.857 | 9.597 | 1.00 | 23.37 O |
| ATOM | 2744 | OE2 | GLU | A | 480 | 20.095 | 51.725 | 9.902 | 1.00 | 23.58 O |
| ATOM | 2745 | C | GLU | A | 480 | 20.506 | 53.322 | 14.084 | 1.00 | 29.49 C |
| ATOM | 2746 | O | GLU | A | 480 | 19.662 | 53.156 | 14.982 | 1.00 | 32.89 O |
| ATOM | 2747 | N | ALA | A | 481 | 21.627 | 52.595 | 14.012 | 1.00 | 29.69 N |
| ATOM | 2748 | CA | ALA | A | 481 | 21.798 | 51.359 | 14.808 | 1.00 | 30.05 C |
| ATOM | 2749 | CB | ALA | A | 481 | 22.736 | 50.389 | 14.103 | 1.00 | 29.29 C |
| ATOM | 2750 | C | ALA | A | 481 | 22.231 | 51.579 | 16.271 | 1.00 | 31.74 C |
| ATOM | 2751 | O | ALA | A | 481 | 22.627 | 50.636 | 16.972 | 1.00 | 32.30 O |
| ATOM | 2752 | N | PHE | A | 482 | 22.143 | 52.821 | 16.731 | 1.00 | 32.59 N |
| ATOM | 2753 | CA | PHE | A | 482 | 22.348 | 53.127 | 18.128 | 1.00 | 33.03 C |
| ATOM | 2754 | CB | PHE | A | 482 | 22.228 | 54.632 | 18.355 | 1.00 | 31.69 C |
| ATOM | 2755 | CG | PHE | A | 482 | 22.209 | 55.008 | 19.801 | 1.00 | 31.48 C |
| ATOM | 2756 | CD1 | PHE | A | 482 | 21.057 | 54.863 | 20.546 | 1.00 | 30.32 C |
| ATOM | 2757 | CE1 | PHE | A | 482 | 21.038 | 55.184 | 21.882 | 1.00 | 30.87 C |
| ATOM | 2758 | CZ | PHE | A | 482 | 22.177 | 55.653 | 22.508 | 1.00 | 31.52 C |
| ATOM | 2759 | CE2 | PHE | A | 482 | 23.344 | 55.792 | 21.780 | 1.00 | 31.64 C |
| ATOM | 2760 | CD2 | PHE | A | 482 | 23.356 | 55.465 | 20.433 | 1.00 | 31.92 C |
| ATOM | 2761 | C | PHE | A | 482 | 21.306 | 52.411 | 18.966 | 1.00 | 35.09 C |
| ATOM | 2762 | O | PHE | A | 482 | 21.593 | 51.866 | 20.043 | 1.00 | 34.35 O |

TABLE 3-continued

GLTP domain of FAPP2 atomic coordinates

| ATOM | 2763 | N | SER | A | 483 | 20.087 | 52.449 | 18.452 | 1.00 | 37.45 | N |
|---|---|---|---|---|---|---|---|---|---|---|---|
| ATOM | 2764 | CA | SER | A | 483 | 18.888 | 52.043 | 19.188 | 1.00 | 40.66 | C |
| ATOM | 2765 | CB | SER | A | 483 | 17.680 | 52.160 | 18.236 | 1.00 | 44.10 | C |
| ATOM | 2766 | OG | SER | A | 483 | 18.060 | 52.783 | 17.000 | 1.00 | 44.77 | O |
| ATOM | 2767 | C | SER | A | 483 | 18.994 | 50.605 | 19.716 | 1.00 | 38.61 | C |
| ATOM | 2768 | O | SER | A | 483 | 18.567 | 50.280 | 20.840 | 1.00 | 33.55 | O |
| ATOM | 2769 | N | ILE | A | 484 | 19.569 | 49.766 | 18.859 | 1.00 | 38.25 | N |
| ATOM | 2770 | CA | ILE | A | 484 | 19.657 | 48.337 | 19.063 | 1.00 | 38.22 | C |
| ATOM | 2771 | CB | ILE | A | 484 | 19.323 | 47.578 | 17.720 | 1.00 | 40.15 | C |
| ATOM | 2772 | CG1 | ILE | A | 484 | 18.266 | 46.469 | 17.940 | 1.00 | 40.68 | C |
| ATOM | 2773 | CD1 | ILE | A | 484 | 16.851 | 46.981 | 18.247 | 1.00 | 40.75 | C |
| ATOM | 2774 | CG2 | ILE | A | 484 | 20.576 | 47.074 | 16.991 | 1.00 | 39.79 | C |
| ATOM | 2775 | C | ILE | A | 484 | 21.041 | 48.049 | 19.641 | 1.00 | 37.31 | C |
| ATOM | 2776 | O | ILE | A | 484 | 21.179 | 47.212 | 20.524 | 1.00 | 34.42 | O |
| ATOM | 2777 | N | GLY | A | 485 | 22.059 | 48.773 | 19.177 | 1.00 | 39.85 | N |
| ATOM | 2778 | CA | GLY | A | 485 | 23.404 | 48.647 | 19.738 | 1.00 | 40.56 | C |
| ATOM | 2779 | C | GLY | A | 485 | 23.330 | 48.757 | 21.246 | 1.00 | 38.90 | C |
| ATOM | 2780 | O | GLY | A | 485 | 23.991 | 48.033 | 21.985 | 1.00 | 39.01 | O |
| ATOM | 2781 | N | MET | A | 486 | 22.493 | 49.658 | 21.705 | 1.00 | 37.62 | N |
| ATOM | 2782 | CA | MET | A | 486 | 22.416 | 49.902 | 23.111 | 1.00 | 41.92 | C |
| ATOM | 2783 | CB | MET | A | 486 | 22.210 | 51.396 | 23.316 | 1.00 | 44.16 | C |
| ATOM | 2784 | CG | MET | A | 486 | 20.791 | 51.866 | 23.456 | 1.00 | 45.48 | C |
| ATOM | 2785 | SD | MET | A | 486 | 20.487 | 52.245 | 25.185 | 1.00 | 49.13 | S |
| ATOM | 2786 | CE | MET | A | 486 | 18.694 | 52.282 | 25.172 | 1.00 | 46.45 | C |
| ATOM | 2787 | C | MET | A | 486 | 21.362 | 49.016 | 23.810 | 1.00 | 43.51 | C |
| ATOM | 2788 | O | MET | A | 486 | 21.236 | 49.010 | 25.037 | 1.00 | 44.09 | O |
| ATOM | 2789 | N | GLN | A | 487 | 20.621 | 48.265 | 23.005 | 1.00 | 46.44 | N |
| ATOM | 2790 | CA | GLN | A | 487 | 19.828 | 47.122 | 23.452 | 1.00 | 46.27 | C |
| ATOM | 2791 | CB | GLN | A | 487 | 18.705 | 46.870 | 22.426 | 1.00 | 46.98 | C |
| ATOM | 2792 | CG | GLN | A | 487 | 17.596 | 45.913 | 22.849 | 1.00 | 48.13 | C |
| ATOM | 2793 | CD | GLN | A | 487 | 17.672 | 44.507 | 22.232 | 1.00 | 47.61 | C |
| ATOM | 2794 | OE1 | GLN | A | 487 | 18.365 | 44.266 | 21.234 | 1.00 | 48.21 | O |
| ATOM | 2795 | NE2 | GLN | A | 487 | 16.936 | 43.565 | 22.836 | 1.00 | 47.13 | N |
| ATOM | 2796 | C | GLN | A | 487 | 20.754 | 45.890 | 23.606 | 1.00 | 46.99 | C |
| ATOM | 2797 | O | GLN | A | 487 | 20.566 | 45.089 | 24.521 | 1.00 | 47.78 | O |
| ATOM | 2798 | N | ARG | A | 488 | 21.747 | 45.751 | 22.717 | 1.00 | 46.14 | N |
| ATOM | 2799 | CA | ARG | A | 488 | 22.829 | 44.753 | 22.876 | 1.00 | 47.15 | C |
| ATOM | 2800 | CB | ARG | A | 488 | 23.861 | 44.842 | 21.737 | 1.00 | 50.23 | C |
| ATOM | 2801 | CG | ARG | A | 488 | 23.866 | 43.681 | 20.755 | 1.00 | 53.21 | C |
| ATOM | 2802 | CD | ARG | A | 488 | 24.194 | 42.350 | 21.410 | 1.00 | 55.06 | C |
| ATOM | 2803 | NE | ARG | A | 488 | 25.039 | 41.530 | 20.544 | 1.00 | 57.05 | N |
| ATOM | 2804 | CZ | ARG | A | 488 | 24.652 | 40.957 | 19.405 | 1.00 | 60.48 | C |
| ATOM | 2805 | NH1 | ARG | A | 488 | 23.408 | 41.094 | 18.949 | 1.00 | 62.17 | N |
| ATOM | 2806 | NH2 | ARG | A | 488 | 25.527 | 40.231 | 18.711 | 1.00 | 61.80 | N |
| ATOM | 2807 | C | ARG | A | 488 | 23.579 | 44.943 | 24.186 | 1.00 | 45.15 | C |
| ATOM | 2808 | O | ARG | A | 488 | 23.582 | 44.059 | 25.041 | 1.00 | 43.32 | O |
| ATOM | 2809 | N | ASP | A | 489 | 24.220 | 46.103 | 24.323 | 1.00 | 42.30 | N |
| ATOM | 2810 | CA | ASP | A | 489 | 24.931 | 46.452 | 25.545 | 1.00 | 40.24 | C |
| ATOM | 2811 | CB | ASP | A | 489 | 25.310 | 47.938 | 25.556 | 1.00 | 40.05 | C |
| ATOM | 2812 | CG | ASP | A | 489 | 26.279 | 48.315 | 24.437 | 1.00 | 42.32 | C |
| ATOM | 2813 | OD1 | ASP | A | 489 | 26.944 | 47.430 | 23.850 | 1.00 | 43.73 | O |
| ATOM | 2814 | OD2 | ASP | A | 489 | 26.385 | 49.519 | 24.143 | 1.00 | 44.17 | O |
| ATOM | 2815 | C | ASP | A | 489 | 24.086 | 46.109 | 26.774 | 1.00 | 38.11 | C |
| ATOM | 2816 | O | ASP | A | 489 | 24.622 | 45.614 | 27.755 | 1.00 | 40.22 | O |
| ATOM | 2817 | N | LEU | A | 490 | 22.773 | 46.335 | 26.719 | 1.00 | 34.38 | N |
| ATOM | 2818 | CA | LEU | A | 490 | 21.897 | 46.018 | 27.875 | 1.00 | 33.66 | C |
| ATOM | 2819 | CB | LEU | A | 490 | 20.519 | 46.694 | 27.740 | 1.00 | 33.89 | C |
| ATOM | 2820 | CG | LEU | A | 490 | 20.094 | 47.844 | 28.674 | 1.00 | 33.37 | C |
| ATOM | 2821 | CD1 | LEU | A | 490 | 21.250 | 48.482 | 29.430 | 1.00 | 34.63 | C |
| ATOM | 2822 | CD2 | LEU | A | 490 | 19.351 | 48.914 | 27.894 | 1.00 | 33.05 | C |
| ATOM | 2823 | C | LEU | A | 490 | 21.698 | 44.527 | 28.194 | 1.00 | 31.42 | C |
| ATOM | 2824 | O | LEU | A | 490 | 21.729 | 44.138 | 29.360 | 1.00 | 30.45 | O |
| ATOM | 2825 | N | SER | A | 491 | 21.495 | 43.694 | 27.179 | 1.00 | 30.94 | N |
| ATOM | 2826 | CA | SER | A | 491 | 21.332 | 42.252 | 27.413 | 1.00 | 30.71 | C |
| ATOM | 2827 | CB | SER | A | 491 | 20.762 | 41.550 | 26.177 | 1.00 | 30.02 | C |
| ATOM | 2828 | OG | SER | A | 491 | 21.642 | 41.664 | 25.085 | 1.00 | 30.25 | O |
| ATOM | 2829 | C | SER | A | 491 | 22.648 | 41.587 | 27.867 | 1.00 | 30.87 | C |
| ATOM | 2830 | O | SER | A | 491 | 22.617 | 40.539 | 28.514 | 1.00 | 29.76 | O |
| ATOM | 2831 | N | LEU | A | 492 | 23.786 | 42.199 | 27.517 | 1.00 | 30.58 | N |
| ATOM | 2832 | CA | LEU | A | 492 | 25.084 | 41.813 | 28.036 | 1.00 | 29.77 | C |
| ATOM | 2833 | CB | LEU | A | 492 | 26.184 | 42.601 | 27.326 | 1.00 | 31.34 | C |
| ATOM | 2834 | CG | LEU | A | 492 | 26.370 | 42.525 | 25.805 | 1.00 | 32.30 | C |
| ATOM | 2835 | CD1 | LEU | A | 492 | 27.623 | 43.313 | 25.414 | 1.00 | 32.61 | C |
| ATOM | 2836 | CD2 | LEU | A | 492 | 26.434 | 41.083 | 25.305 | 1.00 | 31.27 | C |
| ATOM | 2837 | C | LEU | A | 492 | 25.170 | 42.144 | 29.517 | 1.00 | 29.54 | C |
| ATOM | 2838 | O | LEU | A | 492 | 25.679 | 41.368 | 30.327 | 1.00 | 29.87 | O |
| ATOM | 2839 | N | TYR | A | 493 | 24.672 | 43.323 | 29.853 | 1.00 | 29.48 | N |
| ATOM | 2840 | CA | TYR | A | 493 | 24.934 | 43.941 | 31.136 | 1.00 | 30.17 | C |

TABLE 3-continued

| | | | | | | | | | | |
|---|---|---|---|---|---|---|---|---|---|---|
| ATOM | 2841 | CB | TYR | A | 493 | 24.795 | 45.463 | 31.003 | 1.00 | 29.93 C |
| ATOM | 2842 | CG | TYR | A | 493 | 24.847 | 46.209 | 32.306 | 1.00 | 29.58 C |
| ATOM | 2843 | CD1 | TYR | A | 493 | 26.048 | 46.463 | 32.933 | 1.00 | 28.60 C |
| ATOM | 2844 | CE1 | TYR | A | 493 | 26.101 | 47.150 | 34.132 | 1.00 | 28.36 C |
| ATOM | 2845 | CZ | TYR | A | 493 | 24.941 | 47.593 | 34.727 | 1.00 | 29.05 C |
| ATOM | 2846 | OH | TYR | A | 493 | 25.005 | 48.277 | 35.923 | 1.00 | 27.52 O |
| ATOM | 2847 | CE2 | TYR | A | 493 | 23.720 | 47.356 | 34.124 | 1.00 | 30.41 C |
| ATOM | 2848 | CD2 | TYR | A | 493 | 23.680 | 46.665 | 32.915 | 1.00 | 31.30 C |
| ATOM | 2849 | C | TYR | A | 493 | 24.015 | 43.412 | 32.228 | 1.00 | 31.41 C |
| ATOM | 2850 | O | TYR | A | 493 | 24.487 | 43.062 | 33.314 | 1.00 | 31.80 O |
| ATOM | 2851 | N | LEU | A | 494 | 22.712 | 43.352 | 31.955 | 1.00 | 31.60 N |
| ATOM | 2852 | CA | LEU | A | 494 | 21.745 | 43.030 | 33.022 | 1.00 | 32.71 C |
| ATOM | 2853 | CB | LEU | A | 494 | 20.288 | 43.208 | 32.545 | 1.00 | 32.63 C |
| ATOM | 2854 | CG | LEU | A | 494 | 19.883 | 44.645 | 32.159 | 1.00 | 32.78 C |
| ATOM | 2855 | CD1 | LEU | A | 494 | 18.497 | 44.689 | 31.534 | 1.00 | 31.47 C |
| ATOM | 2856 | CD2 | LEU | A | 494 | 19.962 | 45.608 | 33.335 | 1.00 | 33.11 C |
| ATOM | 2857 | C | LEU | A | 494 | 21.953 | 41.651 | 33.691 | 1.00 | 32.97 C |
| ATOM | 2858 | O | LEU | A | 494 | 21.705 | 41.512 | 34.904 | 1.00 | 31.59 O |
| ATOM | 2859 | N | PRO | A | 495 | 22.397 | 40.633 | 32.917 | 1.00 | 32.13 N |
| ATOM | 2860 | CA | PRO | A | 495 | 22.730 | 39.324 | 33.504 | 1.00 | 32.69 C |
| ATOM | 2861 | CB | PRO | A | 495 | 23.094 | 38.486 | 32.280 | 1.00 | 32.31 C |
| ATOM | 2862 | CG | PRO | A | 495 | 22.184 | 39.035 | 31.229 | 1.00 | 31.70 C |
| ATOM | 2863 | CD | PRO | A | 495 | 22.234 | 40.527 | 31.457 | 1.00 | 31.19 C |
| ATOM | 2864 | C | PRO | A | 495 | 23.872 | 39.343 | 34.512 | 1.00 | 34.15 C |
| ATOM | 2865 | O | PRO | A | 495 | 23.796 | 38.656 | 35.526 | 1.00 | 34.21 O |
| ATOM | 2866 | N | ALA | A | 496 | 24.917 | 40.120 | 34.236 | 1.00 | 35.74 N |
| ATOM | 2867 | CA | ALA | A | 496 | 26.006 | 40.333 | 35.200 | 1.00 | 36.64 C |
| ATOM | 2868 | CB | ALA | A | 496 | 27.052 | 41.256 | 34.604 | 1.00 | 38.04 C |
| ATOM | 2869 | C | ALA | A | 496 | 25.484 | 40.936 | 36.494 | 1.00 | 36.19 C |
| ATOM | 2870 | O | ALA | A | 496 | 25.965 | 40.637 | 37.590 | 1.00 | 33.36 O |
| ATOM | 2871 | N | MET | A | 497 | 24.494 | 41.804 | 36.334 | 1.00 | 37.00 N |
| ATOM | 2872 | CA | MET | A | 497 | 23.861 | 42.482 | 37.438 | 1.00 | 37.31 C |
| ATOM | 2873 | CB | MET | A | 497 | 23.058 | 43.639 | 36.883 | 1.00 | 39.12 C |
| ATOM | 2874 | CG | MET | A | 497 | 22.858 | 44.748 | 37.876 | 1.00 | 42.16 C |
| ATOM | 2875 | SD | MET | A | 497 | 21.586 | 45.895 | 37.341 | 1.00 | 44.26 S |
| ATOM | 2876 | CE | MET | A | 497 | 21.367 | 46.728 | 38.922 | 1.00 | 44.32 C |
| ATOM | 2877 | C | MET | A | 497 | 22.958 | 41.537 | 38.234 | 1.00 | 37.23 C |
| ATOM | 2878 | O | MET | A | 497 | 22.946 | 41.561 | 39.473 | 1.00 | 36.66 O |
| ATOM | 2879 | N | GLU | A | 498 | 22.211 | 40.712 | 37.506 | 1.00 | 37.71 N |
| ATOM | 2880 | CA | GLU | A | 498 | 21.339 | 39.692 | 38.087 | 1.00 | 38.92 C |
| ATOM | 2881 | CB | GLU | A | 498 | 20.603 | 38.944 | 36.962 | 1.00 | 41.45 C |
| ATOM | 2882 | CG | GLU | A | 498 | 19.330 | 38.197 | 37.371 | 1.00 | 44.77 C |
| ATOM | 2883 | CD | GLU | A | 498 | 19.568 | 36.908 | 38.164 | 1.00 | 48.73 C |
| ATOM | 2884 | OE1 | GLU | A | 498 | 18.714 | 36.592 | 39.035 | 1.00 | 51.80 O |
| ATOM | 2885 | OE2 | GLU | A | 498 | 20.593 | 36.211 | 37.933 | 1.00 | 49.99 O |
| ATOM | 2886 | C | GLU | A | 498 | 22.078 | 38.674 | 38.974 | 1.00 | 38.21 C |
| ATOM | 2887 | O | GLU | A | 498 | 21.574 | 38.332 | 40.041 | 1.00 | 38.37 O |
| ATOM | 2888 | N | LYS | A | 499 | 23.247 | 38.180 | 38.538 | 1.00 | 37.65 N |
| ATOM | 2889 | CA | LYS | A | 499 | 23.931 | 37.063 | 39.237 | 1.00 | 37.08 C |
| ATOM | 2890 | CB | LYS | A | 499 | 25.143 | 36.531 | 38.463 | 1.00 | 39.09 C |
| ATOM | 2891 | CG | LYS | A | 499 | 24.851 | 36.080 | 37.044 | 1.00 | 42.32 C |
| ATOM | 2892 | CD | LYS | A | 499 | 24.467 | 34.612 | 36.897 | 1.00 | 43.41 C |
| ATOM | 2893 | CE | LYS | A | 499 | 23.887 | 34.371 | 35.499 | 1.00 | 43.96 C |
| ATOM | 2894 | NZ | LYS | A | 499 | 24.397 | 33.125 | 34.868 | 1.00 | 43.85 N |
| ATOM | 2895 | C | LYS | A | 499 | 24.391 | 37.490 | 40.613 | 1.00 | 33.65 C |
| ATOM | 2896 | O | LYS | A | 499 | 24.305 | 36.720 | 41.562 | 1.00 | 31.97 O |
| ATOM | 2897 | N | GLN | A | 500 | 24.907 | 38.716 | 40.678 | 1.00 | 31.62 N |
| ATOM | 2898 | CA | GLN | A | 500 | 25.228 | 39.402 | 41.923 | 1.00 | 29.99 C |
| ATOM | 2899 | CB | GLN | A | 500 | 25.674 | 40.840 | 41.630 | 1.00 | 30.58 C |
| ATOM | 2900 | CG | GLN | A | 500 | 27.129 | 41.130 | 41.950 | 1.00 | 31.36 C |
| ATOM | 2901 | CD | GLN | A | 500 | 28.091 | 40.618 | 40.905 | 1.00 | 31.89 C |
| ATOM | 2902 | OE1 | GLN | A | 500 | 28.062 | 41.044 | 39.758 | 1.00 | 32.34 O |
| ATOM | 2903 | NE2 | GLN | A | 500 | 28.974 | 39.722 | 41.307 | 1.00 | 34.07 N |
| ATOM | 2904 | C | GLN | A | 500 | 24.036 | 39.454 | 42.861 | 1.00 | 28.65 C |
| ATOM | 2905 | O | GLN | A | 500 | 24.136 | 39.080 | 44.035 | 1.00 | 26.95 O |
| ATOM | 2906 | N | LEU | A | 501 | 22.914 | 39.940 | 42.335 | 1.00 | 28.10 N |
| ATOM | 2907 | CA | LEU | A | 501 | 21.703 | 40.118 | 43.132 | 1.00 | 28.11 C |
| ATOM | 2908 | CB | LEU | A | 501 | 20.656 | 40.906 | 42.356 | 1.00 | 29.35 C |
| ATOM | 2909 | CG | LEU | A | 501 | 20.977 | 42.358 | 42.022 | 1.00 | 30.59 C |
| ATOM | 2910 | CD1 | LEU | A | 501 | 19.719 | 43.007 | 41.464 | 1.00 | 30.88 C |
| ATOM | 2911 | CD2 | LEU | A | 501 | 21.481 | 43.132 | 43.230 | 1.00 | 30.61 C |
| ATOM | 2912 | C | LEU | A | 501 | 21.076 | 38.809 | 43.584 | 1.00 | 26.83 C |
| ATOM | 2913 | O | LEU | A | 501 | 20.326 | 38.797 | 44.565 | 1.00 | 26.34 O |
| ATOM | 2914 | N | ALA | A | 502 | 21.362 | 37.728 | 42.854 | 1.00 | 25.52 N |
| ATOM | 2915 | CA | ALA | A | 502 | 20.880 | 36.384 | 43.201 | 1.00 | 24.67 C |
| ATOM | 2916 | CB | ALA | A | 502 | 20.865 | 35.481 | 41.973 | 1.00 | 24.29 C |
| ATOM | 2917 | C | ALA | A | 502 | 21.732 | 35.766 | 44.302 | 1.00 | 23.43 C |
| ATOM | 2918 | O | ALA | A | 502 | 21.239 | 34.956 | 45.084 | 1.00 | 22.96 O |

TABLE 3-continued

GLTP domain of FAPP2 atomic coordinates

| ATOM | 2919 | N | ILE | A | 503 | 23.005 | 36.155 | 44.351 | 1.00 | 22.71 | N |
|---|---|---|---|---|---|---|---|---|---|---|---|
| ATOM | 2920 | CA | ILE | A | 503 | 23.928 | 35.709 | 45.398 | 1.00 | 22.19 | C |
| ATOM | 2921 | CB | ILE | A | 503 | 25.399 | 36.031 | 45.037 | 1.00 | 21.90 | C |
| ATOM | 2922 | CG1 | ILE | A | 503 | 25.886 | 35.075 | 43.942 | 1.00 | 21.45 | C |
| ATOM | 2923 | CD1 | ILE | A | 503 | 27.056 | 35.602 | 43.138 | 1.00 | 21.37 | C |
| ATOM | 2924 | CG2 | ILE | A | 503 | 26.313 | 35.958 | 46.265 | 1.00 | 21.71 | C |
| ATOM | 2925 | C | ILE | A | 503 | 23.565 | 36.360 | 46.721 | 1.00 | 21.94 | C |
| ATOM | 2926 | O | ILE | A | 503 | 23.715 | 35.746 | 47.775 | 1.00 | 21.24 | O |
| ATOM | 2927 | N | LEU | A | 504 | 23.101 | 37.603 | 46.652 | 1.00 | 22.41 | N |
| ATOM | 2928 | CA | LEU | A | 504 | 22.669 | 38.336 | 47.845 | 1.00 | 23.42 | C |
| ATOM | 2929 | CB | LEU | A | 504 | 22.663 | 39.847 | 47.583 | 1.00 | 23.15 | C |
| ATOM | 2930 | CG | LEU | A | 504 | 23.999 | 40.462 | 47.171 | 1.00 | 22.80 | C |
| ATOM | 2931 | CD1 | LEU | A | 504 | 23.846 | 41.947 | 46.890 | 1.00 | 22.76 | C |
| ATOM | 2932 | CD2 | LEU | A | 504 | 25.039 | 40.212 | 48.241 | 1.00 | 22.67 | C |
| ATOM | 2933 | C | LEU | A | 504 | 21.285 | 37.877 | 48.314 | 1.00 | 23.97 | C |
| ATOM | 2934 | O | LEU | A | 504 | 21.062 | 37.727 | 49.517 | 1.00 | 24.15 | O |
| ATOM | 2935 | N | ASP | A | 505 | 20.371 | 37.656 | 47.369 | 1.00 | 24.02 | N |
| ATOM | 2936 | CA | ASP | A | 505 | 19.048 | 37.107 | 47.681 | 1.00 | 24.62 | C |
| ATOM | 2937 | CB | ASP | A | 505 | 18.210 | 36.856 | 46.406 | 1.00 | 24.51 | C |
| ATOM | 2938 | CG | ASP | A | 505 | 17.507 | 38.114 | 45.885 | 1.00 | 24.40 | C |
| ATOM | 2939 | OD1 | ASP | A | 505 | 17.489 | 39.154 | 46.590 | 1.00 | 23.95 | O |
| ATOM | 2940 | OD2 | ASP | A | 505 | 16.967 | 38.049 | 44.756 | 1.00 | 23.55 | O |
| ATOM | 2941 | C | ASP | A | 505 | 19.151 | 35.809 | 48.478 | 1.00 | 25.06 | C |
| ATOM | 2942 | O | ASP | A | 505 | 18.484 | 35.659 | 49.492 | 1.00 | 24.82 | O |
| ATOM | 2943 | N | THR | A | 506 | 19.977 | 34.873 | 48.028 | 1.00 | 26.62 | N |
| ATOM | 2944 | CA | THR | A | 506 | 20.127 | 33.599 | 48.747 | 1.00 | 28.78 | C |
| ATOM | 2945 | CB | THR | A | 506 | 20.673 | 32.473 | 47.836 | 1.00 | 29.14 | C |
| ATOM | 2946 | OG1 | THR | A | 506 | 21.733 | 32.989 | 47.030 | 1.00 | 31.21 | O |
| ATOM | 2947 | CG2 | THR | A | 506 | 19.562 | 31.907 | 46.914 | 1.00 | 28.82 | C |
| ATOM | 2948 | C | THR | A | 506 | 20.977 | 33.712 | 50.034 | 1.00 | 29.58 | C |
| ATOM | 2949 | O | THR | A | 506 | 20.850 | 32.873 | 50.923 | 1.00 | 30.36 | O |
| ATOM | 2950 | N | LEU | A | 507 | 21.820 | 34.743 | 50.137 | 1.00 | 30.54 | N |
| ATOM | 2951 | CA | LEU | A | 507 | 22.585 | 35.011 | 51.363 | 1.00 | 30.73 | C |
| ATOM | 2952 | CB | LEU | A | 507 | 23.655 | 36.080 | 51.116 | 1.00 | 30.51 | C |
| ATOM | 2953 | CG | LEU | A | 507 | 24.484 | 36.505 | 52.333 | 1.00 | 30.35 | C |
| ATOM | 2954 | CD1 | LEU | A | 507 | 25.568 | 35.473 | 52.619 | 1.00 | 30.41 | C |
| ATOM | 2955 | CD2 | LEU | A | 507 | 25.080 | 37.889 | 52.121 | 1.00 | 29.86 | C |
| ATOM | 2956 | C | LEU | A | 507 | 21.650 | 35.484 | 52.468 | 1.00 | 31.88 | C |
| ATOM | 2957 | O | LEU | A | 507 | 21.718 | 35.006 | 53.601 | 1.00 | 30.54 | O |
| ATOM | 2958 | N | TYR | A | 508 | 20.789 | 36.439 | 52.128 | 1.00 | 33.60 | N |
| ATOM | 2959 | CA | TYR | A | 508 | 19.789 | 36.949 | 53.069 | 1.00 | 35.82 | C |
| ATOM | 2960 | CB | TYR | A | 508 | 19.126 | 38.241 | 52.531 | 1.00 | 35.45 | C |
| ATOM | 2961 | CG | TYR | A | 508 | 19.965 | 39.471 | 52.821 | 1.00 | 35.27 | C |
| ATOM | 2962 | CD1 | TYR | A | 508 | 21.225 | 39.622 | 52.246 | 1.00 | 35.37 | C |
| ATOM | 2963 | CE1 | TYR | A | 508 | 22.016 | 40.723 | 52.529 | 1.00 | 35.40 | C |
| ATOM | 2964 | CZ | TYR | A | 508 | 21.558 | 41.687 | 53.404 | 1.00 | 35.10 | C |
| ATOM | 2965 | OH | TYR | A | 508 | 22.363 | 42.768 | 53.667 | 1.00 | 34.55 | O |
| ATOM | 2966 | CE2 | TYR | A | 508 | 20.314 | 41.562 | 53.997 | 1.00 | 34.36 | C |
| ATOM | 2967 | CD2 | TYR | A | 508 | 19.528 | 40.456 | 53.708 | 1.00 | 34.73 | C |
| ATOM | 2968 | C | TYR | A | 508 | 18.749 | 35.879 | 53.446 | 1.00 | 38.81 | C |
| ATOM | 2969 | O | TYR | A | 508 | 18.366 | 35.767 | 54.617 | 1.00 | 38.27 | O |
| ATOM | 2970 | N | GLU | A | 509 | 18.320 | 35.083 | 52.461 | 1.00 | 42.45 | N |
| ATOM | 2971 | CA | GLU | A | 509 | 17.339 | 34.009 | 52.690 | 1.00 | 44.44 | C |
| ATOM | 2972 | CB | GLU | A | 509 | 16.909 | 33.343 | 51.370 | 1.00 | 47.14 | C |
| ATOM | 2973 | CG | GLU | A | 509 | 15.857 | 34.116 | 50.579 | 1.00 | 50.74 | C |
| ATOM | 2974 | CD | GLU | A | 509 | 15.703 | 33.629 | 49.134 | 1.00 | 54.45 | C |
| ATOM | 2975 | OE1 | GLU | A | 509 | 16.157 | 32.498 | 48.821 | 1.00 | 55.06 | O |
| ATOM | 2976 | OE2 | GLU | A | 509 | 15.123 | 34.384 | 48.305 | 1.00 | 54.08 | O |
| ATOM | 2977 | C | GLU | A | 509 | 17.870 | 32.949 | 53.654 | 1.00 | 42.85 | C |
| ATOM | 2978 | O | GLU | A | 509 | 17.173 | 32.566 | 54.592 | 1.00 | 42.06 | O |
| ATOM | 2979 | N | VAL | A | 510 | 19.098 | 32.490 | 53.425 | 1.00 | 42.09 | N |
| ATOM | 2980 | CA | VAL | A | 510 | 19.679 | 31.403 | 54.236 | 1.00 | 42.64 | C |
| ATOM | 2981 | CB | VAL | A | 510 | 20.994 | 30.839 | 53.611 | 1.00 | 43.16 | C |
| ATOM | 2982 | CG1 | VAL | A | 510 | 22.112 | 31.874 | 53.595 | 1.00 | 43.83 | C |
| ATOM | 2983 | CG2 | VAL | A | 510 | 21.454 | 29.590 | 54.354 | 1.00 | 43.14 | C |
| ATOM | 2984 | C | VAL | A | 510 | 19.872 | 31.753 | 55.729 | 1.00 | 40.87 | C |
| ATOM | 2985 | O | VAL | A | 510 | 19.695 | 30.889 | 56.590 | 1.00 | 39.81 | O |
| ATOM | 2986 | N | HIS | A | 511 | 20.205 | 33.012 | 56.028 | 1.00 | 40.28 | N |
| ATOM | 2987 | CA | HIS | A | 511 | 20.410 | 33.474 | 57.416 | 1.00 | 39.10 | C |
| ATOM | 2988 | CB | HIS | A | 511 | 21.602 | 34.448 | 57.479 | 1.00 | 38.89 | C |
| ATOM | 2989 | CG | HIS | A | 511 | 22.915 | 33.813 | 57.134 | 1.00 | 38.78 | C |
| ATOM | 2990 | ND1 | HIS | A | 511 | 23.481 | 33.907 | 55.881 | 1.00 | 38.88 | N |
| ATOM | 2991 | CE1 | HIS | A | 511 | 24.617 | 33.233 | 55.860 | 1.00 | 38.68 | C |
| ATOM | 2992 | NE2 | HIS | A | 511 | 24.815 | 32.715 | 57.059 | 1.00 | 38.65 | N |
| ATOM | 2993 | CD2 | HIS | A | 511 | 23.763 | 33.060 | 57.875 | 1.00 | 38.60 | C |
| ATOM | 2994 | C | HIS | A | 511 | 19.173 | 34.122 | 58.064 | 1.00 | 38.54 | C |
| ATOM | 2995 | O | HIS | A | 511 | 19.261 | 34.604 | 59.182 | 1.00 | 37.93 | O |
| ATOM | 2996 | N | GLY | A | 512 | 18.040 | 34.149 | 57.363 | 1.00 | 39.42 | N |

TABLE 3-continued

GLTP domain of FAPP2 atomic coordinates

| ATOM | 2997 | CA  | GLY | A | 512 | 16.789 | 34.695 | 57.898 | 1.00 | 40.19 | C |
| ATOM | 2998 | C   | GLY | A | 512 | 16.753 | 36.211 | 58.039 | 1.00 | 41.68 | C |
| ATOM | 2999 | O   | GLY | A | 512 | 16.501 | 36.717 | 59.129 | 1.00 | 42.12 | O |
| ATOM | 3000 | N   | LEU | A | 513 | 16.980 | 36.933 | 56.937 | 1.00 | 43.63 | N |
| ATOM | 3001 | CA  | LEU | A | 513 | 17.143 | 38.395 | 56.966 | 1.00 | 44.58 | C |
| ATOM | 3002 | CB  | LEU | A | 513 | 18.544 | 38.804 | 56.467 | 1.00 | 44.83 | C |
| ATOM | 3003 | CG  | LEU | A | 513 | 19.799 | 38.671 | 57.350 | 1.00 | 45.38 | C |
| ATOM | 3004 | CD1 | LEU | A | 513 | 19.882 | 37.335 | 58.064 | 1.00 | 45.31 | C |
| ATOM | 3005 | CD2 | LEU | A | 513 | 21.058 | 38.884 | 56.516 | 1.00 | 45.40 | C |
| ATOM | 3006 | C   | LEU | A | 513 | 16.079 | 39.097 | 56.126 | 1.00 | 46.58 | C |
| ATOM | 3007 | O   | LEU | A | 513 | 16.407 | 39.848 | 55.211 | 1.00 | 44.92 | O |
| ATOM | 3008 | N   | GLU | A | 514 | 14.808 | 38.865 | 56.458 | 1.00 | 51.34 | N |
| ATOM | 3009 | CA  | GLU | A | 514 | 13.666 | 39.514 | 55.778 | 1.00 | 53.18 | C |
| ATOM | 3010 | CB  | GLU | A | 514 | 12.549 | 38.492 | 55.505 | 1.00 | 55.15 | C |
| ATOM | 3011 | CG  | GLU | A | 514 | 13.025 | 37.125 | 55.005 | 1.00 | 56.68 | C |
| ATOM | 3012 | CD  | GLU | A | 514 | 13.832 | 37.197 | 53.719 | 1.00 | 57.42 | C |
| ATOM | 3013 | OE1 | GLU | A | 514 | 13.704 | 38.208 | 52.991 | 1.00 | 59.22 | O |
| ATOM | 3014 | OE2 | GLU | A | 514 | 14.587 | 36.240 | 53.432 | 1.00 | 56.55 | O |
| ATOM | 3015 | C   | GLU | A | 514 | 13.101 | 40.680 | 56.605 | 1.00 | 52.49 | C |
| ATOM | 3016 | O   | GLU | A | 514 | 12.911 | 41.794 | 56.105 | 1.00 | 49.45 | O |

TABLE 4

| Identical | | Similar | | Different (unique to FAPP2) | |
|---|---|---|---|---|---|
| FAPP2-C212 | hGLTP | FAPP2-C212 | hGLTP | FAPP2-C212 | hGLTP |
| L349 | L37  | V342 | L30  | V345 | F33 |
| D360 | D48  | L346 | F34  | N399 | V88 |
| N364 | N52  | V357 | I45  | E403 | L92 |
| K367 | K55  | L361 | I49  | R398 | —   |
| W407 | W96  | L433 | A128 | F311 | —   |
| R410 | R99  | V452 | I147 | F312 | —   |
| F414 | F103 | L488 | I180 |      |     |
| I429 | I124 | Y491 | F183 |      |     |
| Y437 | Y132 |      |      |      |     |
| L441 | L136 |      |      |      |     |
| H445 | H140 |      |      |      |     |
| V449 | V144 |      |      |      |     |
| F453 | F148 |      |      |      |     |
| A456 | A151 |      |      |      |     |
| F466 | F161 |      |      |      |     |
| L470 | L165 |      |      |      |     |

REFERENCES CITED

[1] Thurberg et al., 2002 Kidney International, 62(6): 1933-1946
[2] Tanaka et al., 2005 Clinical Nephrology, 64(4): 281-287
[3] Desnick et al., 2002 Clinical Nephrology, 57(1):1-8
[4] Cho and Kopp, 2004 Pediatr Nephrol, 19(6):583-593
[5] Sessa et al., 2002 Nephron, 91(2): 348-351
[6] Winters et al., 2000 J Clin Apheresis, 15(1-2):53-73
[7] D'Angelo et al. 2013 Nature 501, 116-120
[8] Kamlekar et al., 2013 Biochim. Biophys Acta 1831(2)
[9] Cherezov V et al. 2007 Science 318(5854):1258-65
[10] Jaakola V et al, 2008 Science 322(5905):1211-7
[11] Zou et al 2012 PLOS ONE 7(10):e46039
[12] Tats et al. 2008 BMC Genomics, 9:e463
[13] Buchan et al. 2006 Nucleic Acids Res, 34:1015-1027
[14] Moura et al. 2007 PLoS ONE, 2(9):e847
[15] Good et al. 1966 Biochemistry 5:467-477
[16] Principles of protein X-ray crystallography by J. Drenth. 2nd ed. (1999) Springer-Verlag, Heidelberg, Germany
[17] Structure Determination by X-ray Crystallography by M. Ladd and. Palmer. 4th ed. (2003) Kluwer Academic/Plenum Publishers, New York, N.Y.
[18] The CCP4 suite: Acta Crystallogr. D., 50:760-763
[19] Navaza 1994 Acta Cryst., A50:157-163
[20] Acta Crystallogr. D., 54:905-921.
[21] Malakhova et al 2005 JBC 280(28): 26312-26320,
[22] Enzyme Kinetics by Segel (1975) J. Wiley & Sons
[23] Brown R E et al. 1990 Biochim Biophys Acta. 1990; 1044:77-83
[24] Mattjus P et al. 2000 Biochemistry 39:1067-1075
[25] Mattjus P et al. 1999 Anal Biochem. 1999; 268:297-304
[26] Rao C S et al. 2004 Biochemistry 43:13805-13815
[27] Samygina V R et al. 2011 Structure 19:1644-1654
[28] Goodford 1985 J. Med. Chem. 28:849 857
[29] Miranker, A. and M. Karplus, (1991) Proteins: Structure. Function and Genetics, 1 1:29-34
[30] Goodsell, D. S et al (1990) Proteins: Structure. Function, and Genetics 8:195 202
[31] Kuntz, I. D. et al. (1982) J Mol. Biol 161:269-288
[32] Bartlett, (1989) Molecular Recognition in Chemical and Biological Problems, Special Pub., Royal Chem. Soc. 78:182-196
[33] Martin, Y. C, (1992) J Med. Chem, 35:2145 2154
[34] Bohrn, (1992) J. Comp. Aid Molec. Design 6:61-78
[35] Nishibata, Y. and A. Itai, (1991) Tetrahedron 47:8985
[36] Cohen, N. C. et al. (1990) J Med. Chem. 33: 883-894
[37] Navia (1992) Current Opinions in Structural Biology 2:202-210
[38] Remington's Pharmaceutical Sciences; Mack Pub. Co., N.J. 1991

The invention claimed is:

1. A method of identifying a compound that binds to phosphoinositol 4-phosphate adaptor protein-2 (FAPP2), comprising computationally identifying a compound that binds to FAPP2 using the atomic coordinates of at least the amino acids which make up the substrate binding pocket of FAPP2, as set forth in Table 2.

2. The method of claim 1, wherein the compound binds to the substrate binding pocket of FAPP2 or binds adjacent to the substrate binding pocket of FAPP2.

3. The method of claim 1, wherein the compound is an inhibitor of FAPP2.

4. The method of claim 3 wherein the compound is a substrate of FAPP2.

5. The method of claim 1, wherein the compound is specific to FAPP2, preferably over GLTP.

6. The method of claim 1, wherein the compound is a small molecule.

7. The method of claim 1 wherein said computationally identifying includes identifying said compound from a library of compounds or identifying said compound in a database.

8. A polypeptide comprising an amino acid sequence with at least 95% sequence identity to amino acids 308-519 of FAPP2 (SEQ ID NO: 1) and an amino acid sequence with at least 95% sequence identity to amino acids 2-164 of lysozyme T4L (SEQ ID NO:2).

9. The polypeptide of claim 8 comprising residues D360, N364, W407 of human FAPP2, wherein the numbering is in accordance with SEQ ID NO:4.

10. The polypeptide of claim 8 comprising the sequence SEQ ID NO:3 or a fragment thereof.

11. The polypeptide of claim 10 consisting of the sequence SEQ ID NO:3.

12. The crystalline form of the polypeptide of claim 8.

13. The crystalline form of claim 12, wherein the crystal is characterized with space group $P2_12_12$ and has unit cell parameters of +/−5% of a=100.02 Å, b=130.87 Å, c=88.73 Å, α=90°, β=90°, γ=90°.

14. The crystalline form of claim 12 wherein the crystal diffracts x-rays for a determination of structure coordinates to a resolution of between approximately 2.0 Å to 4.0 Å.

* * * * *